(12) United States Patent
Strum et al.

(10) Patent No.: US 10,829,490 B2
(45) Date of Patent: Nov. 10, 2020

(54) SUBSTITUTED DIHYDROPYRAZINO[1', 2':1,5] PYRROLO[2,3-D]PYRIMIDINE-BASED ANTIPROLIFERATIVE AGENTS

(71) Applicant: G1 Therapeutics, Inc., Research Triangle Park, NC (US)

(72) Inventors: Jay Copeland Strum, Hillsborough, NC (US); David Jung, Durham, NC (US)

(73) Assignee: GI Therapeutics, Inc., Research Triangle Park, NC (US)

( * ) Notice: Subject to any disclaimer, the term of this patent is extended or adjusted under 35 U.S.C. 154(b) by 0 days.

(21) Appl. No.: 16/230,396

(22) Filed: Dec. 21, 2018

(65) Prior Publication Data

US 2019/0135811 A1 May 9, 2019

Related U.S. Application Data

(63) Continuation of application No. PCT/US2017/040093, filed on Jun. 29, 2017.

(60) Provisional application No. 62/357,630, filed on Jul. 1, 2016.

(51) Int. Cl.
| | | |
|---|---|---|
| *C07D 487/04* | (2006.01) | |
| *C07D 471/14* | (2006.01) | |
| *C07D 487/14* | (2006.01) | |
| *C07D 491/147* | (2006.01) | |
| *C07D 491/22* | (2006.01) | |
| *C07D 495/14* | (2006.01) | |
| *C07D 498/22* | (2006.01) | |
| *C07D 487/22* | (2006.01) | |
| *C07D 401/14* | (2006.01) | |
| *C07D 473/00* | (2006.01) | |

(52) U.S. Cl.
CPC ......... *C07D 471/14* (2013.01); *C07D 401/14* (2013.01); *C07D 473/00* (2013.01); *C07D 487/14* (2013.01); *C07D 487/22* (2013.01); *C07D 491/147* (2013.01); *C07D 491/22* (2013.01); *C07D 495/14* (2013.01); *C07D 498/22* (2013.01); *Y02P 20/55* (2015.11)

(58) Field of Classification Search
CPC .................................................. C07D 487/04
USPC ................................................. 544/343, 346
See application file for complete search history.

(56) References Cited

U.S. PATENT DOCUMENTS

| | | |
|---|---|---|
| 2004/0236084 A1 | 11/2004 | Biwersi et al. |
| 2011/0152244 A1 | 6/2011 | Besong et al. |
| 2014/0106870 A1 | 4/2014 | Naicker |
| 2014/0271466 A1 | 9/2014 | Sharpless et al. |
| 2014/0315888 A1 | 10/2014 | Ho et al. |
| 2019/0328874 A1 | 10/2019 | Wong |

FOREIGN PATENT DOCUMENTS

| | | |
|---|---|---|
| WO | WO 2001/068648 A1 | 9/2001 |
| WO | WO 2003/062236 A1 | 7/2003 |
| WO | WO 2004/065378 A1 | 8/2004 |
| WO | WO 2009/151589 A1 | 12/2009 |
| WO | WO 2010/020675 A1 | 2/2010 |
| WO | WO 2011/101409 A1 | 8/2011 |
| WO | WO 2012/061156 A1 | 5/2012 |
| WO | WO 2012/078859 A2 | 6/2012 |
| WO | WO 2012/082997 A1 | 6/2012 |
| WO | WO 2013/048214 A2 | 4/2013 |
| WO | WO 2013/148748 A1 | 10/2013 |
| WO | WO 2013/163239 A1 | 10/2013 |
| WO | WO 2015/061407 A1 | 4/2015 |
| WO | WO 2015/161283 A1 | 10/2015 |
| WO | WO 2015/161285 A1 | 10/2015 |
| WO | WO 2015/161287 A1 | 10/2015 |
| WO | WO 2015/161288 A1 | 10/2015 |
| WO | WO 2015/180642 A1 | 12/2015 |

(Continued)

OTHER PUBLICATIONS

U.S. Pat. No. 8,598,186, B2, U.S. Appl. No. 13/869,520 Tavares et al., Dec. 3, 2013.
U.S. Pat. No. 8,598,197, B2, U.S. Appl. No. 13/869,576, Tavares et al., Dec. 3, 2013.
U.S. Pat. No. 8,691,830, B2, U.S. Appl. No. 13/869,594, Tavares et al., Apr. 8, 2014.
U.S. Pat. No. 8,822,683, B2, U.S. Appl. No. 14/162,637, Tavares et al., Sep. 2, 2014.
U.S. Pat. No. 8,829,012, B2, U.S. Appl. No. 14/162,649, Tavares et al., Sep. 9, 2014.
U.S. Pat. No. 9,102,682, B2, U.S. Appl. No. 14/452,296, Tavares et al., Aug. 11, 2015.

(Continued)

*Primary Examiner* — Douglas M Willis
(74) *Attorney, Agent, or Firm* — Knowles Intellectual Property Strategies, LLC

(57) ABSTRACT

This invention is in the area of pyrimidine-based compounds for the treatment of disorders involving abnormal cellular proliferation, including but not limited to tumors and cancers. Representative examples of compounds of the present invention include

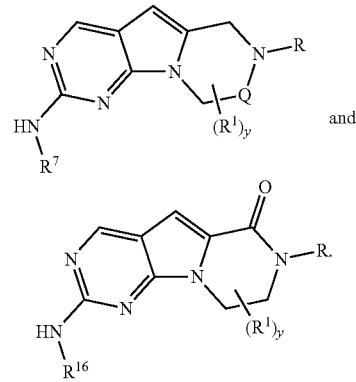

29 Claims, 3 Drawing Sheets

(56) References Cited

FOREIGN PATENT DOCUMENTS

WO     WO 16/040858     *    3/2016
WO     WO 2018/106870 A1    6/2018

OTHER PUBLICATIONS

U.S. Pat. No. 9,260,442, B2, U.S. Appl. No. 14/498,796, Tavares, Jan. 27, 2016.
U.S. Pat. No. 9,464,092, B2, U.S. Appl. No. 14/212,911, Strum et al., Oct. 11, 2016.
U.S. Pat. No. 9,481,691, B2, U.S. Appl. No. 14/712,630, Tavares et al., Nov. 1, 2016.
U.S. Pat. No. 9,487,530, B2, U.S. Appl. No. 14/212,430, Strum et al., Nov. 8, 2016.
U.S. Pat. No. 9,499,564, B2, U.S. Appl. No. 14/712,582, Tavares et al., Nov. 22, 2016.
U.S. Pat. No. 9,527,857, B2, U.S. Appl. No. 14/214,048, Strum et al., Dec. 27, 2016.
U.S. Pat. No. 9,717,735, B2, U.S. Appl. No. 14/690,180, Strum et al., Aug. 1, 2017.
U.S. Pat. No. 9,745,316, B2, U.S. Appl. No. 14/982,443, Tavares, Aug. 29, 2017.
U.S. Pat. No. 9,856,268, B2, U.S. Appl. No. 15/348,862, Tavares, Jan. 2, 2018.
U.S. Pat. No. 9,931,345, B2, U.S. Appl. No. 15/288,878, Strum et al., Apr. 3, 2018.
U.S. Pat. No. 9,957,276, B2, U.S. Appl. No. 15/348,770, Tavares et al., May 1, 2018.
U.S. Pat. No. 10,076,523, B2, U.S. Appl. No. 15/387,083, Strum et al., Sep. 18, 2018.
U.S. Pat. No. 10,085,992, A1, U.S. Appl. No. 15/342,990, Strum et al., Oct. 2, 2018.
U.S. Pat. No. 10,189,849, B2, U.S. Appl. No. 15/918,834, Tavares et al., Jan. 29, 2019.
U.S. Pat. No. 10,189,850, B2, U.S. Appl. No. 15/918,852, Tavares et al., Jan. 29, 2019.
U.S. Pat. No. 10,189,851, B2, U.S. Appl. No. 15/918,877, Tavares et al., Jan. 29, 2019.
U.S. Pat. No. 10,231,969, B2, U.S. Appl. No. 15/457,699, Strum, et al., Mar. 19, 2019.
2017/0333440, A1, U.S. Appl. No. 15/665,071, Strum, et al., Nov. 23, 2017.
2018/0127431, A1, U.S. Appl. No. 15/860,483, Tavares et al., May 10, 2018.
2018/0221378, A1, U.S. Appl. No. 15/943,278, Strum, et al., Aug. 9, 2018.
2018/0303838, A1, U.S. Appl. No. 15/839,685, Strum, et al., Oct. 25, 2018.
2018/0360840, A1, U.S. Appl. No. 16/112,360, Strum, et al., Dec. 20, 2018.
2018/0015096, A1, U.S. Appl. No. 15/713,385, Strum, et al., Jan. 18, 2018.
2018/0360841, A1, U.S. Appl. No. 16/112,362, Strum, et al., Dec. 20, 2018.
2019/0030034, A1, U.S. Appl. No. 16/142,574, Strum, et al., Jan. 31, 2019.
2019/0070185, A1, U.S. Appl. No. 16/178,419, Strum, et al., Mar. 7, 2019.
Johnson et al., "Mitigation of hematological radiation toxicity in mice through pharmacological quiescence induced by CDK4/6 inhibition." J. Clin. Invest. 2010; 120(7); 2528-2536.
VanderWel et al., Pyrido[2,3-d]pyrimidin-7-ones as Specific Inhibitors of Cyclin-Dependent Kinase 4, J. Med. Chem. 2005, 48, 2371-2387.
International Search Report and Written Opinion of International Application No. PCT/US17/40093 dated Nov. 20, 2017.

* cited by examiner

SUBSTITUTED DIHYDROPYRAZINO[1', 2':1,5]PYRROLO[2,3-D]PYRIMIDINE-BASED ANTIPROLIFERATIVE AGENTS

CROSS-REFERENCE TO RELATED APPLICATIONS

This application is a continuation of International Application No. PCT/US2017/040093, filed with the Patent Cooperation Treaty, U.S. Receiving Office on Jun. 29, 2017, which claims the benefit of U.S. Provisional Application 62/357,630 which was filed on Jul. 1, 2016. The entirety of these applications are hereby incorporated by reference herein for all purposes.

FIELD OF THE INVENTION

This invention is in the area of pyrimidine-based compounds for the treatment of disorders involving abnormal cellular proliferation, including but not limited to tumors and cancers.

BACKGROUND

In normal tissue, cellular proliferation is generally restricted to cells that are required to replenish the tissue. Once cells have terminally differentiated, they have a specialized function and no longer divide. Most tissues are made up of non-dividing cells. Thus normal cell proliferation is tightly controlled to ensure that only the necessary cells divide. There is also a careful balance between cell division and programmed cell death (apoptosis).

Cell division, sometimes referred to as the cell cycle, has four phases: $G_1$ phase (synthesis of various enzymes required for DNA replication), S phase (DNA replication producing two identical sets of chromosomes), $G_2$ (significant protein synthesis, including production of microtubules) and M phase (nuclear division, cytoplasmic division and formation of new cell membrane). Cell division also includes a complex system of cell signaling networks that allow cells to interpret information from numerous extracellular signals, including through receptor proteins, inflammatory factors and pro-apoptotic and anti-apoptotic signals.

Dysfunctional signals include those from genetic mutation, infection, exposure to environmental factors including toxins, system stress, autoimmune disorders, and inflammation.

A range of disorders can occur when the process of cell proliferation becomes dysfunctional, including benign growths, neoplasms, tumorigenesis, cancerogenesis, autoimmune disorders, inflammatory disorders graft-versus-host rejection, and fibrotic disorders.

A number of broad-spectrum anti-neoplastic agents have been developed. Cytoskeletal drugs like paclitaxel target tubulin to arrest mitotic cell division and are used to treat a variety of cancers including ovarian, breast, lung, pancreatic, and testicular tumors (See e.g., Jordan, Wilson, Nature Reviews Cancer (2004) 4: 253-265). Organometallic-based drugs such as cisplatin have been used to treat lymphomas, sarcomas, germ cell tumors, and some carcinomas including bladder, small cell lung cancer, and ovarian cancer. Cisplatin has the ability to bind nitrogenous bases and cause extensive DNA cross-linking that ultimately leads to apoptosis (See e.g., Siddick, Oncogene (2003) 22: 7265-7279). Intercalating and alkylating agents have also been extensive use in the clinic for the treatment of various neoplasms, however, the global toxicity associated with these drugs presents a critical concern for patients requiring long-term therapy.

Palbociclib (PD-033299; Ibrance) is sold by Pfizer for the treatment of estrogen-positive, HER2-negative breast cancer in combination with letrozole. The compound inhibits CDK4 and CDK6. The structure of palbociclib is:

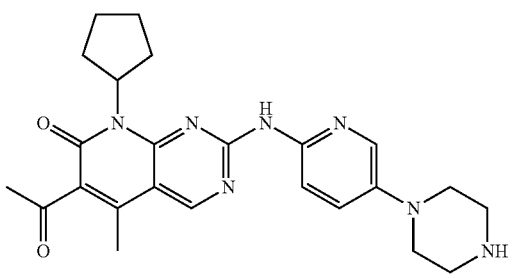 [SMILES: CC(=O)c1c(C)c2cnc(Nc3ccc(N4CCNCC4)cn3)nc2n(C2CCCC2)c1=O]

Abemaciclib (LY2835219) is a CDK 4/6 inhibitor currently in human clinical trials for the treatment of various types of cancers. It is in a phase III trial for stage IV non-small cell lung carcinoma; in combination with Fulvestrant for women with breast cancer; and with either anastrozole or letrozole for first line treatment of breast cancer. The structure of abemaciclib is:

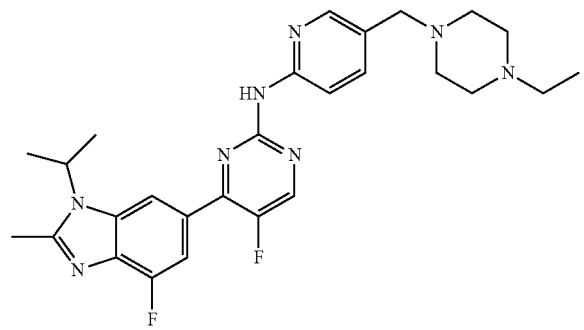 [SMILES: CCN1CCN(Cc2ccc(Nc3ncc(F)c(-c4cc(F)c5nc(C)n(C(C)C)c5c4)n3)nc2)CC1]

Ribociclib (Lee011; Kisqali), is a CDK 4/6 inhibitor approved for use in combination with an aromatase inhibitor to treat some metastatic breast cancers, and is in clinical trials for the treatment of certain other tumors. The structure of ribociclib is:

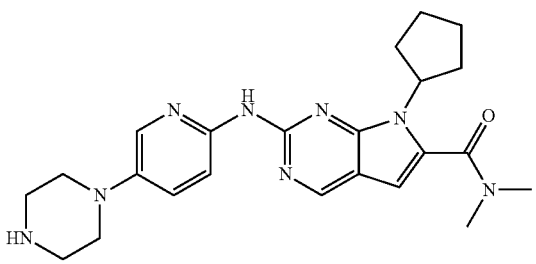 [SMILES: CN(C)C(=O)c1cc2cnc(Nc3ccc(N4CCNCC4)cn3)nc2n1C1CCCC1]

Various other pyrimidine-based agents have been developed for the treatment of hyperproliferative diseases. U.S. Pat. Nos. 8,822,683; 8,598,197; 8,598,186; 8,691,830; 8,829,102; 8,822,683; 9,102,682; 9,499,564; 9,481,591; and 9,260,442, filed by Tavares and Strum and assigned to G1 Therapeutics describe a class of N-(heteroaryl)-pyrrolo[3,2- d]pyrimidin-2-amine cyclin dependent kinase inhibitors including those of the formula (with variables as defined therein):

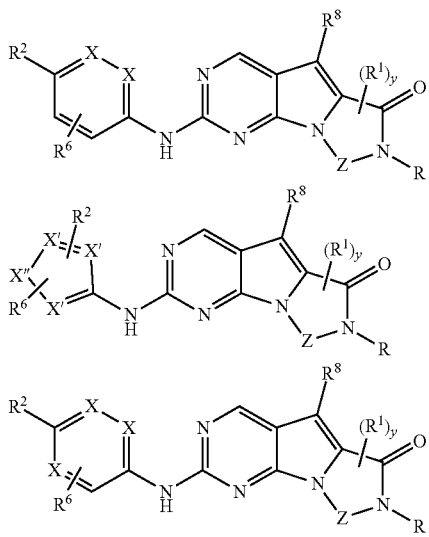

WO 2013/148748 (U.S. Ser. No. 61/617,657) titled "Lactam Kinase Inhibitors", WO 2013/163239 (U.S. Ser. No. 61/638,491) titled "Synthesis of Lactams" and WO 2015/061407 filed by Tavares and also assigned to G1 Therapeutics describes the synthesis of N-(heteroaryl)-pyrrolo[3,2-d]pyrimidin-2-amines and their use as lactam kinase inhibitors.

Other publications include the following. WO 2014/144326 filed by Strum et al. and assigned to G1 Therapeutics describes compounds and methods for protection of normal cells during chemotherapy using pyrimidine-based CDK4/6 inhibitors. WO 2014/144596 filed by Strum et al. and assigned to G1 Therapeutics describes compounds and methods for protection of hematopoietic stem and progenitor cells against ionizing radiation using pyrimidine-based CDK4/6 inhibitors. WO 2014/144847 filed by Strum et al. and assigned to G1 Therapeutics describes HSPC-sparing treatments of abnormal cellular proliferation using pyrimidine-based CDK4/6 inhibitors. WO 2014/144740 filed by Strum et al. and assigned to G1 Therapeutics describes highly active anti-neoplastic and anti-proliferative pyrimidine-based CDK 4/6 inhibitors. WO 2015/161285 filed by Strum et al. and assigned to G1 Therapeutics describes tricyclic pyrimidine-based CDK inhibitors for use in radioprotection. WO 2015/161287 filed by Strum et al. and assigned to G1 Therapeutics describes analogous tricyclic pyrimidine-based CDK inhibitors for the protection of cells during chemotherapy. WO 2015/161283 filed by Strum et al. and assigned to G1 Therapeutics describes analogous tricyclic pyrimidine-based CDK inhibitors for use in HSPC-sparing treatments of RB-positive abnormal cellular proliferation. WO 2015/161288 filed by Strum et al. and assigned to G1 Therapeutics describes analogous tricyclic pyrimidine-based CDK inhibitors for use as anti-neoplastic and anti-proliferative agents. WO 2016/040858 filed by Strum et al. and assigned to G1 Therapeutics describes the use of combinations of pyrimidine-based CDK4/6 inhibitors with other anti-neoplastic agents. WO 2016/040848 filed by Strum et al. and assigned to G1 Therapeutics describes compounds and methods for treating certain Rb-negative cancers with CDK4/6 inhibitors and topoisomerase inhibitors.

WO 03/062236 identifies a series of 2-(pyridin-2-ylamino-pyrido[2,3]pyrimidin-7-ones for the treatment of Rb positive cancers that show selectivity for CDK4/6, including 6-acetyl-8-cyclopentyl-5-methyl-2-(5-piperazin-1-yl-pyridin-2-ylammino)-8H-pyrido-[2,3-d]-pyrimidin-7-one (PD0332991), which was given fast-track approval by the FDA and is currently sold as Ibrance (Palbociclib) by Pfizer for the treatment of metastatic breast cancer.

VanderWel et al. describe an iodine-containing pyrido[2,3-d]pyrimidine-7-one (CKIA) as a potent and selective CDK4 inhibitor (see VanderWel et al., J. Med. Chem. 48 (2005) 2371-2387).

WO 2010/020675 filed by Novartis AG describes pyrrolopyrimidine compounds as CDK inhibitors. WO 2011/101409 also filed by Novartis describes pyrrolopyrimidines with CDK 4/6 inhibitory activity.

Johnson et al. reported that pharmacological inhibition of CDK4/6 using the CDK4/6 inhibitors 6-acetyl-8-cyclopentyl-5-methyl-2-(5-piperazin-1-yl-pyridin-2-ylammino)-8H-pyrido-[2,3-d]-pyrimidin-7-one (PD0332991) and 2-bromo-12,13-dihydro-5H-indolo[2,3-a]pyrrolo[3,4]carbazole-5,6-dione (2BrIC) exhibited IR protective characteristics in CDK4/6-dependent cell lines. (Johnson et al. Mitigation of hematological radiation toxicity in mice through pharmacological quiescence induced by CDK4/6 inhibition. J Clin. Invest. 2010; 120(7): 2528-2536).

There remains a need for additional compounds to treat disorders associated with abnormal cellular proliferation, including a tumor or cancer.

SUMMARY

Compounds are presented that have advantageous antiproliferative activity, including anticancer and antitumor activity. Based on this discovery, compounds and methods are presented for the treatment of a patient with a proliferative disorder including a tumor or cancer that includes administering an effective amount of one or a combination of the compounds described herein to a patient in need thereof, optionally in a pharmaceutically acceptable carrier. In certain embodiments the antiproliferative disorder is selected from a benign growth, neoplasm, tumor, cancer, autoimmune disorder, inflammatory disorder, graft-versus-host rejection and a fibrotic disorder. In a typical embodiment the patient is a human.

The invention includes an active compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, or Formula XXIII or a pharmaceutically acceptable salt or composition thereof. In one embodiment, an active compound or its salt, composition, or prodrug thereof is used to treat a medical disorder involving abnormal cellular proliferation.

The invention includes an antiproliferative (including antineoplastic) compound of Formula I, Formula II, Formula III Formula IV, Formula V, Formula VI, Formula VII, Formula VIII, Formula IX, Formula X, Formula XI, Formula XII, Formula XIII, Formula XIV, Formula XV Formula XVI, Formula XVII, Formula XVIII, or Formula XIX:

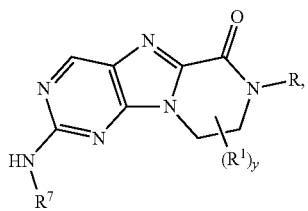 (I)
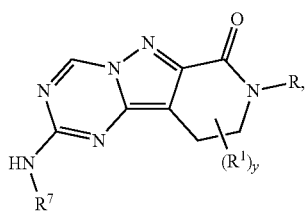 (II)
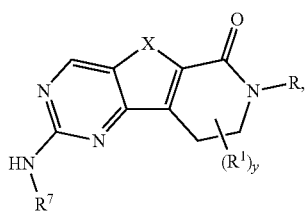 (III)
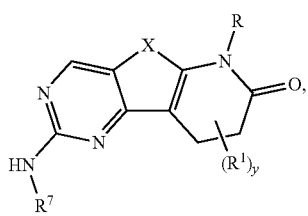 (IV)
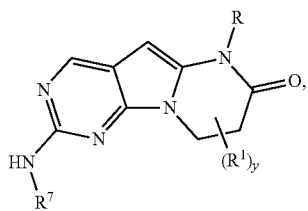 (V)
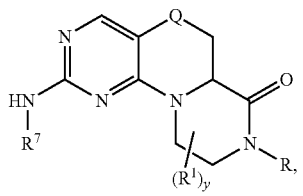 (VI)
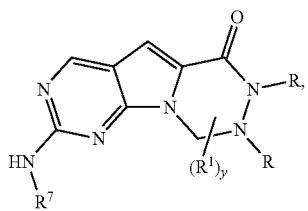 (VII)
-continued
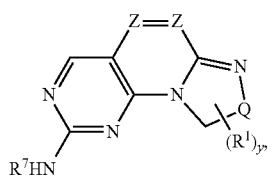 (VIII)
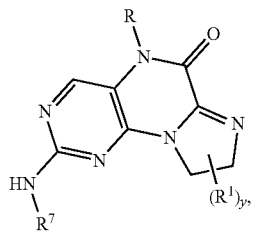 (IX)
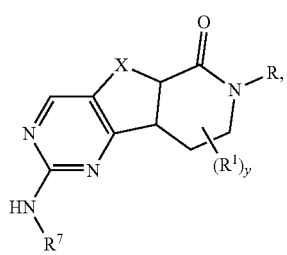 (X)
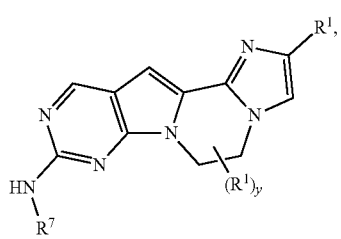 (XI)
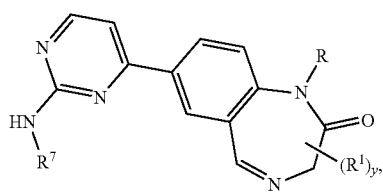 (XII)
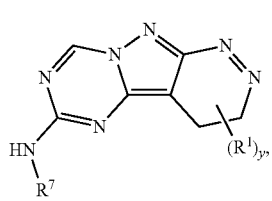 (XIII)
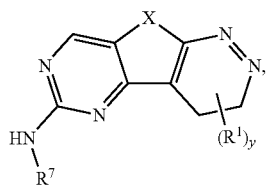 (XIV)

-continued (XV)

(XVI)

(XVII)

(XVIII)

(XIX)

or a pharmaceutically acceptable salt, N-oxide, isotopic derivative, prodrug, and/or a pharmaceutically acceptable composition thereof;
wherein:
X is NH, NR$^9$, S, or O;
y is 0, 1, 2, 3 or 4;
m is 0, 1, or 2;
n is 0, 1, or 2;
Z is independently CH, CR$^9$, or N;
Q is CH$_2$ or CO;
R is hydrogen, C$_1$-C$_6$alkyl, —(C$_0$-C$_2$alkyl)(C$_3$-C$_8$carbocyclyl), —(C$_0$-C$_2$alkyl)(C$_3$-C$_8$heterocyclyl), —(C$_0$-C$_2$alkyl)(aryl), —(C$_0$-C$_2$alkyl)(heteroaryl), —COOalkyl, —COOarylalkyl, or —COOH;
each R$^1$ is independently alkyl, aryl, cycloalkyl or haloalkyl, wherein each of said alkyl, cycloalkyl and haloalkyl groups optionally includes heteroatoms O, N, or S in place of a carbon in the chain and two R$^1$'s on adjacent ring atoms or on the same ring atom together with the ring atom(s) to which they are attached optionally form a 3-8-membered cycle or two R$^1$'s on adjacent ring atoms together with the ring atom(s) to which they are attached optionally form a 6-membered aryl ring;
or R$^1$ is hydrogen;

R$^2$ is -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-C(O)—O-alkyl; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atom may optionally combine to form a ring;
R$^3$ and R$^4$ at each occurrence are independently selected from:
  (i) hydrogen or
  (ii) alkyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance, and wherein two R$^x$ groups bound to the same or adjacent atom may optionally combine to form a ring; or R$^3$ and R$^4$ together with the nitrogen atom to which they are attached may combine to form a heterocyclo ring optionally independently substituted with one or more R$^x$ groups as allowed by valance, and wherein two R$^x$ groups bound to the same or adjacent atom may optionally combine to form a ring;
R$^5$ is independently selected at each occurrence from:
  (i) hydrogen or
  (ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance;
R$^x$ at each occurrence is independently selected from halo, cyano, nitro, oxo, alkyl, haloalkyl, alkenyl, alkynyl, cycloalkyl, heterocyclo, aryl, heteroaryl, arylalkyl, heteroarylalkyl, cycloalkylalkyl, heterocycloalkyl, -(alkylene)$_m$-OR$^5$, -(alkyalkylene)$_m$-O-alkylene-OR$^5$, (alkylene)$_m$-S(O)$_n$—R$^5$, -(alkyalkylene)$_m$-NR$^3$R$^4$, -(alkyalkylene)$_m$-CN, -(alkylene)$_m$-C(O)—R$^5$, -(alkyalkylene)$_m$-C(S)—R$^5$, -(alkyalkylene)$_m$-C(O)—OR$^5$, -(alkyalkylene)$_m$-O—C(O)—R$^5$, -(alkylene)$_m$-C(S)—OR$^5$, -(alkyalkylene)$_m$-C(O)-(alkylene)$_m$-NR$^3$R$^4$, -(alkyalkylene)$_m$-C(S)—NR$^3$R$^4$, -(alkylene)$_m$-N(R$^3$)—C(O)—NR$^3$R$^4$, -(alkyalkylene)$_m$-N(R$^3$)—C(S)—NR$^3$R$^4$, -(alkyalkylene)$_m$-N(R$^3$)—C(O)—R$^5$, -(alkyalkylene)$_m$-N(R$^3$)—C(S)—R$^5$, -(alkyalkylene)$_m$-O—C(O)—NR$^3$R$^4$, -(alkyalkylene)$_m$-O—C(S)—NR$^3$R$^4$, -(alkyalkylene)$_m$-SO$_2$—NR$^3$R$^4$, -(alkyalkylene)$_m$-N(R$^3$)—SO$_2$—R$^5$, -(alkyalkylene)$_m$-N(R$^3$)—SO$_2$—NR$^3$R$^4$, -(alkyalkylene)$_m$-N(R$^3$)—C(O)—OR$^5$) -(alkylene)$_m$-N(R$^3$)—C(S)—OR$^5$, or -(alkylene)$_m$-N(R$^3$)—SO$_2$—R$^5$,
wherein: said alkyl, haloalkyl, alkenyl, alkynyl, cycloalkyl, heterocyclo, aryl, heteroaryl, arylalkyl, heteroarylalkyl, cycloalkylalkyl, and heterocycloalkyl groups may be further independently substituted as described herein;
R$^6$ is selected independently at each instance from: hydrogen, halogen, alkyl, alkenyl, alkynyl cycloalkyl, heterocyclo, aryl, heteroaryl, cycloalkylalkyl, heterocycloalkyl, arylalkyl, or heteroarylalkyl;
R$^7$ is selected from:

-continued

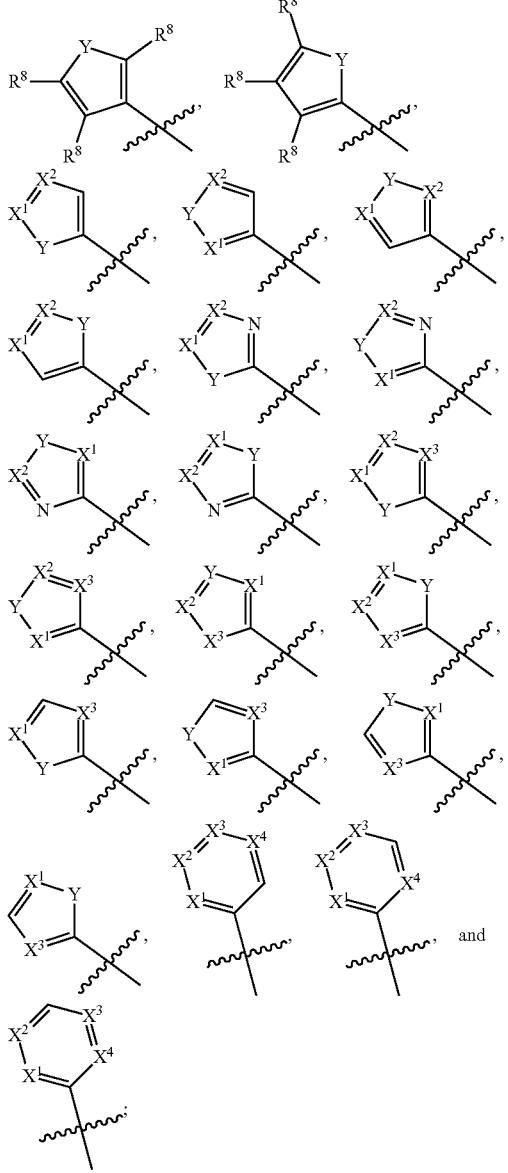

or R⁷ is selected from cycloalkyl, heterocycle, and alkyl, each of which cycloalkyl, heterocycle, and alkyl groups is optionally substituted with one or more substituents selected from amino, —NHR¹⁴, —NR¹⁴R¹⁵, hydroxyl, OR¹⁴, R⁶, and R²;

R¹⁴ and R¹⁵ are independently selected from: hydrogen, alkyl, alkenyl, alkynyl, —C(O)H, —C(O)alkyl, —C(S)alkyl, aryl, —SO₂alkyl, heteroaryl, arylalkyl, and heteroarylalkyl.

Y is NH, O, S, or NR⁹;

X¹, X², X³, and X⁴, are independently N or CR⁸, wherein at least one of X¹, X², X³, and X⁴, is CRS;

R⁸ is selected independently at each instance from: R⁶ and R², wherein one R⁸ is R²;

R⁹ is selected from: —C(O)H, —C(O)alkyl, —C(S)alkyl, alkyl, aryl, heteroaryl, arylalkyl, and heteroarylalkyl;

R¹⁰ is selected from: hydrogen, —COOalkyl, —COOarylalkyl, —COOH, —OH, —C(O)H, —C(O)alkyl, —C(S)alkyl, alkyl, aryl, heteroaryl, arylalkyl, and heteroarylalkyl; and wherein for compounds of Formula VII y is 0, 1, or 2.

In an additional aspect the invention includes an active compound of Formula XX, Formula XXI, Formula XXII, Formula XXIII, or Formula XXIV or a pharmaceutically acceptable salt or composition thereof. The compounds of Formula XX, Formula XXI, Formula XXII, Formula XXIII, and XXIV have the following structures:

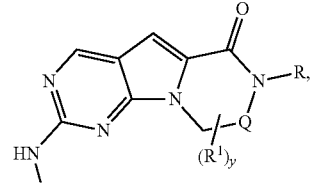
(XX)

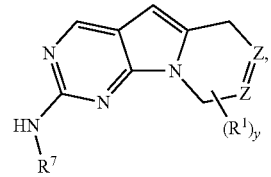
(XXI)

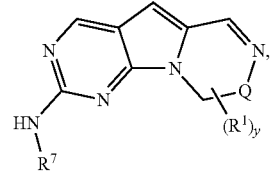
(XXII)

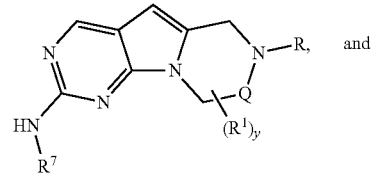
(XXIII)

and

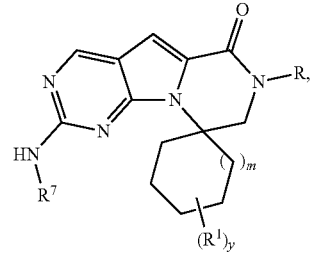
(XXIV)

wherein m, R, R¹, R⁷, Q, and y are defined above.

In one embodiment the compound of Formula XX is:

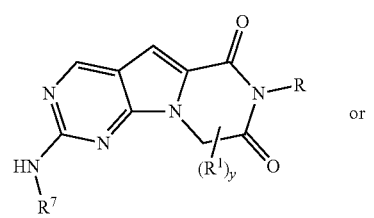

or

-continued

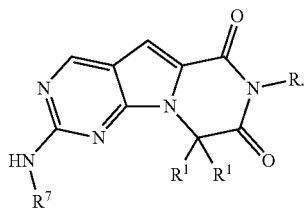

In an additional aspect the invention includes an active compound of Formula XXV:

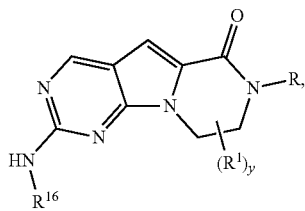

(XXV)

wherein R, $R^1$, $R^2$, $R^6$, and y are defined above;

$R^{16}$ is selected from cycloalkyl, heterocycle, and alkyl, each of which cycloalkyl, heterocycle, and alkyl groups is optionally substituted with one or more substituents selected from amino, —$NHR^{14}$, —$NR^{14}R^{15}$, hydroxyl, $OR^{14}$, $R^6$, and $R^2$;

$R^{14}$ and $R^{15}$ are independently selected from: hydrogen, alkyl, alkenyl, alkynyl, —C(O)H, —C(O)alkyl, —C(S)alkyl, aryl, —$SO_2$alkyl, heteroaryl, arylalkyl, and heteroarylalkyl.

In an alternative embodiment the compound of the present invention is selected from

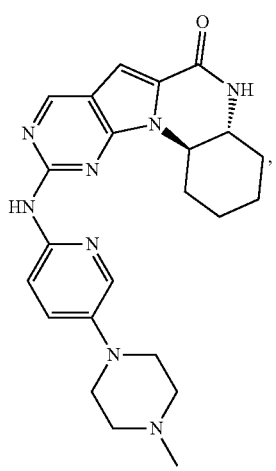

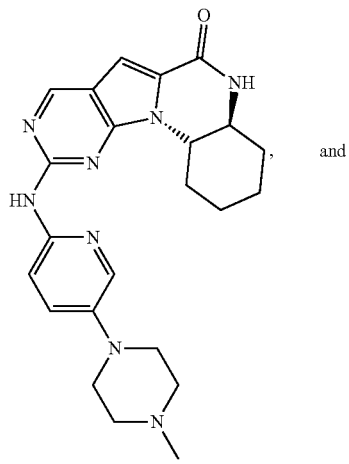

and

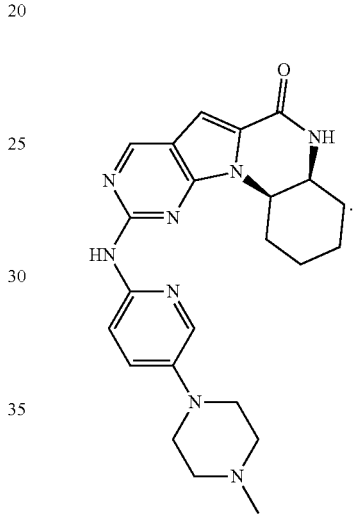

In another alternative embodiment the compound of the present invention is selected from

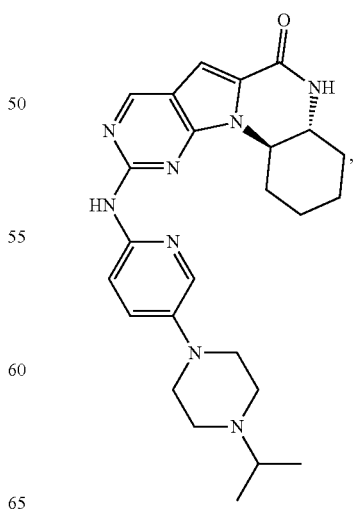

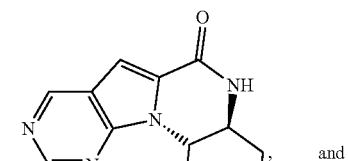
and
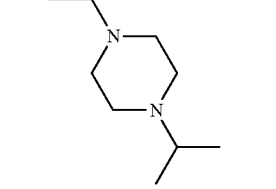
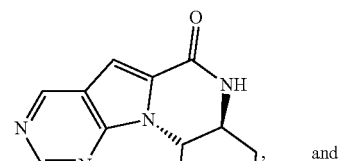
and
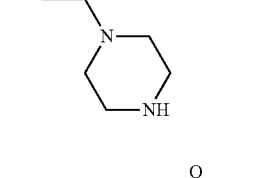
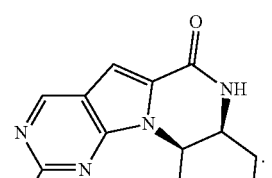
In an alternative embodiment the compound of the present invention is:
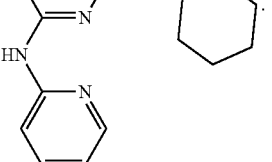
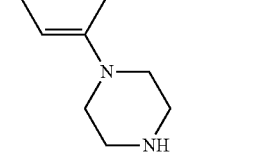
In another alternative embodiment the compound of the present invention is selected from
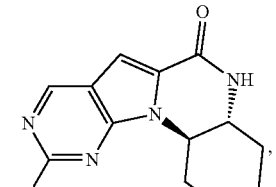
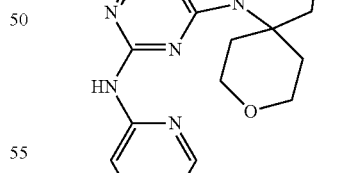
In another alternative embodiment the compound of the present invention is:
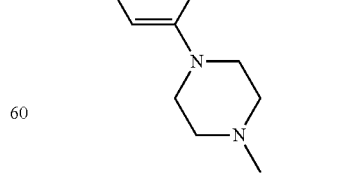

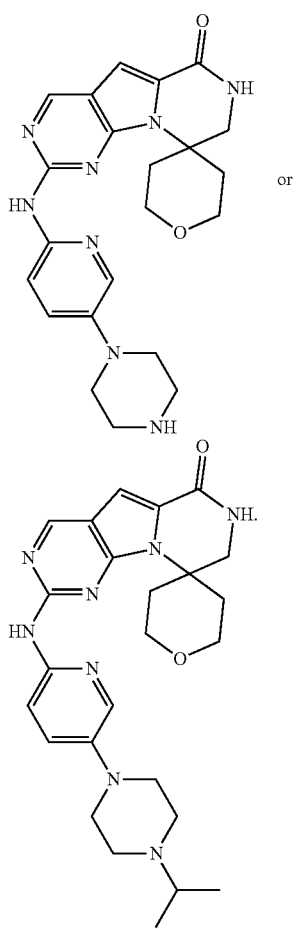

These compounds can be used to treat such condition in a host in need thereof, typically a human.

In one embodiment, the active compound acts as an inhibitor of a cyclin-dependent kinase (CDK), for example CDK4 and/or CDK6. In an aspect, the compound is a selective inhibitor of CDK4 and/or CDK6. In another embodiment, the selectivity is for CDK4 and/or CDK6 over CDK2. Based on this, in one embodiment, the method for the treatment of a disorder of abnormal cellular proliferation that is mediated by CDK4 and or CDK6 is provided that includes the administration of an effective amount of a compound of the present invention or a pharmaceutically acceptable salt thereof, optionally in a pharmaceutically acceptable carrier, as described in more detail below.

In an alternative embodiment, a method for the treatment of a disorder of abnormal cellular proliferation that is not mediated by CDK4 and or CDK6 is provided that includes the administration of an effective amount of a compound of the present invention or a pharmaceutically acceptable salt thereof, optionally in a pharmaceutically acceptable carrier, as described in more detail below.

In another embodiment, a method for the treatment of a fibrotic disorder in a host is provided that includes the administration of an effective amount of a compound of the present invention or a pharmaceutically acceptable salt thereof, optionally in a pharmaceutically acceptable carrier.

In another embodiment, a method for the treatment of rheumatoid arthritis or psoriasis in a host is provided that includes the administration of an effective amount of a compound of the present invention or a pharmaceutically acceptable salt thereof, optionally in a pharmaceutically acceptable carrier.

In yet another embodiment, a method for the treatment of an autoimmune disorder in a host is provided that includes the administration of an effective amount of a compound of the present invention or a pharmaceutically acceptable salt thereof, optionally in a pharmaceutically acceptable carrier.

In a principal embodiment, a method for the treatment of a tumor or cancer in a host is provided that includes the administration of an effective amount of a compound of the present invention or a pharmaceutically acceptable salt thereof, optionally in a pharmaceutically acceptable carrier. In an aspect of this embodiment, the cancer is an Rb-positive tumor or cancer. In another aspect of this embodiment, the cancer is an Rb-negative tumor or cancer. In certain aspects, the cancer is selected from breast cancer, prostate cancer (including androgen-resistant prostate cancer), another cancer of the reproductive system such as endometrial, ovarian or testicular cancer, small cell lung carcinoma, glioblastoma and head and/or neck cancer.

In yet another embodiment, a method for the treatment of a disorder of abnormal cellular proliferation in a host such as a human is provided that includes administering an effective amount of a combination of one or more of the active compounds described herein in combination or alternation with another active compound. In certain aspects of the invention, the second compound is a chemotherapeutic agent. In another aspect of this embodiment, the second active compound is an immune modulator, including but not limited to a checkpoint inhibitor such as an anti-PD1, anti-CTLA, anti-LAG-3, anti-Tim, etc antibody, small molecule, peptide, nucleotide or other inhibitor (including but not limited to ipilimumab (Yervoy), Pembrolimumab (Keytruda) and nivolumab (Opdivo).

In yet another embodiment, one of the active compounds described herein is administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist.

In another embodiment, one of the active compounds described herein is administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant.

In one embodiment, the compounds described herein inhibit Cyclin Dependent Kinase. For example, a compound described in the present invention provides a dose-dependent G1-arresting effect on a subject's CDK replication dependent healthy cells, for example HSPCs or renal epithelial cells. The methods provided for herein are sufficient to afford chemoprotection to targeted CDK replication dependent healthy cells during chemotherapeutic agent exposure, for example, during the time period that a DNA-damaging chemotherapeutic agent is capable of DNA-damaging effects on CDK replication dependent healthy cells in the subject.

In one embodiment, the use of the compounds or methods described herein is combined with the use of hematopoietic growth factors including, but not limited to, granulocyte colony stimulating factor (G-CSF), granulocyte-macrophage colony stimulating factor (GM-CSF), thrombopoietin, interleukin (IL)-12, steel factor, and erythropoietin (EPO), or their derivatives. In one embodiment, the compound is administered prior to administration of the hematopoietic growth factor. In one embodiment, the hematopoietic growth factor administration is timed so that the compound's effect on HSPCs has dissipated.

The present invention thus includes at least the following features:

(a) a compound of the present invention as described herein, and pharmaceutically acceptable salts and prodrugs thereof;

(b) a compound of the present invention as described herein, and pharmaceutically acceptable salts and prodrugs thereof that are useful in the treatment of a disorder of abnormal cellular proliferation, including a tumor or cancer;

(c) use of a compound of the present invention, or pharmaceutically acceptable salts and prodrugs thereof in the manufacture of a medicament for the treatment of a disorder of abnormal cellular proliferation, such as a tumor or cancer;

(d) a method for manufacturing a medicament intended for the therapeutic use of treating a disorder of abnormal cellular proliferation including a tumor or cancer, characterized in that a compound of the present invention as described herein is used in the manufacture;

(e) a compound of the present invention as described herein, and pharmaceutically acceptable salts and prodrugs thereof that are useful in the treatment of cancer, including any of the cancers described herein;

(f) use of a compound of the present invention, and pharmaceutically acceptable salts and prodrugs thereof in the manufacture of a medicament for the treatment of cancer, including any of the cancers described herein;

(g) a method for manufacturing a medicament intended for the therapeutic use of treating cancer, including any of the cancers described herein, characterized in that a compound of the present invention as described herein is used in the manufacture;

(h) a compound of the present invention as described herein, and pharmaceutically acceptable salts and prodrugs thereof that are useful in the treatment of a tumor, including any of the tumors described herein;

(i) use of a compound of the present invention, and pharmaceutically acceptable salts and prodrugs thereof in the manufacture of a medicament for the treatment of a tumor, including any of the tumors described herein;

(j) a method for manufacturing a medicament intended for the therapeutic use of treating a tumor, including any of the tumors described herein, characterized in that a compound of the present invention as described herein is used in the manufacture;

(k) a compound of the present invention as described herein, and pharmaceutically acceptable salts and prodrugs thereof that are useful in the treatment of a fibrotic disorder;

(l) use of a compound of the present invention, and pharmaceutically acceptable salts and prodrugs thereof in the manufacture of a medicament for the treatment of a fibrotic disorder;

(m) a method for manufacturing a medicament intended for the therapeutic use of treating a fibrotic disorder, characterized in that a compound of the present invention as described herein is used in the manufacture;

(n) a compound of the present invention as described herein, and pharmaceutically acceptable salts and prodrugs thereof that are useful in the treatment of an autoimmune or inflammatory disorder;

(o) use of a compound of the present invention, and pharmaceutically acceptable salts and prodrugs thereof in the manufacture of a medicament for the treatment of an autoimmune or inflammatory disorder;

(p) a method for manufacturing a medicament intended for the therapeutic use of treating an autoimmune or inflammatory disorder, characterized in that a compound of the present invention as described herein is used in the manufacture;

(q) a pharmaceutical formulation comprising an effective host-treating amount of the compound of the present invention or a pharmaceutically acceptable salt or prodrug thereof together with a pharmaceutically acceptable carrier or diluent;

(r) a compound of the present invention as described herein as a mixture of enantiomers or diastereomers (as relevant), including as a racemate;

(s) a compound of the present invention as described herein in enantiomerically or diastereomerically (as relevant) enriched form, including as an isolated enantiomer or disastereomer (i.e., greater than 85, 90, 95, 97 or 99% pure); and, (t) a process for the preparation of therapeutic products that contain an effective amount of a compound of the present invention, as described herein.

(u) a compound of the present invention as described herein, and pharmaceutically acceptable salts and prodrugs thereof that are useful in chemoprotection;

(v) use of a compound of the present invention, and pharmaceutically acceptable salts and prodrugs thereof in the manufacture of a medicament for chemoprotection; and (w) a method for manufacturing a medicament intended for the therapeutic use of chemoprotection, characterized in that a compound of the present invention as described herein is used in the manufacture.

DETAILED DESCRIPTION

I. Compounds

Figure 1:
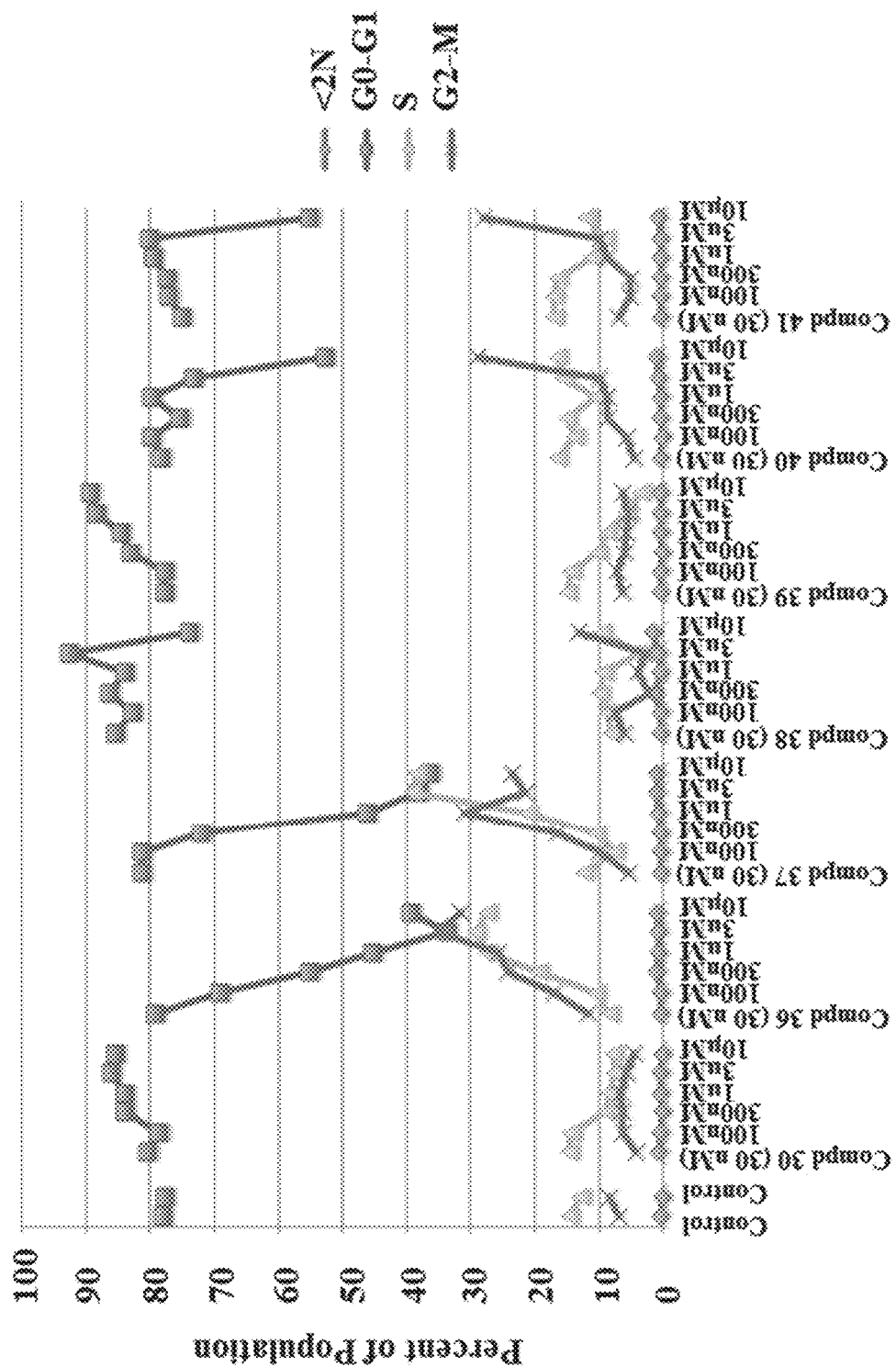
FIG. 1 is a bar graph showing the population of cells with a DNA content less than 2N, cells in the G0-G1 phase, cells in the S phase, and cells in the G2-M phase as a way to measure the relative amount of apoptotic cells following administration of control, Compound 30, Compound 36, Compound 37, Compound 38, Compound 39, Compound 40, and Compound 41. The Compound number and dose, measured in M and nM) are shown on the x-axis and the cell population, measured in percent, is shown on the y-axis.
Figure 2:
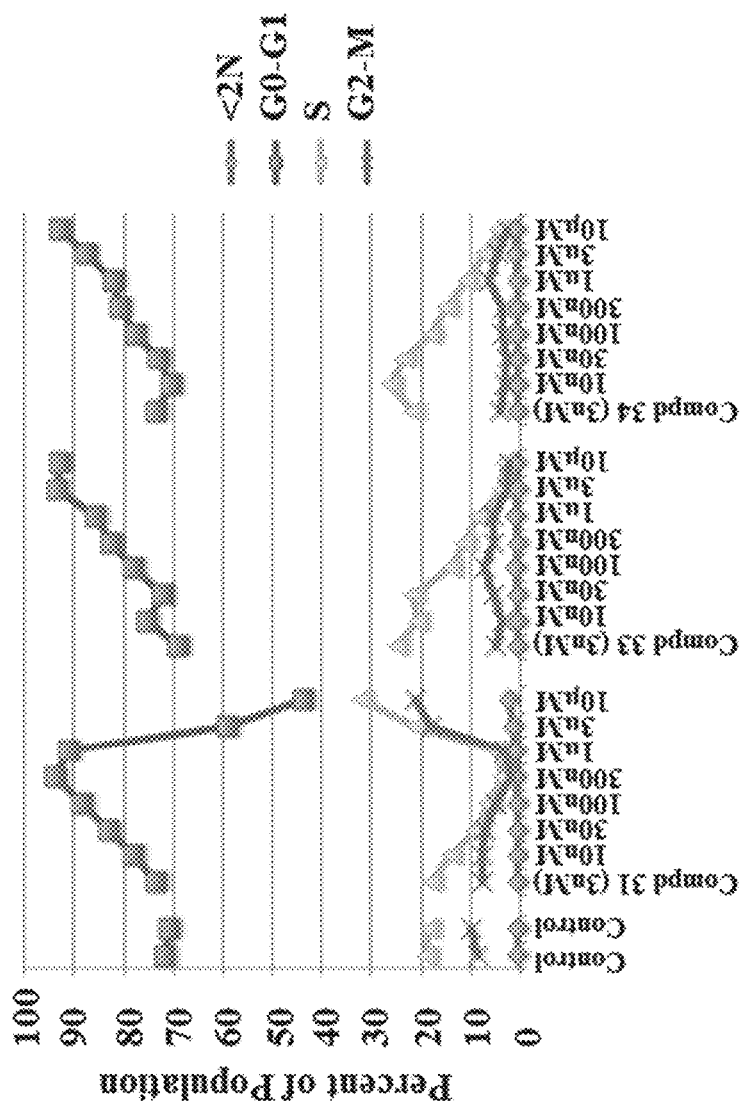
FIG. 2 is a bar graph showing the population of cells with a DNA content less than 2N, cells in the G0-G1 phase, cells in the S phase, and cells in the G2-M phase as a way to measure the relative amount of apoptotic cells following administration of control, Compound 31, Compound 33, and Compound 34. The Compound number and dose, measured in μM and nM) are shown on the x-axis and the cell population, measured in percent, is shown on the y-axis.
Figure 4:
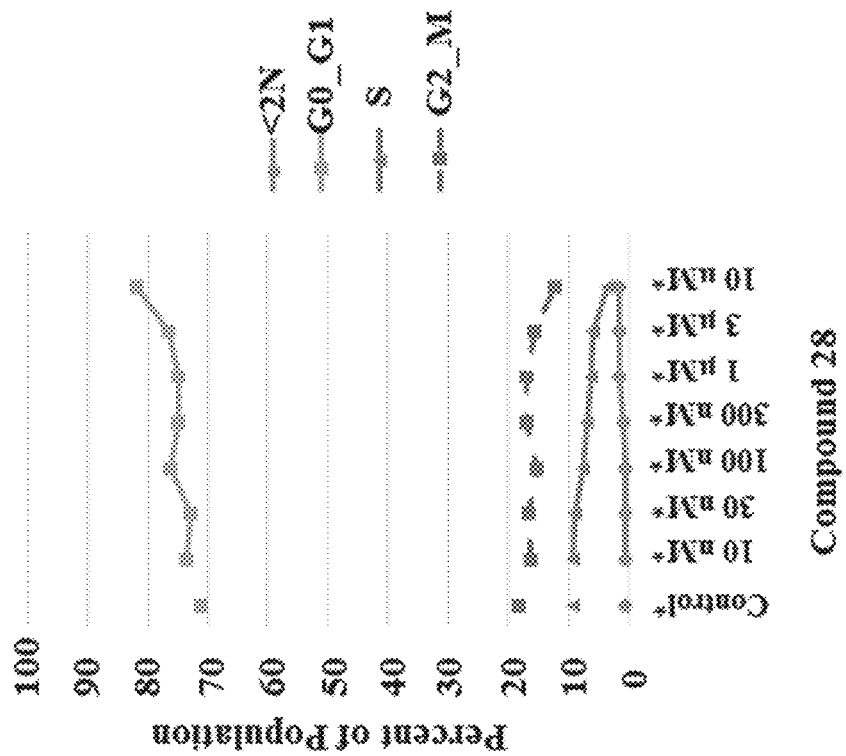
FIG. 4 is a bar graph showing the population of cells with a DNA content less than 2N, cells in the G0-G1 phase, cells in the S phase, and cells in the G2-M phase as a way to measure the relative amount of apoptotic cells following administration of control and Compound 28. The population of apoptotic cells after exposure to Compound 28 was greater than 70% at every dose administered. The assay was done in a population of Hs68 cells. * is <2000 events. The Compound number and dose, measured in µM and nM, are shown on the x-axis and the cell population, measured in percent, is shown on the y-axis.
Figure 3:
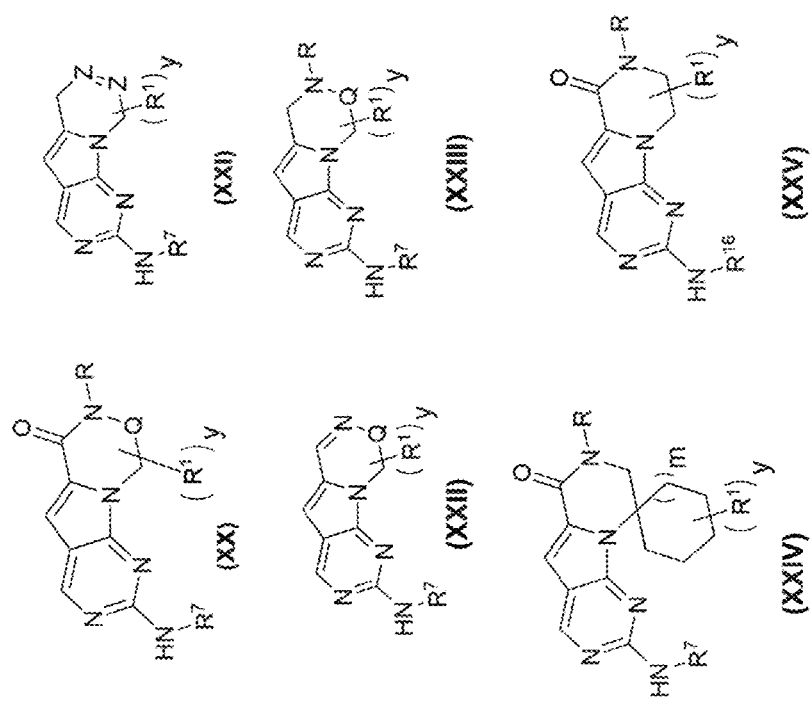
FIG. 3 is Formula XX, Formula XXI, Formula XXII, Formula XXIII, Formula XXIV, and Formula XXV.

In one embodiment, compounds of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, or Formula XIX are provided:

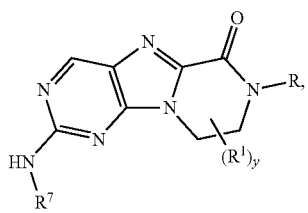
(I)

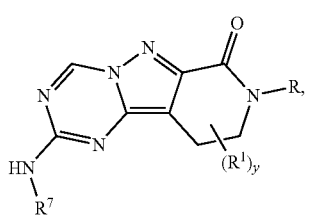
(II)

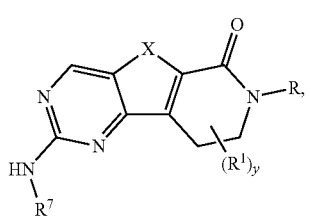
(III)

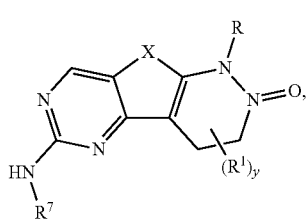
(IV)

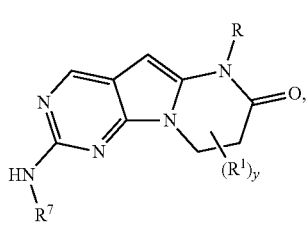
(V)

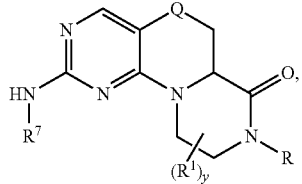
(VI)

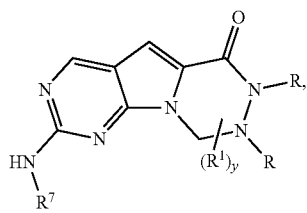
(VII)

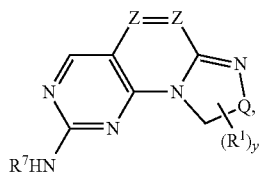
(VIII)

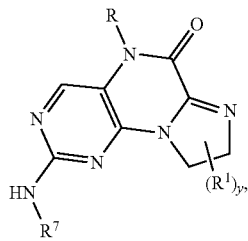
(IX)

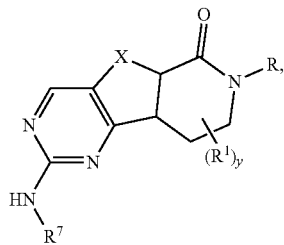
(X)

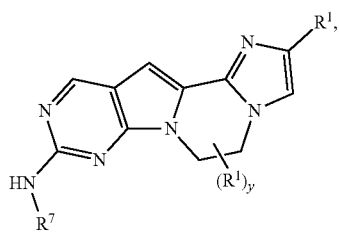
(XI)

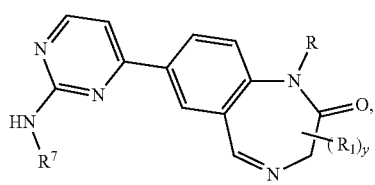
(XII)

-continued

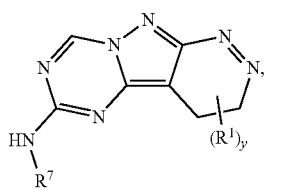
(XIII)

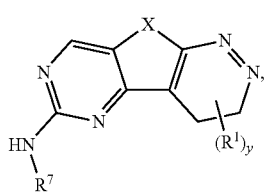
(XIV)

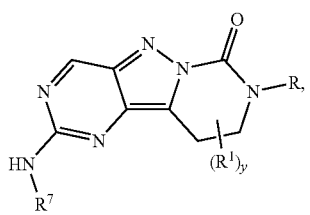
(XV)

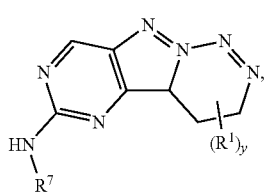
(XVI)

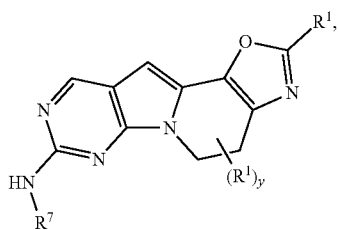
(XVII)

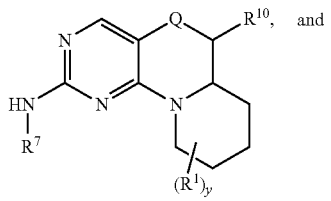
(XVIII)

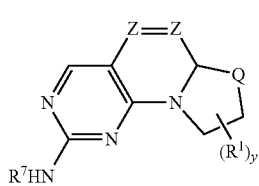
(XIX)

or a pharmaceutically acceptable salt, N-oxide, isotopic derivative, or prodrug, optionally in a pharmaceutically acceptable carrier to form a pharmaceutically acceptable composition thereof; wherein the variables are as defined above in the Summary section.

In an alternative embodiment, a compound of Formula XX, Formula XXI, Formula XXII, Formula XXIII or Formula XXIV is provided:

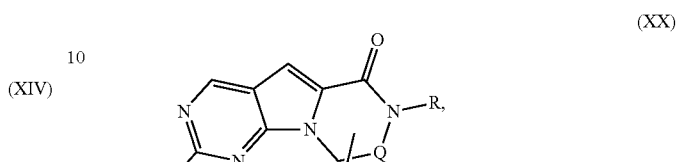
(XX)

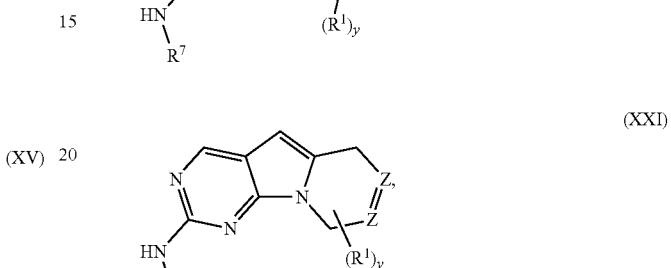
(XXI)

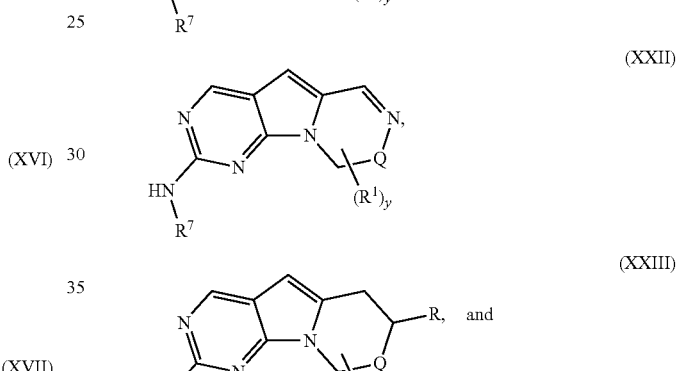
(XXII)

(XXIII)

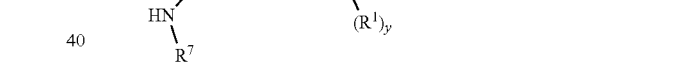

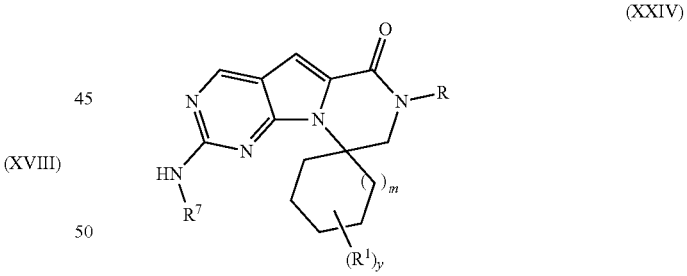
(XXIV)

or a pharmaceutically acceptable salt, N-oxide, isotopic derivative, or prodrug, optionally in a pharmaceutically acceptable carrier to form a pharmaceutically acceptable composition thereof, wherein the variables are as defined above in the Summary section.

In another embodiment, a compound of Formula I-1, Formula II-1, Formula III-1, Formula IV-1, Formula V-1, Formula VI-1, Formula VII-1, Formula VIII-1, Formula IX-1, Formula X-1, Formula XI-1, Formula XII-1, Formula XIII-1, Formula XIV-1, Formula XV-1, Formula XVI-1, Formula XVII-1, Formula XVIII-1, Formula XIX-1, Formula XX-1, Formula XXI-1, Formula XXII-1, Formula XXIII-1, Formula XXIV-1, or Formula XXV-1 is provided:

(I-1) 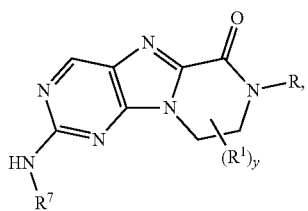
(II-1) 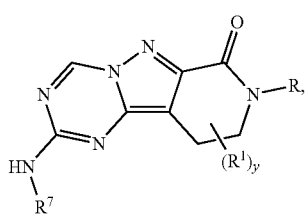
(III-1) 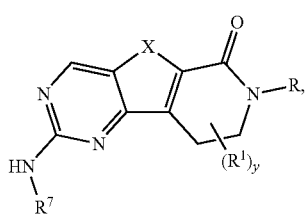
(IV-1) 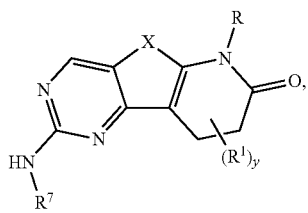
(V-1) 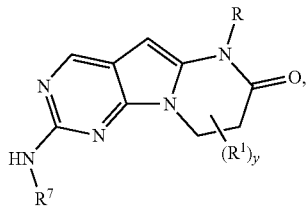
(VI-1) 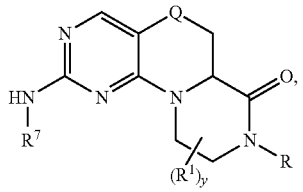
(VII-1) 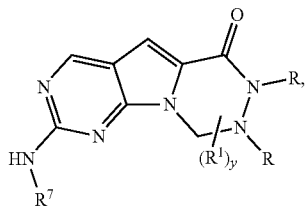
(VIII-1) 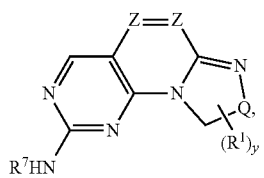
(IX-1) 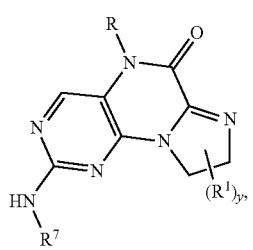
(X-1) 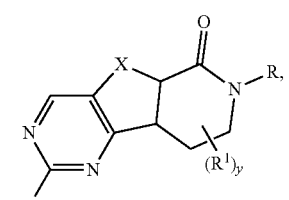
(XI-1) 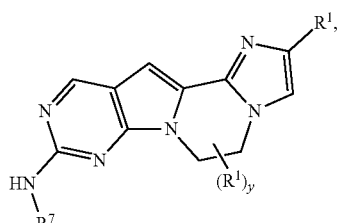
(XII-1) 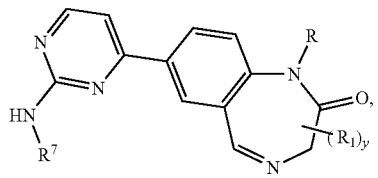
(XIII-1) 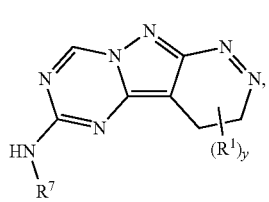
(XIV-1) 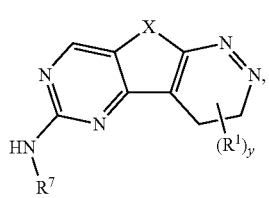

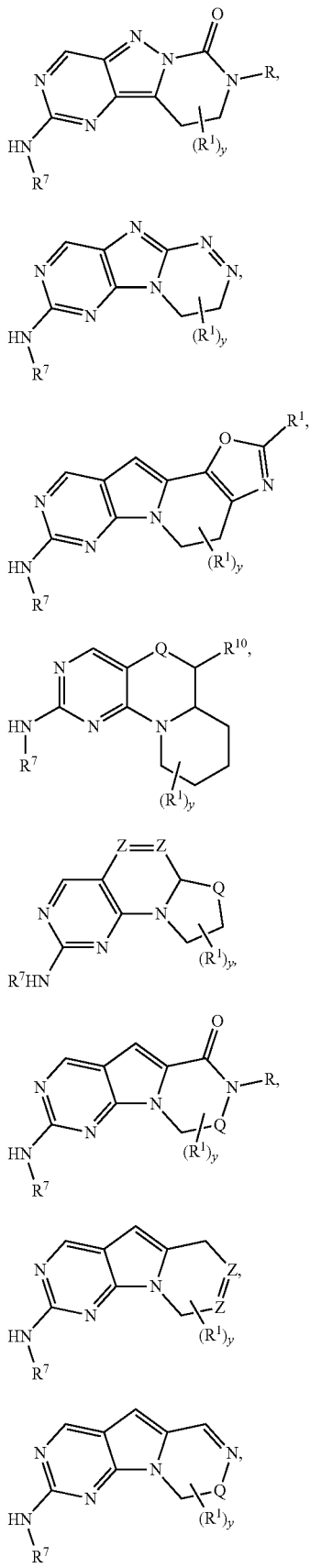
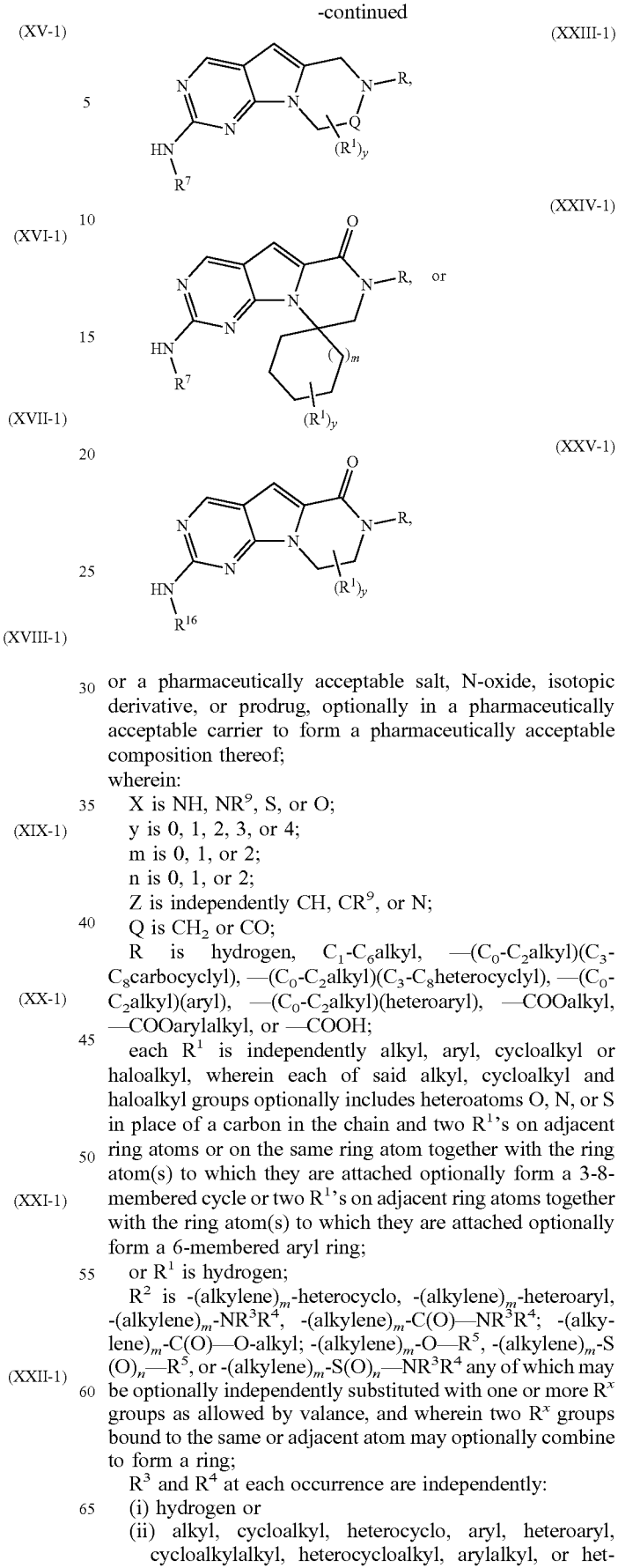

or a pharmaceutically acceptable salt, N-oxide, isotopic derivative, or prodrug, optionally in a pharmaceutically acceptable carrier to form a pharmaceutically acceptable composition thereof;

wherein:

X is NH, $NR^9$, S, or O;
y is 0, 1, 2, 3, or 4;
m is 0, 1, or 2;
n is 0, 1, or 2;
Z is independently CH, $CR^9$, or N;
Q is $CH_2$ or CO;
R is hydrogen, $C_1$-$C_6$alkyl, —($C_0$-$C_2$alkyl)($C_3$-$C_8$carbocyclyl), —($C_0$-$C_2$alkyl)($C_3$-$C_8$heterocyclyl), —($C_0$-$C_2$alkyl)(aryl), —($C_0$-$C_2$alkyl)(heteroaryl), —COOalkyl, —COOarylalkyl, or —COOH;

each $R^1$ is independently alkyl, aryl, cycloalkyl or haloalkyl, wherein each of said alkyl, cycloalkyl and haloalkyl groups optionally includes heteroatoms O, N, or S in place of a carbon in the chain and two $R^1$'s on adjacent ring atoms or on the same ring atom together with the ring atom(s) to which they are attached optionally form a 3-8-membered cycle or two $R^1$'s on adjacent ring atoms together with the ring atom(s) to which they are attached optionally form a 6-membered aryl ring;

or $R^1$ is hydrogen;

$R^2$ is -(alkylene)$_m$-heterocyclo, -(alkylene)$_m$-heteroaryl, -(alkylene)$_m$-$NR^3R^4$, -(alkylene)$_m$-C(O)—$NR^3R^4$; -(alkylene)$_m$-C(O)—O-alkyl; -(alkylene)$_m$-O—$R^5$, -(alkylene)$_m$-S(O)$_n$—$R^5$, or -(alkylene)$_m$-S(O)$_n$—$NR^3R^4$ any of which may be optionally independently substituted with one or more $R^x$ groups as allowed by valance, and wherein two $R^x$ groups bound to the same or adjacent atom may optionally combine to form a ring;

$R^3$ and $R^4$ at each occurrence are independently:
(i) hydrogen or
(ii) alkyl, cycloalkyl, heterocyclo, aryl, heteroaryl, cycloalkylalkyl, heterocycloalkyl, arylalkyl, or heteroarylalkyl; or $R^3$ and $R^4$ together with the nitrogen atom to which they are attached may combine to form a heterocyclo ring;

$R^5$ is independently:
(i) hydrogen or
(ii) alkyl, alkenyl, alkynyl, cycloalkyl, heterocyclo, aryl, heteroaryl, cycloalkylalkyl, heterocycloalkyl, arylalkyl, or heteroarylalkyl;

$R^x$ at each occurrence is independently selected from halo, cyano, nitro, oxo, alkyl, haloalkyl, alkenyl, alkynyl, cycloalkyl, heterocyclo, aryl, heteroaryl, arylalkyl, heteroarylalkyl, cycloalkylalkyl, heterocycloalkyl, -(alkylene)$_m$-OR$^5$, -(alkyalkylene)$_m$-O-alkylene-OR$^5$, -(alkylene)$_m$-S(O)$_n$—R$^5$, -(alkyalkylene)$_m$-NR$^3$R$^4$, -(alkyalkylene)$_m$-CN, -(alkylene)$_m$-C(O)—R$^5$, -(alkyalkylene)$_m$-C(S)—R$^5$, -(alkyalkylene)$_m$-C(O)—OR$^5$, -(alkyalkylene)$_m$-O—C(O)—R$^5$, -(alkylene)$_m$-C(S)—OR$^5$, -(alkyalkylene)$_m$-C(O)-(alkylene)$_m$-NR$^3$R$^4$, -(alkyalkylene)$_m$-C(S)—NR$^3$R$^4$, -(alkylene)$_m$-N(R$^3$)—C(O)—NR$^3$R$^4$, -(alkyalkylene)$_m$-N(R$^3$)—C(S)—NR$^3$R$^4$, -(alkylene)$_m$-N(R$^3$)—C(O)—R$^5$, -(alkyalkylene)$_m$-N(R$^3$)—C(S)—R$^5$, -(alkyalkylene)$_m$-O—C(O)—NR$^3$R$^4$, -(alkyalkylene)$_m$-O—C(S)—NR$^3$R$^4$, -(alkyalkylene)$_m$-SO$_2$—NR$^3$R$^4$, -(alkyalkylene)$_m$-N(R$^3$)—SO$_2$—R$^5$, -(alkyalkylene)$_m$-N(R$^3$)—SO$_2$—NR$^3$R$^4$, -(alkyalkylene)$_m$-N(R$^3$)—C(O)—OR$^5$, -(alkylene)$_m$-N(R$^3$)—C(S)—OR$^5$, or -(alkylene)$_m$-N(R$^3$)—SO$_2$—R$^5$;

$R^6$ is selected independently at each instance from: hydrogen, halogen, alkyl, alkenyl, alkynyl cycloalkyl, heterocyclo, aryl, heteroaryl, cycloalkylalkyl, heterocycloalkyl, arylalkyl, or heteroarylalkyl;

$R^7$ is selected from:

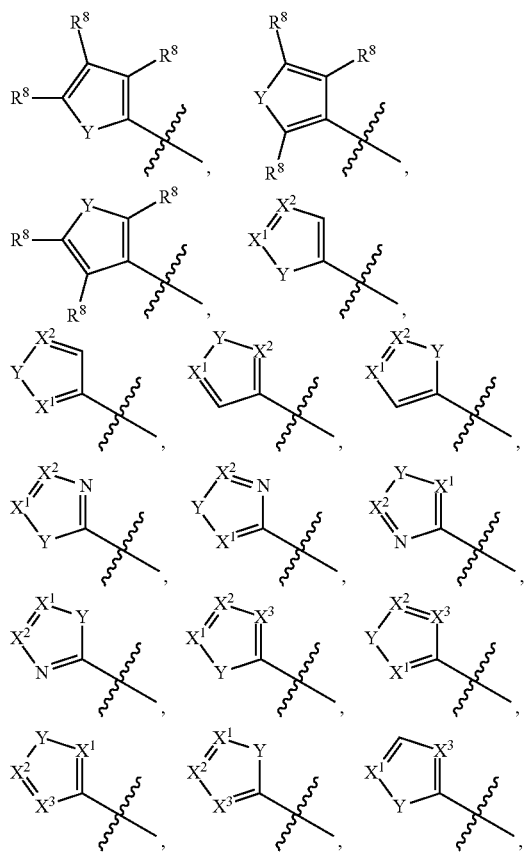

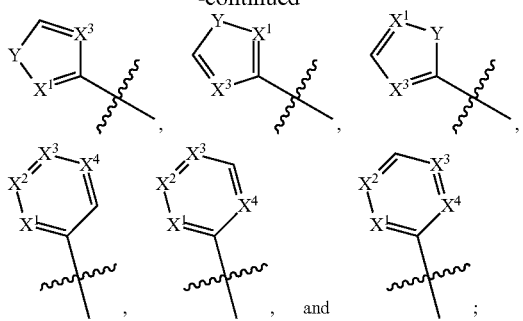

or $R^7$ is selected from cycloalkyl, heterocycle, and alkyl, each of which cycloalkyl, heterocycle, and alkyl groups is optionally substituted with one or more substituents selected from amino, —NHR$^{14}$, —NR$^{14}$R$^{15}$, hydroxyl, OR$^{14}$, R$^6$, and R$^2$;

$R^{14}$ and $R^{15}$ are independently selected from: hydrogen, alkyl, alkenyl, alkynyl, —C(O)H, —C(O)alkyl, —C(S) alkyl, aryl, —SO$_2$alkyl, heteroaryl, arylalkyl, and heteroarylalkyl;

$R^{16}$ is selected from cycloalkyl, heterocycle, and alkyl, each of which cycloalkyl, heterocycle, and alkyl groups is optionally substituted with one or more substituents selected from amino, —NHR$^{14}$, —NR$^{14}$R$^{15}$, hydroxyl, OR$^{14}$, R$^6$, and R$^2$;

Y is NH, O, S, or NR$^9$;

$X^1$, $X^2$, $X^3$ and $X^4$, are independently N or CR$^8$, wherein at least one of $X^1$, $X^2$, $X^3$, and $X^4$, is CR$^8$;

$R^8$ is selected independently at each instance from: R$^6$ and R$^2$, wherein one R$^8$ is R$^2$;

$R^9$ is selected from: —C(O)H, —C(O)alkyl, —C(S)alkyl, alkyl, aryl, heteroaryl, arylalkyl, and heteroarylalkyl;

$R^{10}$ is selected from: hydrogen, —COOalkyl, —COOarylalkyl, —COOH, —OH, —C(O)H, —C(O)alkyl, —C(S) alkyl, alkyl, aryl, heteroaryl, arylalkyl, and heteroarylalkyl; and wherein for compounds of Formula VII y is 0, 1, or 2.

In an additional embodiment, $R^7$ is selected from:

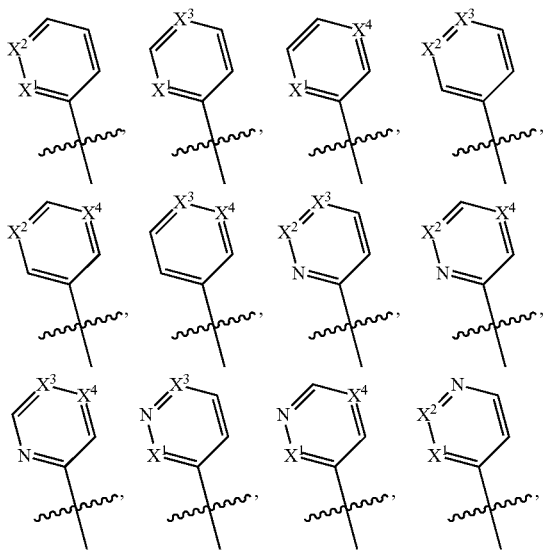

-continued
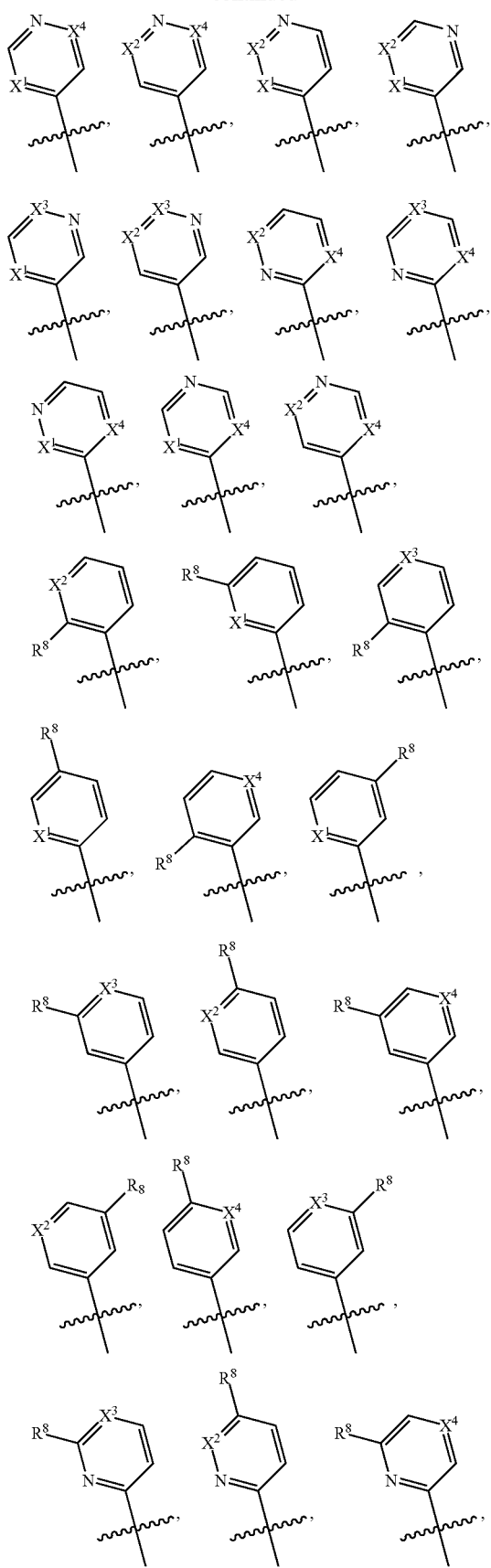
-continued
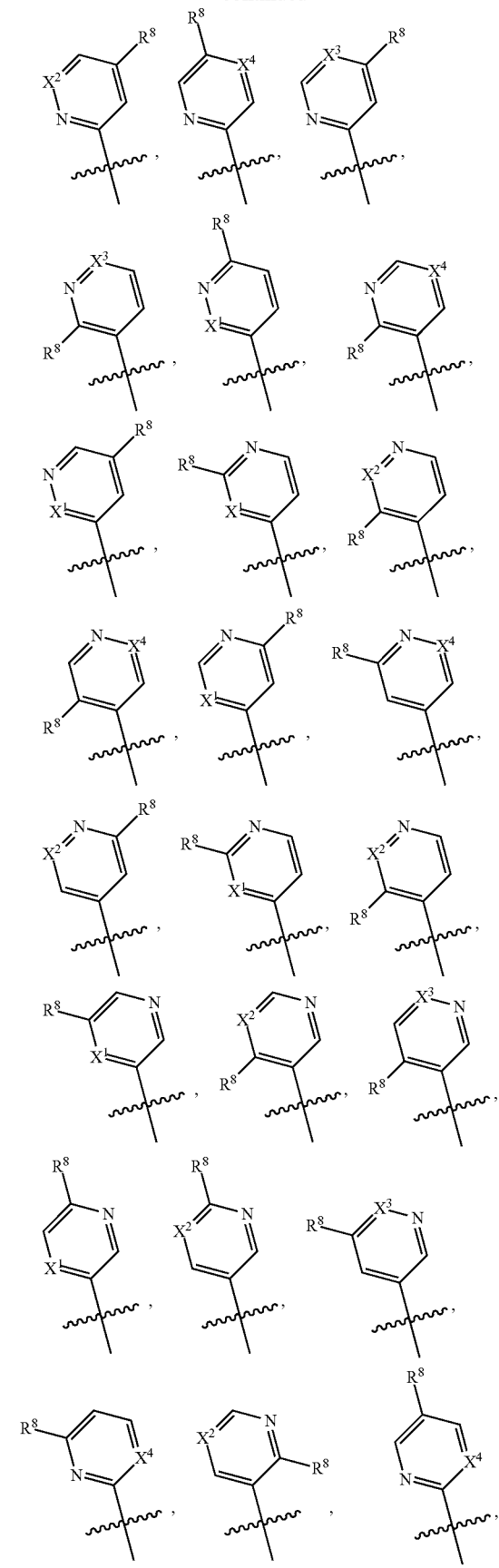

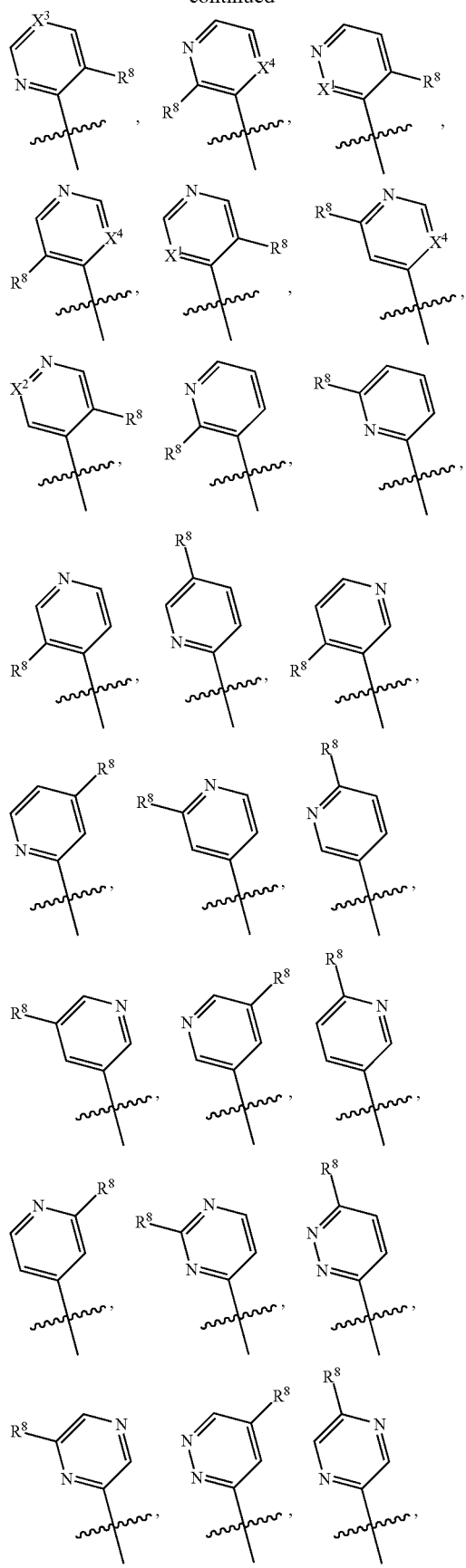
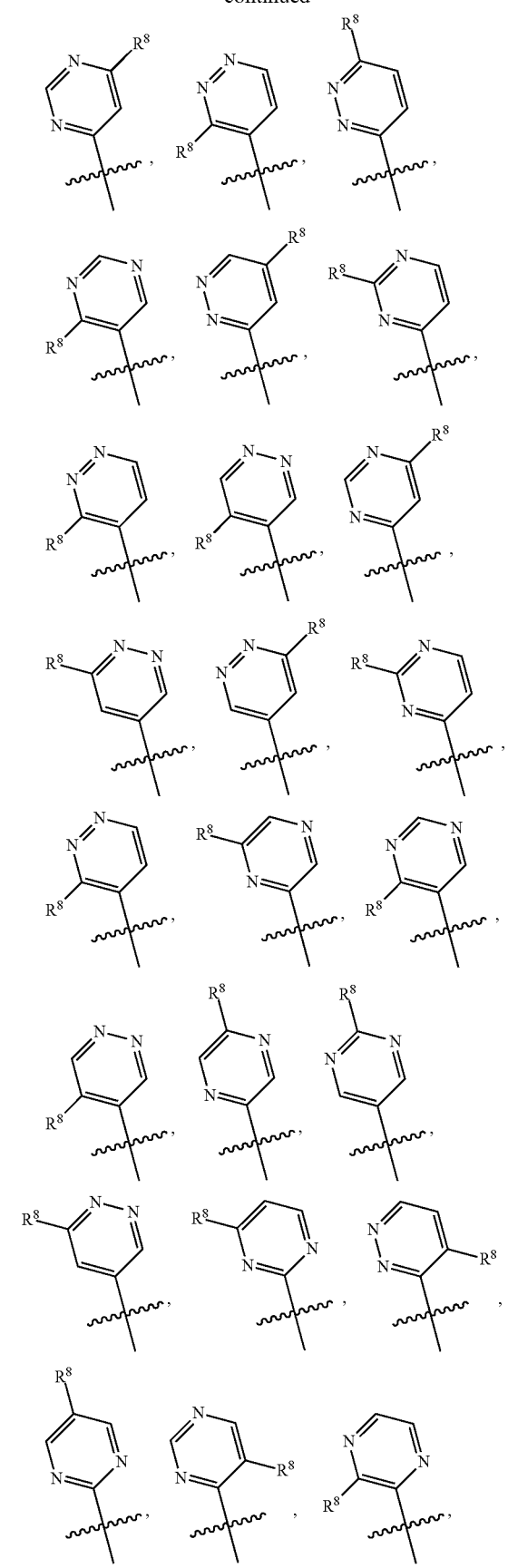

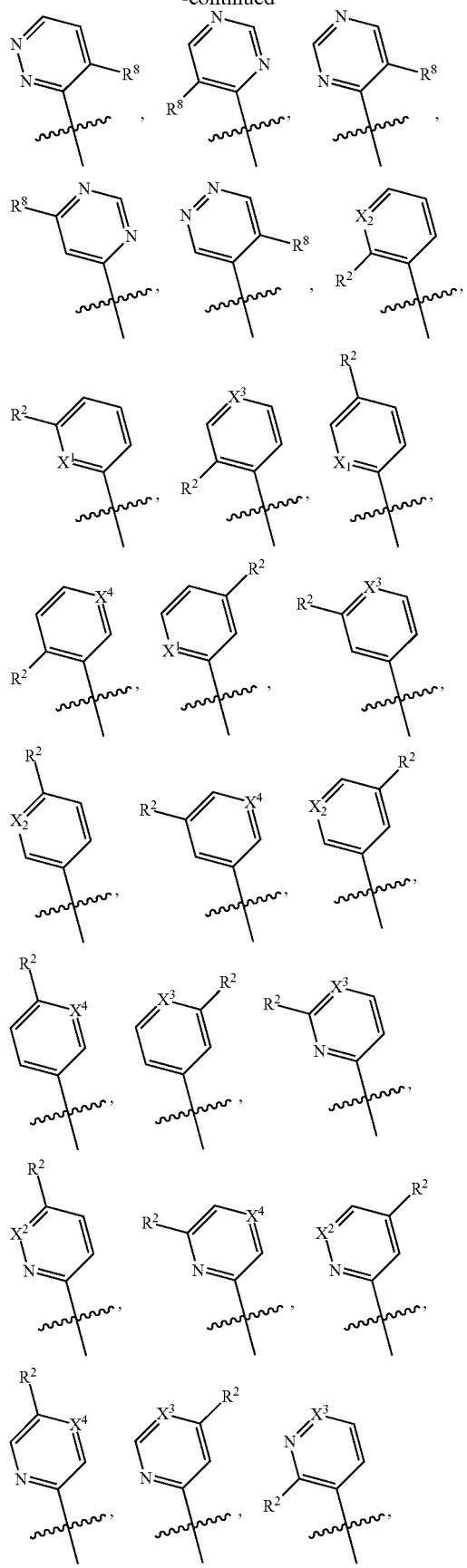
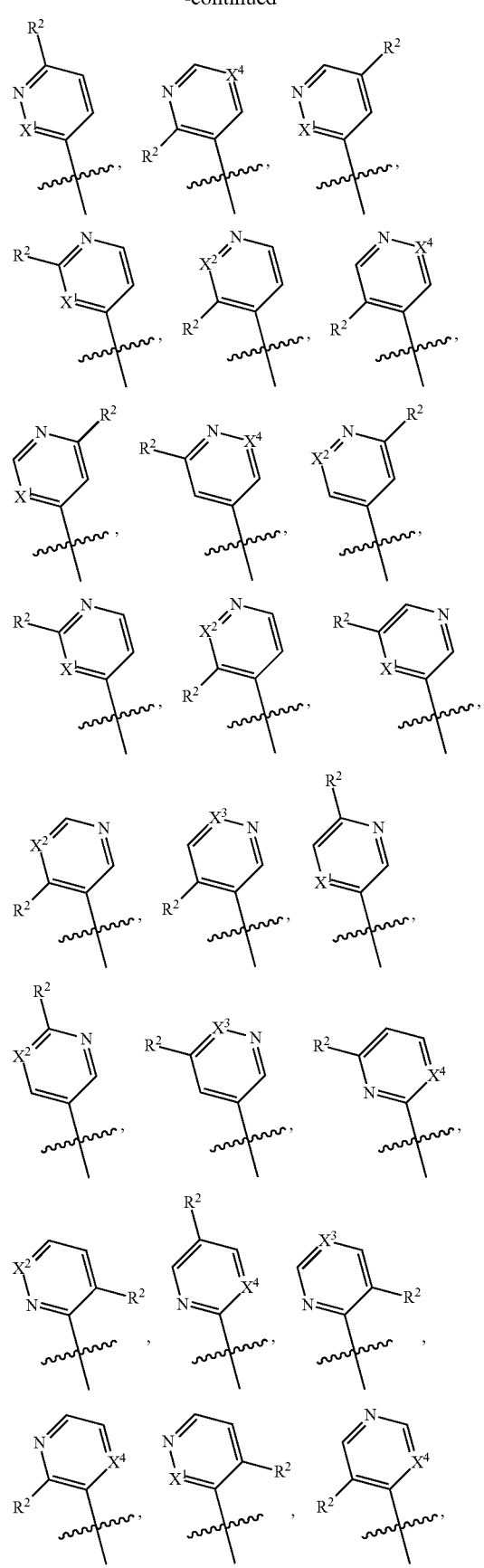

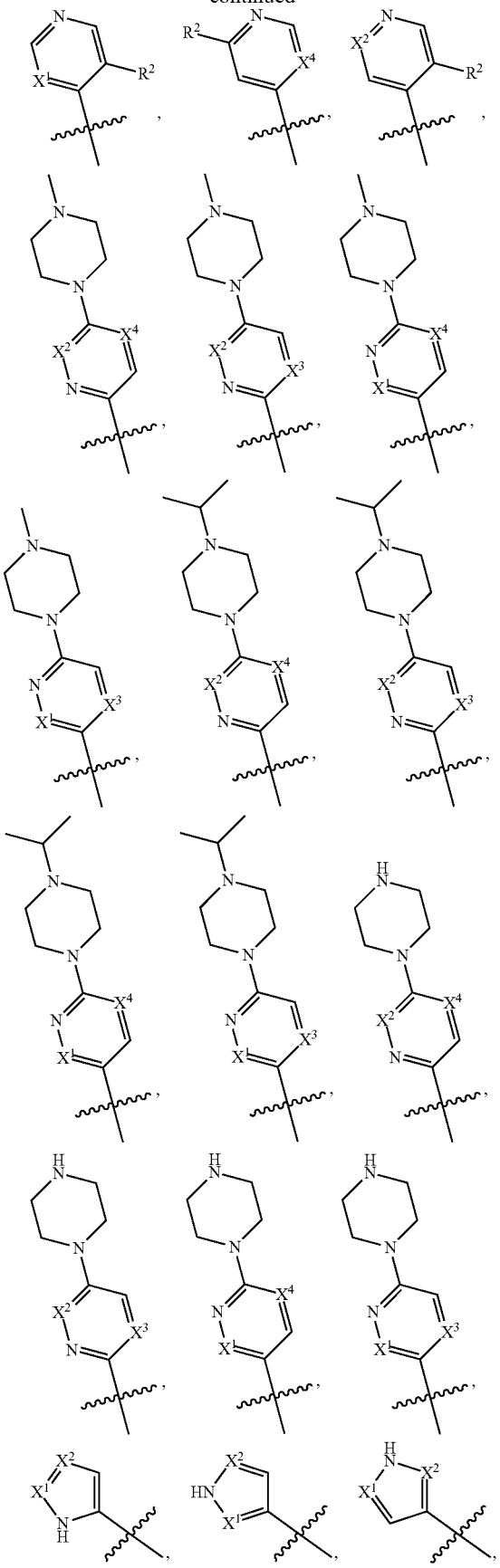

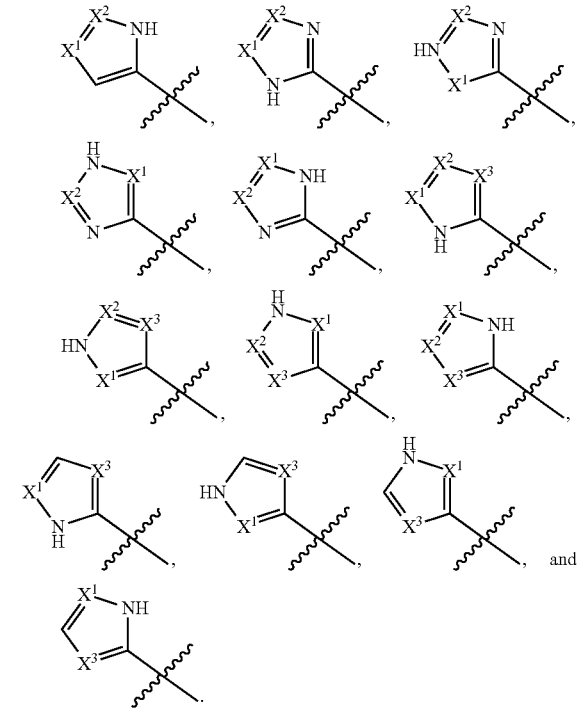

In an additional embodiment, R⁷ is selected from:

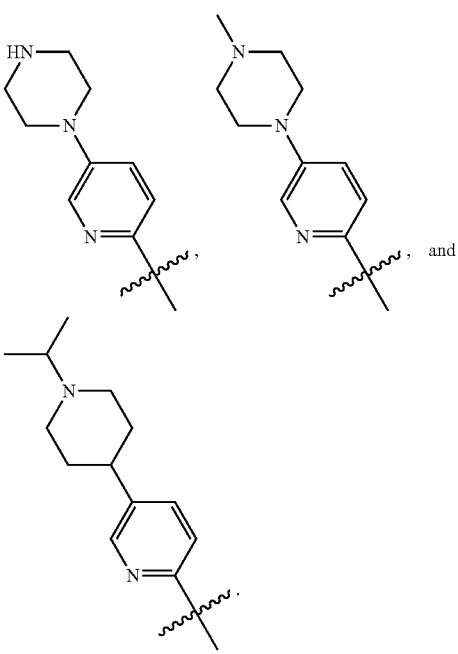

In another embodiment, a compound of Formula I-2, Formula II-2, Formula III-2, Formula IV-2, Formula V-2, Formula VI-2, Formula VII-2, Formula VIII-2, Formula IX-2, Formula X-2, Formula XI-2, Formula XII-2, Formula XIII-2, Formula XIV-2, Formula XV-2, Formula XVI-2, Formula XVII-2, Formula XVIII-2, Formula XIX-2, Formula XX-2 Formula XXI-2, Formula XXII-2, Formula XXIII-2, or Formula XXIV-2 is provided:

(I-2) 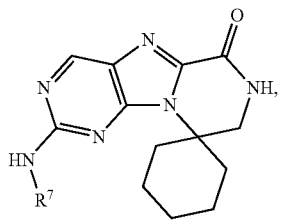
(II-2) 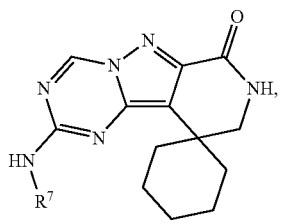
(III-2) 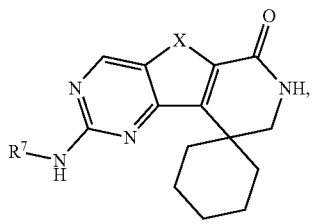
(IV-2) 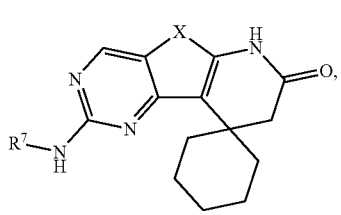
(V-2) 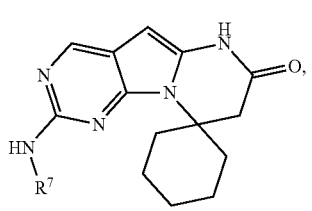
(VI-2) 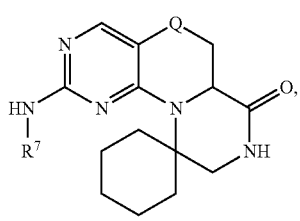
(VII-2) 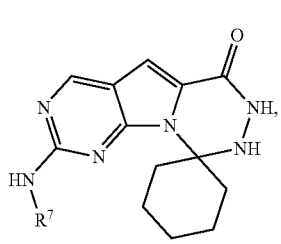
-continued
(VIII-2) 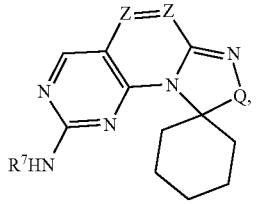
(IX-2) 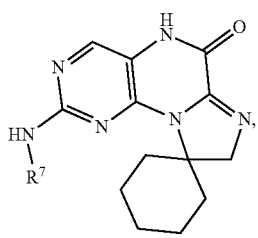
(X-2) 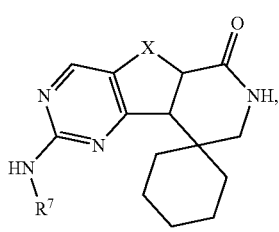
(XI-2) 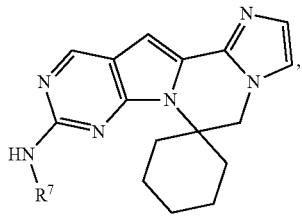
(XII-2) 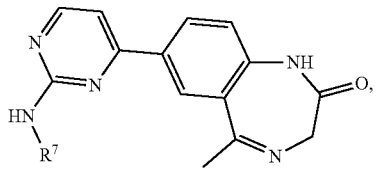
(XIII-2) 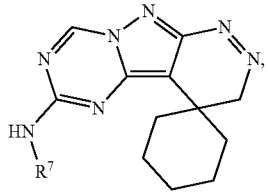
(XIV-2) 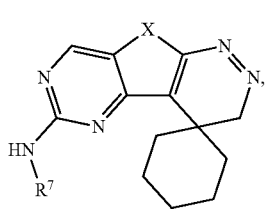

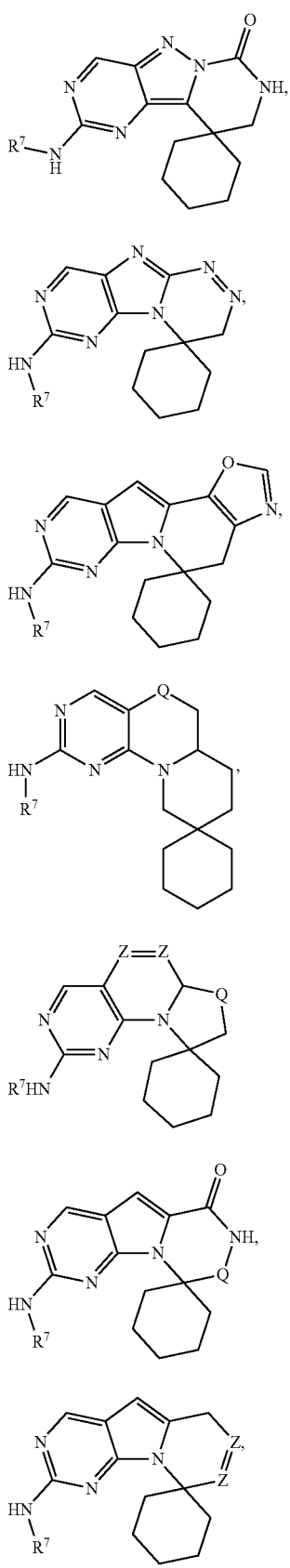
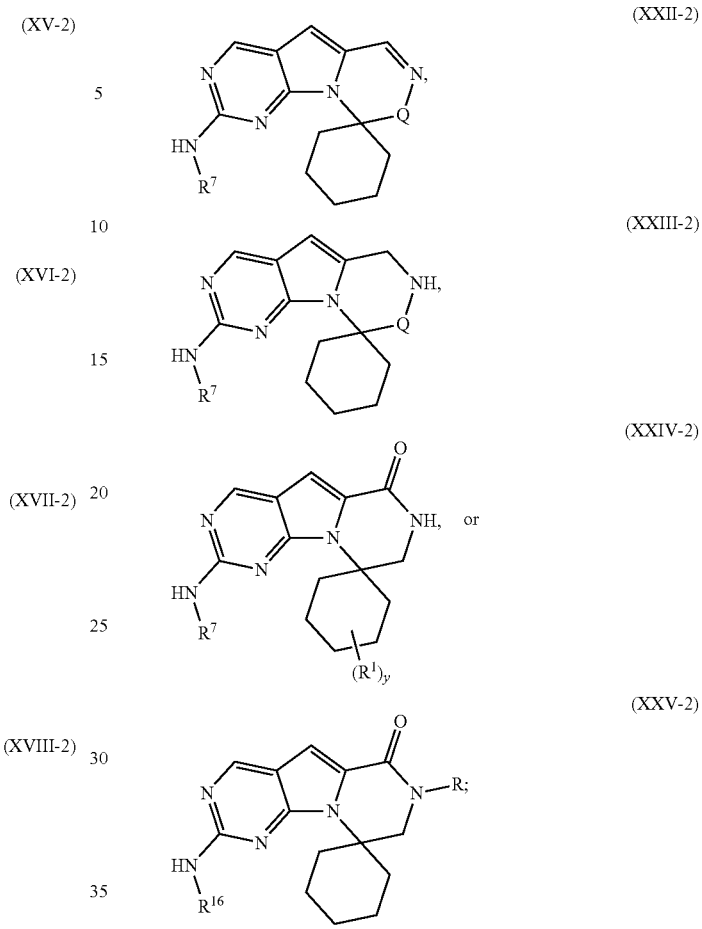

or a pharmaceutically acceptable salt, N-oxide, isotopic derivative, or prodrug, optionally in a pharmaceutically acceptable carrier to form a pharmaceutically acceptable composition thereof; wherein $R^{16}$, $R^7$, Q, Z, $R^1$, y, and X are as defined in Formula X-1 and Formula XIX-1 above.

In some aspects, $R^6$ is hydrogen.

In some aspects, $R^x$ is not further substituted.

In some aspects, $R^2$ is -(alkylene)$_m$-heterocyclo, -(alkylene)$_m$-heteroaryl, -(alkylene)$_m$-NR$^3$R$^4$, -(alkyalkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more $R^x$ groups as allowed by valance, and wherein two $R^x$ groups bound to the same or adjacent atom may optionally combine to form a ring and wherein m is 0 or 1 and n is 0, 1 or 2.

In some aspects, $R^2$ is -(alkylene)$_m$-heterocyclo, -(alkylene)$_m$-NR$^3$R$^4$, -(alkylene)$_m$-C(O)—NR$^3$R$^4$, -(alkyalkylene)$_m$-C(O)—O-alkyl or -(alkylene)$_m$-OR$^5$ any of which may be optionally independently substituted with one or more $R^x$ groups as allowed by valance, and wherein two $R^x$ groups bound to the same or adjacent atom may optionally combine to form a ring.

In some aspects, $R^2$ is -(alkylene)$_m$-heterocyclo, -(alkylene)$_m$-NR$^3$R$^4$, -(alkylene)$_m$-C(O)—NR$^3$R$^4$, -(alkyalkylene)$_m$-C(O)—O-alkyl or -(alkylene)$_m$-OR$^5$ without further substitution.

In some aspects, m in $R^2$ is 1. In a further aspect, the alkylene in $R^2$ is methylene.

In some aspects, R² is

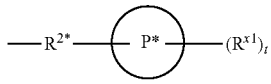

wherein:
R²* is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- and -(alkylene)$_m$-NH-(alkylene)$_m$- wherein each m is independently 0 or 1;

P is a 4- to 8-membered mono- or bicyclic saturated heterocyclyl group;

each $R^{x1}$ is independently -(alkylene)$_m$-(C(O))$_m$-(alkylene)$_m$-(N($R^N$))$_m$-(alkyl)$_m$ wherein each m is independently 0 or 1 provided at least one m is 1, —C(O))—O-alkyl, -(alkylene)$_m$-cycloalkyl wherein m is 0 or 1, —N($R^N$)-cycloalkyl, —C(O)-cycloalkyl, -(alkylene)$_m$-heterocyclyl wherein m is 0 or 1, or —N($R^N$)-heterocyclyl, —C(O)-heterocyclyl, —S(O)$_2$-(alkylene)$_m$ wherein m is 1 or 2, wherein:

$R^N$ is H, C$_1$ to C$_4$ alkyl or C$_1$ to C$_6$ heteroalkyl, and
wherein two $R^{x1}$ can, together with the atoms to which they attach on P, which may be the same atom, form a ring; and
t is 0, 1 or 2.

In some aspects, each $R^{x1}$ is only optionally substituted by unsubstituted alkyl, halogen or hydroxy.

In some aspects, $R^{x1}$ is hydrogen or unsubstituted C$_1$-C$_4$ alkyl.

In some aspects, at least one $R^{x1}$ is -(alkylene)$_m$-heterocyclyl wherein m is 0 or 1.

In some aspects, R² is

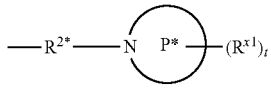

wherein P* is a 4- to 8-membered mono- or bicyclic saturated heterocyclyl group.

In some aspects, R² is

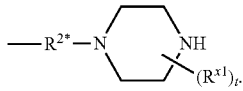

In some aspects, R² is

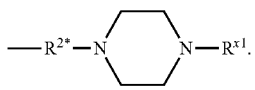

In some aspects, R² is

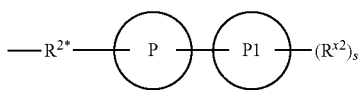

wherein:
R²* is a bond, alkylene, -(alkylene)$_m$-O-(alkylene)$_m$-, -(alkylene)$_m$-C(O)-(alkylene)$_m$-, -(alkylene)$_m$-S(O)$_2$-(alkylene)$_m$- and -(alkylene)$_m$-NH-(alkylene)$_m$- wherein each m is independently 0 or 1;

P is a 4- to 8-membered mono- or bicyclic saturated heterocyclyl group;

P1 is a 4- to 6-membered monocyclic saturated heterocyclyl group;

each $R^{x2}$ is independently hydrogen or alkyl; and
s is 0, 1 or 2.

In some aspects, R² is

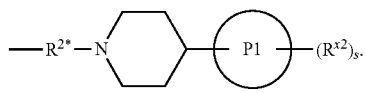

In some aspects, P1 includes at least one nitrogen.

In some aspects, any alkylene in R²* in any previous aspect is not further substituted.

In some aspects, R² is

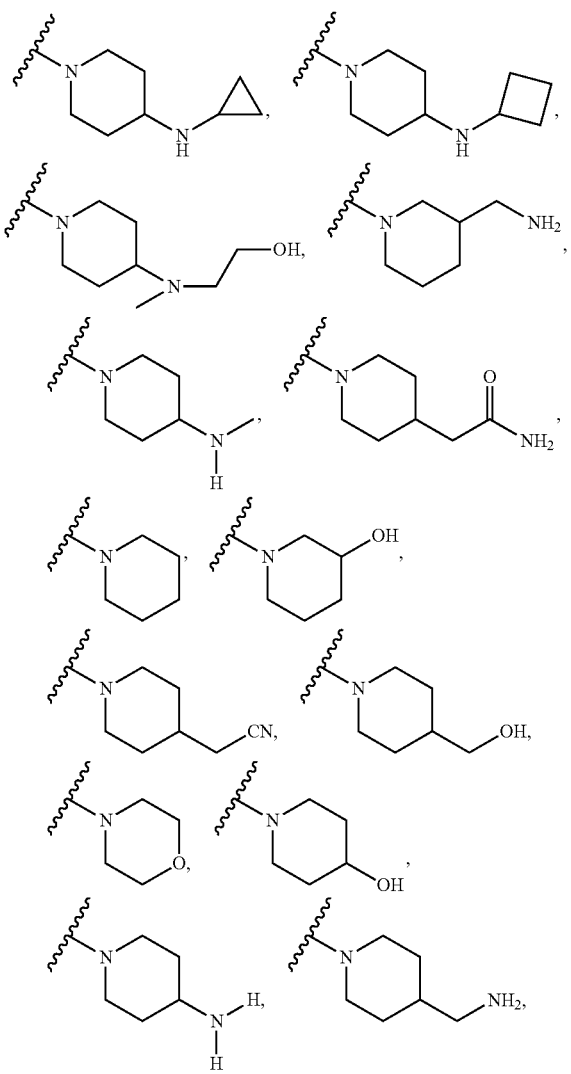

-continued
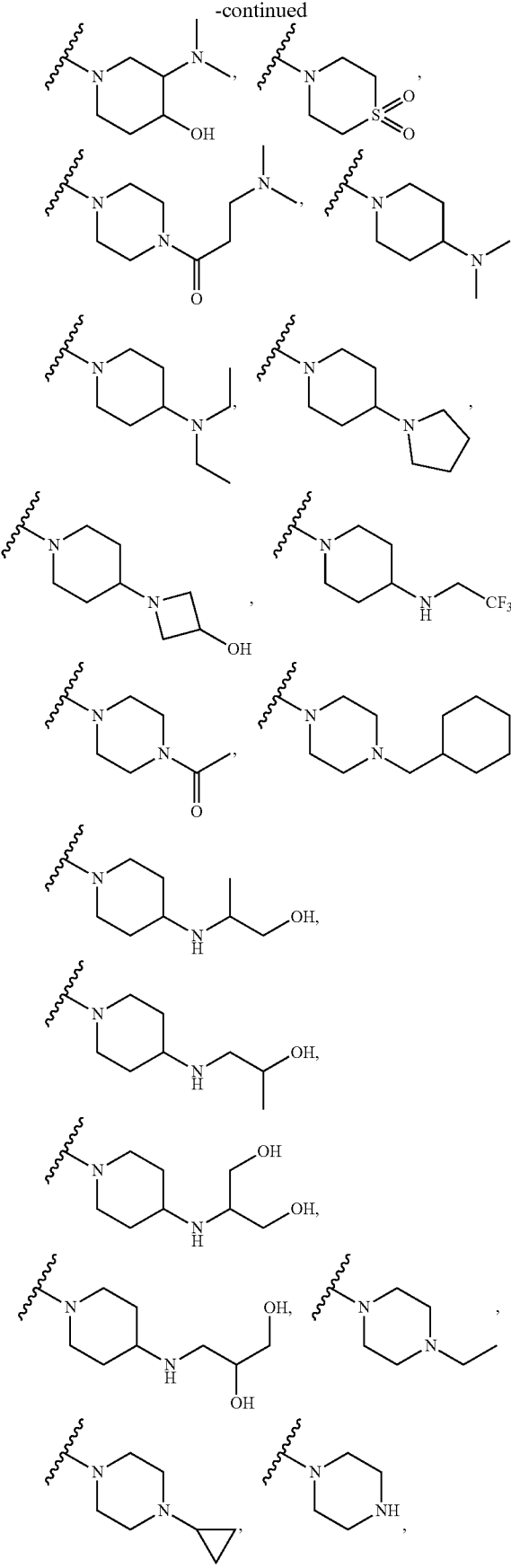
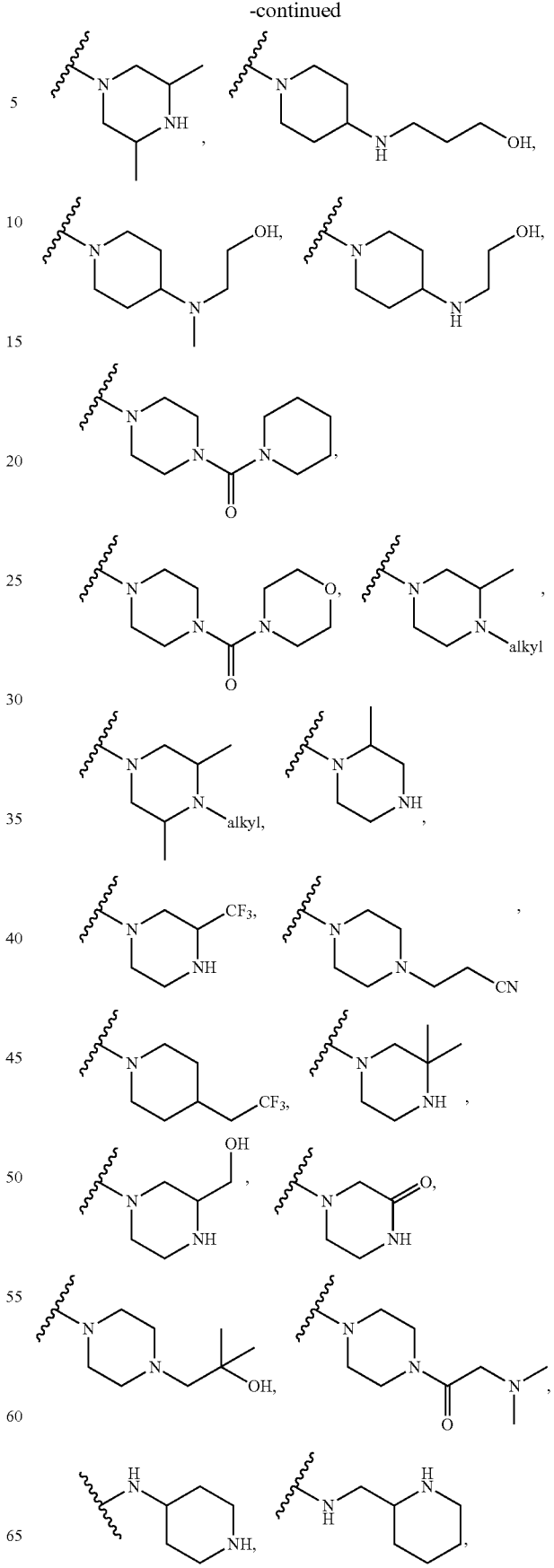

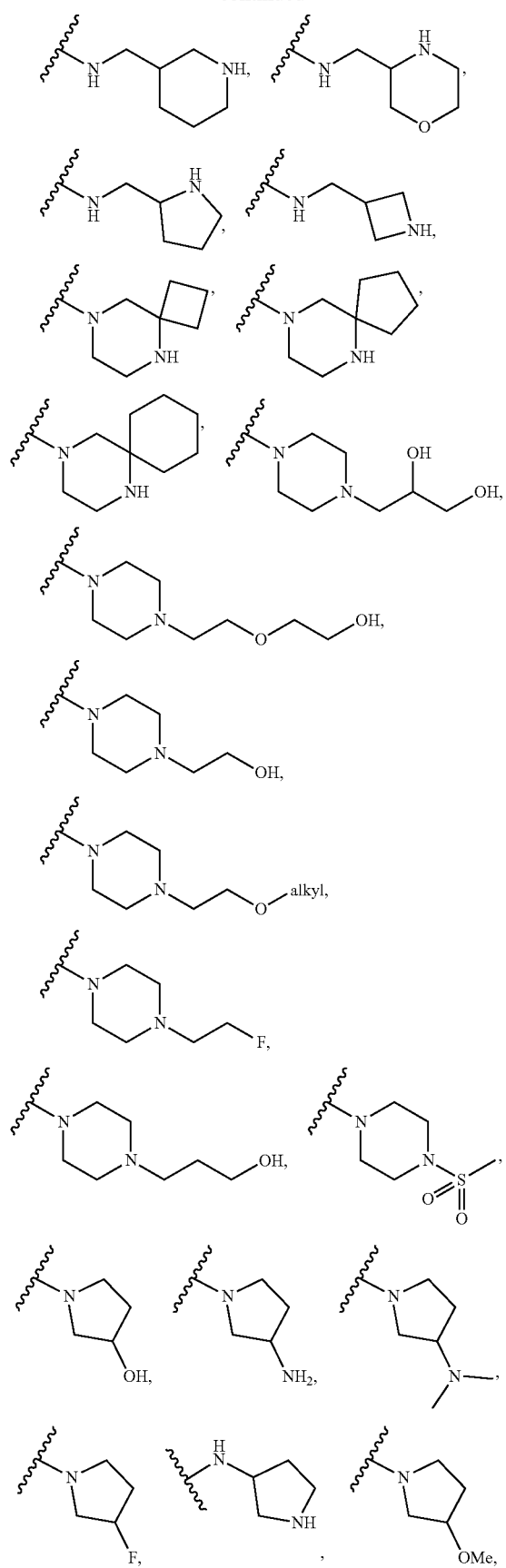
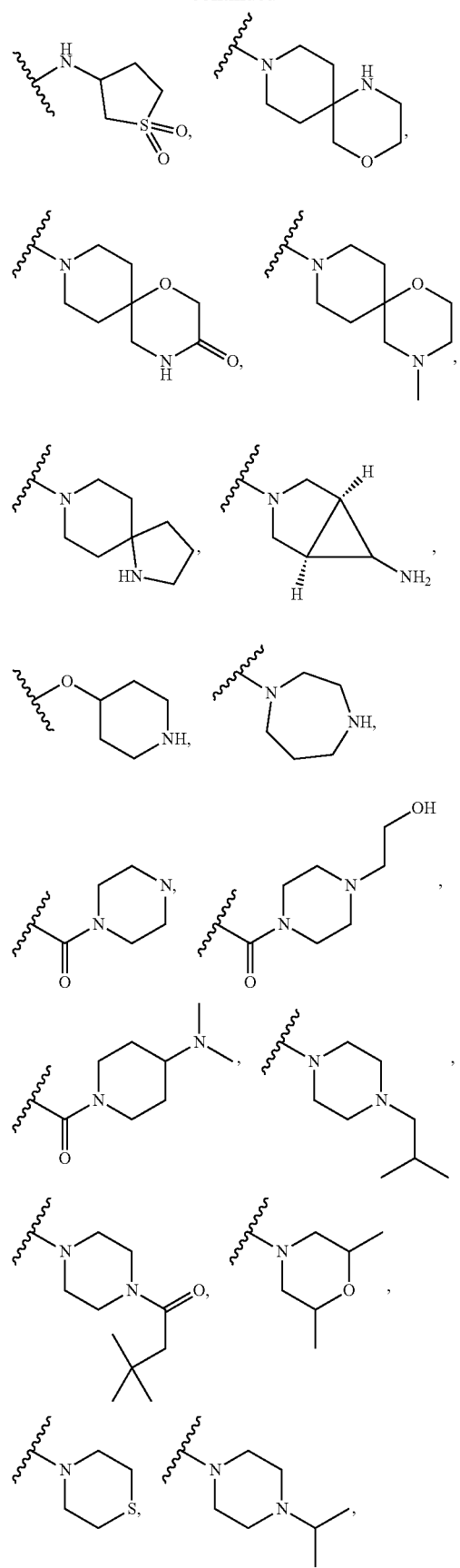

-continued

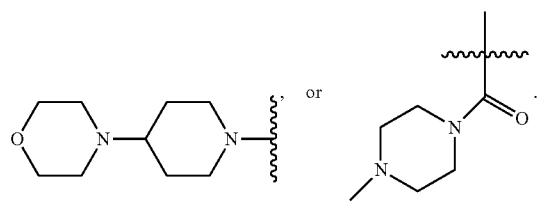

In some aspects, the compound has general Formula Ia:

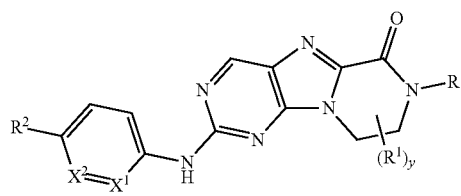

Ia wherein R, $R^1$, $R^2$, $X^1$, $X^2$ and y are as previously defined.

In some aspects, the compound has general Formula Ib:

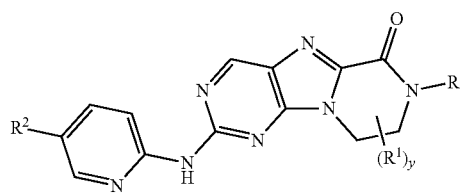

Ib wherein R, $R^1$, $R^2$, and y are as previously defined.

In some aspects, the compound has general Formula Ic:

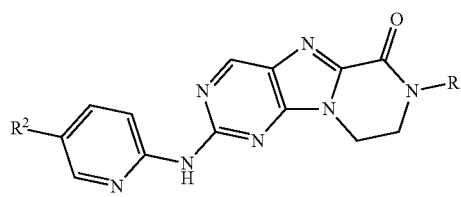

Ic wherein R and $R^2$ are as previously defined.

In some aspects, the compound has general Formula Id:

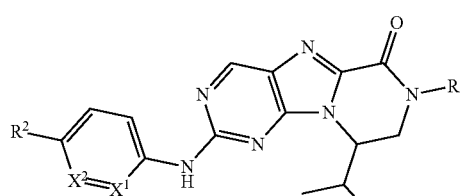

Id wherein R, $R^2$, $X^1$ and $X^2$ are as previously defined.

In some aspects, the compound has general Formula Ie:

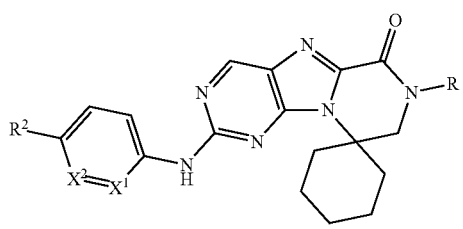

Ie wherein R, $R^2$, $X^1$ and $X^2$ are as previously defined.

In some aspects, the compound has general Formula If:

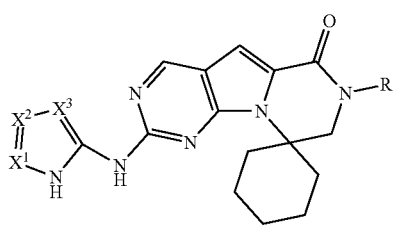

If wherein R, $R^2$, $X^1$, $X^2$, and $X^3$ are as previously defined.

In some aspects, the compound has general Formula IIa:

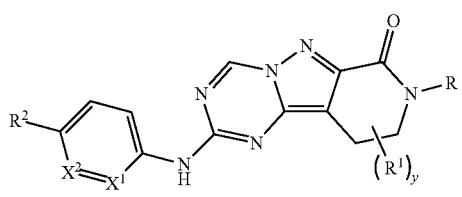

IIa wherein R, $R^1$, $R^2$, $X^1$, $X^2$, and y are as previously defined.

In some aspects, the compound has general Formula IIb:

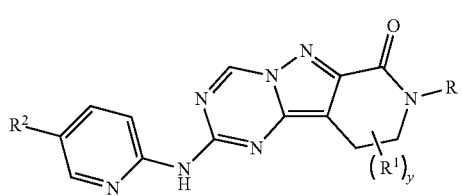

IIb wherein R, $R^1$, $R^2$, and y are as previously defined.

In some aspects, the compound has general Formula IIc:

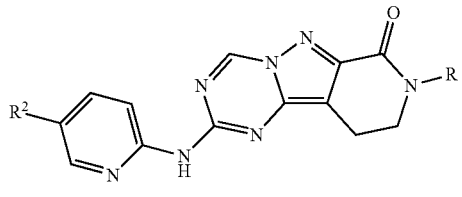

IIc wherein R and $R^2$, are as previously defined.

In some aspects, the compound has general Formula IId:

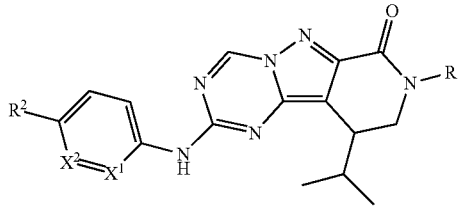

IId wherein R, R², X¹ and X² are as previously defined.

In some aspects, the compound has general Formula IIe:

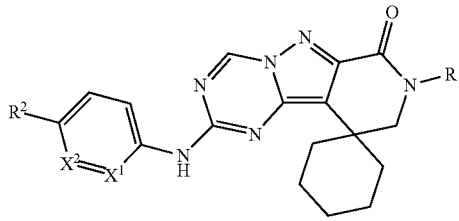

IIe wherein R, R², X¹ and X² are as previously defined.

In some aspects, the compound has general Formula IIf:

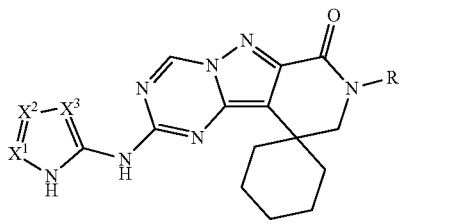

IIf wherein R, R², X¹, X², and X³ are as previously defined.

In some aspects, the compound has general Formula IIIa:

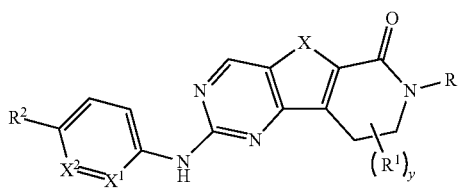

IIIa wherein R, R¹, R², X¹, X², and y are as previously defined.

In some aspects, the compound has general Formula IIIb:

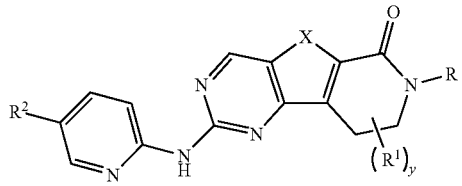

IIIb wherein R, R¹, R², X, and y are as previously defined.

In some aspects, the compound has general Formula IIIc:

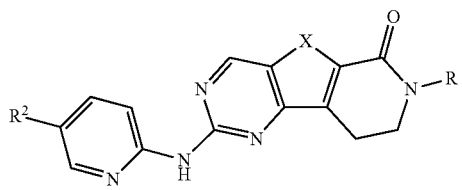

IIIc wherein R, X, and R are as previously defined.

In some aspects, the compound has general Formula IIId:

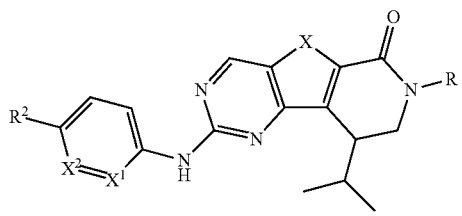

IIId wherein R, R², X¹, and X² are as previously defined.

In some aspects, the compound has general Formula IIIe:

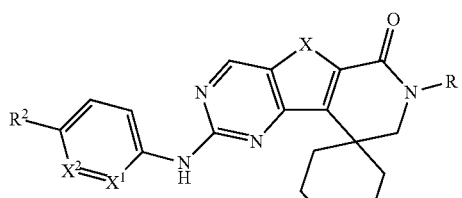

IIIe wherein R, R², X¹, and X² are as previously defined.

In some aspects, the compound has general Formula IIIf:

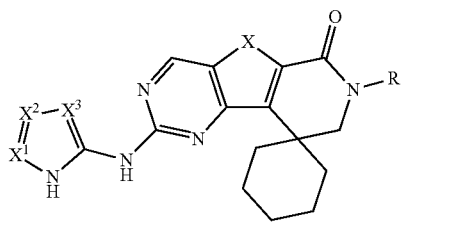

IIIf wherein R, R², X¹, X², and X³ are as previously defined.

In some aspects, the compound has general Formula IVa:

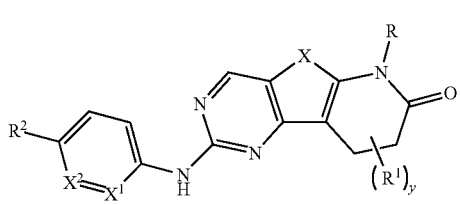

IVa wherein R, $R^1$, $R^2$, X, $X^2$ and y are as previously defined.

In some aspects, the compound has general Formula IVb:

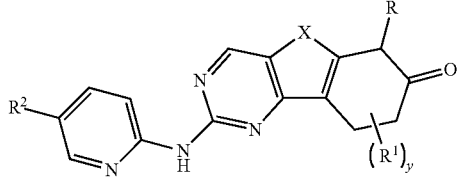

IVb wherein R, $R^1$, $R^2$, X, and y are as previously defined.

In some aspects, the compound has general Formula IVc:

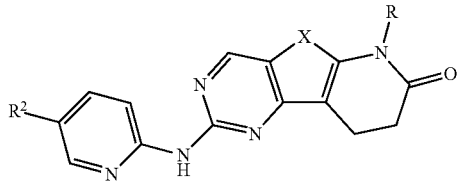

IVc wherein R, X, and $X^2$ are as previously defined.

In some aspects, the compound has general Formula IVd:

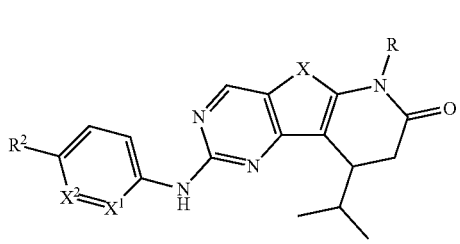

IVd wherein R, $R^2$, $X^1$, and $X^2$ are as previously defined.

In some aspects, the compound has general Formula IVe:

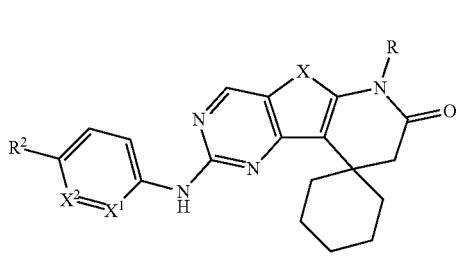

IVe wherein R, $R^2$, $X^1$, and $X^2$ are as previously defined.

In some aspects, the compound has general Formula IVf:

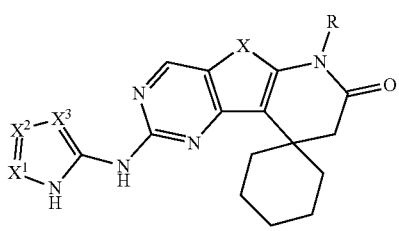

IVf wherein R, $R^2$, $X^1$, $X^2$, and $X^3$ are as previously defined.

In some aspects, the compound has general Formula Va:

Va wherein R, $R^1$, $R^2$, $X^1$, $X^2$ and y are as previously defined.

In some aspects, the compound has general Formula Vb:

Vb wherein R, $R^1$, $R^2$, and y are as previously defined.

In some aspects, the compound has general Formula Vc:

Vc wherein R and $R^2$ are as previously defined.

In some aspects, the compound has general Formula Vd:

Vd wherein R, $R^2$, $X^1$, and $X^2$ are as previously defined.

In some aspects, the compound has general Formula Ve:

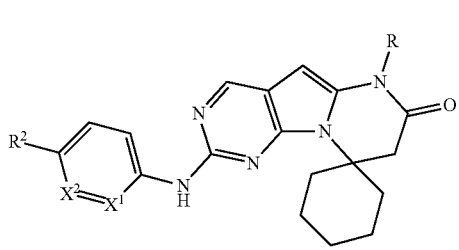

Ve wherein R, R², X¹, and X² are as previously defined.

In some aspects, the compound has general Formula Vf:

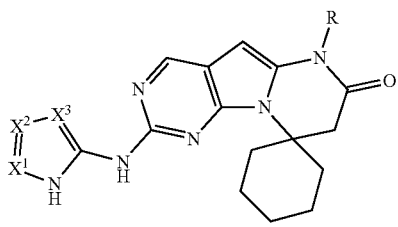

Vf wherein R, R², X¹, X², and X³ are as previously defined.

In some aspects, the compound has general Formula VIa:

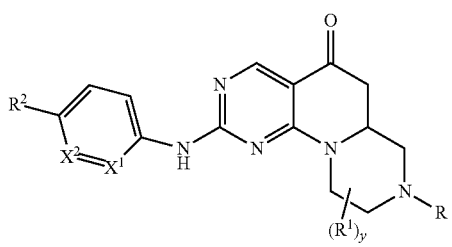

VIa wherein R, R¹, R², X¹, and X² are as previously defined.

In some aspects, the compound has general Formula VIb:

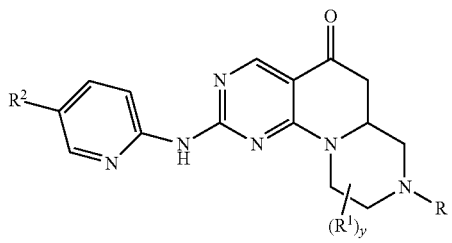

VIb wherein R, R¹, R², and y are as previously defined.

In some aspects, the compound has general Formula VIc:

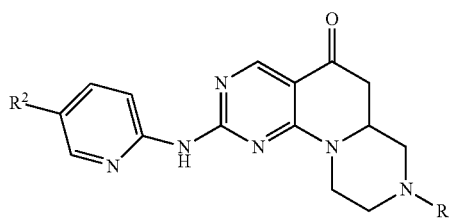

VIc wherein R and R² are as previously defined.

In some aspects, the compound has general Formula VId:

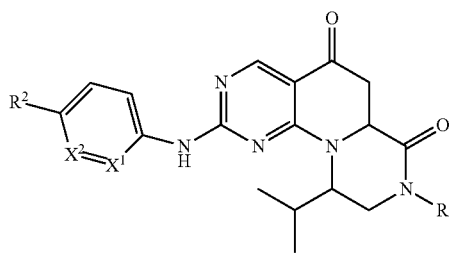

VId wherein R, R², X¹, and X² are as previously defined.

In some aspects, the compound has general Formula VIe:

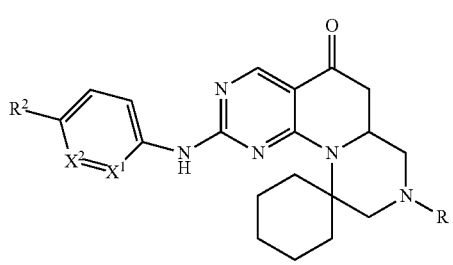

VIe wherein R, R², X¹, and X² are as previously defined.

In some aspects, the compound has general Formula VIf:

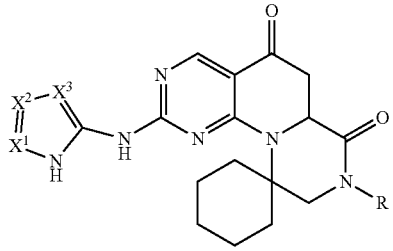

VIf wherein R, R², X¹, X², and X³ are as previously defined.

In some aspects, the compound has general Formula VIIa:

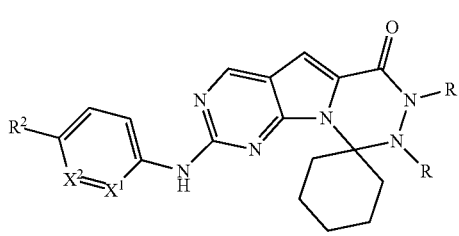

VIIa wherein R, R², X¹, and X² are as previously defined.

In some aspects, the compound has general Formula VIIb:

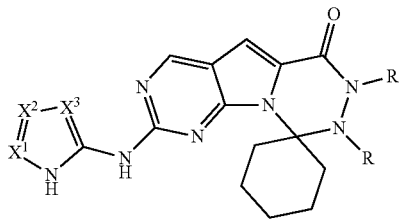

VIIb wherein R, R², X¹, X², and X³ are as previously defined.

In some aspects, the compound has general Formula VIIIa:

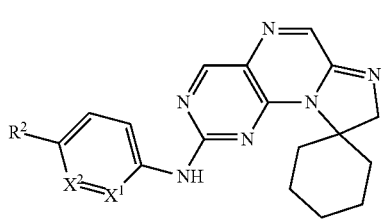

VIIIa wherein R², X¹, and X² are as previously defined.

In some aspects, the compound has general Formula VIIIb:

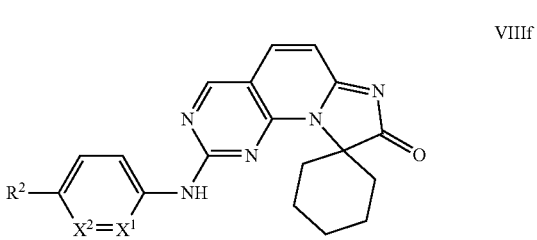

VIIIb wherein R², X¹, and X² are as previously defined.

In some aspects, the compound has general Formula VIIIc:

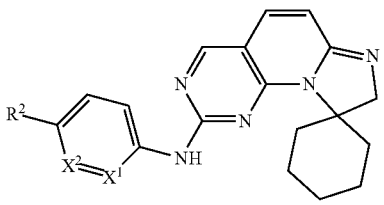

VIIIc wherein R², X¹, and X² are as previously defined.

In some aspects, the compound has general Formula VIIId:

VIIId wherein R², X¹, and X² are as previously defined.

In some aspects, the compound has general Formula VIIIe:

VIIIe wherein R², X¹, and X² are as previously defined.

In some aspects, the compound has general Formula VIIIf:

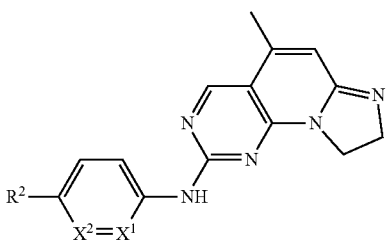

VIIIf wherein R², X¹, and X² are as previously defined.

In some aspects, the compound has general Formula IXa:

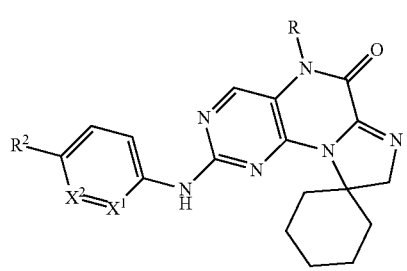

IXa wherein R, R², X¹, and X² are as previously defined.

In some aspects, the compound has general Formula IXb:

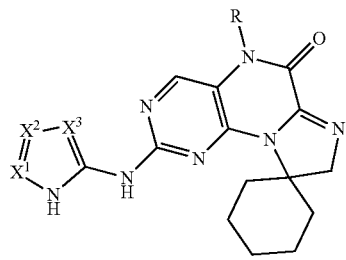

IXb wherein R, R², X¹, X², and X³ are as previously defined.

In some aspects, the compound has general Formula Xa:

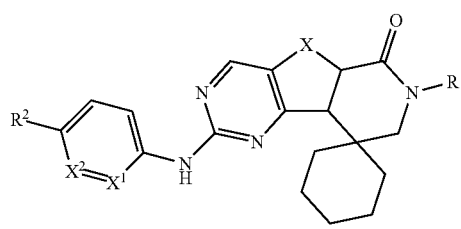

Xa wherein R, R², X¹, and X² are as previously defined.

In some aspects, the compound has general Formula Xb:

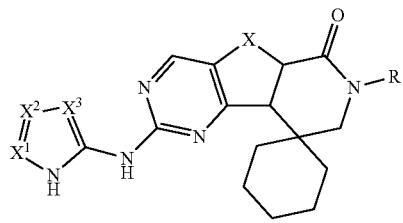

Xb wherein R, R², X¹, X², and X³ are as previously defined.

In some aspects, the compound has general Formula XIa:

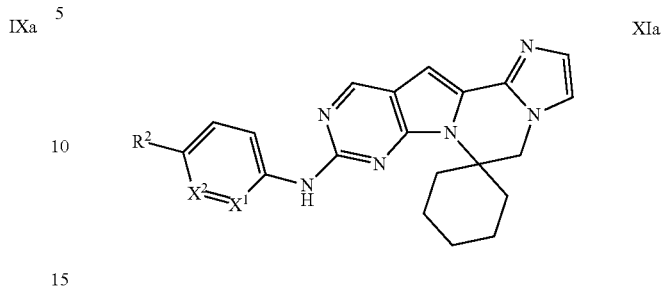

XIa wherein R, R², X¹, and X² are as previously defined.

In some aspects, the compound has general Formula XIb:

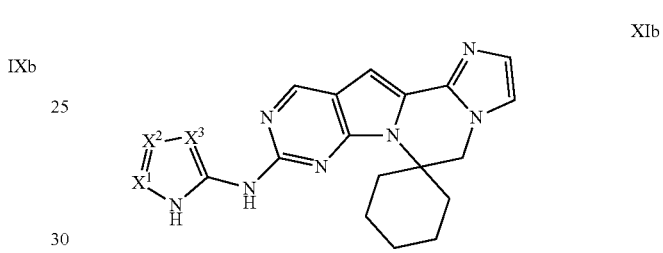

XIb wherein R, R², X¹, X², and X³ are as previously defined.

In some aspects, the compound has general Formula XIIa:

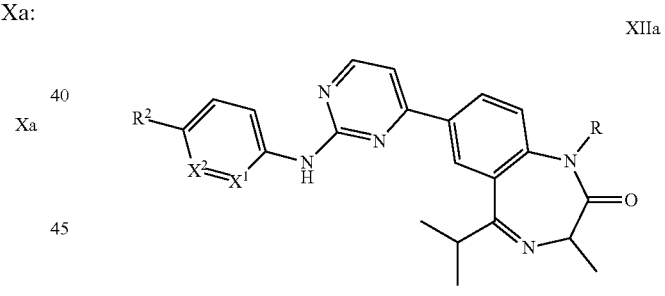

XIIa wherein R, R², X¹, and X² are as previously defined.

In some aspects, the compound has general Formula XIIb:

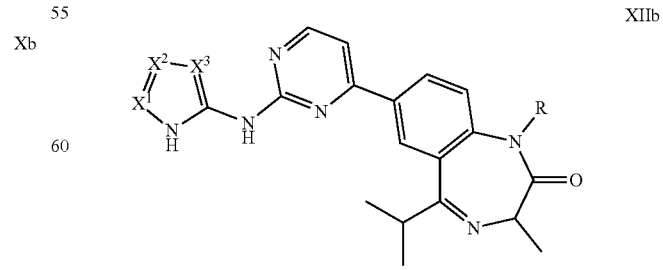

XIIb wherein R, R², X¹, X², and X³ are as previously defined.

In some aspects, the compound has general Formula XIIIa:

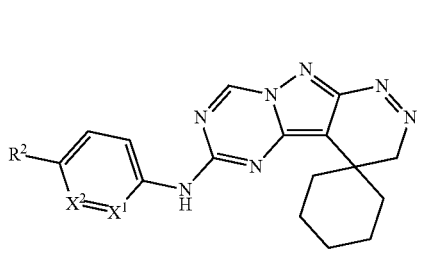

XIIIa wherein $R^2$, $X^1$, and $X^2$ are as previously defined.

In some aspects, the compound has general Formula XIIIb:

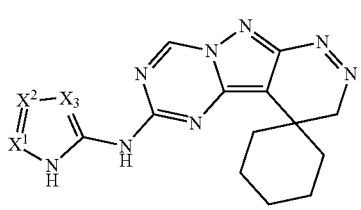

XIIIb wherein $R^2$, $X^1$, $X^2$, and $X^3$ are as previously defined.

In some aspects, the compound has general Formula XIVa:

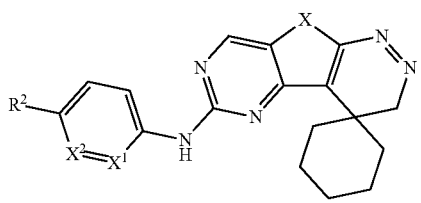

XIVa wherein X, $R^2$, $X^1$, and $X^2$ are as previously defined.

In some aspects, the compound has general Formula XIVb:

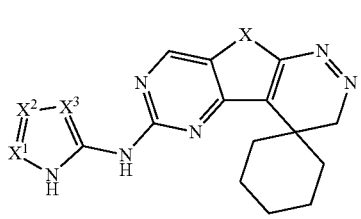

XIVb wherein X, $R^2$, $X^1$, $X^2$, and $X^3$ are as previously defined.

In some aspects, the compound has general Formula XVa:

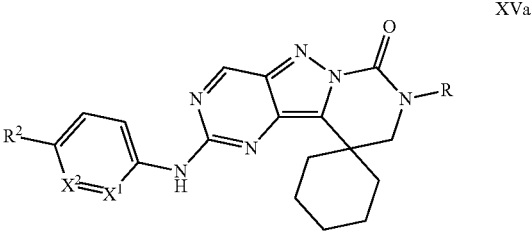

XVa wherein R, $R^2$, $X^1$, and $X^2$ are as previously defined.

In some aspects, the compound has general Formula XVb:

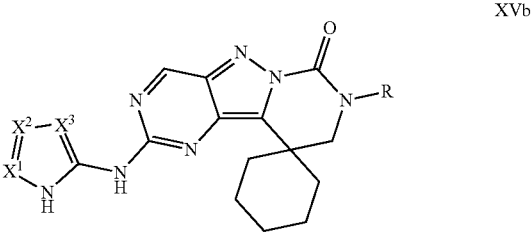

XVb wherein R, $R^2$, $X^1$, $X^2$, and $X^3$ are as previously defined.

In some aspects, the compound has general Formula XVIa:

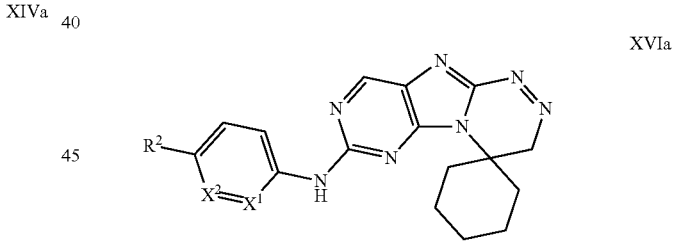

XVIa wherein $R^2$, $X^1$, and $X^2$ are as previously defined.

In some aspects, the compound has general Formula XVIb:

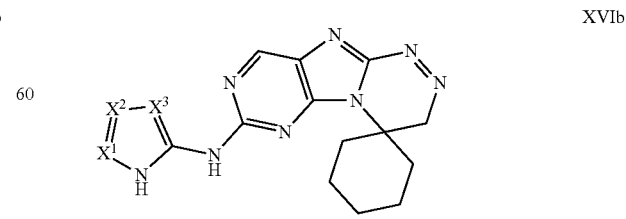

XVIb wherein $R^2$, $X^1$, $X^2$, and $X^3$ are as previously defined.

In some aspects, the compound has general Formula XVIIa:

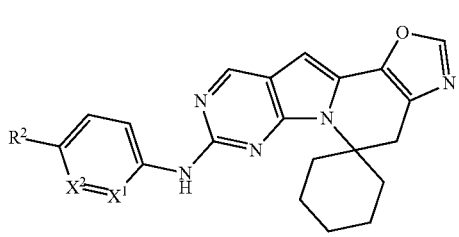

XVIIa wherein R, R², X¹, and X² are as previously defined.

In some aspects, the compound has general Formula XVIIb:

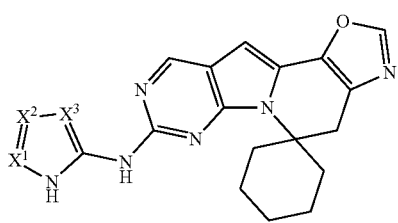

XVIIb wherein R, R², X¹, X², and X³ are as previously defined.

In some aspects, the compound has general Formula XVIIIa:

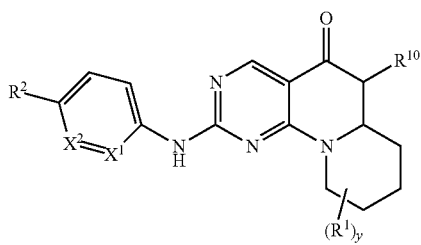

XVIIIa wherein R¹, R², R¹⁰, X¹, X², X³, and y are as previously defined.

In some aspects, the compound has general Formula XVIIIb:

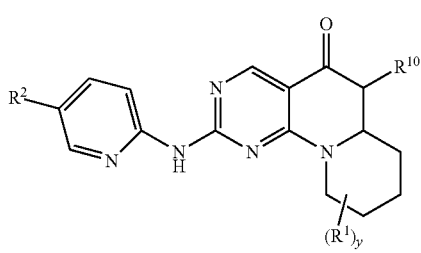

XVIIIb wherein R, R¹, R², R¹⁰ and y are as previously defined.

In some aspects, the compound has general Formula XVIIIc:

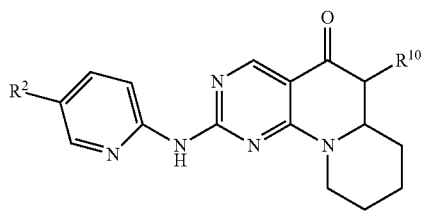

XVIIIc wherein R, R² and R¹⁰ are as previously defined.

In some aspects, the compound has general Formula XVIIId:

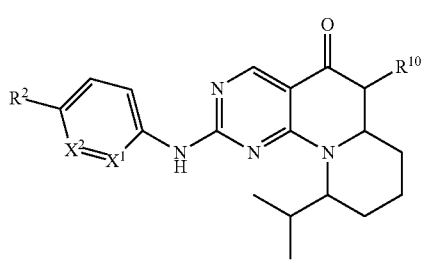

XVIIId wherein R, R², R¹⁰, X¹, and X² are as previously defined.

In some aspects, the compound has general Formula XVIIIe:

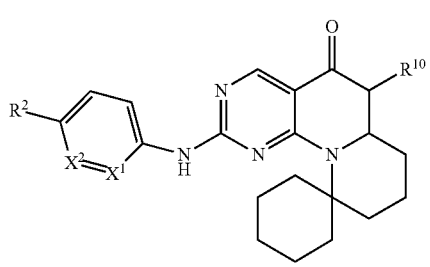

XVIIIe wherein R, R², R¹⁰ X¹, and X² are as previously defined.

In some aspects, the compound has general Formula XIVa:

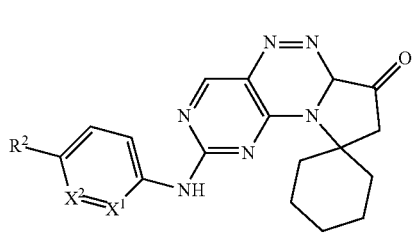

XIXa wherein R², X¹, and X² are as previously defined.

In some aspects, the compound has general Formula XIXb:

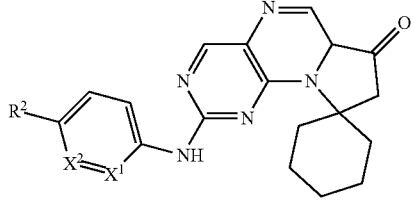

XIXb wherein $R^2$, $X^1$, and $X^2$ are as previously defined.

In some aspects, the compound has general Formula XIXc:

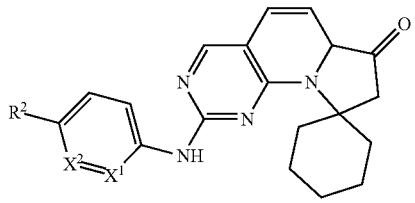

XIXc wherein $R^2$, $X^1$, and $X^2$ are as previously defined.

In some aspects, the compound has general Formula XIXd:

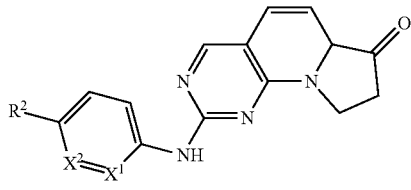

XIXd wherein $R^2$, $X^1$, and $X^2$ are as previously defined.

In some aspects, the compound has general Formula XIXe:

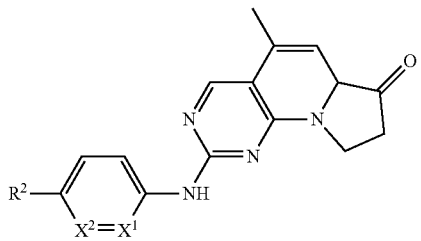

XIXe wherein $R^2$, $X^1$, and $X^2$ are as previously defined.

In some aspects, the compound has general Formula XXa:

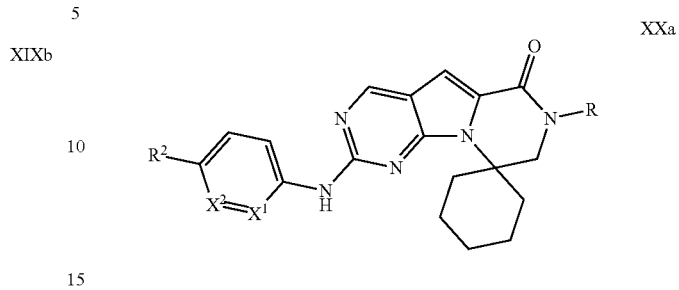

XXa wherein R, $R^2$, $X^1$, and $X^2$ are as previously defined.

In some aspects, the compound has general Formula XXb:

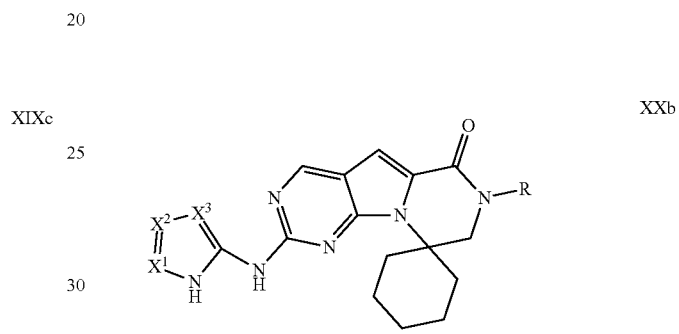

XXb wherein R, $X^1$, $X^2$, and $X^3$ are as previously defined.

In some aspects, the compound has general Formula XXc:

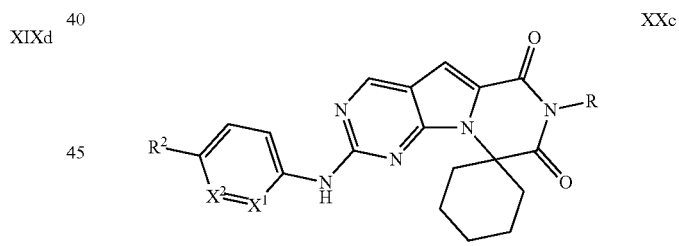

XXc wherein R, $R^2$, $X^1$, and $X^2$ are as previously defined.

In some aspects, the compound has general Formula XXd:

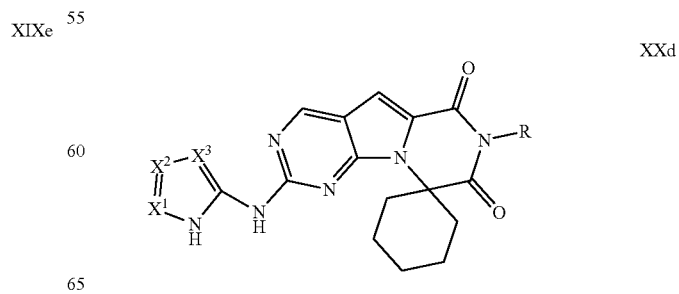

XXd wherein R, $X^1$, $X^2$, and $X^3$ are as previously defined.

In some aspects, the compound has general Formula XXIa:

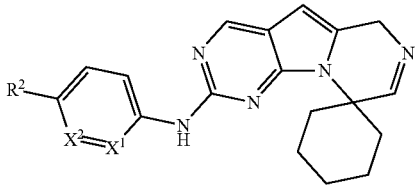

XXIa wherein $R^2$, $X^1$, and $X^2$ are as previously defined.

In some aspects, the compound has general Formula XXIb:

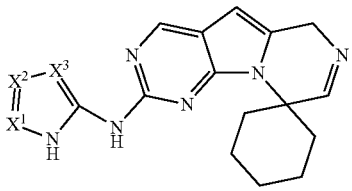

XXIb wherein $X^1$, $X^2$, and $X^3$ are as previously defined.

In some aspects, the compound has general Formula XXIIa:

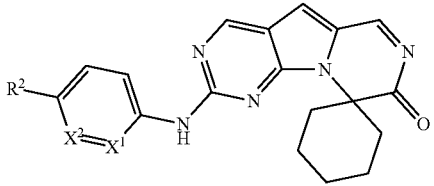

XXIIa wherein $R^2$, $X^1$, and $X^2$ are as previously defined.

In some aspects, the compound has general Formula XXIIb:

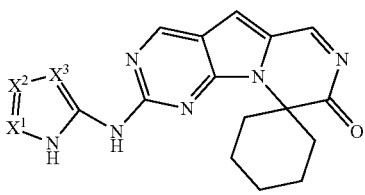

XXIIb wherein $X^1$, $X^2$, and $X^3$ are as previously defined.

In some aspects, the compound has general Formula XXIIIa:

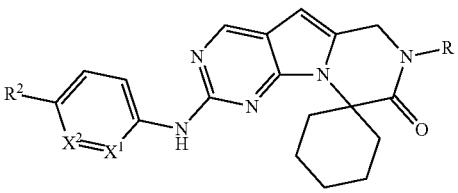

XXIIIa wherein R, $R^2$, $X^1$, and $X^2$ are as previously defined.

In some aspects, the compound has general Formula XXIIIb:

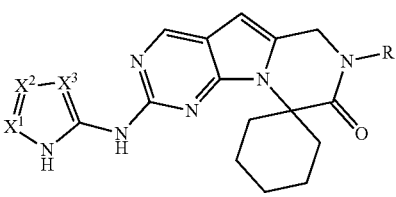

XXIIIb wherein R, $X^1$, $X^2$, and $X^3$ are as previously defined.

In some embodiments, the compound is selected from a Formula presented above and $X^1$ is N and $X^2$ is CH. In other embodiments, the compound is selected from a Formula presented above and $X^1$ is N and $X^2$ is N. In other embodiments, the compound is selected from a Formula presented above and $X^1$ is CH and $X^2$ is CH. In other embodiments, the compound is selected from a Formula presented above and $X^1$ is CH and $X^2$ is N.

In some embodiments, the compound is selected from a Formula presented above and $X^1$ is N, $X^2$ is CH, $X^3$ is CH, and $X^4$ is CH. In other embodiments, the compound is selected from a Formula presented above and $X^1$ is CH, $X^2$ is N, $X^3$ is CH, and $X^4$ is CH. In other embodiments, the compound is selected from a Formula presented above and $X^1$ is CH, $X^2$ is N, $X^3$ is N, and $X^4$ is CH. In other embodiments, the compound is selected from a Formula presented above and $X^1$ is CH, $X^2$ is N, $X^3$ is CH, and $X^4$ is N. In other embodiments, the compound is selected from a Formula presented above and $X^1$ is N, $X^2$ is CH, $X^3$ is N, and $X^4$ is CH. In other embodiments, the compound is selected from a Formula presented above and $X^1$ is N, $X^2$ is CH, $X^3$ is CH, and $X^4$ is N.

In some embodiments, the compound is selected from a Formula presented above and
$R^2$ is

wherein P* is a 4- to 8-membered mono- or bicyclic saturated heterocyclyl group and $R^{2*}$, $R^{x1}$ and t are as previously defined.

In some embodiments, the compound is selected from a Formula presented above and $R^2$ is

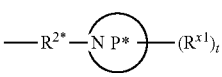

wherein P* is a 4- to 8-membered mono- or bicyclic saturated heterocyclyl group, $R^{x1}$ is hydrogen or unsubstituted $C_1$-$C_4$ alkyl and $R^{2*}$ is as previously defined.

In some embodiments, the compound is selected from a Formula presented above and $R^2$ is selected from

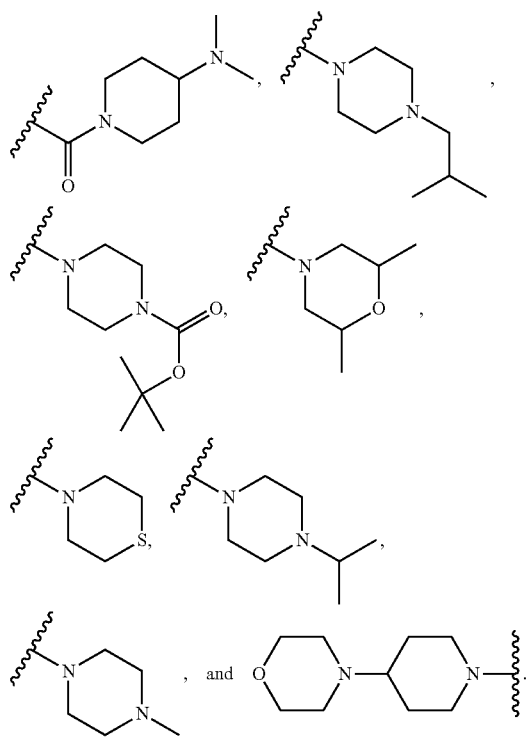

In some embodiments, the compound is selected from a Formula presented above and $R^2$ is selected from,

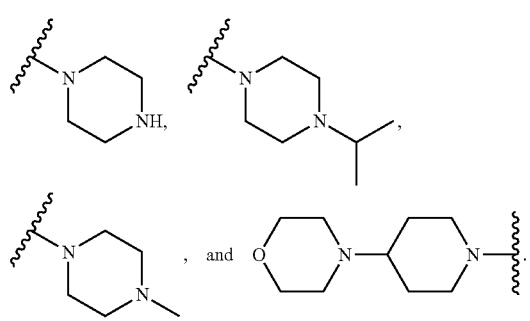

In some embodiments, the compound is selected from a Formula presented above and R is alkyl.

In some embodiments, the compound is selected from a Formula presented above and R is hydrogen.

In some embodiments $R^x$ is further substituted with a substituent chosen from:

-(alkylene)$_m$-CN, -(alkylene)$_m$-OR$^{5*}$, -(alkylene)$_m$-S(O)$_n$—R$^{5*}$, -(alkylene)$_m$-NR$^{3*}$R$^{4*}$, -(alkylene)$_m$-C(O)—R$^{5*}$, -(alkylene)$_m$-C(=S)R$^{5*}$, -(alkylene)$_m$-C(=O)O R$^{5*}$, -(alkylene)$_m$-OC(=O)R$^{5*}$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$-O—C(O)—NR$^{3*}$R$^{4*}$, -(alkylene)$_m$-O—C(S)—NR$^{3*}$R$^{4*}$, -(alkylene)$_m$-SO$_2$—NR$^{3*}$R$^{4*}$, -(alkylene)$_m$-N(R$^{3*}$)—SO$_2$—R$^{5*}$, -(alkylene)$_m$-N(R$^{3*}$)—SO$_2$—NR$^{3*}$R$^{4*}$, -(alkylene)$_m$-N(R$^{3*}$)—C(O)—OR$^{5*}$, -(alkylene)$_m$-N(R$^{3*}$)—C(S)—OR$^{5*}$, and -(alkylene)$_m$-N(R$^{3*}$)—SO$_2$—R$^{5*}$;

$R^{3*}$ and $R^{4*}$ at each occurrence are independently selected from:

(i) hydrogen or (ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance; or $R^{3*}$ and $R^{4*}$ together with the nitrogen atom to which they are attached may combine to form a heterocyclo ring optionally independently substituted with one or more $R^x$ groups as allowed by valance.

$R^{5*}$ is independently selected at each occurrence from:

(i) hydrogen or (ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;

In some embodiments the compound of the present invention is selected from:

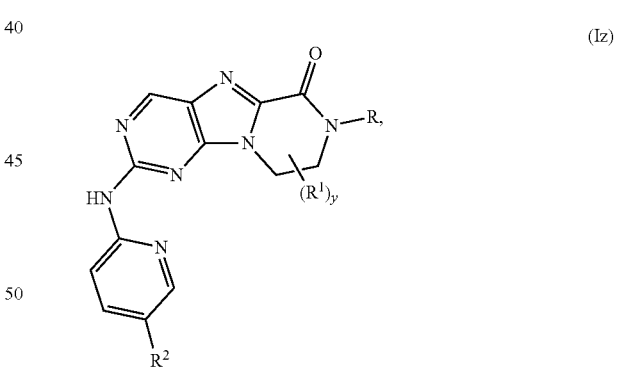

(Iz)

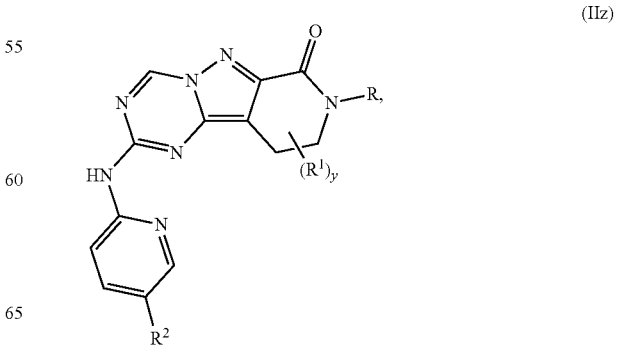

(IIz)

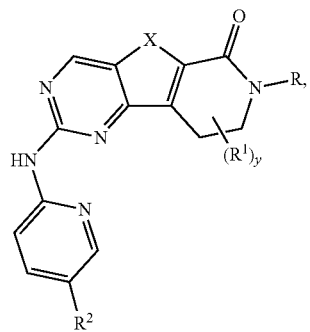
(IIIz)
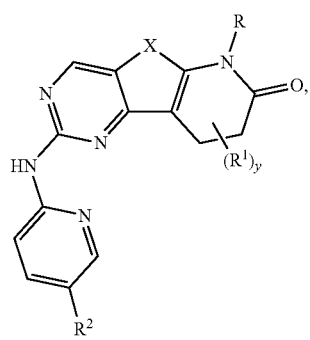
(IVz)
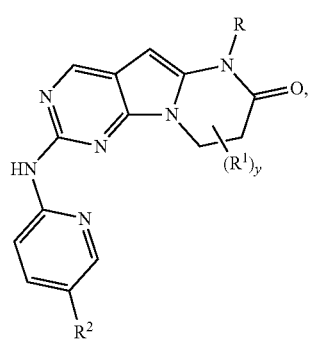
(Vz)
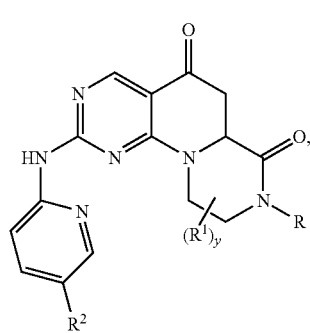
(VIz)
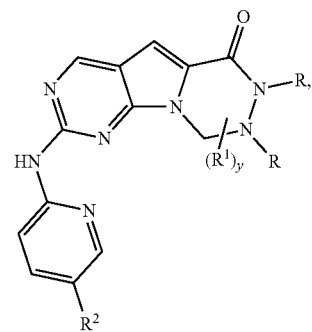
(VIIz)
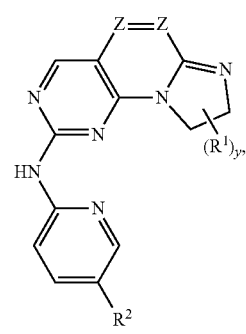
(VIIIz)
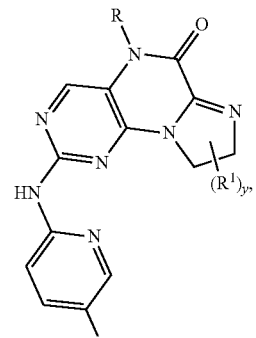
(IXz)
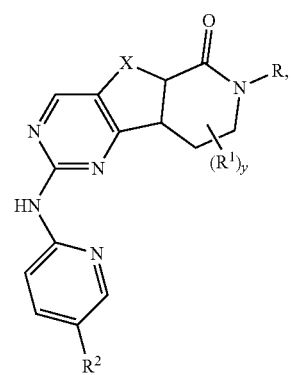
(Xz)

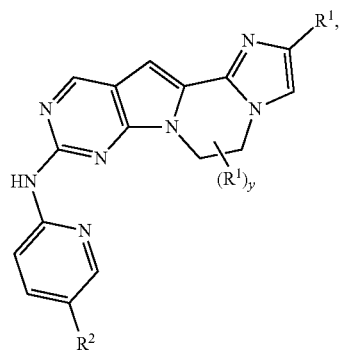
(XIz)
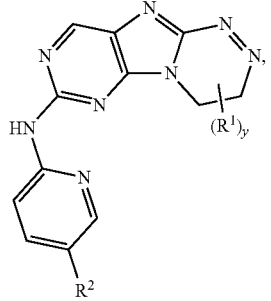
(XVIz)
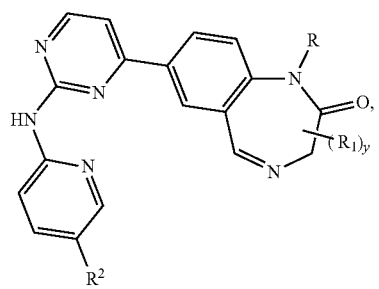
(XIIz)
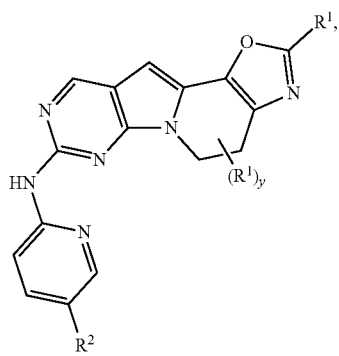
(XVIIz)
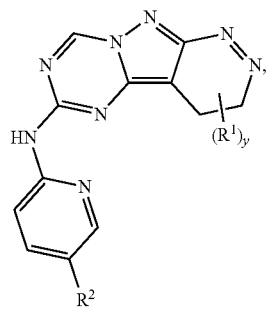
(XIIIz)
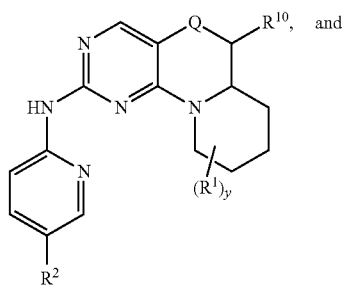
(XVIIIz)
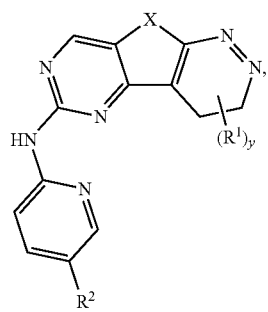
(XIVz)
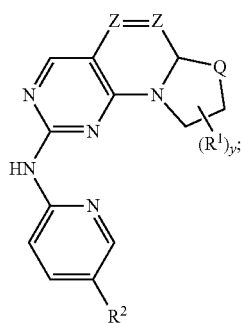
(XIXz)
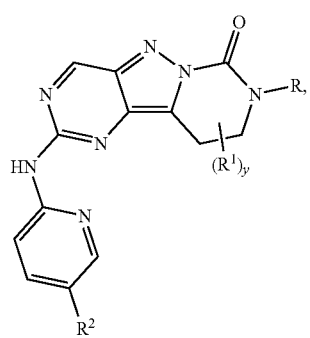
(XVz)
wherein:
R² is selected from,
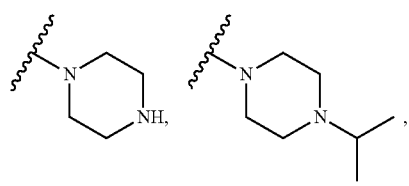

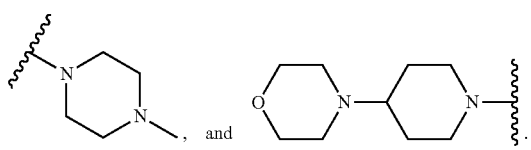

In an alternative embodiment, the compound of the present invention is selected from:

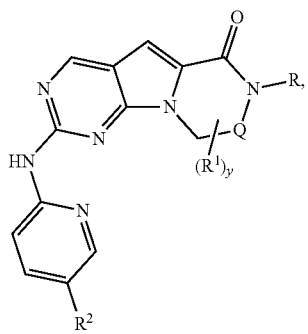
(XX)

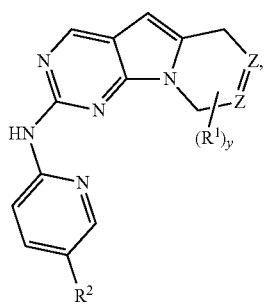
(XXI)

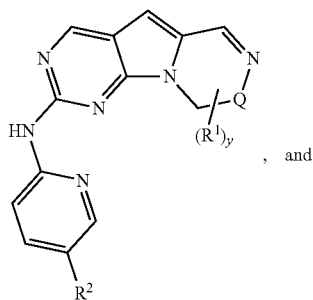
(XXII), and

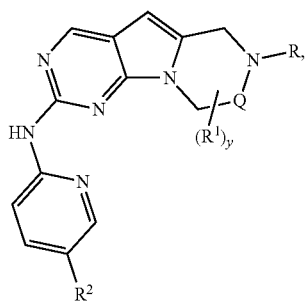
(XXIII)

wherein:
R² is selected from,

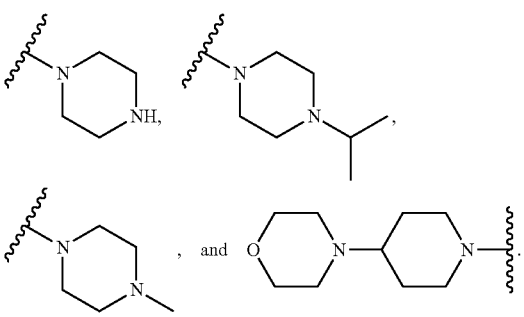

II. Terminology

Compounds are described using standard nomenclature. Unless defined otherwise, all technical and scientific terms used herein have the same meaning as is commonly understood by one of skill in the art to which this invention belongs.

The compounds in any of the Formulas described herein include racemates, enantiomers, mixtures of enantiomers, diastereomers, mixtures of diastereomers, tautomers, N-oxides, isomers; such as rotamers, as if each is specifically described.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein.

The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, and Formula XIX with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2$H, $^3$H, $^{11}$C, $^{13}$C, $^{14}$C, $^{15}$N, $^{18}$F $^{31}$P, $^{32}$P, $^{35}$S, $^{36}$Cl, and $^{125}$I respectively. In one non-limiting embodiment, isotopically labelled compounds can be used in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2$H) and tritium ($^3$H) may be used anywhere in described structures that achieves the desired result. Alternatively or in addition, isotopes of carbon, e.g., $^{13}$C and $^{14}$C, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, or Formula XXIII. In one non-limiting embodiment, the substitution of a hydrogen atom for a deuterium atom occurs within a group selected from any of R, $R^1$, $R^2$, $R^3$, $R^4$, $R^5$, $R^6$, $R^7$, $R^8$, $R^9$, and $R^x$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)NH$_2$ is attached through carbon of the keto (C═O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example, and without limitation, the terms alkyl, alkoxy, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl.

The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one point of unsaturation.

"Halo" and "Halogen" is fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

"Haloalkoxy" indicates a haloalkyl group as defined herein attached through an oxygen bridge (oxygen of an alcohol radical).

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("C$_6$ aryl"; e.g., phenyl). In some embodiments, an aryl group has 10 ring carbon atoms ("C$_{10}$ aryl"; e.g., naphthyl such as 1-naphthyl and 2-naphthyl). In some embodiments, an aryl group has 14 ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2 or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted C$_{6-14}$ aryl. In certain embodiments, the aryl group is a substituted C$_{6-14}$ aryl. An aryl group may be optionally substituted with one or more functional groups that include but are not limited to, halo, hydroxy, nitro, amino, cyano, haloalkyl, aryl, heteroaryl, and heterocyclo.

The term "heterocyclyl" (or "heterocyclo") includes saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may be optionally substituted with 1 to 3 substituents that include but are not limited to, hydroxyl, Boc, halo, haloalkyl, cyano, alkyl, aralkyl, oxo, alkoxy, and amino. Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl. Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl.

Heterocyclo groups also include radicals where heterocyclic radicals are fused/condensed with aryl radicals: such as unsaturated condensed heterocyclic group containing 1 to 5 nitrogen atoms, for example, indoline, isoindoline, unsaturated condensed heterocyclic group containing 1 to 2 oxygen atoms and 1 to 3 nitrogen atoms, unsaturated condensed heterocyclic group containing 1 to 2 sulfur atoms and 1 to 3 nitrogen atoms, and saturated, partially unsaturated and unsaturated condensed heterocyclic group containing 1 to 2 oxygen or sulfur atoms.

The term "heteroaryl" denotes aryl ring systems that contain one or more heteroatoms selected from O, N and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "sulfonyl", whether used alone or linked to other terms such as alkylsulfonyl, denotes respectively divalent radicals —SO$_2$—.

The terms "carboxy" or "carboxyl", whether used alone or with other terms, such as "carboxyalkyl", denotes —C(O)—OH.

The term "carbonyl", whether used alone or with other terms, such as "aminocarbonyl", denotes —C(O)—.

The term "aminocarbonyl" denotes an amide group of the formula —C(O)—NH$_2$.

The terms "heterocycloalkyl" denotes heterocyclic-substituted alkyl radicals. Examples include but are not limited to, piperidylmethyl and morpholinylethyl.

"Arylalkyl" is an aryl group as defined herein attached through an alkyl group. Non-limiting examples of arylalkyl groups include:

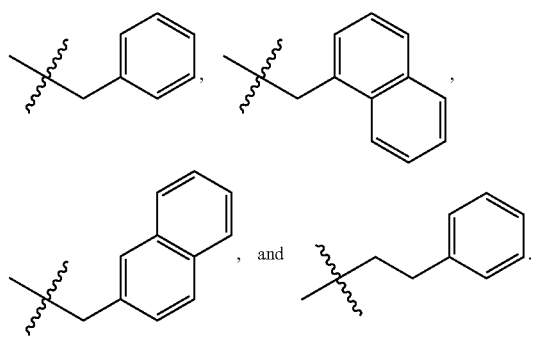

"Heteroarylalkyl" is a heteroaryl group as defined herein attached through an alkyl group. Non-limiting examples of heteroarylalkyl groups include:

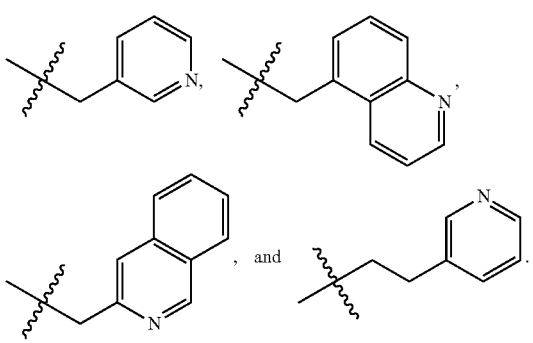

"Aryloxy" is an aryl group as defined herein attached through a —O— linker. Non-limiting examples of aryloxy groups include:

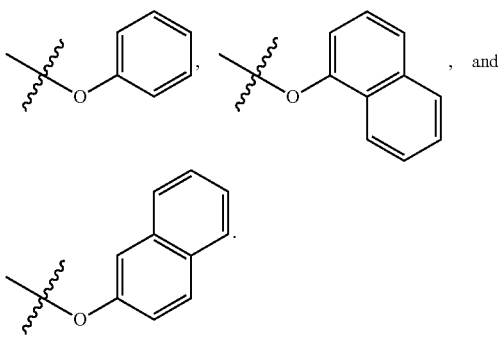

As used herein, "carbocyclyl", "carbocyclic", "carbocycle" or "cycloalkyl" is a saturated or partially unsaturated (i.e., not aromatic) group containing all carbon ring atoms and from 3 to 14 ring carbon atoms ("$C_3$-14 carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 9 ring carbon atoms ("$C_{3-9}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the carbocyclyl group can be saturated or can contain one or more carbon-carbon double or triple bonds. In an alternative embodiment, "Carbocyclyl" also includes ring systems wherein the carbocyclyl ring, as defined above, is fused with one or more heterocyclyl, aryl or heteroaryl groups wherein the point of attachment is on the carbocyclyl ring, and in such instances, the number of carbons continue to designate the number of carbons in the carbocyclic ring system. In an alternative embodiment, each instance of carbocycle is optionally substituted with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

"Cycloalkylalkyl" is an cycloalkyl group as defined herein attached through an alkyl group. Non-limiting examples of cycloalkylalkyl groups include:

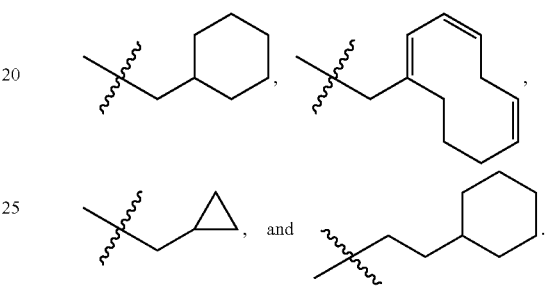

The term "oxo" as used herein contemplates an oxygen atom attached with a double bond.

III. Methods of Treatment

In one aspect, a method of treating a proliferative disorder in a host, including a human, is provided comprising administering an effective amount of a compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV.

or its pharmaceutically acceptable salt, N-oxide, deuterated derivative, prodrug, and/or a pharmaceutically acceptable composition thereof as described herein optionally in a pharmaceutically acceptable carrier. Non-limiting examples of disorders include tumors, cancers, disorders related to abnormal cellular proliferation, inflammatory disorders, immune disorders, and autoimmune disorders.

A compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV is useful as therapeutic agents when administered in an effective amount to a host, including a human, to treat a tumor, cancer (solid, non-solid, diffuse, hematological, etc), abnormal cellular proliferation, immune disorder, inflammatory disorder, blood disorder, a myelo- or lymphoproliferative disorder such as B- or T-cell lymphomas, multiple myeloma, breast cancer, prostate cancer, AML, ALL, ACL, lung cancer, pancreatic cancer, colon cancer, skin cancer, melanoma, Waldenstrom's macroglobulinemia, Wiskott-Aldrich syndrome, or a post-transplant lymphoproliferative disorder; an autoimmune disorder, for example, Lupus, Crohn's Disease, Addison disease, Celiac disease, dermatomyositis, Graves disease, thyroiditis, multiple sclerosis, pernicious anemia, reactive arthritis, or type I diabetes; a disease of cardiologic malfunction, including hypercholesterolemia; an infectious disease, including a viral and/or bacterial infection; an inflammatory condition, including asthma, chronic peptic ulcers, tuberculosis, rheumatoid arthritis, periodontitis, ulcerative colitis, or hepatitis.

Exemplary proliferative disorders include, but are not limited to, benign growths, neoplasms, tumors, cancer (Rb positive or Rb negative), autoimmune disorders, inflammatory disorders graft-versus-host rejection, and fibrotic disorders.

Non-limiting examples of cancers that can be treated according to the present invention include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma, Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In another embodiment, the disorder is myelodysplastic syndrome (MDS).

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML).

In certain embodiments, the proliferative disorder is a myeloproliferative neoplasm. In certain embodiments, the myeloproliferative neoplasm (MPN) is primary myelofibrosis (PMF).

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

In certain embodiments, the condition treated with a compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV is a disorder related to abnormal cellular proliferation.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

In certain embodiments, a compound of the present invention and its pharmaceutically acceptable derivatives or pharmaceutically acceptable formulations containing these compounds are also useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In certain embodiments, the condition is associated with an immune response.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

The term "neoplasia" or "cancer" is used throughout the specification to refer to the pathological process that results in the formation and growth of a cancerous or malignant neoplasm, i.e., abnormal tissue (solid) or cells (non-solid) that grow by cellular proliferation, often more rapidly than normal and continues to grow after the stimuli that initiated the new growth cease. Malignant neoplasms show partial or complete lack of structural organization and functional coordination with the normal tissue and most invade surrounding tissues, can metastasize to several sites, are likely to recur after attempted removal and may cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present disclosed compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In another aspect, a method of increasing BIM expression (e.g., BCLC2L11 expression) is provided to induce apoptosis in a cell comprising contacting a compound of the present invention or a pharmaceutically acceptable composition, salt, isotopic analog, or prodrug thereof with the cell. In certain embodiments, the method is an in vitro method. In certain embodiments, the method is an in vivo method. BCL2L11 expression is tightly regulated in a cell. BCL2L11 encodes for BIM, a proapoptotic protein. BCL2L11 is down-regulated in many cancers and BIM is inhibited in many cancers, including chronic myelocytic leukemia (CML) and non-small cell lung cancer (NSCLC) and that suppression of BCL2L11 expression can confer resistance to tyrosine kinase inhibitors. See, e.g., Ng et al., Nat. Med. (2012) 18:521-528.

In yet another aspect, a method of treating a condition associated with angiogenesis is provided, such as, for example, a diabetic condition (e.g., diabetic retinopathy), an inflammatory condition (e.g., rheumatoid arthritis), macular degeneration, obesity, atherosclerosis, or a proliferative disorder, comprising administering to a subject in need thereof a compound of the present invention or a pharmaceutically acceptable composition, salt, isotopic analog, or prodrug thereof.

In certain embodiments, the condition associated with angiogenesis is macular degeneration. In certain embodiments, provided is a method of treating macular degeneration comprising administering to a subject in need thereof a compound of the present invention or a pharmaceutically acceptable composition, salt, isotopic analog, or prodrug thereof.

In certain embodiments, the condition associated with angiogenesis is obesity. As used herein, "obesity" and "obese" as used herein, refers to class I obesity, class II obesity, class III obesity and pre-obesity (e.g., being "overweight") as defined by the World Health Organization. In certain embodiments, a method of treating obesity is provided comprising administering to a subject in need thereof a compound of the present invention or a pharmaceutically acceptable composition, salt, isotopic analog, or prodrug thereof.

In certain embodiments, the condition associated with angiogenesis is atherosclerosis. In certain embodiments, provided is a method of treating atherosclerosis comprising administering to a subject in need thereof a compound of the present invention or a pharmaceutically acceptable composition, salt, isotopic analog, or prodrug thereof.

In certain embodiments, the condition associated with angiogenesis is a proliferative disorder. In certain embodiments, provided is a method of treating a proliferative disorder comprising administering to a subject in need thereof a compound of the present invention or a pharmaceutically acceptable composition, salt, isotopic analog, or prodrug thereof.

IV. Methods to Reduce the Side Effects Related to Chemotherapy

In certain embodiments, compounds of the present invention decrease the effect of chemotherapeutic agent toxicity on CDK4/6 replication dependent healthy cells, such as hematopoietic stem cells and hematopoietic progenitor cells (together referred to as HSPCs), and/or renal epithelial cells, in subjects, typically humans, that will be, are being, or have been exposed to the chemotherapeutic agent (typically a DNA-damaging agent).

In one embodiment, the subject has been exposed to a chemotherapeutic agent, and, using a compound described herein, the subject's CDK4/6-replication dependent healthy cells are placed in G1 arrest following exposure in order to mitigate, for example, DNA damage. In one embodiment, the compound is administered at least 1/2 hour, at least 1 hour, at least 2 hours, at least 3 hours, at least 4 hours, at least 5 hours, at least 6 hours, at least 7 hours, at least 8 hours, at least 10 hours, at least 12 hours, at least 14 hours, at least 16 hours, at least 18 hours, at least 20 hours or more post chemotherapeutic agent exposure.

In one embodiment, the compound can allow for dose intensification (e.g., more therapy can be given in a fixed period of time) in medically related chemotherapies, which will translate to better efficacy. Therefore, the presently disclosed methods can result in chemotherapy regimens that are less toxic and more effective.

In some embodiments, the use of a compound described herein may result in reduced or substantially free of off-target effects, for example, related to inhibition of kinases other than CDK4 and/or CDK6 such as CDK2. Furthermore, in certain embodiments, the use of the compounds described herein should not induce cell cycle arrest in CDK4/6 replication independent cells.

In some embodiments, the use of a compound described herein reduces the risk of undesirable off-target effects including, but not limited to, long term toxicity, anti-oxidant effects, and estrogenic effects. Anti-oxidant effects can be determined by standard assays known in the art. For example, a compound with no significant anti-oxidant effects is a compound that does not significantly scavenge free-radicals, such as oxygen radicals. The anti-oxidant effects of a compound can be compared to a compound with known anti-oxidant activity, such as genistein. Thus, a compound with no significant anti-oxidant activity can be one that has less than about 2, 3, 5, 10, 30, or 100 fold anti-oxidant activity relative to genistein. Estrogenic activities can also be determined via known assays. For instance, a non-estrogenic compound is one that does not significantly bind and activate the estrogen receptor. A compound that is substantially free of estrogenic effects can be one that has less than about 2, 3, 5, 10, 20, or 100 fold estrogenic activity relative to a compound with estrogenic activity, e.g., genistein.

V. Methods to Treat Abnormal Proliferation of T-Cells, B-Cells and/or NK-Cells In certain aspects, the invention includes the use of an effective amount of a compound described herein, or its pharmaceutically acceptable salt, prodrug or isotopic variant optionally in a pharmaceutical composition, to treat a host, typically a human, with a selected cancer, tumor, hyperproliferative condition or an inflammatory or immune disorder. Some of the disclosed compounds are highly active against T-cell proliferation. Given the paucity of drugs for T-cell cancers and abnormal proliferation, the identification of such uses represents a substantial improvement in the medical therapy for these diseases.

Abnormal proliferation of T-cells, B-cells, and/or NK-cells can result in a wide range of diseases such as cancer, proliferative disorders and inflammatory/immune diseases. A host, for example a human, afflicted with any of these disorders can be treated with an effective amount of a compound as described herein to achieve a decrease in symptoms (a palliative agent) or a decrease in the underlying disease (a disease modifying agent).

Examples include T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, a compound disclosed herein, or its salt, prodrug, or isotopic variant can be used in an effective amount to treat a host, for example a human, with a lymphoma or lymphocytic or myelocytic proliferation disorder or abnormality. For example, the compounds as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, a compound disclosed herein, or its salt, prodrug, or isotopic variant can be used in an effective amount to treat a host, for example a human, with a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

Alternatively, a compound disclosed herein, or its salt, prodrug, or isotopic variant can be used in an effective amount to treat a host, for example a human with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In one embodiment, a compound disclosed herein, or its salt, prodrug, or isotopic variant can be used in an effective amount to treat a host, for example a human with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

VI. Pharmaceutical Compositions and Dosage Forms

An active compound described herein, or its salt, isotopic analog, or prodrug can be administered in an effective amount to a host to treat any of the disorders described herein using any suitable approach which achieves the desired therapeutic result. The amount and timing of active compound administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

The therapeutically effective dosage of any active compound described herein will be determined by the health care practitioner depending on the condition, size and age of the patient as well as the route of delivery. In one non-limited embodiment, a dosage from about 0.1 to about 200 mg/kg has therapeutic efficacy, with all weights being calculated based upon the weight of the active compound, including the cases where a salt is employed. In one embodiment the dosage is at about or greater than 0.1, 0.5, 1, 5, 10, 25, 50, 75, 100, 125, 150, 175, or 200 mg/kg. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments, the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples of dosage forms with at least 5, 10, 15, 20, 25, 50, 100, 200, 250, 300, 400, 500, 600, 700, or 750 mg of active compound, or its salt. The pharmaceutical composition may also include a molar ratio of the active compound and an additional active agent, in a ratio that achieves the desired results.

Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intraveneous, intramuscular, inhalation, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcomeal, or tear duct injections, or through a mucus, mucin, or a mucosal barrier, in an immediate or controlled release fashion or via an ocular device.

In accordance with the presently disclosed methods, an oral administration can be in any desired form such as a solid, gel or liquid, including a solution, suspension, or emulsion. In some embodiments, the compounds or salts are administered by inhalation, intravenously, or intramuscularly as a liposomal suspension. When administered through inhalation the active compound or salt may be in the form of a plurality of solid particles or droplets having any desired particle size, and for example, from about 0.01, 0.1 or 0.5 to about 5, 10, 20 or more microns, and optionally from about 1 to about 2 microns. Compounds as disclosed in the present invention have demonstrated good pharmacokinetic and pharmacodynamics properties, for instance when administered by the oral or intravenous routes.

The pharmaceutical formulations can comprise an active compound described herein or a pharmaceutically acceptable salt thereof, in any pharmaceutically acceptable carrier. If a solution is desired, water may sometimes be the carrier of choice for water-soluble compounds or salts. With respect to the water-soluble compounds or salts, an organic vehicle, such as glycerol, propylene glycol, polyethylene glycol, or mixtures thereof, can be suitable. In the latter instance, the organic vehicle can contain a substantial amount of water. The solution in either instance can then be sterilized in a suitable manner known to those in the art, and for illustration by filtration through a 0.22-micron filter. Subsequent to sterilization, the solution can be dispensed into appropriate receptacles, such as depyrogenated glass vials. The dispensing is optionally done by an aseptic method. Sterilized closures can then be placed on the vials and, if desired, the vial contents can be lyophilized.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of a solution suspension, tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules. Materials in this connection also include lactose or milk sugar as well as high molecular weight polyethylene glycols. When aqueous suspensions and/or elixirs are desired for oral administration, the compounds of the presently disclosed host matter can be combined with various sweetening agents, flavoring agents, coloring agents, emulsifying agents and/or suspending agents, as well as such diluents as water, ethanol, propylene glycol, glycerin and various like combinations thereof.

In yet another embodiment of the host matter described herein, there are provided injectable, stable, sterile formulations comprising an active compound as described herein, or a salt thereof, in a unit dosage form in a sealed container. The compound or salt is provided in the form of a lyophilizate, which is capable of being reconstituted with a suitable pharmaceutically acceptable carrier to form liquid formulation suitable for injection thereof into a host. When the compound or salt is substantially water-insoluble, a sufficient amount of emulsifying agent, which is physiologically acceptable, can be employed in sufficient quantity to emulsify the compound or salt in an aqueous carrier. Particularly useful emulsifying agents include phosphatidyl cholines and lecithin.

Additional embodiments provided herein include liposomal formulations of the active compounds disclosed herein. The technology for forming liposomal suspensions is well known in the art. When the compound is an aqueous-soluble salt, using conventional liposome technology, the same can be incorporated into lipid vesicles. In such an instance, due to the water solubility of the active compound, the active compound can be substantially entrained within the hydrophilic center or core of the liposomes. The lipid layer employed can be of any conventional composition and can either contain cholesterol or can be cholesterol-free. When the active compound of interest is water-insoluble, again employing conventional liposome formation technology, the salt can be substantially entrained within the hydrophobic lipid bilayer that forms the structure of the liposome. In either instance, the liposomes that are produced can be reduced in size, as through the use of standard sonication and homogenization techniques. The liposomal formulations comprising the active compounds disclosed herein can be lyophilized to produce a lyophilizate, which can be reconstituted with a pharmaceutically acceptable carrier, such as water, to regenerate a liposomal suspension.

Pharmaceutical formulations also are provided which are suitable for administration as an aerosol by inhalation. These formulations comprise a solution or suspension of a desired compound described herein or a salt thereof, or a plurality of solid particles of the compound or salt. The desired formulations can be placed in a small chamber and nebulized. Nebulization can be accomplished by compressed air or by ultrasonic energy to form a plurality of liquid droplets or solid particles comprising the compounds or salts. The liquid droplets or solid particles may for example have a particle size in the range of about 0.5 to about 10 microns, and optionally from about 0.5 to about 5 microns. In one embodiment, the solid particles provide for controlled release through the use of a degradable polymer. The solid particles can be obtained by processing the solid compound or a salt thereof, in any appropriate manner known in the art, such as by micronization. Optionally, the size of the solid particles or droplets can be from about 1 to about 2 microns. In this respect, commercial nebulizers are available to achieve this purpose. The compounds can be administered via an aerosol suspension of respirable particles in a manner set forth in U.S. Pat. No. 5,628,984, the disclosure of which is incorporated herein by reference in its entirety.

Pharmaceutical formulations also are provided which provide a controlled release of a compound described herein, including through the use of a degradable polymer, as known in the art.

When the pharmaceutical formulations suitable for administration as an aerosol is in the form of a liquid, the formulations can comprise a water-soluble active compound in a carrier that comprises water. A surfactant can be present, which lowers the surface tension of the formulations sufficiently to result in the formation of droplets within the desired size range when hosted to nebulization.

The term "pharmaceutically acceptable salts" as used herein refers to those salts which are, within the scope of sound medical judgment, suitable for use in contact with hosts (e.g., human hosts) without undue toxicity, irritation, allergic response, and the like, commensurate with a reasonable benefit/risk ratio, and effective for their intended use, as well as the zwitterionic forms, where possible, of the compounds of the presently disclosed host matter.

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilic hydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

VII. Combination Therapy

The disclosed compounds of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV can be used in an effective amount alone or in combination with another compound of the present invention or another bioactive agent to treat a host such as a human with a disorder as described herein.

The disclosed compounds described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chlormadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478, 847; 5,393,763; and 5,457,117, WO2011/156518, U.S. Pat. Nos. 8,455,534 and 8,299,112, 9,078,871; 8,853,423; 8,703, 810; US 2015/0005286; and WO 2014/205138, US2016/ 0175289, US2015/0258080, WO 2014/191726, WO 2012/ 084711; WO 2002/013802; WO 2002/004418; WO 2002/ 003992; WO 2002/003991; WO 2002/003990; WO 2002/ 003989; WO 2002/003988; WO 2002/003986; WO 2002/ 003977; WO 2002/003976; WO 2002/003975; WO 2006/ 078834; U.S. Pat. No. 6,821,989; US 2002/0128276; U.S. Pat. No. 6,777,424; US 2002/0016340; U.S. Pat. Nos. 6,326, 392; 6,756,401; US 2002/0013327; U.S. Pat. Nos. 6,512, 002; 6,632,834; US 2001/0056099; U.S. Pat. Nos. 6,583, 170; 6,479,535; WO 1999/024027; U.S. Pat. No. 6,005,102; EP 0802184; U.S. Pat. Nos. 5,998,402; 5,780,497, 5,880, 137, WO 2012/048058 and WO 2007/087684.

In another embodiment, an active compound described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (navitoclax), ABT-263 ((R)-4-(4-((4'-chloro-4,4-dimethyl-3,4,5,6-tetrahydro-[1, 1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one aspect, a treatment regimen is provided comprising the administration of a compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV in combination with at least one additional chemotherapeutic agent. The combinations disclosed herein can be administered for beneficial, additive, or synergistic effect in the treatment of abnormal cellular proliferative disorders.

In specific embodiments, the treatment regimen includes the administration of a compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV in combination with at least one kinase inhibitor. In one embodiment, the at least one kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3k inhibitors that may be used in the present invention are well known. Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib), (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10, 13,16-tetraazaoctadecan-18-oate), PF-05212384 (N-[4-[[4-(Dimethylamino)-1-piperidinyl]carbonyl]phenyl]-N'-[4-(4, 6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo [4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E, 9S,9aR,10R,11aS)-6-[[bis(prop-2-enyl)amino] methylidene]-5-hydroxy-9-(methoxymethyl)-9a,11a-dimethyl-1,4,7-trioxo-2,3,3a,9,10,11-hexahydroindeno[4, 5h]isochromen-10-yl] acetate (also known as sonolisib)) LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, $CH_{5132799}$, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109.

In one embodiment, the compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV is combined in a single dosage form with the PIk3 inhibitor.

BTK inhibitors for use in the present invention are well known. Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo [h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference. In one embodiment, the compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV is combined in a single dosage form with the BTK inhibitor.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl) amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), R09021 (6-[(1R, 2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R, 2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), piceatannol (3-Hydroxyresveratol), YM193306(see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein). In one embodiment, the compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV is combined in a single dosage form with the Syk inhibitor.

In one embodiment, the at least one additional chemotherapeutic agent is a protein cell death-1 (PD-1) inhibitor. PD-1 inhibitors are known in the art, and include, for example, nivolumab (BMS), pembrolizumab (Merck), pidilizumab (CureTech/Teva), AMP-244 (Amplimmune/GSK), BMS-936559 (BMS), and MEDI4736 (Roche/Genentech). In one embodiment, the compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV is combined in a single dosage form with the PD-1 inhibitor.

In one embodiment, the at least one additional chemotherapeutic agent is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide), ABT-263 ((R)-4-(4-((4'-chloro-4,4-dimethyl-3,4,5,6-tetrahydro-[1, 1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), or G3139 (Oblimersen). In one embodiment, the compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV is combined in a single dosage form with the at least one BCL-2 inhibitor.

In one embodiment, a combination described herein can be further combined with an additional therapeutic to treat the cancer. The second therapy can be an immunotherapy. As discussed in more detail below, the compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV can be conjugated to an antibody, radioactive agent, or other targeting agent that directs the compound to the diseased or abnormally proliferating cell. In another embodiment, the combination is used in combination with another pharmaceutical or a biologic agent (for example an antibody) to increase the efficacy of treatment with a combined or a synergistic approach. In an embodiment, combination can be used with T-cell vaccination, which typically involves immunization with inactivated autoreactive T cells to eliminate a cancer cell population as described herein. In another embodiment, the combination is used in combination with a bispecific T-cell Engager (BiTE), which is an antibody designed to simultaneously bind to specific antigens on endogenous T cells and cancer cells as described herein, linking the two types of cells.

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the additional therapy is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Another group of cancer therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a cancer cell, and the cell-killing substance is taken up by the cell. FDA-approved conjugated MAbs that work this way include ado-trastuzumab emtansine, which targets the HER-2 molecule to deliver the drug DM1, which inhibits cell proliferation, to HER-2 expressing metastatic breast cancer cells.

Immunotherapies with T cells engineered to recognize cancer cells via bispecific antibodies (bsAbs) or chimeric antigen receptors (CARs) are approaches with potential to ablate both dividing and non/slow-dividing subpopulations of cancer cells.

Bispecific antibodies, by simultaneously recognizing target antigen and an activating receptor on the surface of an immune effector cell, offer an opportunity to redirect immune effector cells to kill cancer cells. The other approach is the generation of chimeric antigen receptors by fusing extracellular antibodies to intracellular signaling domains. Chimeric antigen receptor-engineered T cells are able to specifically kill tumor cells in a MHC-independent way.

In some embodiments, the combination can be administered to the subject in further combination with other chemotherapeutic agents. If convenient, the combination described herein can be administered at the same time as another chemotherapeutic agent, in order to simplify the treatment regimen. In some embodiments, the combination and the other chemotherapeutic can be provided in a single formulation. In one embodiment, the use of the compounds described herein is combined in a therapeutic regime with other agents. Such agents may include, but are not limited to, tamoxifen, midazolam, letrozole, bortezomib, anastrozole, goserelin, an mTOR inhibitor, a PI3 kinase inhibitors, dual mTOR-PI3K inhibitors, MEK inhibitors, RAS inhibitors, ALK inhibitors, HSP inhibitors (for example, HSP70 and HSP 90 inhibitors, or a combination thereof), BCL-2 inhibitors, apopototic inducing compounds, AKT inhibitors, including but not limited to, MK-2206, GSK690693, Perifosine, (KRX-0401), GDC-0068, Triciribine, AZD5363, Honokiol, PF-04691502, and Miltefosine, PD-1 inhibitors including but not limited to, Nivolumab, CT-011, MK-3475, BMS936558, and AMP-514 or FLT-3 inhibitors, including but not limited to, P406, Dovitinib, Quizartinib (AC220), Amuvatinib (MP-470), Tandutinib (MLN518), ENMD-2076, and KW-2449, or combinations thereof.

In one embodiment, the bioactive agent is an mTOR inhibitor. Examples of mTOR inhibitors include but are not limited to rapamycin and its analogs, everolimus (Afinitor), temsirolimus, ridaforolimus, sirolimus, and deforolimus.

Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H, 8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is an ALK inhibitor. Examples of ALK inhibitors include but are not limited to Crizotinib, AP26113, and LDK378.

In one embodiment, the bioactive agent is a HSP inhibitor. HSP inhibitors include but are not limited to Geldanamycin or 17-N-Allylamino-17-demethoxygeldanamycin (17AAG), and Radicicol. In a particular embodiment, a compound described herein is administered in combination with letrozole and/or tamoxifen. Other chemotherapeutic agents that can be used in combination with the compounds described herein include, but are not limited to, chemotherapeutic agents that do not require cell cycle activity for their anti-neoplastic effect.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdRi KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C$_{11}$, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafamib, BMS-214662, tipifamib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, a compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV described herein can be combined with a chemotherapeutic selected from, but are not limited to, Imatinib mesylate (Gleevac®), Dasatinib (Sprycel®), Nilotinib (Tasigna®), Bosutinib (Bosulif®), Trastuzumab (Herceptin®), Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the additional therapeutic agent is an anti-inflammatory agent, a chemotherapeutic agent, a radiotherapeutic, additional therapeutic agents, or immunosuppressive agents.

Suitable chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifamib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one aspect of the present invention, a compound described herein can be combined with at least one immunosuppressive agent. The immunosuppressive agent is preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g., ridaforolimus, azathioprine, campath 1H, a SIP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD$_{25}$, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, anti-thymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In certain embodiments, a compound described herein is administered to the subject prior to treatment with another chemotherapeutic agent, during treatment with another chemotherapeutic agent, after administration of another chemotherapeutic agent, or a combination thereof.

In some embodiments, the compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV can be administered to the subject such that the other chemotherapeutic agent can be administered either at higher doses (increased chemotherapeutic dose intensity) or more frequently (increased chemotherapeutic dose density). Dose-dense chemotherapy is a chemotherapy treatment plan in which drugs are given with less time between treatments than in a standard chemotherapy treatment plan. Chemotherapy dose intensity represents unit dose of chemotherapy administered per unit time. Dose intensity can be increased or decreased through altering dose administered, time interval of administration, or both.

In one embodiment of the invention, the compounds described herein can be administered in a concerted regimen with another agent such as a non-DNA-damaging, targeted anti-neoplastic agent or a hematopoietic growth factor agent. It has been recently reported that the untimely administration of hematopoietic growth factors can have serious side effects. For example, the use of the EPO family of growth factors has been associated with arterial hypertension, cerebral convulsions, hypertensive encephalopathy, thromboembolism, iron deficiency, influenza like syndromes and venous thrombosis. The G-CSF family of growth factors has been associated with spleen enlargement and rupture, respiratory distress syndrome, allergic reactions and sickle cell complications. As such, in one embodiment, the use of the compounds or methods described herein is combined with the use of hematopoietic growth factors including, but not limited to, granulocyte colony stimulating factor (G-CSF, for example, sold as Neupogen (filgrastin), Neulasta (peg-filgrastin), or lenograstin), granulocyte-macrophage colony stimulating factor (GM-CSF, for example sold as molgramostim and sargramostim (Leukine)), M-CSF (macrophage colony stimulating factor), thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbopoetin, Epocept, Nanokine, Epofit, Epogin, Eprex and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Reacrit) as well as for example Epocept, EPOTrust, Erypro Safe, Repoeitin, Vintor, Epofit, Erykine, Wepox, Espogen, Relipoeitin, Shanpoietin, Zyrop and EPIAO). In one embodiment, the compound of Formula I, Formula II, Formula III Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Formula XXI, Formula XXII, Formula XXIII, Formula XXIV, or Formula XXV is administered prior to administration of the hematopoietic growth factor. In one embodiment, the hematopoietic growth factor administration is timed so that the compound's effect on HSPCs has dissipated. In one embodiment, the growth factor is administered at least 20 hours after the administration of a compound described herein.

If desired, multiple doses of a compound described herein can be administered to the subject. Alternatively, the subject can be given a single dose of a compound described herein.

In one aspect of the invention, a compound disclosed herein can be beneficially administered in combination with any therapeutic regimen entailing radiotherapy, chemotherapy, or other therapeutic agents. In additional embodiments the compounds disclosed herein can be beneficially administered in combination with therapeutic agents targeting auto-immune disorders.

VIII. Synthesis

The compounds described herein can be prepared by methods known by those skilled in the art. In one non-limiting example the disclosed compounds can be made by the following schemes.

The disclosed compounds can be made by the following general schemes:

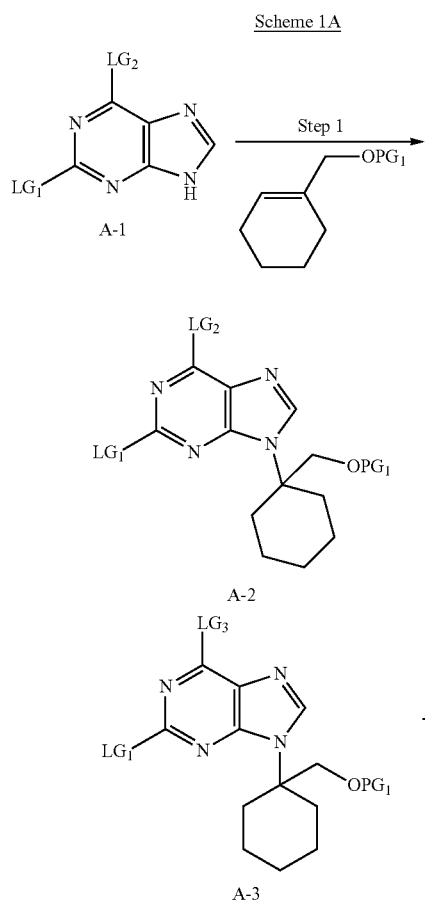

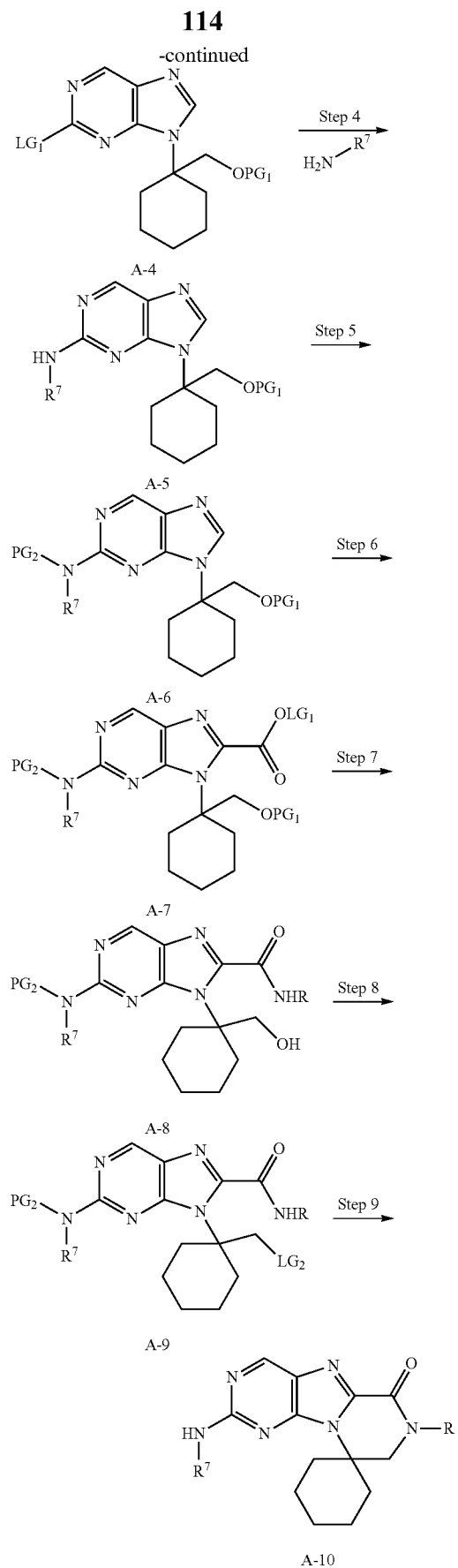

As demonstrated in Scheme 1A, compounds that adhere to Formula 1 can be prepared from readily available purines. In Step 1, an appropriately substituted purine A-1 can be reacted with an appropriate substituted olefin at elevated temperature in the presence of an organometallic catalyst in organic solvent to furnish A-2. $LG_1$ and $LG_2$ are leaving groups known by those skilled in the art. In one embodiment, $LG_1$ and $LG_2$ are chloro. $PG_1$ is a protecting group known by those skilled in the art. In one embodiment, $PG_1$ is TBDMS. In one embodiment, the solvent is toluene. In one embodiment, the catalyst is Au(I) salt bound to appropriate ligands. In one embodiment, the temperature is greater than 80° C. The olefin shown in Scheme 1 is a non-limiting example and other olefins may be used by those skilled in the art to generate derivatives of structure A-2. In Step 2, $LG_2$ is replaced by another leaving group $LG_3$ to yield A-3. In one embodiment, $LG_3$ is amino, —$NH_2$. In Step 3, $LG_3$ is removed by methods known to those skilled in the art to generate structure A-4. In a limiting example, $LG_3$ is replaced by hydrogen. In Step 4, structure A-4 is coupled with an appropriately substituted amine at elevated temperature in the presence of base and an organometallic catalyst in organic solvent. In one embodiment, the amine is pyridin-2-amine. In one embodiment, the base is potassium t-butoxide. In one embodiment, the catalyst is $Pd(OAc)_2$ attached to a [1,1'-biphenyl]-2-yldi-tert-butylphosphane ligand. In one embodiment, the temperature is greater than 60° C. In one embodiment, the solvent is toluene. Structure A-5 is then protected with a protecting group known to those in the art. In one embodiment, $PG_2$ is trityl. Structure A-6 is then transformed to structure A-7 in Step 6 according to methods known in the art. In one embodiment, $LG_1$ is phenyl. In Step 7, $PG_1$ is removed by methods known in the art to afford A-8. Alcohol A-8 is then converted to a leaving group, $LG_2$ in Step 8 to afford compound A-9. In one embodiment, $LG_2$ is bromo. In Step 9, $LG_2$ is displaced to form A-10 which is a compound of Formula I.

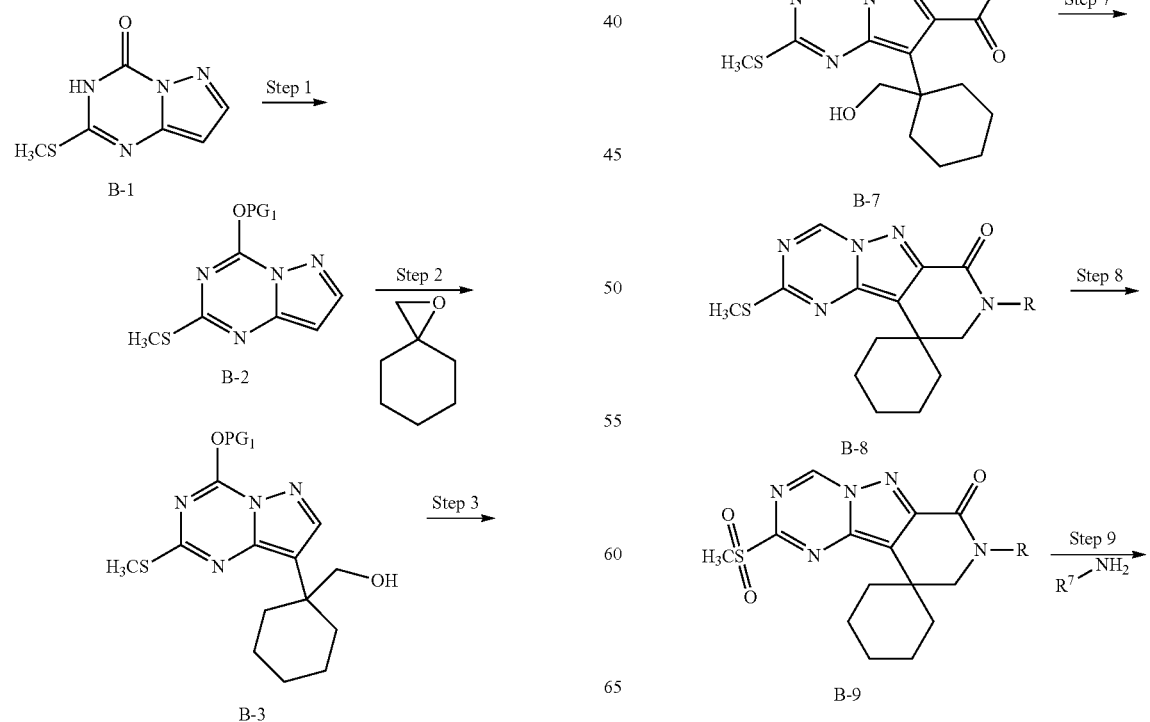

117

-continued

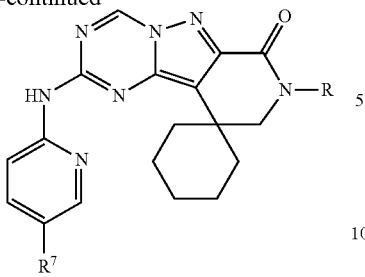

B-10

As demonstrated in Scheme 1B, compounds that adhere to Formula II can be prepared from readily available starting materials such as B-1. In Step 1, B-1 is protected with protecting group PG$_1$ known by those skilled in the art to furnish B-2. In one embodiment, PG$_1$ is TBDMS. In Step 2, B-2 is reacted with an appropriately substituted epoxide in the presence of a Lewis acid to generate B-3. In one embodiment, the Lewis acid is boron trifluoride etherate. The epoxide shown in Scheme 2 is a non-limiting example and other epoxides may be used by those skilled in the art to access derivatives of B-3. In Step 3, alcohol B-3 is protected with protecting group PG$_2$ to furnish B-4. In one embodiment, PG$_2$ is TBDMS. B-4 is then converted to structure B-5 by methods known in the art. LG is a leaving group known by those in the art. In one embodiment, LG is phenyl. In Step 6, PG$_2$ is removed according to methods known in the art to yield B-7. In Step 7, B-7 is cyclized by methods known in the art to generate lactam B-8. In Step 8, sulfide B-8 is oxidized to afford B-9. Sulfone B-9 is then displaced by an appropriately substituted amine to produce compound B-10 which is a compound of Formula II.

Scheme 1C

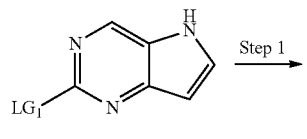

C-1

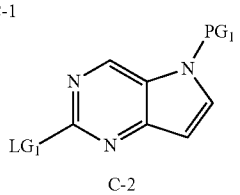

C-2

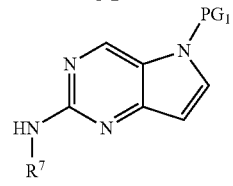

C-3

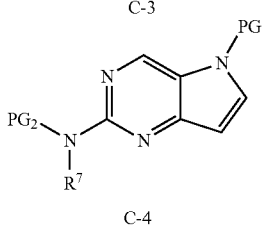

C-4

118

-continued

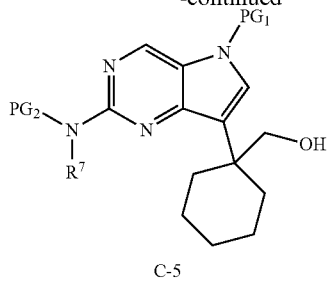

C-5

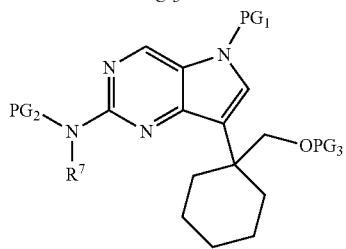

C-6

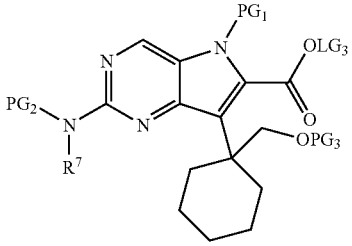

C-7

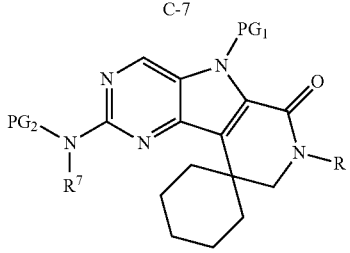

C-8

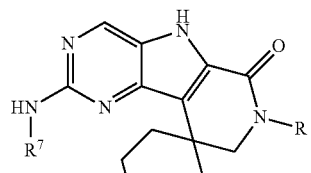

C-9

As demonstrated in Scheme IC, compounds that adhere to Formula III can be prepared from readily available pyrimidines. In Step 1, an appropriately substituted pyrimidine C-1 is protected with a protecting group, PG$_1$, known to those skilled in the art to furnish C-2. In one embodiment, PG$_1$ is trityl. LG$_1$ is a leaving group known by those skilled in the art. In one embodiment, LG$_1$ is chloro. In Step 2, C-2 is coupled with an appropriately substituted amine at elevated temperature in the presence of base and an organometallic catalyst in organic solvent to yield structure C-3. In one embodiment, the amine is pyridin-2-amine. In one embodiment, the base is potassium t-butoxide. In one embodiment, the catalyst is Pd(OAc)$_2$ attached to a [1,1'-biphenyl]-2-ylditert-butylphosphane ligand. In one embodiment, the temperature is greater than 60° C. In one embodiment, the solvent is toluene. In Step 3, structure C-3 is protected with protecting group PG₂ known to those skilled in the art to generate structure C-4. In one embodiment, PG₂ is trityl. In Step 4, C-4 can be reacted with an appropriate substituted epoxide in the presence of a Lewis acid to produce structure C-5. In one embodiment, the Lewis acid is trifluoroboron etherate. The epoxide shown in Scheme 3 is a non-limiting example and other epoxides may be used by those skilled in the art to generate derivatives of structure C-5. In Step 6, alcohol C-5 is protected with protecting group PG₃ known to those skilled in the art to generate C-6. In one embodiment, PG₃ is TBDMS. In Step 6, C-6 is transformed to structure C-7 according to methods known in the art where LG₂ is a leaving group. In one embodiment, LG₂ is phenyl. In Step 7, C-7 is cyclized to afford lactam C-8 according to methods known in the art. In Step 8, PG₁ and PG₂ are removed to furnish compound C-9 which is a compound of Formula III.

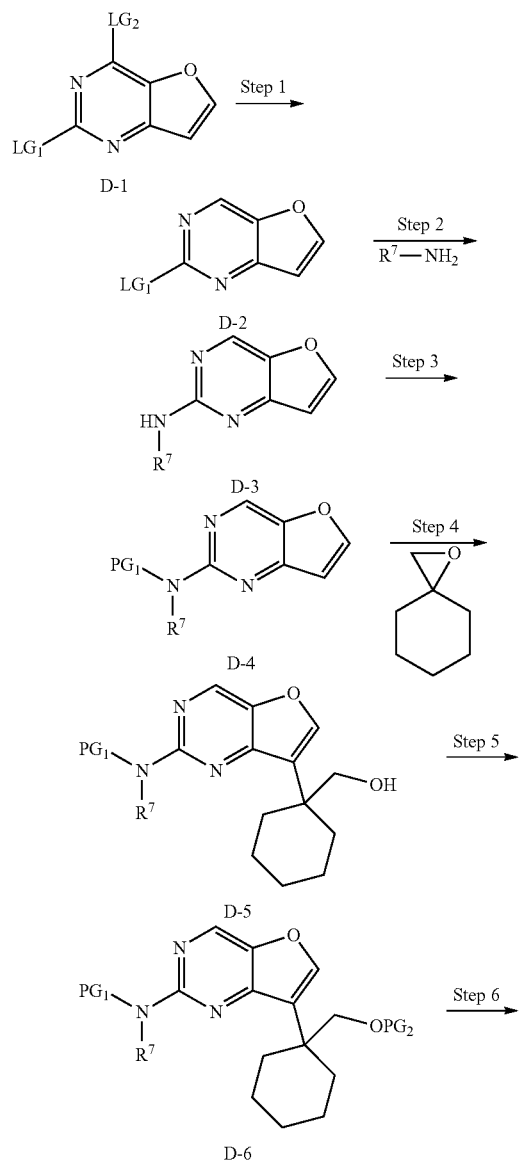

Scheme 1D

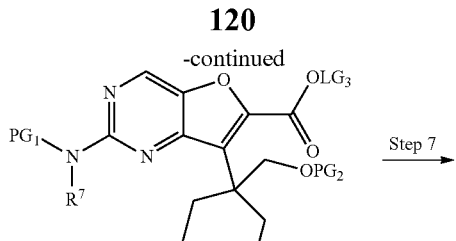

D-7

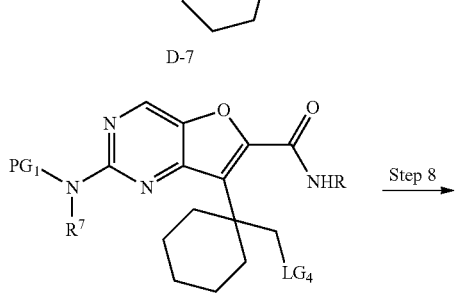

D-8

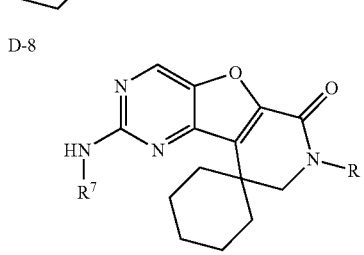

D-9

As demonstrated in Scheme 1D, compounds that adhere to Formula III can be prepared from readily available pyrimidines. LG₁ and LG₂ are leaving groups known by those skilled in the art. In one embodiment, LG₁ and LG₂ are chloro. In Step 1, LG₂ is removed according to methods known in the art to furnish structure D-2. In Step 2, D-2 is coupled with an appropriately substituted amine at elevated temperature in the presence of base and an organometallic catalyst in organic solvent to yield structure D-3. In one embodiment, the amine is pyridin-2-amine. In one embodiment, the base is potassium t-butoxide. In one embodiment, the catalyst is Pd(OAc)₂ attached to a [1,1'-biphenyl]-2-yldi-tert-butylphosphane ligand. In one embodiment, the temperature is greater than 60° C. In one embodiment, the solvent is toluene. In Step 3, structure D-3 is protected with protecting group PG₁ known by those skilled in the art. In one embodiment, PG₁ is trityl. In Step 4, pyrimidine D-4 is reacted with an appropriately substituted epoxide in the presence of a Lewis acid to produce structure D-5. In one embodiment, the Lewis acid is trifluoroboron etherate. The epoxide shown in Scheme 3 is a non-limiting example and other epoxides may be used by those skilled in the art to generate derivatives of structure D-5. In Step 5, alcohol D-5 is protected with protecting group PG₂ known to those skilled in the art to generate D-6. In one embodiment, PG₂ is TBDMS. In Step 6, D-6 is transformed to structure D-7 according to methods known in the art where LG₃ is a leaving group. In one embodiment, LG₃ is phenyl. In Step 7, ester D-7 is converted to amido species and the PG₂ is subsequently removed to furnish the free alcohol which is then converted to leaving group LG₄ by methods known in the art to produce structure D-8. In one embodiment, LG₄ is bromo. In Step 9, D-8 is cyclized by methods known in the art to afford lactam D-9 which is a compound of Formula III.

Scheme 1E

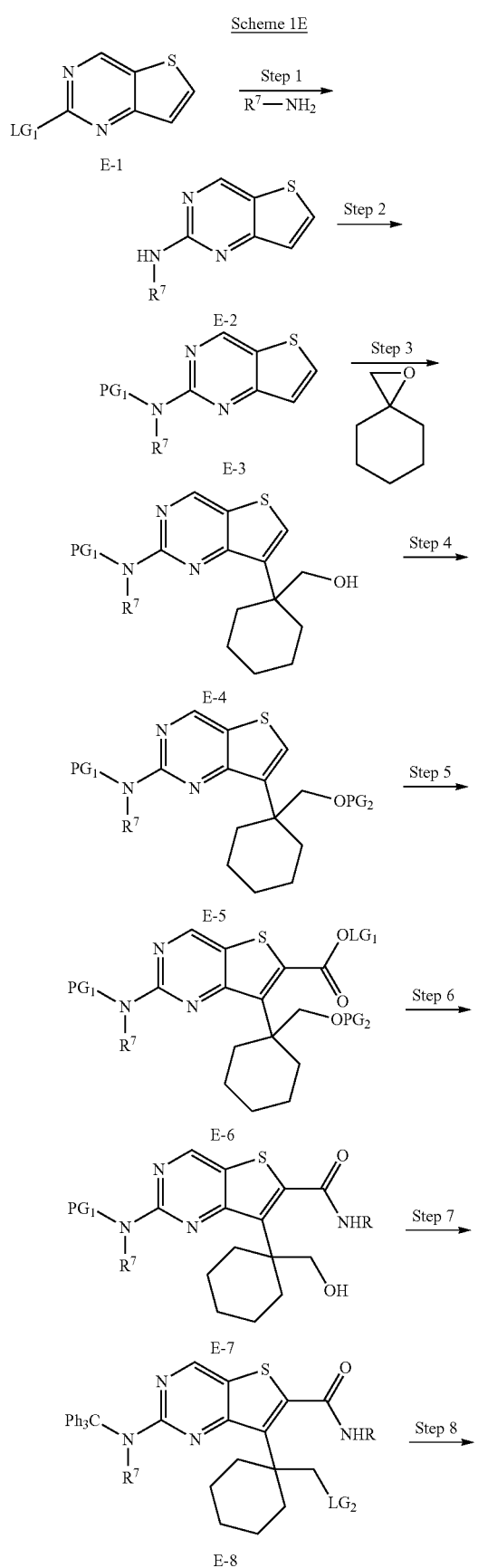

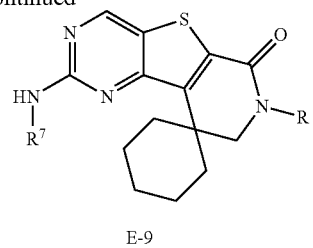

E-9

As demonstrated in Scheme 1E, compounds that adhere to Formula III can be prepared from readily available pyrimidines. In structure E-1, $LG_1$ is a leaving group known by those skilled in the art. In one embodiment, $LG_1$ is chloro. In Step 1, E-1 is coupled with an appropriately substituted amine at elevated temperature in the presence of base and an organometallic catalyst in organic solvent to yield structure E-2. In one embodiment, the amine is pyridin-2-amine. In one embodiment, the base is potassium t-butoxide. In one embodiment, the catalyst is $Pd(OAc)_2$ attached to a [1,1'-biphenyl]-2-yldi-tert-butylphosphane ligand. In one embodiment, the temperature is greater than 60° C. In one embodiment, the solvent is toluene. In Step 2, E-2 is protected with a protecting group, $PG_1$, known to those skilled in the art to furnish E-3. In one embodiment, $PG_1$ is trityl. In Step 3, E-3 can be reacted with an appropriately substituted epoxide in the presence of a Lewis acid to produce structure E-4. In one embodiment, the Lewis acid is trifluoroboron etherate. The epoxide shown in Scheme 5 is a non-limiting example and other epoxides may be used by those skilled in the art to generate derivatives of structure E-4. In Step 4, alcohol E-4 is protected with protecting group $PG_2$ known to those skilled in the art to generate E-5. In one embodiment, $PG_2$ is TBDMS. In Step 5, E-5 is transformed to structure E-6 according to methods known in the art where $LG_1$ is a leaving group. In one embodiment, $LG_1$ is phenyl. In step 6, ester E-6 is transformed to an amido species and $PG_2$ is removed to yield E-7. In Step 7, the alcohol is converted to leaving group $LG_2$ known by those skilled in the art. In one embodiment, $LG_2$ is bromo. In Step 8, E-8 is cyclized to afford lactam E-9 which is a compound of Formula III.

Scheme 1F

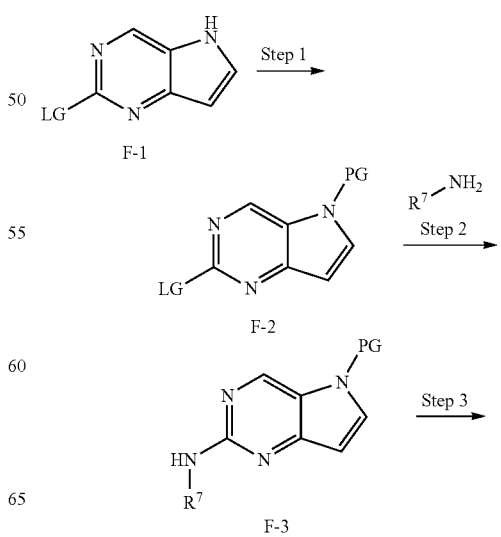

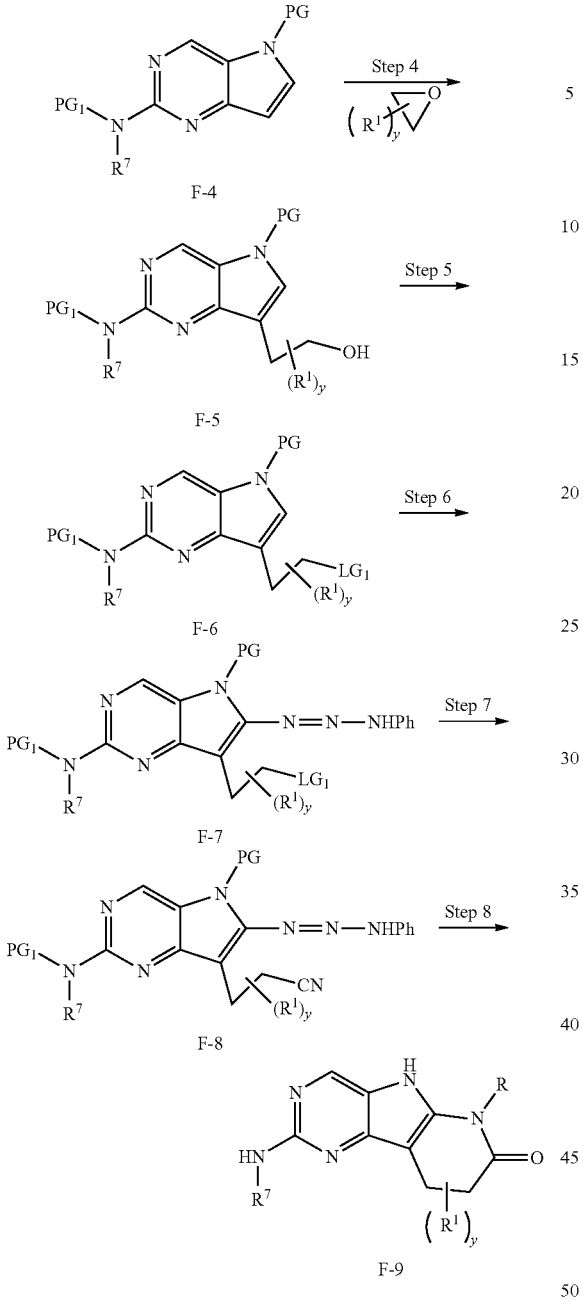

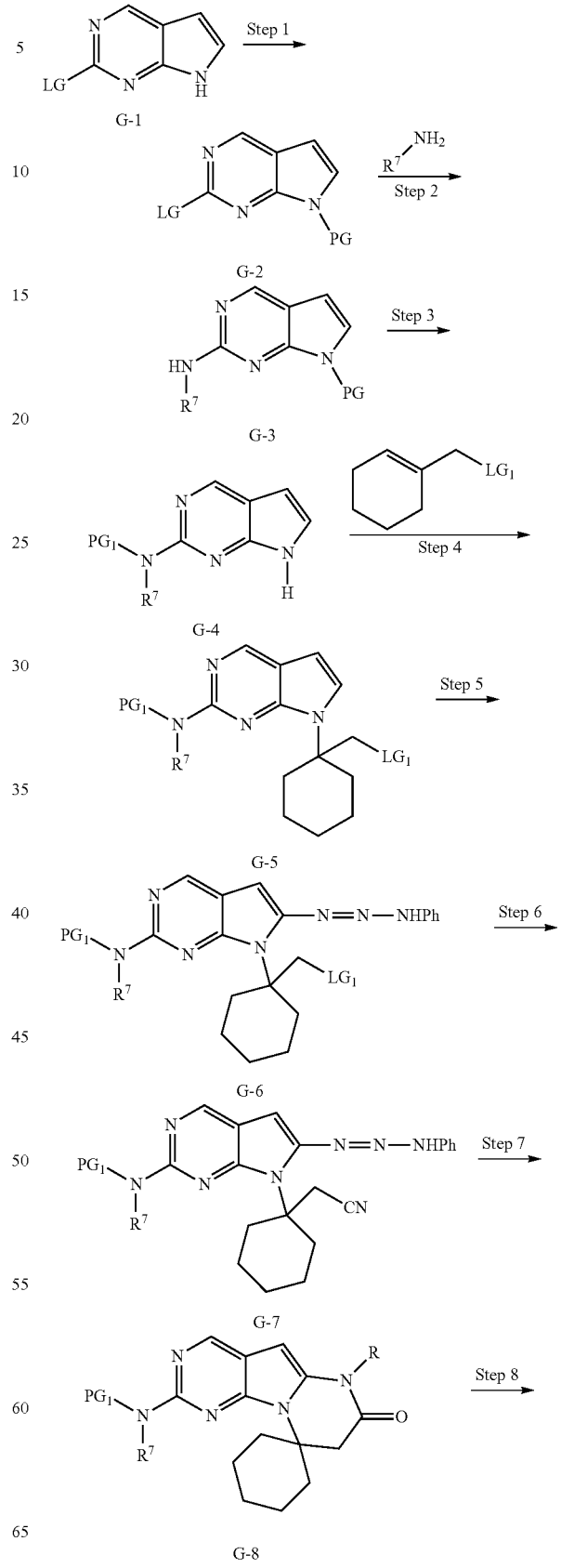

As demonstrated in Scheme 1F, compounds of Formula IV can be prepared from readily available starting materials such as F-1. In Step 1, F-1 is protected by methods known by those skilled in the art to furnish F-2. In one embodiment, LG is chlorine. In one embodiment PG is trityl. In Step 2, F-2 undergoes SNAr nucleophilic addition, yielding F-3.

In Step 3, F-3 is protected to afford F-4. In Step 4, an appropriately substituted F-4 can be reacted with an appropriate substituted epoxide to furnish F-5. In Step 5, the hydroxyl of F-5 is converted to an appropriate leaving group to afford F-6. In Step 6, F-6 is converted to azide F-7. In Step 7, F-7 undergoes nucleophilic attack to install a cyano group and yield F-8. In Step 8, F-8 is cyclized by methods known by those skilled in the art to afford F-9 which is a compound of Formula IV.

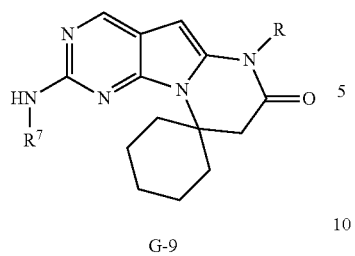

G-9

As demonstrated in Scheme 1G, compounds of Formula V can be prepared from readily available starting materials such as G-1. In Step 1, G-1 is protected by methods known by those skilled in the art to furnish G-2. In one embodiment, LG is chlorine. In one embodiment PG is trityl. In Step 2, G-2 undergoes SNAr nucleophilic addition, yielding G-3. In Step 3, G-3 is protected to afford G-4. In Step 4, an appropriately substituted G-4 can be reacted with an appropriate substituted olefin at elevated temperature in the presence of an organometallic catalyst in organic solvent to furnish G-5. In one embodiment, the solvent is toluene. In one embodiment, the catalyst is Au(I) salt bound to appropriate ligands. In one embodiment, the temperature is greater than 80° C. The olefin shown in Scheme 1G is a non-limiting example and other olefins may be used by those skilled in the art to generate derivatives of structure G-5. In Step 5 G-5 is converted to azide G-6. In Step 6, G-6 is undergoes nucleophilic attack to install a cyano group and yield G-7. In Step 7, G-7 is cyclized by methods known by those skilled in the art to afford G-8. In Step 8, G-8 is deprotected to afford G-9 which is a compound of Formula V.

Scheme 1H

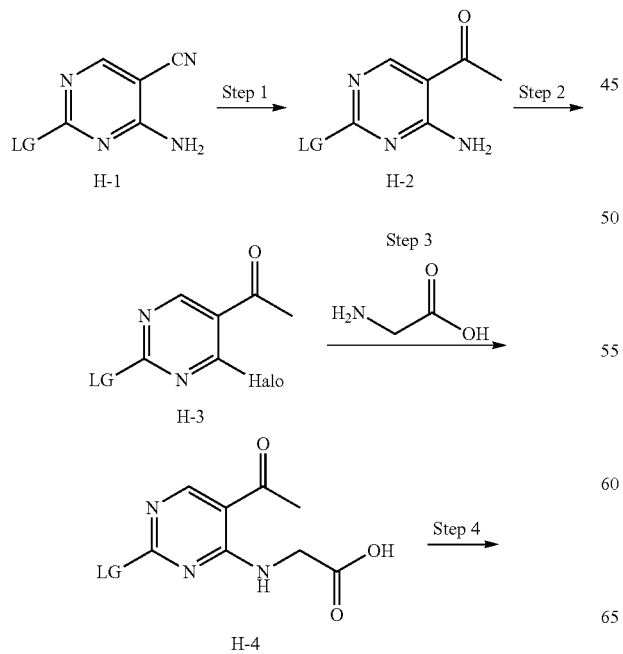

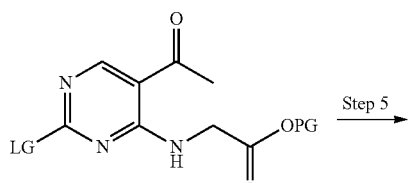

H-5

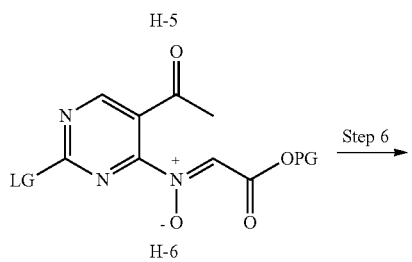

H-6

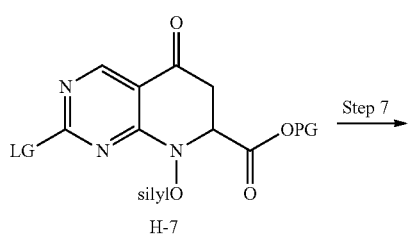

H-7

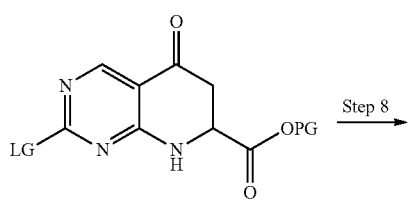

H-8

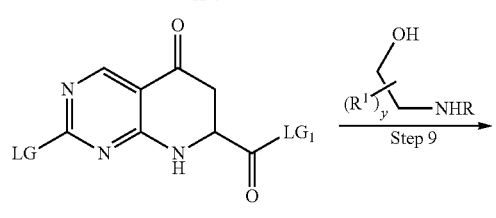

H-9

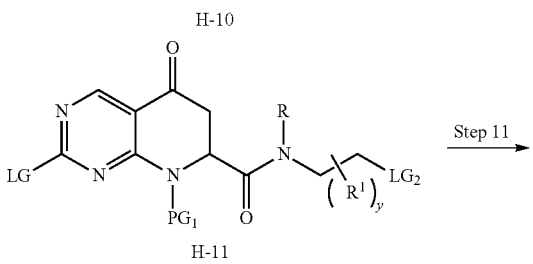

H-10

H-11

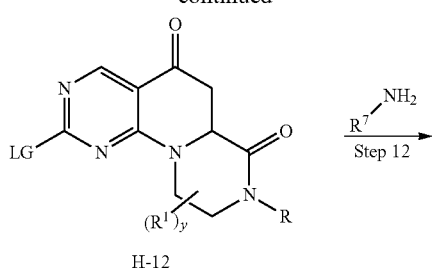

H-12

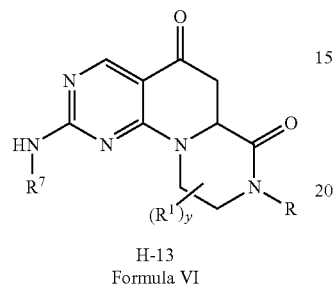

H-13
Formula VI

As demonstrated in Scheme 1H, compounds of Formula VI can be prepared from readily available starting materials such as H-1. In Step 1, H-1 is converted to a ketone by methods known by those skilled in the art to furnish H-2. In one embodiment, LG is chlorine. In Step 2, H-2 is converted to an appropriate halide for subsequent displacement, yielding H-3. In Step 3, halide H-3 is displaced by glycine to afford H-4. H-4 is then protected to afford structure H-5 by methods known in the art. In one embodiment PG is ethyl. In Step 5 H-5 is converted to zwitterion H-6. In Step 6, H-6 is cyclized by methods known in the art to yield H-7. In one embodiment silyl is TMS. In Step 7, H-7 is dehydrated to afford H-8. In Step 8, H-8 is converted to an appropriate leaving group containing compound H-9. In one embodiment LG$_1$ is hydroxyl. In Step 9, the secondary amine is protected and then the LG$_1$ of H-9 is displaced by an appropriately substituted amine to produce compounds of Formula H010. In one embodiment PG$_1$ is a carbamate. In Step 10, the hydroxyl group of H-10 is converted to an appropriate leaving group to afford H-11. In Step 11, H-11 is cyclized to afford H-12. In Step 12 SNAr nucleophilic addition of an amine displacing the leaving group of H-12 affords a compound of Formula VI.

Scheme 2

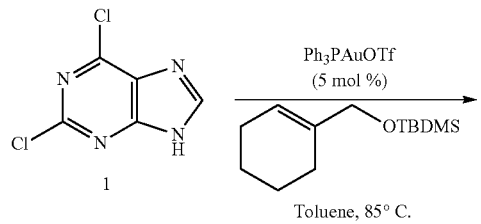

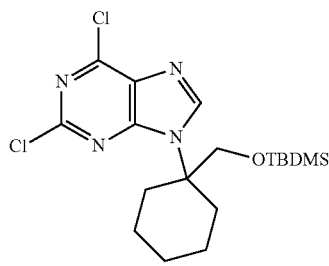

2

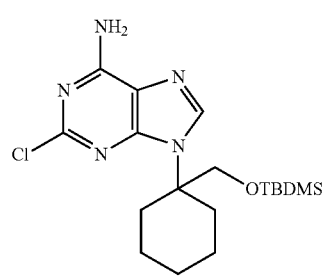

3

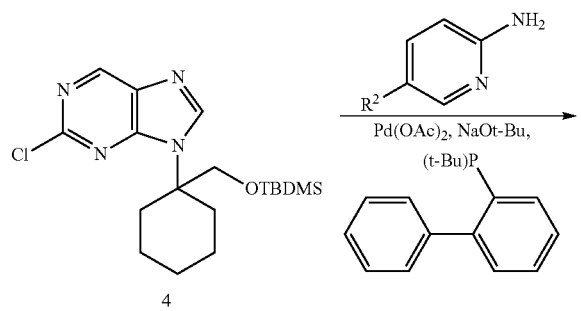

4

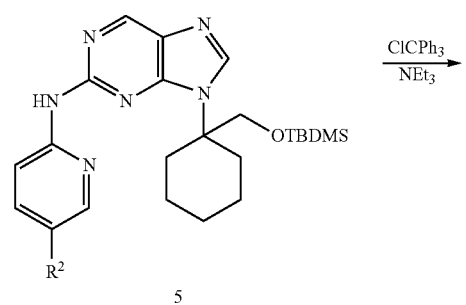

5

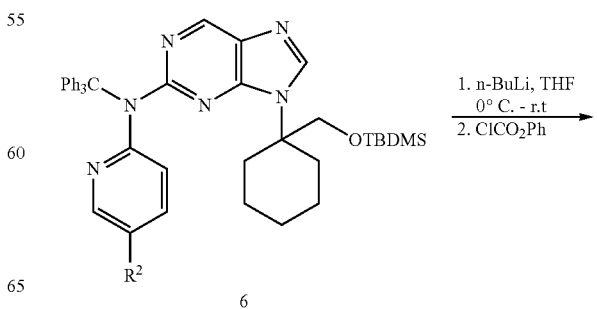

6

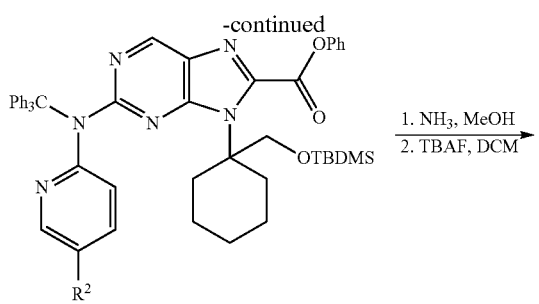
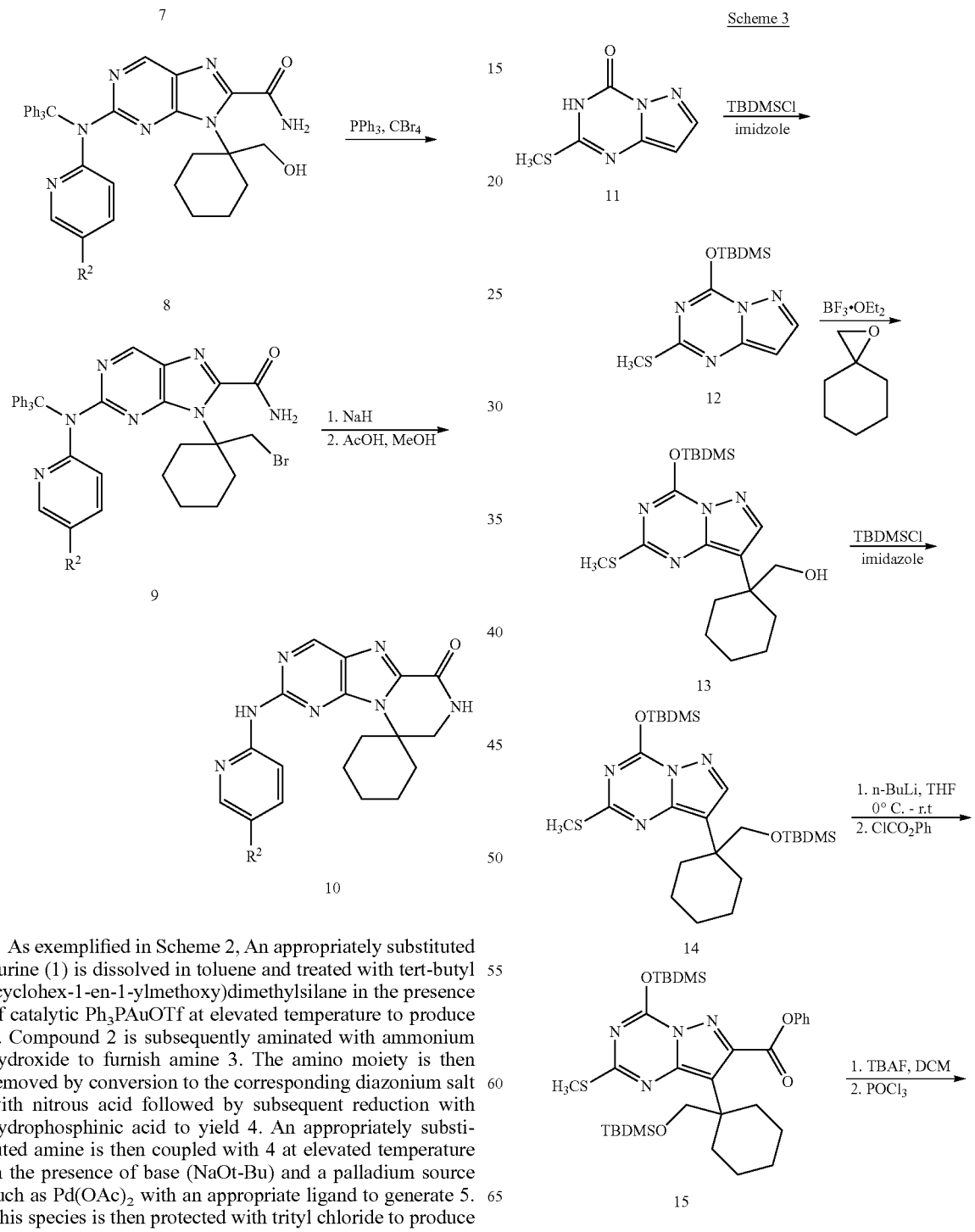

with an organolithium reagent and quenched with an appropriately substituted electrophile to furnish compound 7. Amidation of 7 with ammonia, followed by subsequent deprotection of the silyl ether with TBAF yields an amido alcohol 8 that is converted to bromo species 9 with triphenylphosphine and carbon tetrabromide. Finally, cyclization of the alkyl bromide with the amide moiety, followed by acidic deprotection of trityl affords the title compound 10 which is a representative compound of Formula I.

As exemplified in Scheme 2, An appropriately substituted purine (1) is dissolved in toluene and treated with tert-butyl (cyclohex-1-en-1-ylmethoxy)dimethylsilane in the presence of catalytic Ph₃PAuOTf at elevated temperature to produce 2. Compound 2 is subsequently aminated with ammonium hydroxide to furnish amine 3. The amino moiety is then removed by conversion to the corresponding diazonium salt with nitrous acid followed by subsequent reduction with hydrophosphinic acid to yield 4. An appropriately substituted amine is then coupled with 4 at elevated temperature in the presence of base (NaOt-Bu) and a palladium source such as Pd(OAc)₂ with an appropriate ligand to generate 5. This species is then protected with trityl chloride to produce compound 6. The trityl-protected species is then lithiated

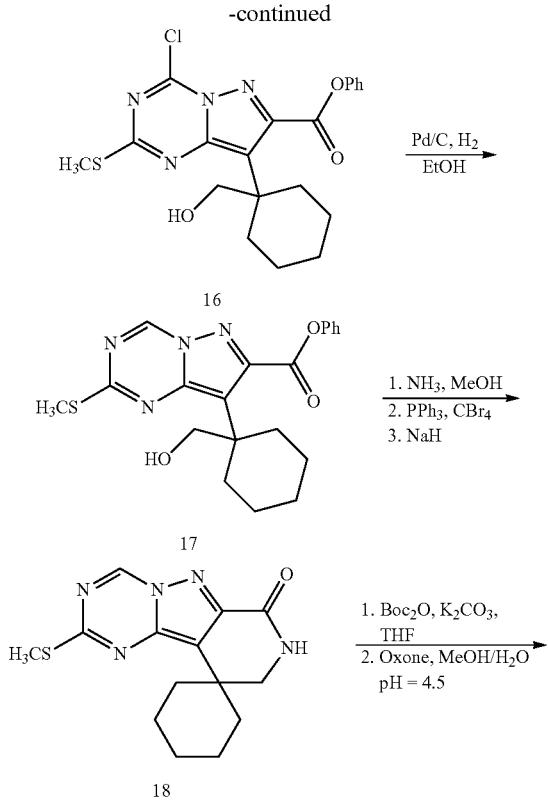

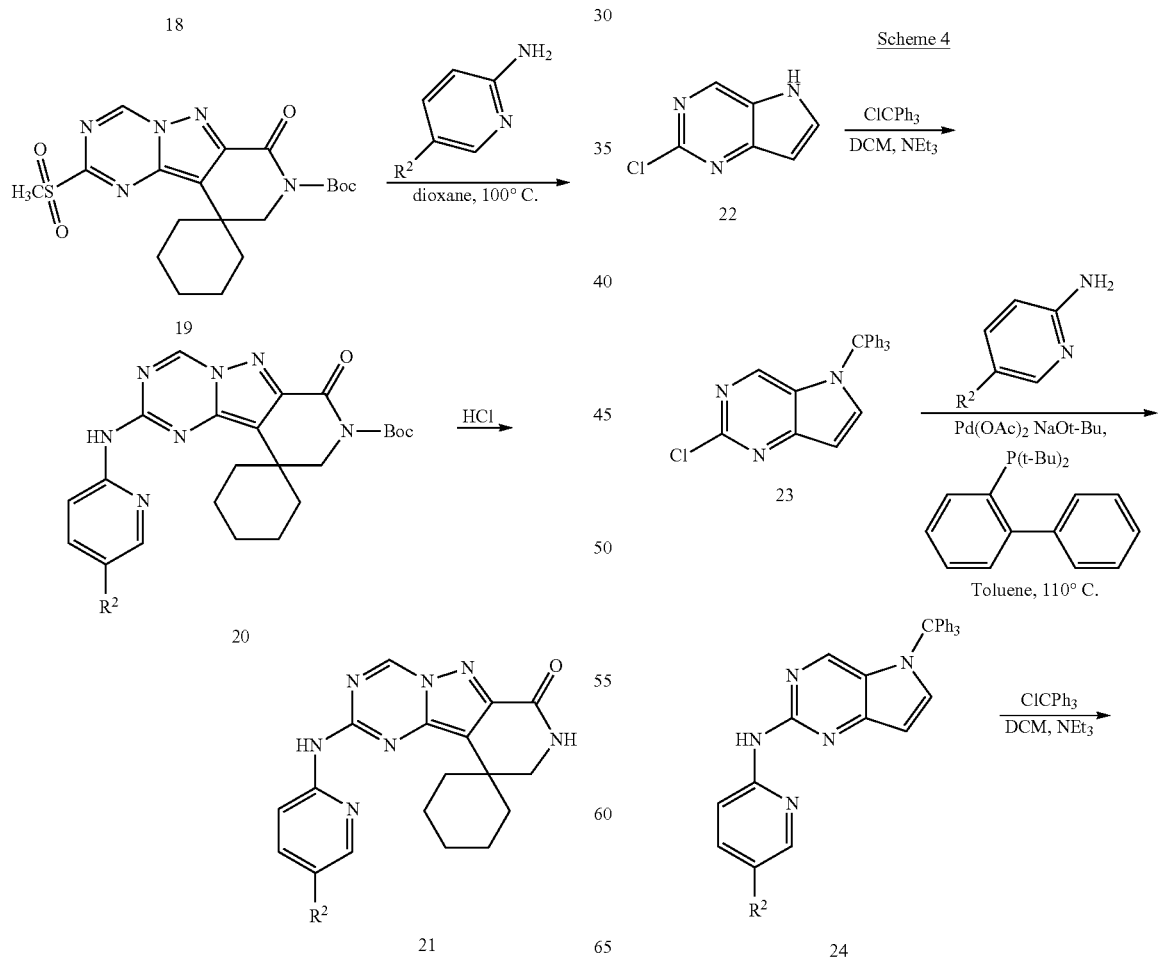

As exemplified in Scheme 3, Compound 11 is first protected with TBDMSCl to yield silyl ether 12 which reacts with an appropriately substituted epoxide in the presence of a suitable Lewis acid to produce alcohol 13. Silylation of 13 affords 14 and subsequent lithiation of the aromatic ring with an n-butyllithium followed by treatment with an appropriately substituted electrophile produces 15. Treatment of 15 with excess TBAF removes both silyl ethers and the free amide is then converted to chloride 16 with POCl₃. Chloride 16 is reduced to compound 17 in the presence of finely dispersed palladium on carbon with molecular hydrogen as the reductant. Treatment of 17 with ammonia in methanol followed by a subsequent reaction with PPh₃ CBr₄ yields an intermediate bromide that undergoes cyclization in the presence of base such as NaH under elevated temperature to afford lactam 18. The amide is protected as a carbamate with Boc₂O and the sulfide is subsequently oxidized to the sulfone by the action of oxone in aqueous media buffered to approximately pH 4.5. This procedure furnishes compound 19 which readily undergoes aromatic substitution with an appropriately substituted amine at elevated temperature to generate 20. The Boc protecting group is then removed under acidic conditions to yield title compound 21 which is a representative compound of Formula II.

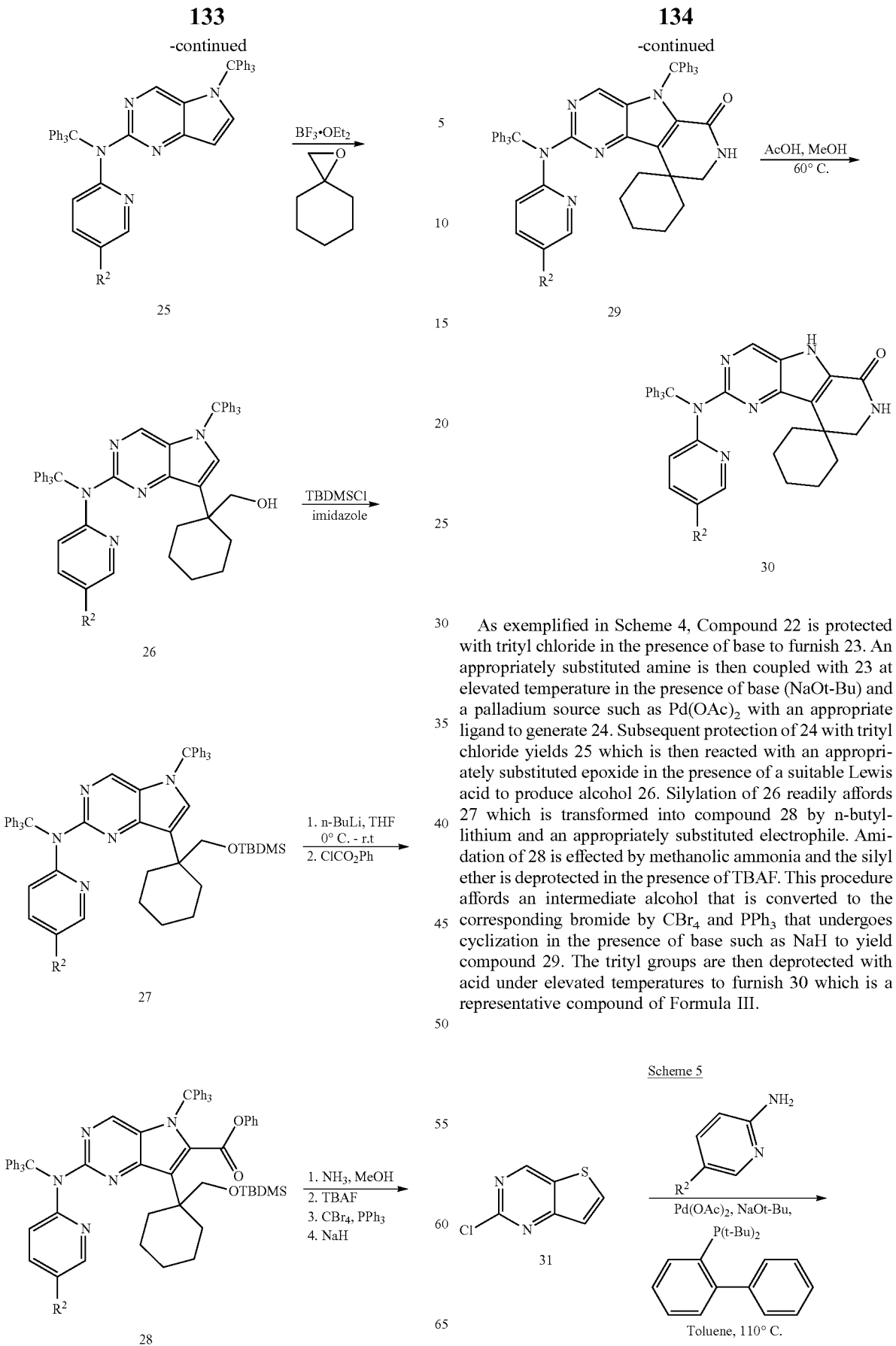

As exemplified in Scheme 4, Compound 22 is protected with trityl chloride in the presence of base to furnish 23. An appropriately substituted amine is then coupled with 23 at elevated temperature in the presence of base (NaOt-Bu) and a palladium source such as Pd(OAc)$_2$ with an appropriate ligand to generate 24. Subsequent protection of 24 with trityl chloride yields 25 which is then reacted with an appropriately substituted epoxide in the presence of a suitable Lewis acid to produce alcohol 26. Silylation of 26 readily affords 27 which is transformed into compound 28 by n-butyllithium and an appropriately substituted electrophile. Amidation of 28 is effected by methanolic ammonia and the silyl ether is deprotected in the presence of TBAF. This procedure affords an intermediate alcohol that is converted to the corresponding bromide by CBr$_4$ and PPh$_3$ that undergoes cyclization in the presence of base such as NaH to yield compound 29. The trityl groups are then deprotected with acid under elevated temperatures to furnish 30 which is a representative compound of Formula III.

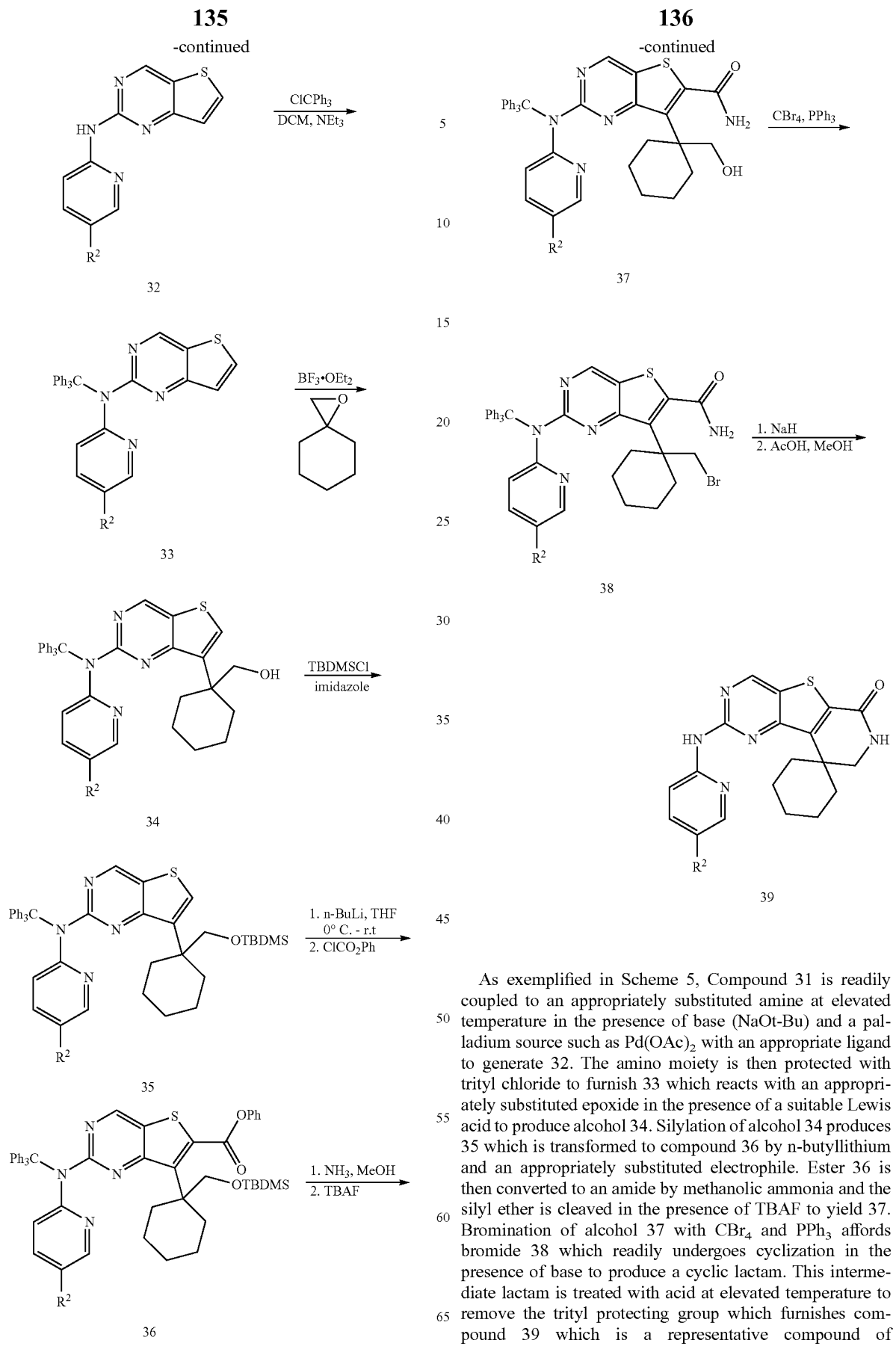

As exemplified in Scheme 5, Compound 31 is readily coupled to an appropriately substituted amine at elevated temperature in the presence of base (NaOt-Bu) and a palladium source such as Pd(OAc)$_2$ with an appropriate ligand to generate 32. The amino moiety is then protected with trityl chloride to furnish 33 which reacts with an appropriately substituted epoxide in the presence of a suitable Lewis acid to produce alcohol 34. Silylation of alcohol 34 produces 35 which is transformed to compound 36 by n-butyllithium and an appropriately substituted electrophile. Ester 36 is then converted to an amide by methanolic ammonia and the silyl ether is cleaved in the presence of TBAF to yield 37. Bromination of alcohol 37 with CBr$_4$ and PPh$_3$ affords bromide 38 which readily undergoes cyclization in the presence of base to produce a cyclic lactam. This intermediate lactam is treated with acid at elevated temperature to remove the trityl protecting group which furnishes compound 39 which is a representative compound of Formula III.

Scheme 6

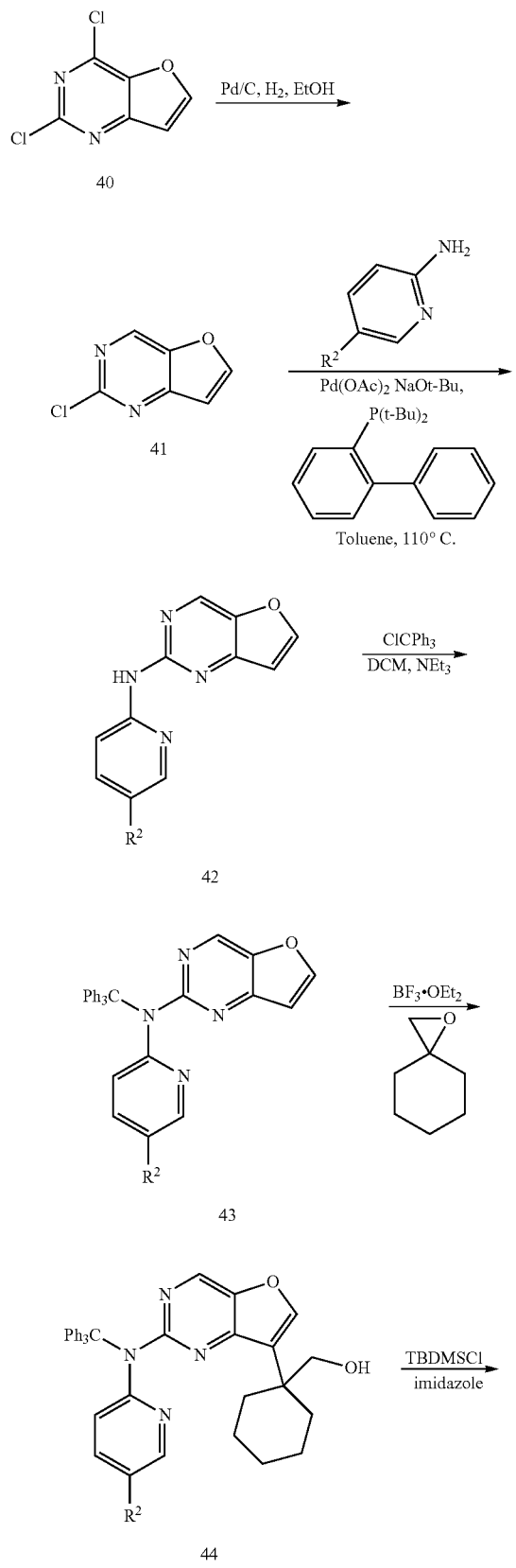

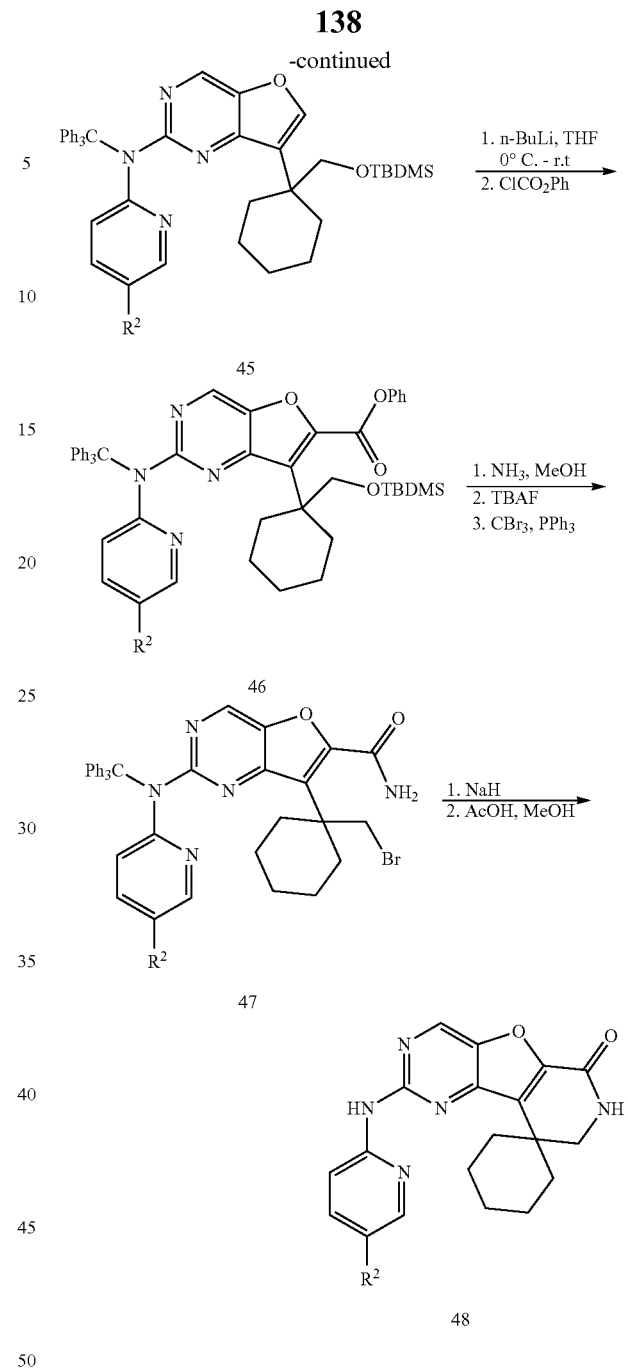

As exemplified in Scheme 6, Compound 40 is reduced with finely dispersed palladium on carbon in the presence of molecular hydrogen to furnish monochloridate 41. An appropriately substituted amine is then coupled with 41 at elevated temperature in the presence of base (NaOt-Bu) and a palladium source such as Pd(OAc)$_2$ with an appropriate ligand to generate 42. Compound 42 is then protected with trityl chloride to yield 43 which is then reacted with an appropriately substituted epoxide in the presence of a suitable Lewis acid to produce alcohol 44. Silylation of alcohol 44 produces 45 which is transformed to compound 46 by n-butyllithium and an appropriately substituted electrophile. Ester 46 is then converted to an amide by methanolic ammonia and the silyl ether is cleaved in the presence of TBAF. Subsequent bromination of the intermediate alcohol with CBr$_4$ and PPh$_3$ affords bromide 47 which readily undergoes cyclization in the presence of base to produce a cyclic lactam. This intermediate lactam is treated with acid at elevated temperature to remove the trityl protecting group which furnishes compound 48 which is a representative compound of Formula III.
Scheme 7
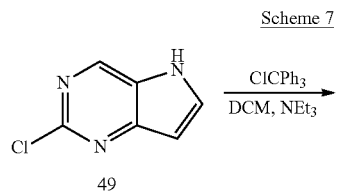
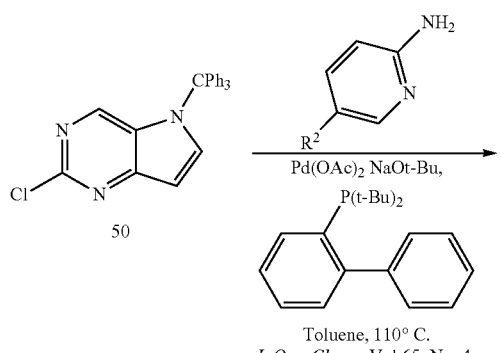
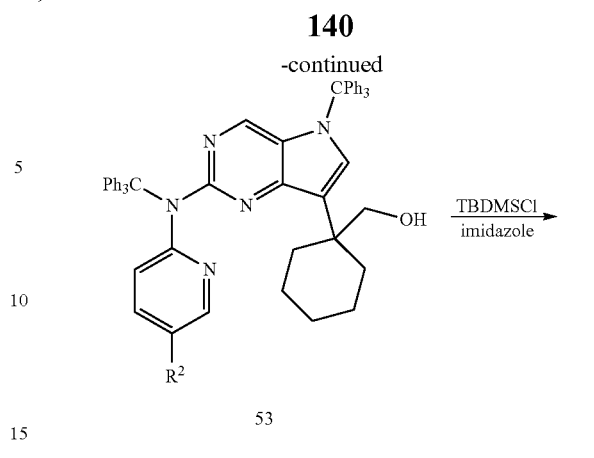
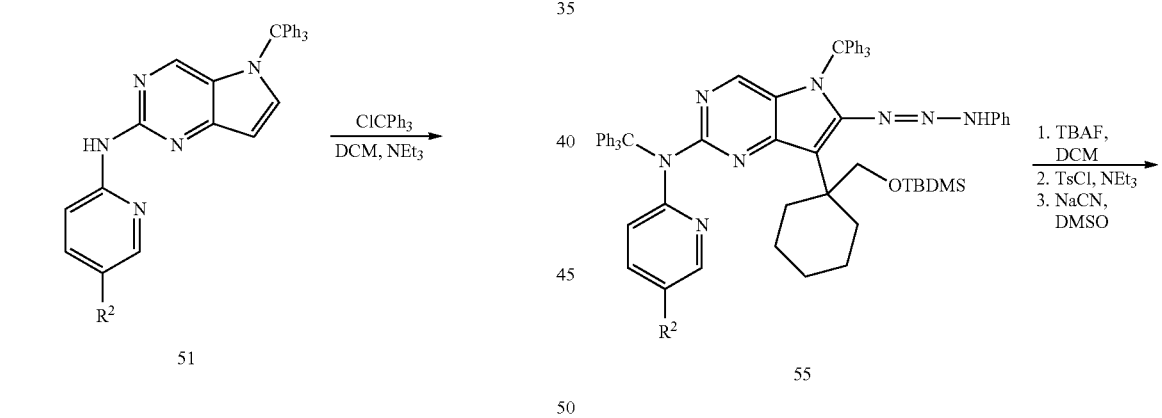
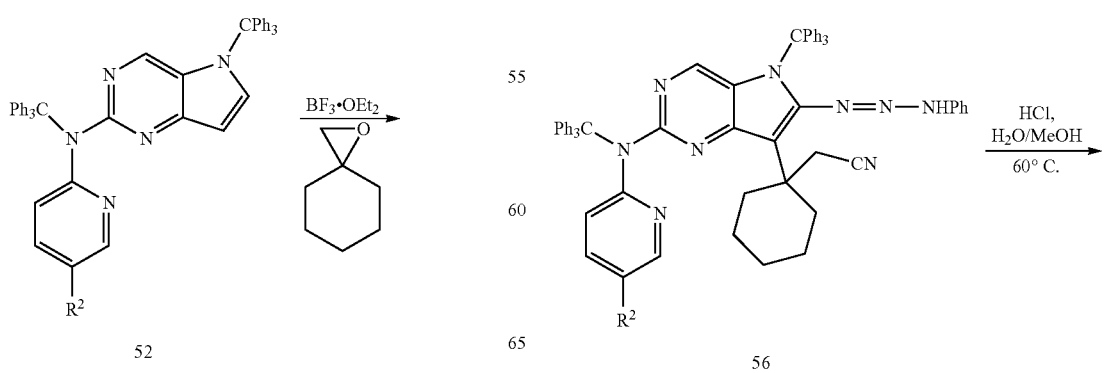

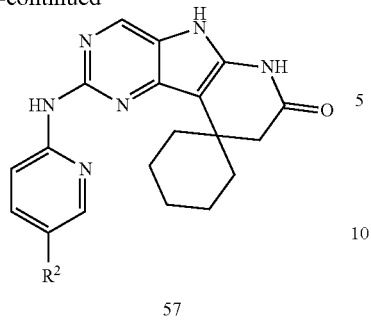

57

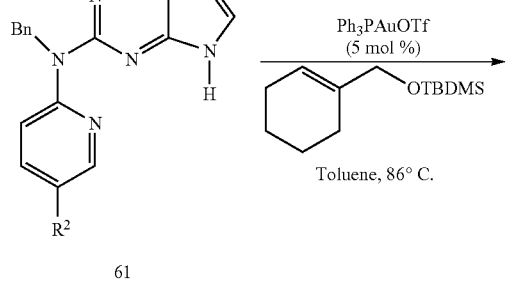

61

As exemplified in Scheme 7, Compound 49 is protected with trityl chloride in the presence of base to yield 50. An appropriately substituted amine is then coupled with 50 at elevated temperature in the presence of base (NaOt-Bu) and a palladium source such as $Pd(OAc)_2$ with an appropriate ligand to generate 51. Subsequent trityl protection of 51 furnishes 52 which reacts with an appropriately substituted epoxide in the presence of a suitable Lewis acid to produce alcohol 53. Silylation of 53 readily affords 54 which is transformed into compound 55 by n-butyllithium and phenylazide. The siyl ether is then cleaved with TBAF and the resulting alcohol is tosylated and displaced by NaCN to yield nitrile 56. Heating compound 8 at elevated temperature in the presence of acid cleaves the trityl protecting groups and promotes hydrolysis of the nitrile and azo moieties to generate lactam 57 which is a representative compound of Formula IV.

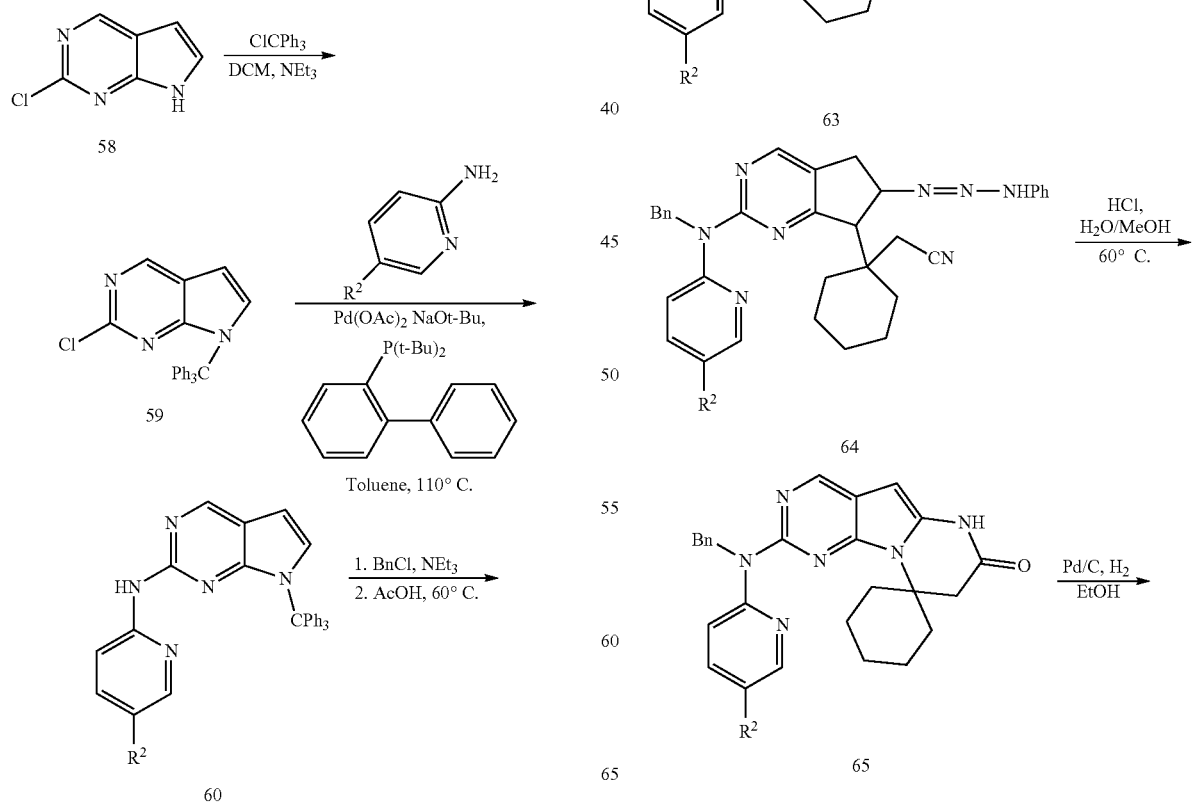

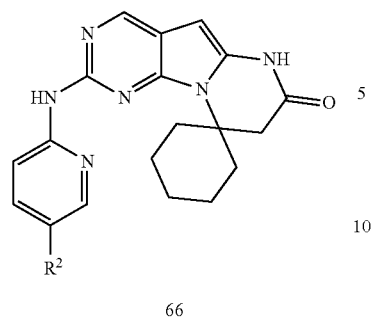

66

As exemplified in Scheme 8, Compound 58 is protected with trityl chloride in the presence of base to yield 59. An appropriately substituted amine is then coupled with 59 at elevated temperature in the presence of base (NaOt-Bu) and a palladium source such as Pd(OAc)$_2$ with an appropriate ligand to generate 60. Subsequent protection of 3 with benzyl chloride and acid-mediated hydrolysis of the pre-existing trityl protecting group yields 61. Compound 61 is then reacted with tert-butyl(cyclohex-1-en-1-ylmethoxy)dimethylsilane in the presence of catalytic Ph3PAuOTf at elevated temperature to produce 62. Treatment of 62 with n-butyllithium followed by phenylazide furnishes 63. The silyl ether is deprotected with TBAF and the resulting alcohol is transformed into an alkyl halide with PPh$_3$ and CB$_4$ and is displaced by NaCN to produce nitrile 64. Hydrolysis of the nitrile and azo moieties in the presence of acid at elevated temperature promotes cyclization to lactam 65. Reductive cleavage of the benzyl protecting group by finely dispersed palladium with molecular hydrogen affords compound 66 which is a representative compound of Formula V.

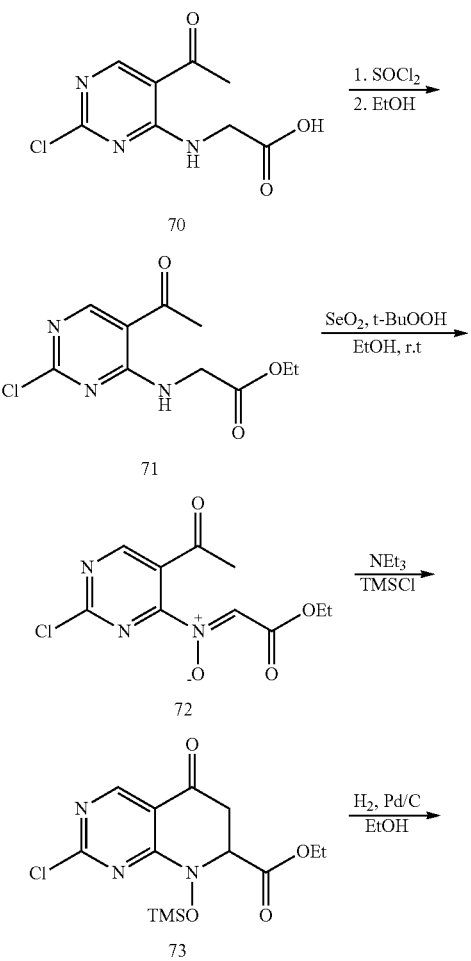

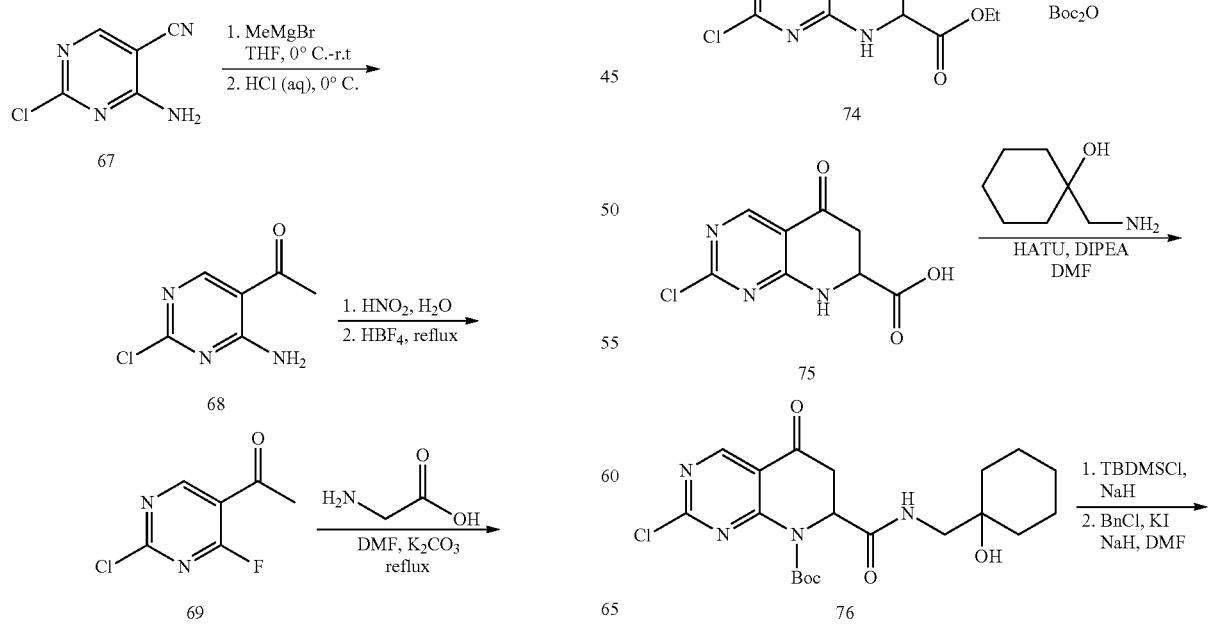

-continued

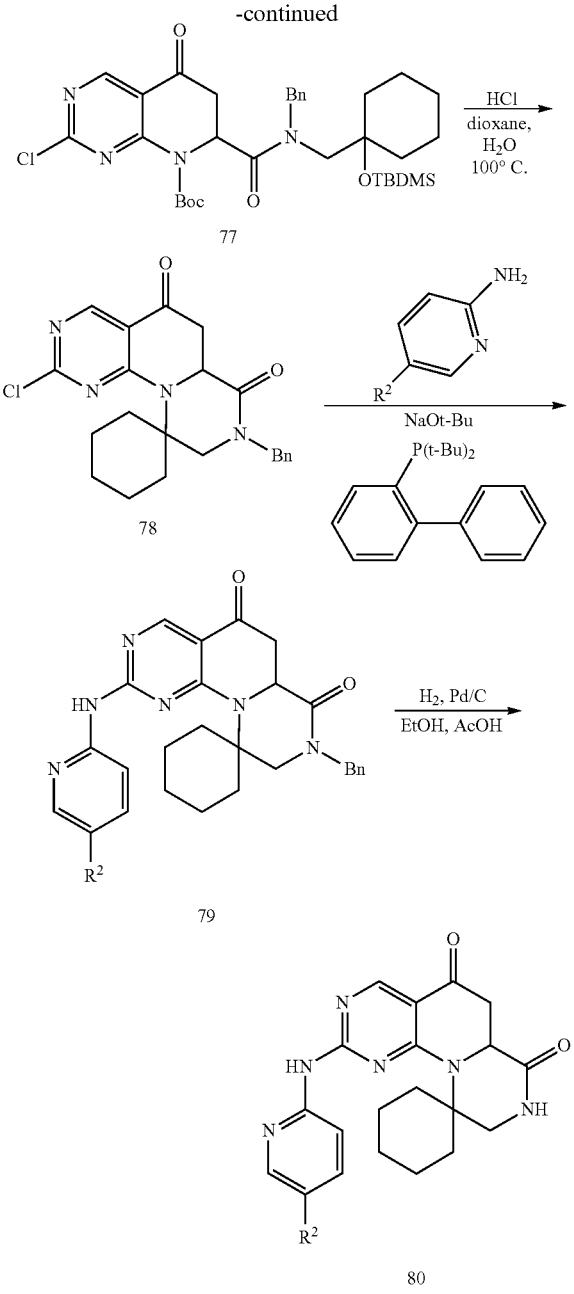

As exemplified in Scheme 9, Compound 67 is chilled to reduced temperatures and treated with methyl magnesium bromide. Acidic workup of the reaction mixture yields 68. Diazotination of 68 with nitrous acid followed by subsequent treatment with HBF$_4$ at elevated temperatures produces fluoride 69. This intermediate is heated with glycine in the presence of base to furnish 70. Carboxylic acid 70 is converted to the acid chloride and esterified with EtOH to afford ethyl ester 71. Oxidation of the secondary nitrogen to nitrone 72 is accomplished with SeO$_2$ and t-BuOOH. Cyclization of 72 with TMSCl in the presence of base yields 73 which is reduced with Pd/C in the presence of molecular hydrogen to generate amine 74. Ethyl ester 74 is then hydrolyzed with aqueous base and simultaneously protected with Boc to afford carboxylic acid 75. Acid 75 is then coupled with an appropriately substituted amine to yield amide 76. The tertiary alcohol is silylated with TBDMSCl and the amide is benzylated with sodium hydride and benzyl bromide to furnish 77. Hydrolysis of Boc and the silane protecting group in aqueous acid produces a tertiary carbocation that undergoes cyclization at elevated temperature to produce 78. Chloride 78 is then coupled with an appropriately substituted amine to generate 79 which undergoes a Pd catalyzed reduction to cleave the benzyl protecting group which yields compound 80 which is a representative compound of Formula VI.

Scheme 10

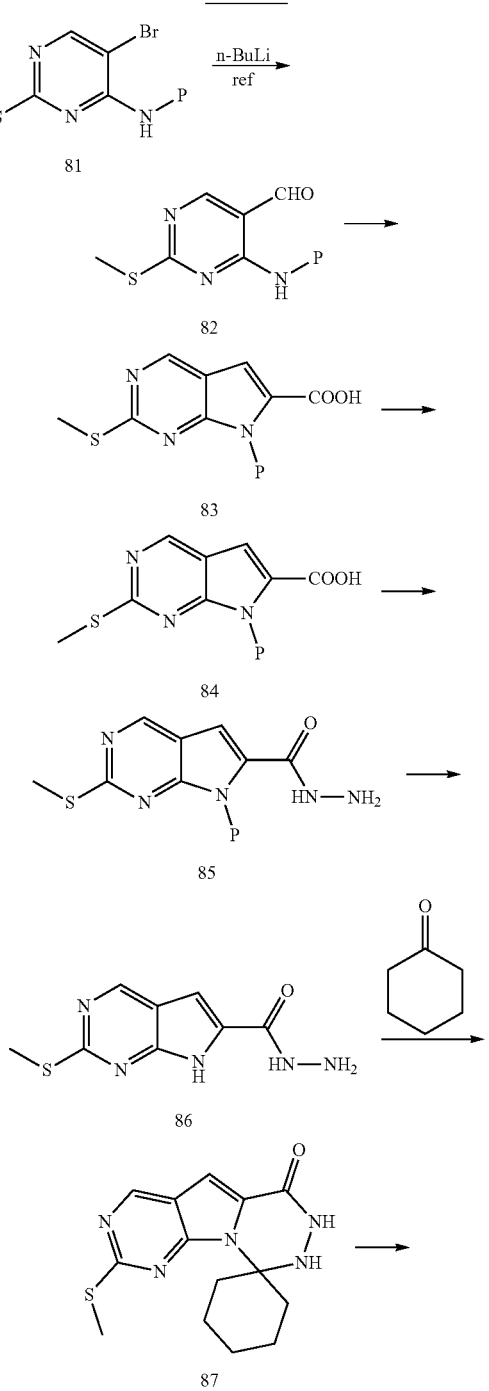

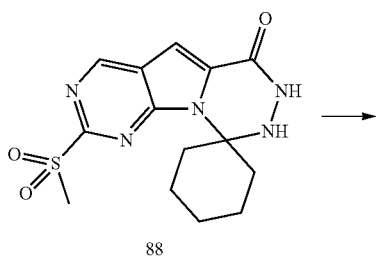

88

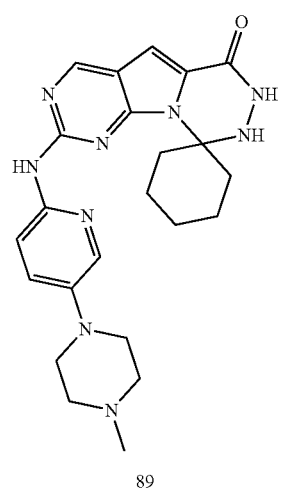

89

As shown in Scheme 10, bromide 81 is converted to aldehyde 82 followed by subsequent cyclization and oxidation to furnish carboxylic acid 83. Acid 83 is then transformed to an alkyl ester 84 and transamidated to yield amide 85. Deprotection of the protecting group P produces 86 which undergoes aminal formation in the presence of a ketone to generate aminal 87. Sulfonation of 87 affords 88 which subsequently undergoes nucleophilic aromatic substitution to furnish desired compound 89 which is a representative compound of Formula VII.

Scheme 11

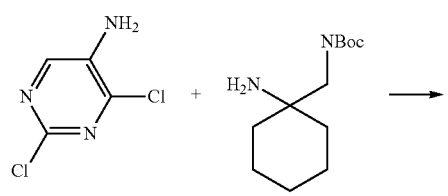

90

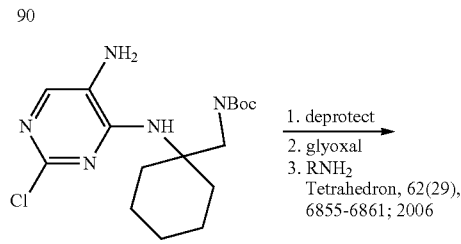

91

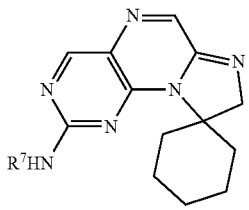

92

1. Anti-Cancer Drug Design (1993), 8(6), 439-61.
2. Indian Journal of Chemistry, Section B: Organic Chemistry Including Medicinal Chemisty (1983), 22B(12), 1233-5.

As shown in Scheme 11, commercially available chloride 90 is coupled with an appropriate amine via nucleophilic aromatic substitution to afford intermediate 91. Amine 91 is then deprotected, subjected to cyclization in the presence of glyoxal, and coupled with the desired amine to yield compound 92 which is a representative compound of Formula VIII.

Scheme 12

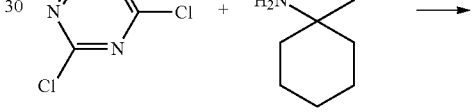

93

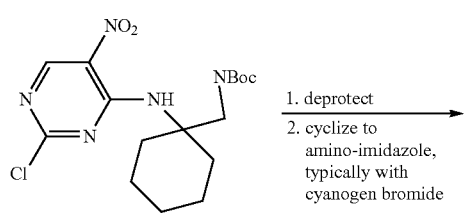

94

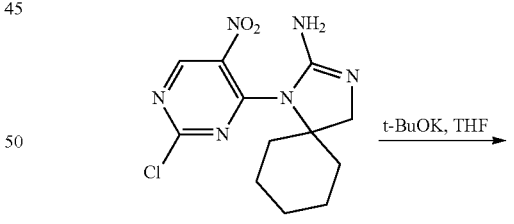

95

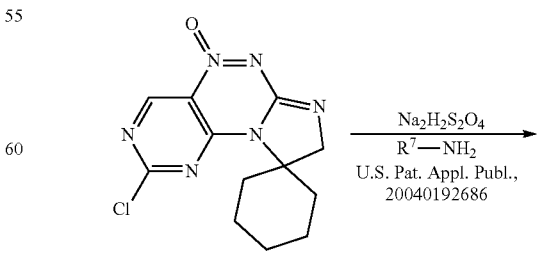

96

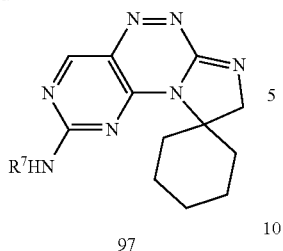

97

Journal of Medicinal Chemistry, 46(1), 169-182; 2003
Journal of Organic Chemisty, 79(16), 7520-7531; 2014
Synthesis, (8), 855-857; 1997
Science of Synthesis, 17, 357-447; 2004

Alternatively compounds of Formula VIII can be formed as shown in Scheme 12. Commercially available chloride 93 is coupled with an appropriate amine via nucleophilic aromatic substitution to afford intermediate 94. Amine 94 is then deprotected and subjected to cyclization in the presence of cyanogen bromide or an analogous reagent to afford compound 95. Compound 95 is further cyclized in the presence of a base to afford compound 96, which is reduced and subjected to an appropriately substituted amine to afford compound 97, which is a compound of Formula VIII.

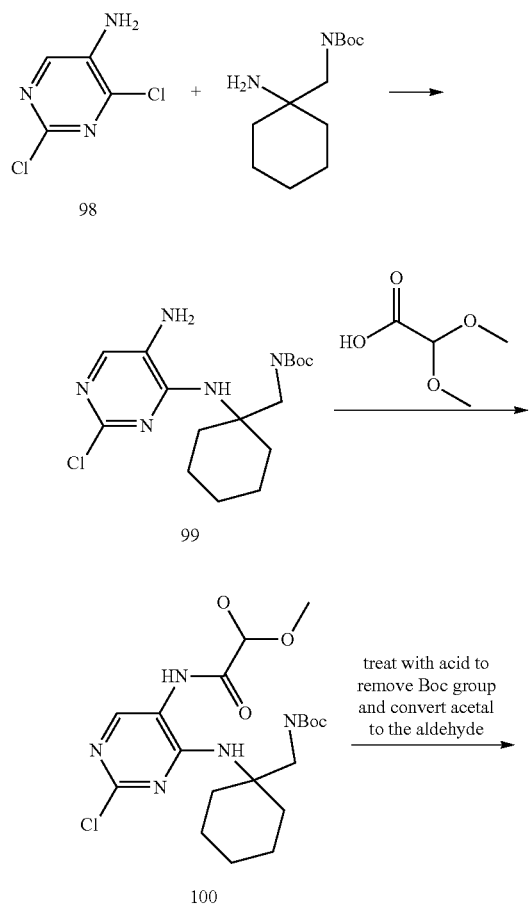

Scheme 13

98

99

100

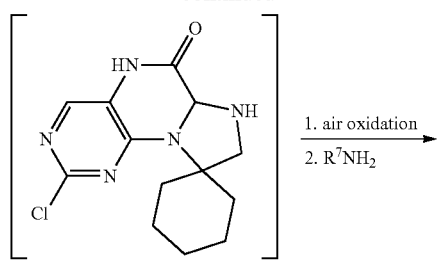

100

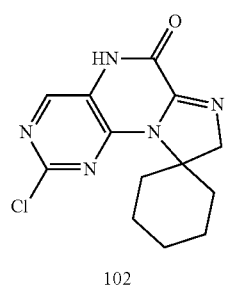

102

As shown in Scheme 13, bichloride 98 is coupled with an amine via nucleophilic aromatic substitution to furnish intermediate 99 which then undergoes amidation in the presence of a carboxylic acid to produce amide 100. Removal of Boc triggers intramolecular cyclization to yield intermediate 101 which is then oxidized upon exposure to air or other oxidants and coupled with a desired amine to afford target 102 which is a compound of Formula IX.

Scheme 14

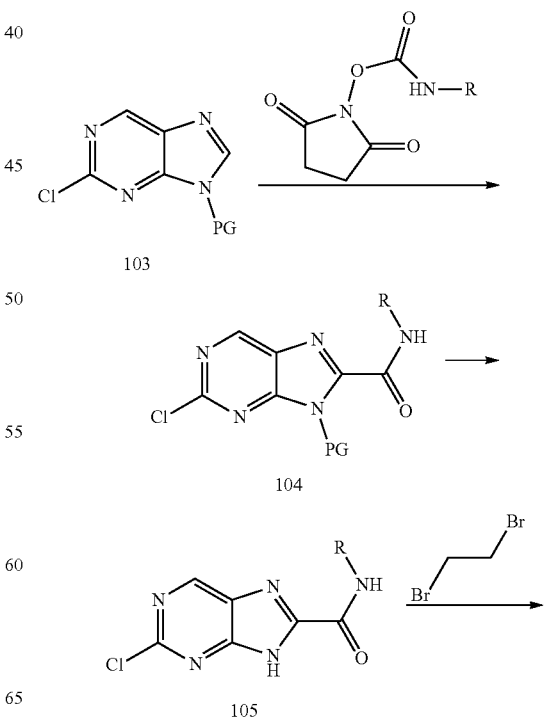

103

104

105

151

-continued

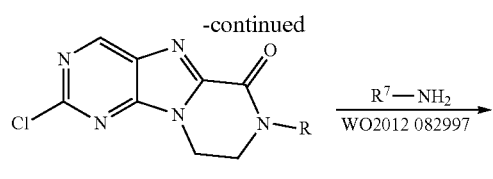
106

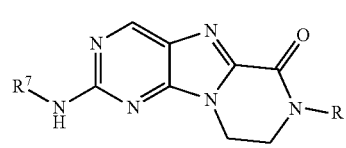
107

As shown in Scheme 14, protected heterocycle 103 is reacted with an electrophile as known in the art to furnish intermediate 104 which then undergoes deprotection to produce amide 105. Nucleophilic attack of dibromoethane by 105 followed by intramolecular cyclization affords 106 which is coupled with a desired amine to afford compound 107 which is a compound of Formula I.

152

-continued

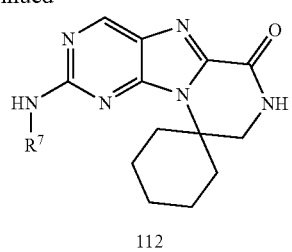
112

X, X1 are halogens

As shown in Scheme 15, protected heterocycle 108 is coupled with a desired amine to furnish intermediate 109. Intermediate 109 is then converted to an anilino compound 110 as known in the art. The anilino compound 110 is condensed into an oxalate derivative 111 which is subsequently deprotected and cyclized to form compound 112, which is a compound of Formula I.

Scheme 15

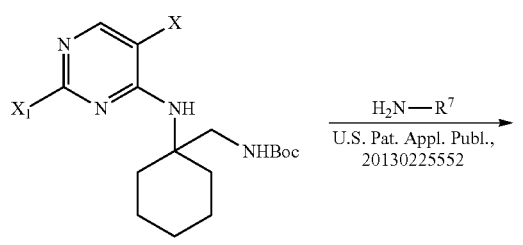
108

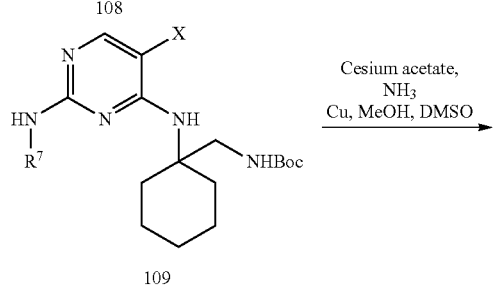
109

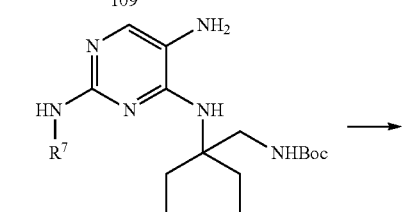
110

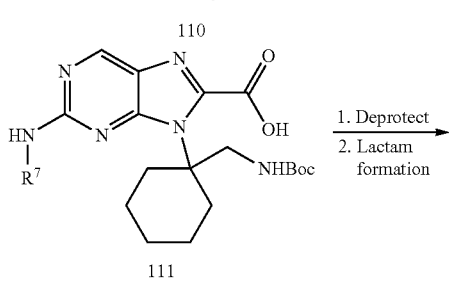
111

Scheme 16

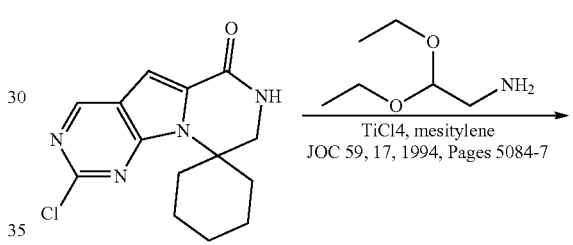
113

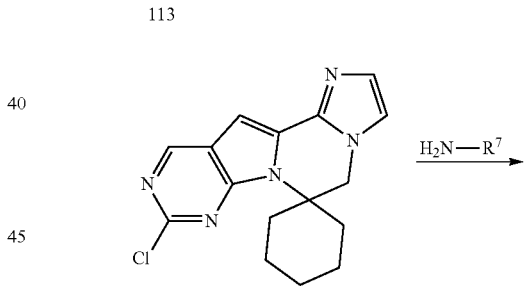
114

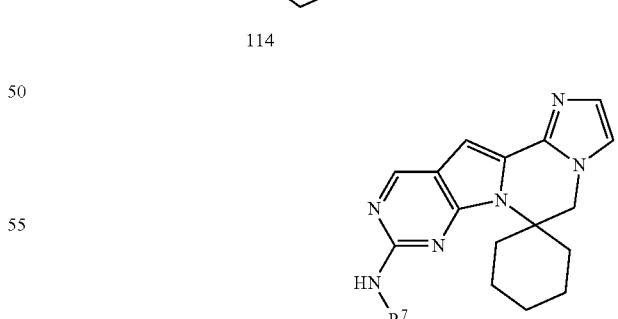
115

As shown in Scheme 16, known compound 113 can be reacted with an amino ketal to form compound 114. Compound 114 is subsequently reacted with a desired amine to form compound 115, which is a representative compound of Formula XI.

Scheme 17

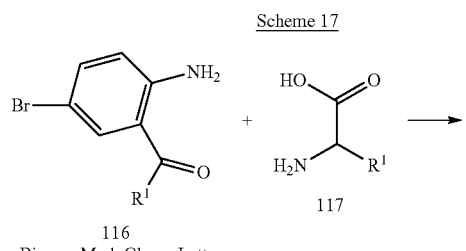

116
Bioorg. Med. Chem. Lett.
18, 2008, pp 5015-17

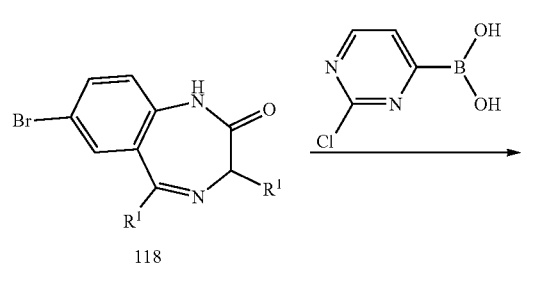

118

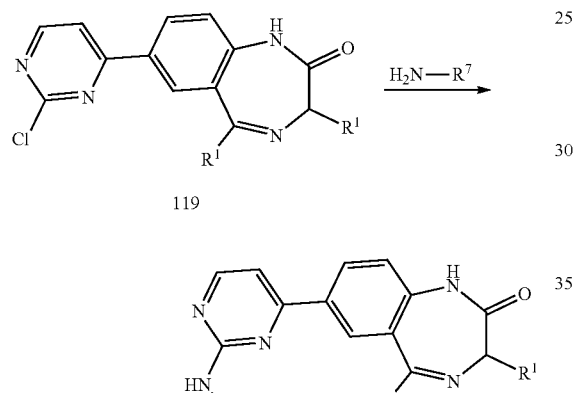

119

120

Scheme 18

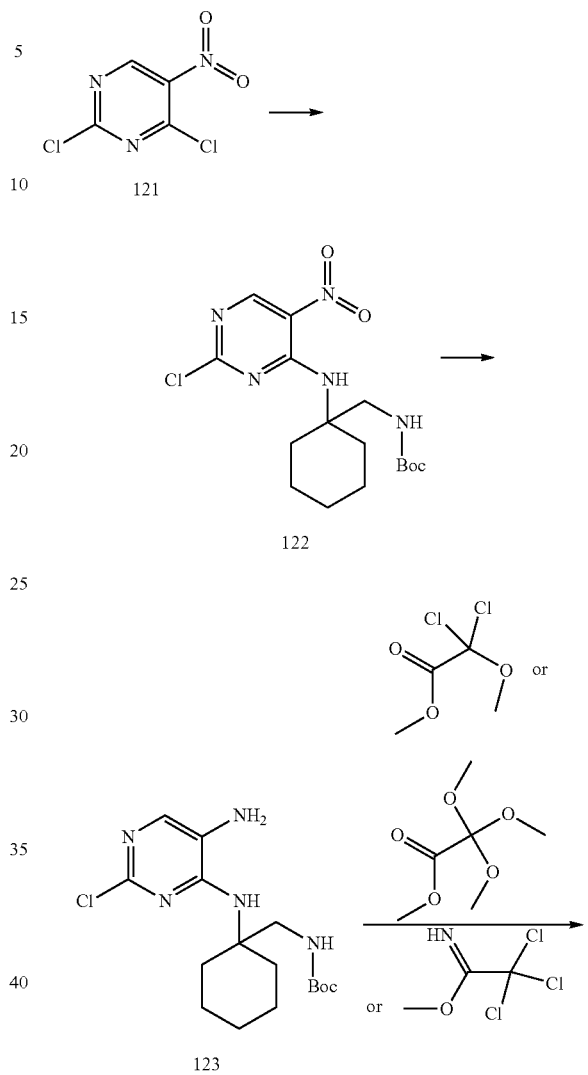

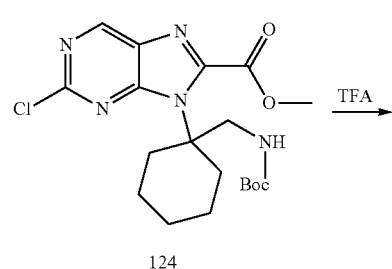

124

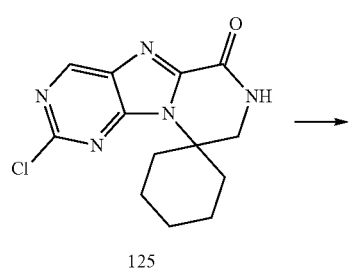

125

General Procedure for the Synthesis of Diazepinones 118. A mixture of the suitable 2-aminobenzophenone derivative 116 (6.0 mmol) in pyridine (40 mL) containing 9.0 mmol of alanine derivative 117 is refluxed for 20 h under nitrogen. The reaction mixture is concentrated under reduced pressure, poured into ice-water and extracted with $CH_2Cl_2$. The organic layer is washed with 0.1 N HCl, dried over $Na_2SO_4$, and evaporated in vacuo. The residue is purified by flash-chromatography eluting with the suitable solvent to afford the expected compounds, which after re-crystallization from the appropriate solvent gives 118.

Diazepinone 118 is then coupled with a pyrimidine to afford 119 which is subjected to an appropriate amine in a nucleophilic attack to afford 120, which is a compound of Formula XII.

In the following schemes methyl piperazines products and intermediates are synthesized. One skilled in the art, will appreciate that a variety of different heterocycles could be used in place of methylpiperazine (such as piperazine, isopropylpiperazine, morpholine, etc) by selection of the heteroaryl amine reactant in the following schemes.

155

-continued

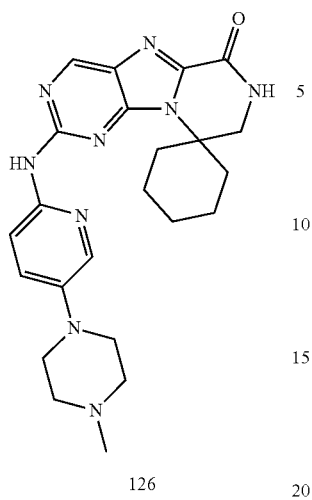

126

Scheme 18 provides a synthetic preparation of compound 126 of Formula I. First commercially available dichloride 121 undergoes nucleophilic addition to install a diamine moiety and afford 122. Intermediate 122 is then reduced to an anilino compound and subsequently reacted with either methyl 2,2-dichloro-2-methoxyacetate, methyl 2,2,2-trimethoxyacetate, methyl 2,2,2-trichloroacetimidate, or a similar reagent to afford cyclization precursor 124. 124 is then deprotected and subsequently undergoes intramolecular cyclization to afford 125 which then undergoes nucleophilic attack to afford final compound 126.

Scheme 19

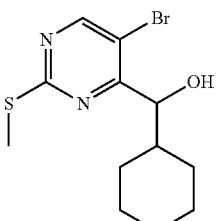

127

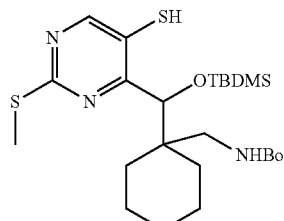

Journal of Heterocyclic Chemistry, 2003, vol. 40, #2 p. 219-224
128

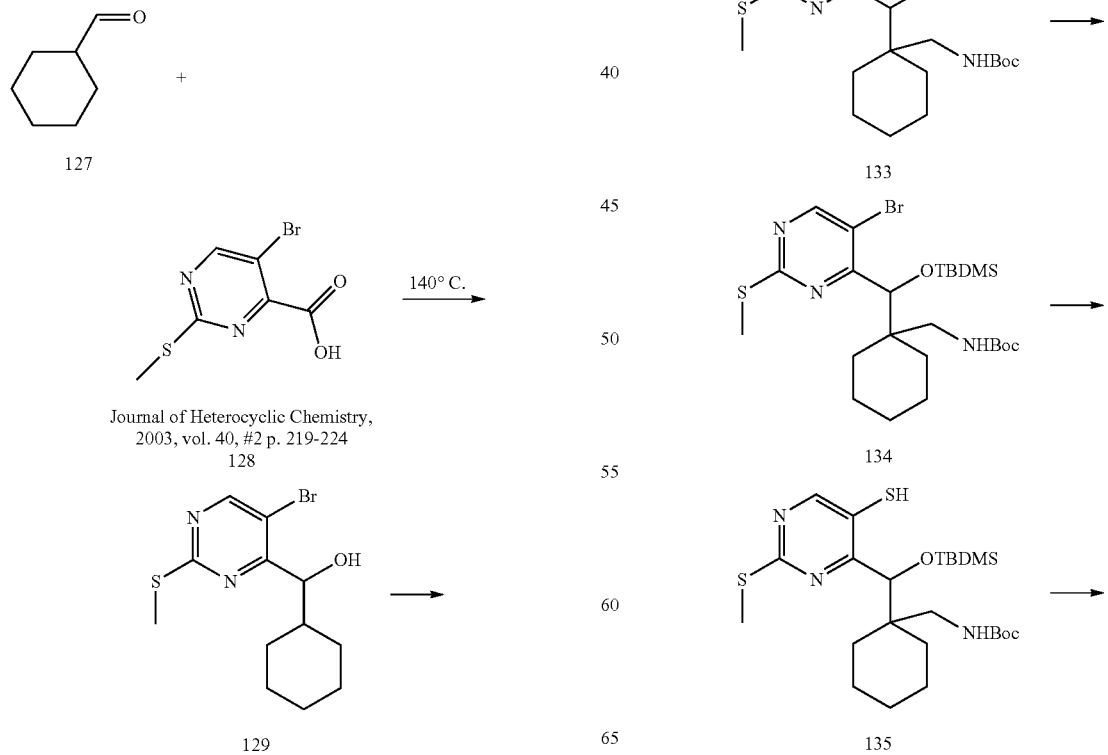

129

156

-continued

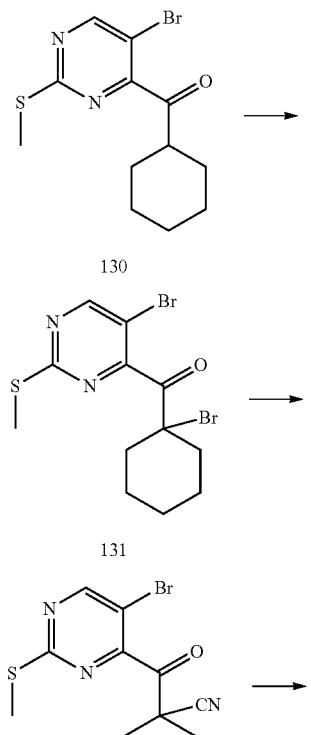

130

131

132

133

134

135

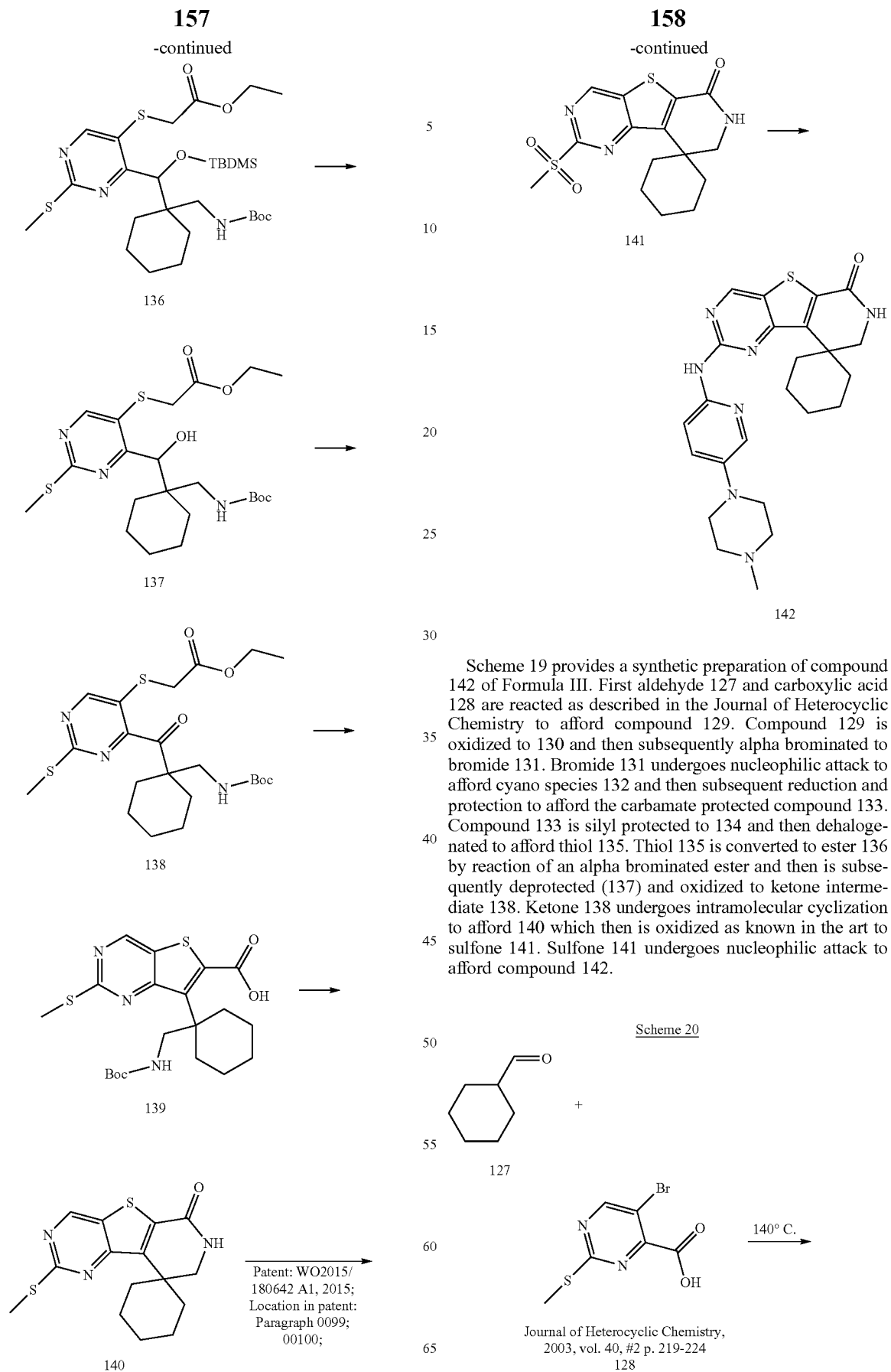

Scheme 19 provides a synthetic preparation of compound 142 of Formula III. First aldehyde 127 and carboxylic acid 128 are reacted as described in the Journal of Heterocyclic Chemistry to afford compound 129. Compound 129 is oxidized to 130 and then subsequently alpha brominated to bromide 131. Bromide 131 undergoes nucleophilic attack to afford cyano species 132 and then subsequent reduction and protection to afford the carbamate protected compound 133. Compound 133 is silyl protected to 134 and then dehalogenated to afford thiol 135. Thiol 135 is converted to ester 136 by reaction of an alpha brominated ester and then is subsequently deprotected (137) and oxidized to ketone intermediate 138. Ketone 138 undergoes intramolecular cyclization to afford 140 which then is oxidized as known in the art to sulfone 141. Sulfone 141 undergoes nucleophilic attack to afford compound 142.

-continued
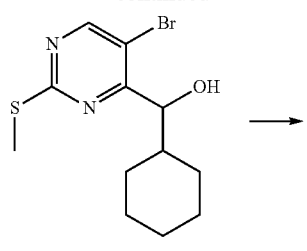
129
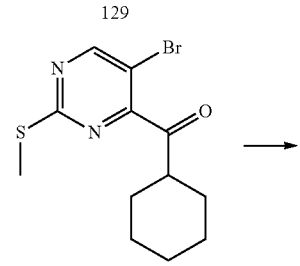
130
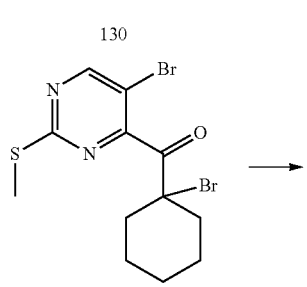
131
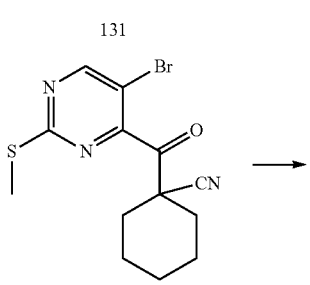
132
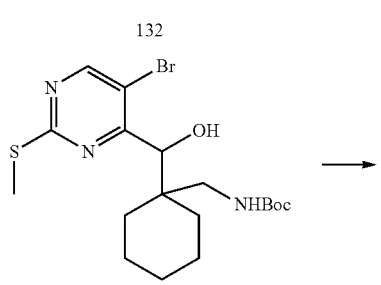
133
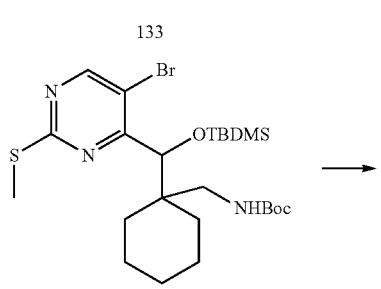
134
-continued
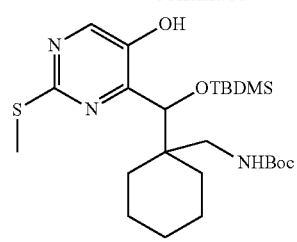
143
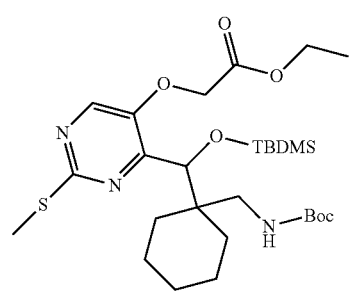
144
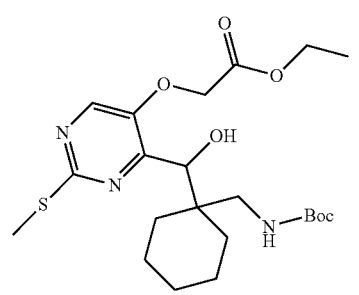
145
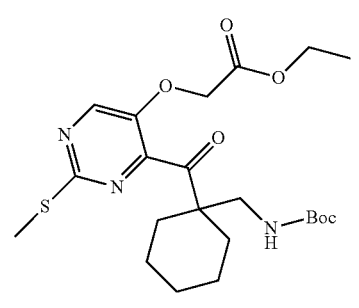
146
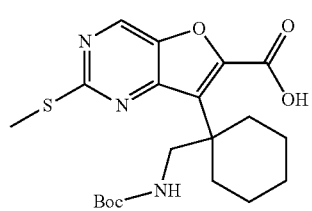
147

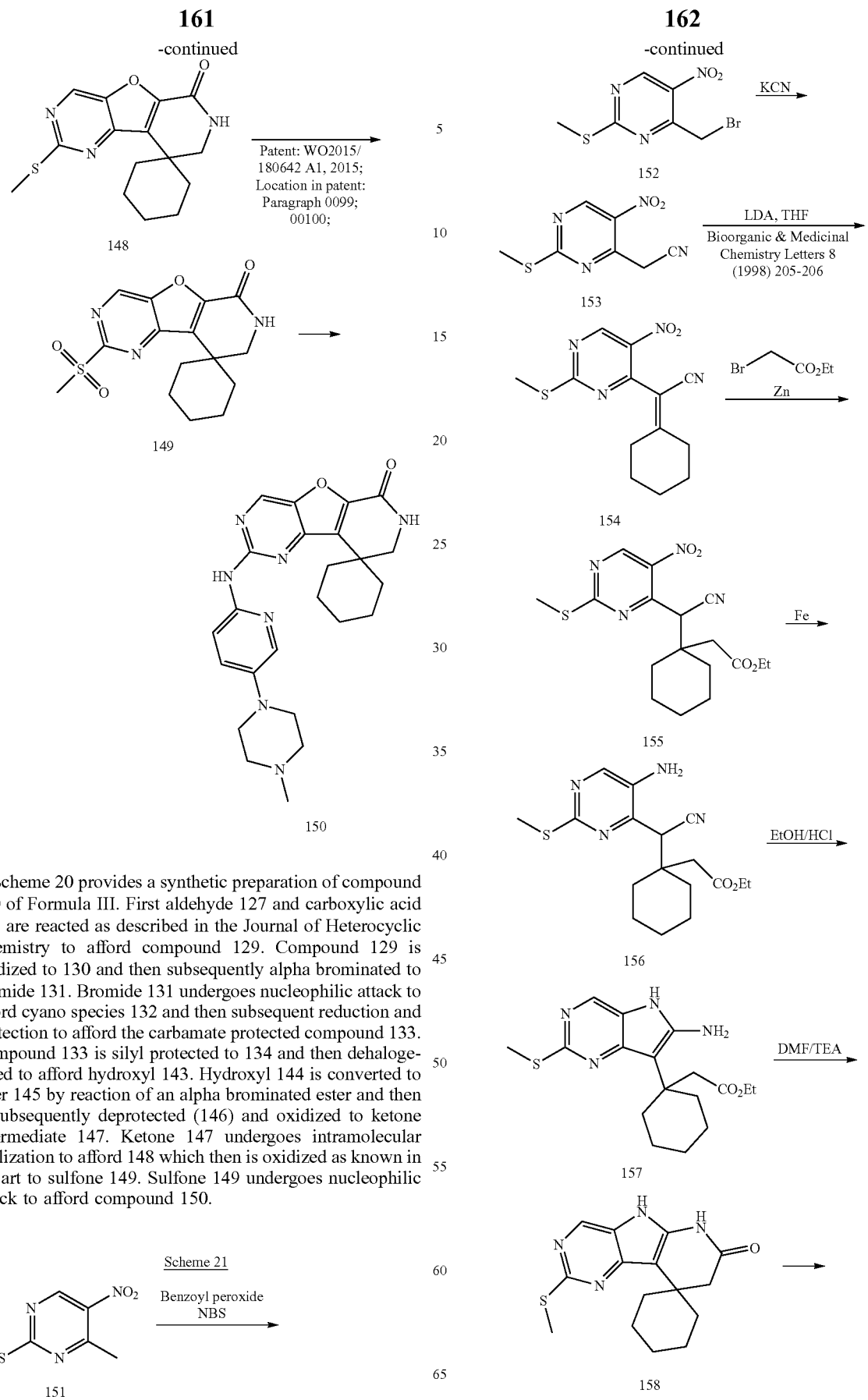

Scheme 20 provides a synthetic preparation of compound 150 of Formula III. First aldehyde 127 and carboxylic acid 128 are reacted as described in the Journal of Heterocyclic Chemistry to afford compound 129. Compound 129 is oxidized to 130 and then subsequently alpha brominated to bromide 131. Bromide 131 undergoes nucleophilic attack to afford cyano species 132 and then subsequent reduction and protection to afford the carbamate protected compound 133. Compound 133 is silyl protected to 134 and then dehalogenated to afford hydroxyl 143. Hydroxyl 144 is converted to ester 145 by reaction of an alpha brominated ester and then is subsequently deprotected (146) and oxidized to ketone intermediate 147. Ketone 147 undergoes intramolecular cyclization to afford 148 which then is oxidized as known in the art to sulfone 149. Sulfone 149 undergoes nucleophilic attack to afford compound 150.

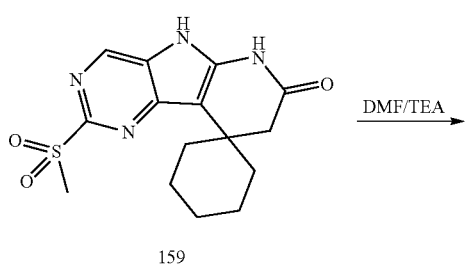

159

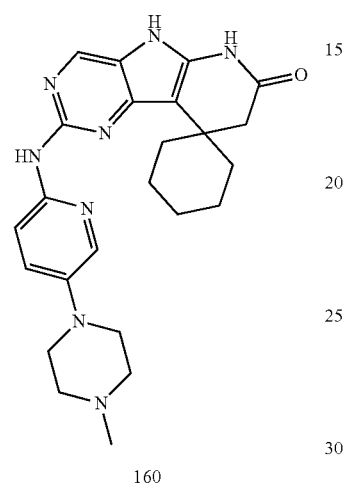

160

Scheme 21 provides a synthetic preparation of compound 160 of Formula IV. Commercially available compound 151 is brominated in a radical reaction to afford 152 which then can be displaced by a nucleophilic source of cyano (such as potassium cyanide) to afford cyano 153. Cyano 153 is then deprotonated as described in BMCL to afford alkene 154. Alkene 154 is coupled with a metal such as zinc to afford ester 155. Ester 155 is then reduced with another metal (such as iron) to afford aniline 156. Aniline 156 then undergoes intramolecular cyclization to afford pyrazolopyrimindine 157 which then undergoes a base catalyzed intramolecular cyclization to afford the trifused cycle 158. Compound 158 is then oxidized to the sulfone 159 which is subsequently displaced with an appropriate amine in the presence of an appropriate base to afford the final compound 160.

Scheme 22

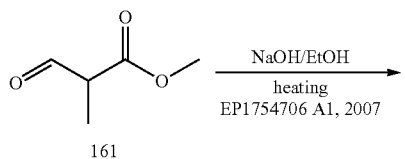

161

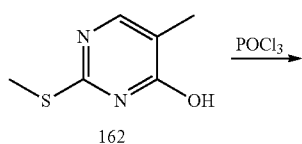

162

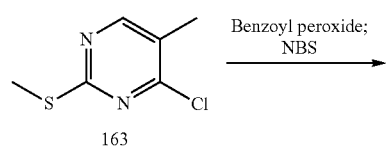

163

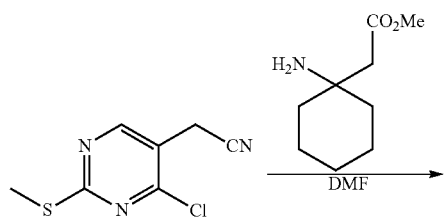

164

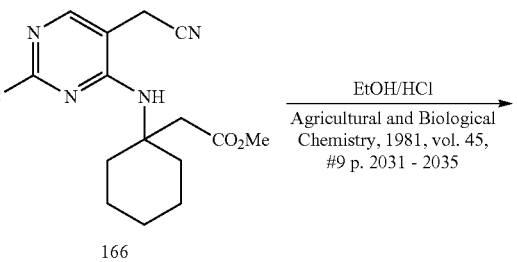

165

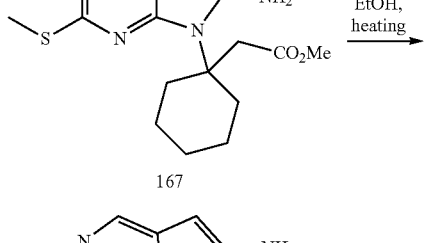

166

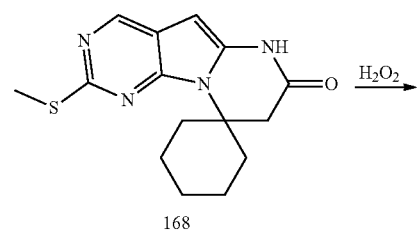

167

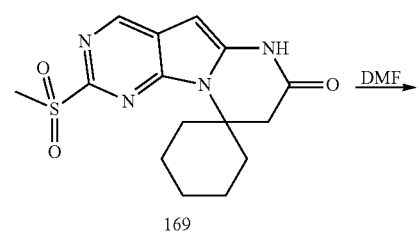

168

169

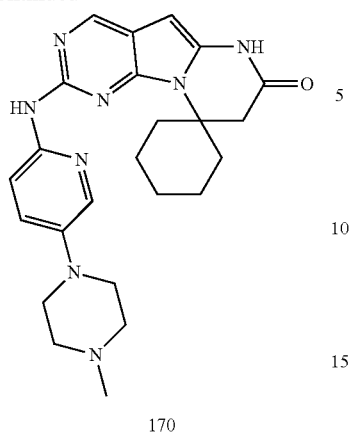

170

Scheme 22 provides a synthetic preparation of compound 170 of Formula V. Commercially available reagent 161 is subjected to base and head as described in EP1754706 to afford 162. Compound 162 is then chlorinated as known in the art to afford 163. Compound 163 undergoes bromination in a radical reaction to afford bromide 164. Bromide 164 undergoes nucleophilic attack with a cyano source (such as potassium cyanide) to afford cyano 165.

Cyano 165 is subjected to an amine to afford 166 and then intramolecular cyclization affords 167 as known in the art. Compound 167 undergoes intramolecular cyclization again to afford 168 then subsequent oxidation to afford 169. The selectivity of the oxidation can be controlled by choice of reagents. Sulfone 169 is then displaced in a nucleophilic SNAr type reaction to afford 170.

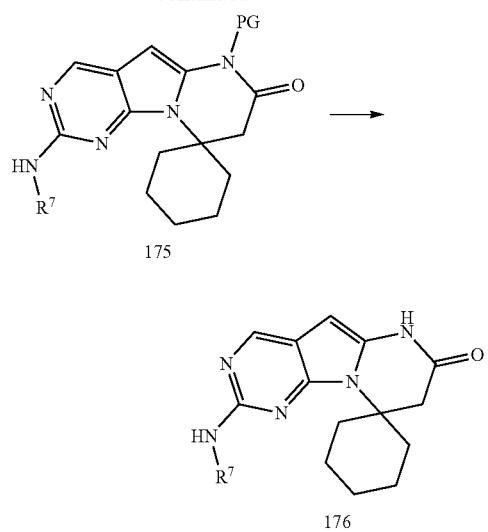

Scheme 23 provides an alternative synthetic preparation of compound of Formula V.

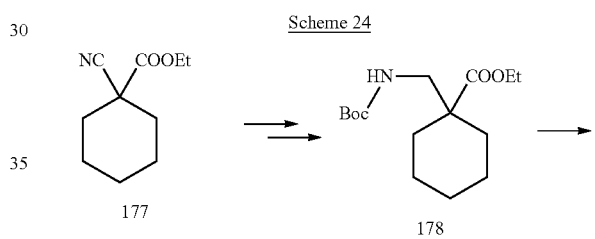

Helvetica Chimica Acta, 1998, vol. 81, # 12 p. 2218-2243

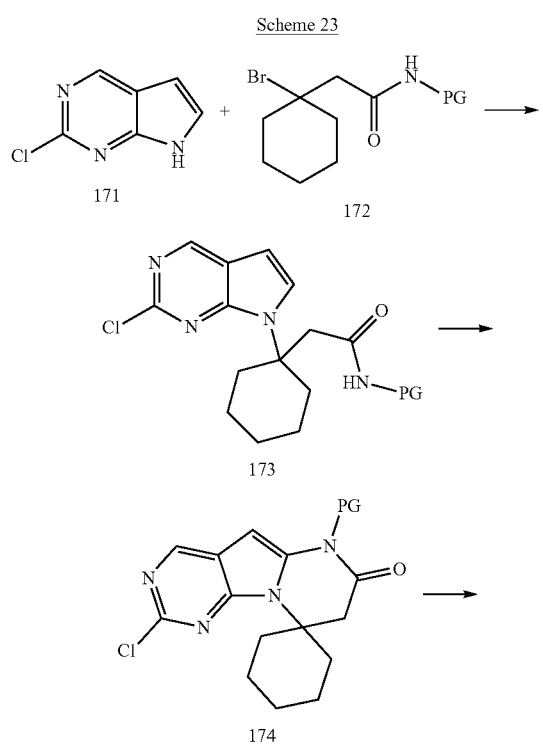

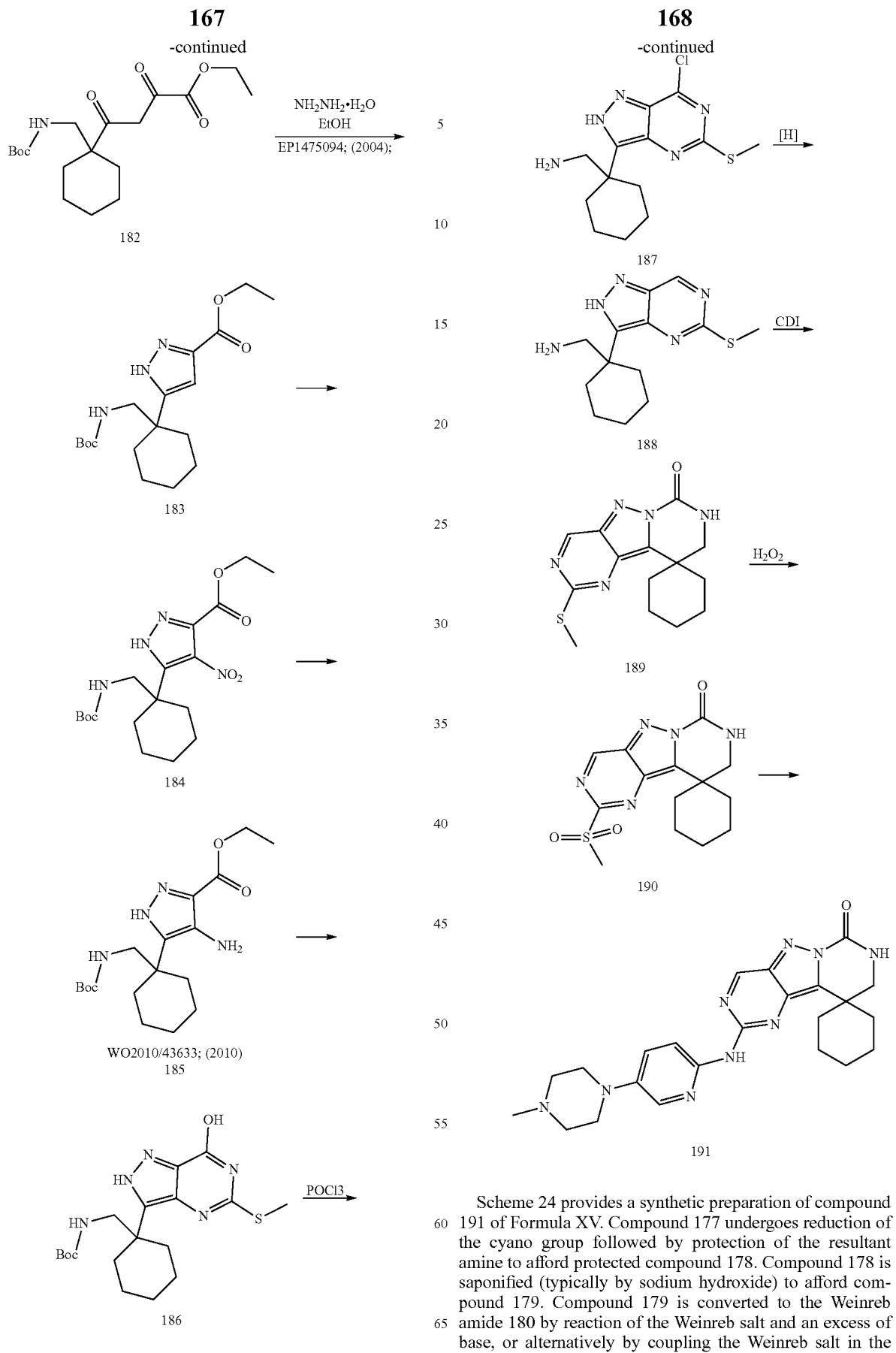

Scheme 24 provides a synthetic preparation of compound 191 of Formula XV. Compound 177 undergoes reduction of the cyano group followed by protection of the resultant amine to afford protected compound 178. Compound 178 is saponified (typically by sodium hydroxide) to afford compound 179. Compound 179 is converted to the Weinreb amide 180 by reaction of the Weinreb salt and an excess of base, or alternatively by coupling the Weinreb salt in the presence of HATU or a similar reagent. The Weinreb amide is then reacted with a nucleophilic methyl source, such as methyl lithium or methyl magnesium bromide to afford a ketone 181. Ketone 181 is deprotonated and condensed to afford compound 182 which undergoes subsequent cyclization with hydrazine to form pyrazole 183 which undergoes subsequent installation of a nitro group to afford compound 184. Compound 184 is reduced to amine 185 as performed in WO2010/43633 which is then cyclized to afford 186. Compound 186 is chlorinated with any suitable reagent (such as POCl$_3$) to afford chloride 187. Chloride 187 is then dehalogenated with a proton source to afford 188. Compound 188 is coupled to an appropriate acid and then undergoes intramolecular cyclization to afford compound 189. Compound 189 is oxidized to compound 190 and undergoes subsequent nucleophilic attack to afford compound 191.

IX. Exemplary Compounds

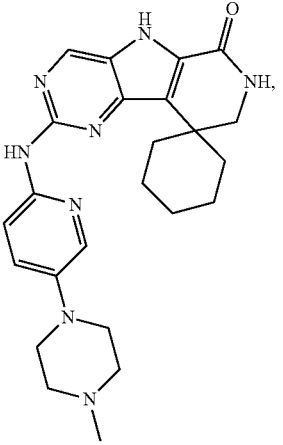

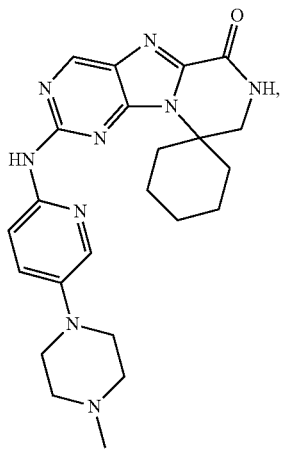

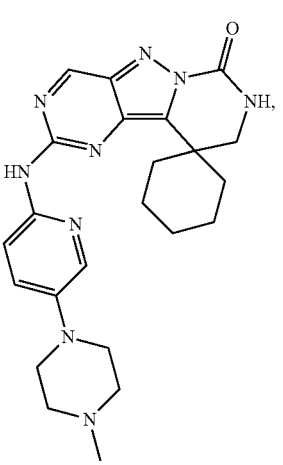

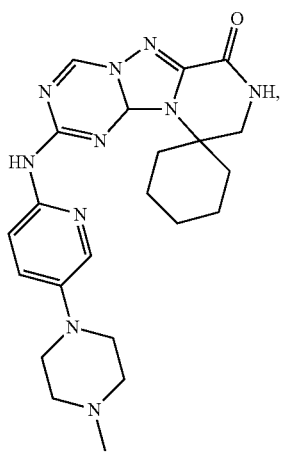

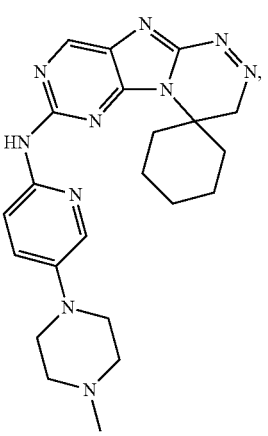

171
-continued
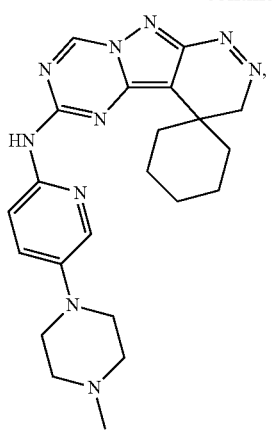
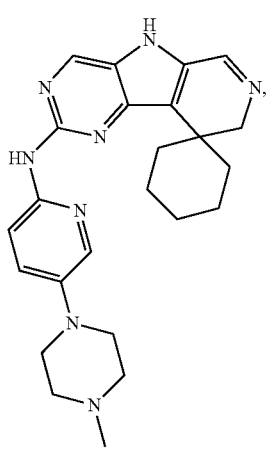
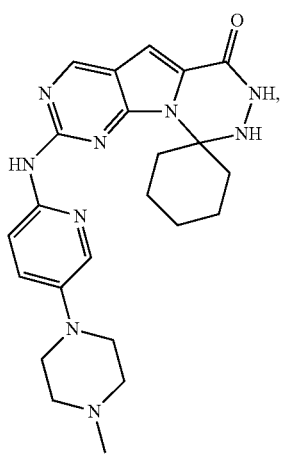
172
-continued
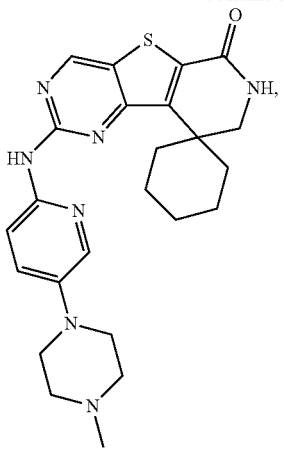
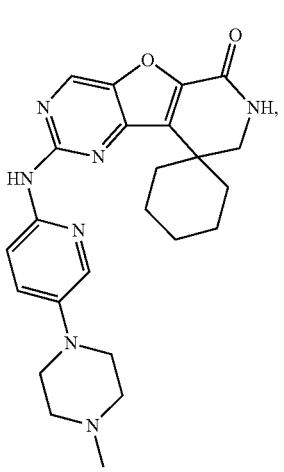
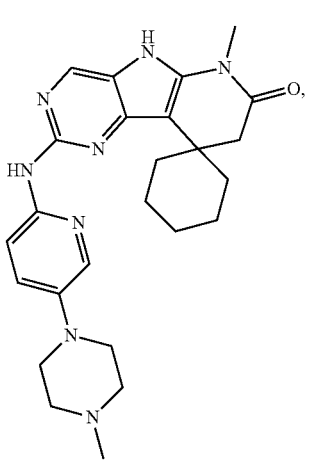

173
-continued
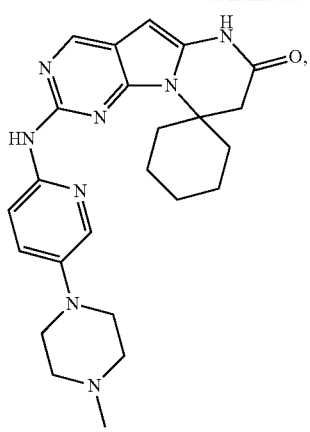
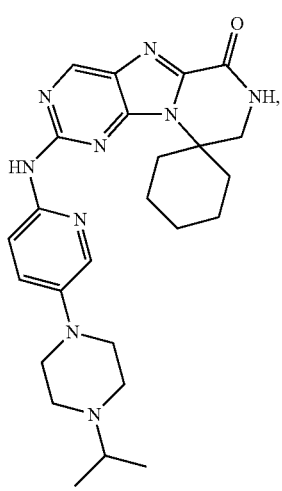
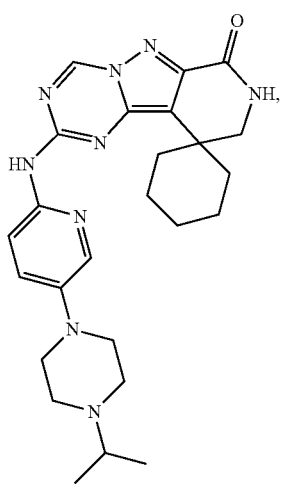
174
-continued
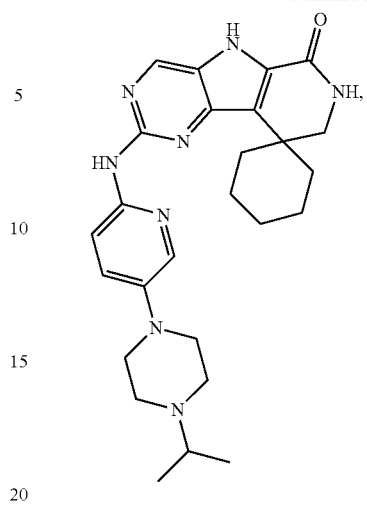
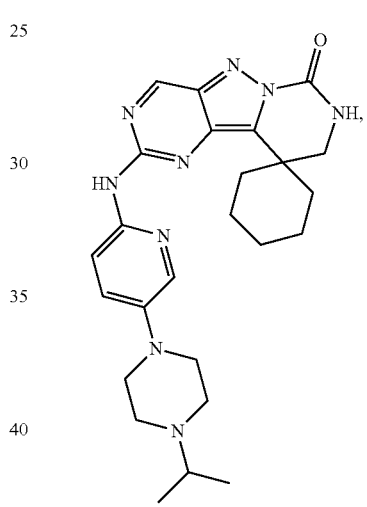
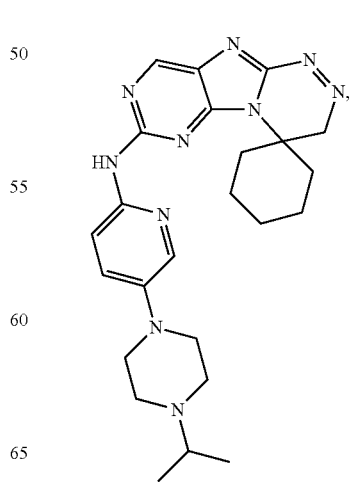

175
-continued
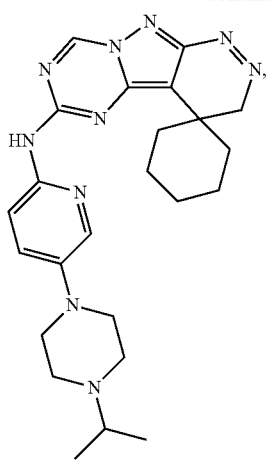
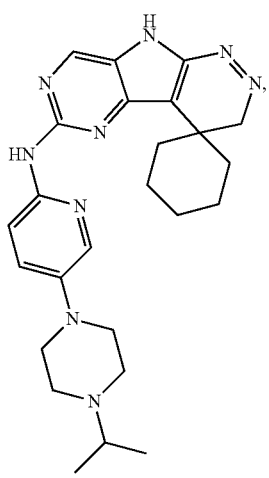
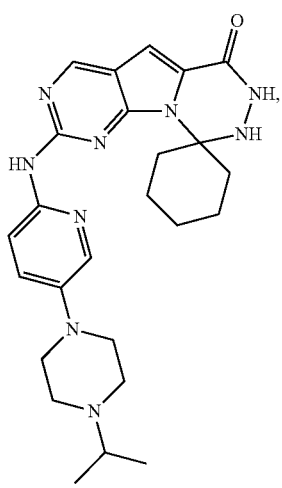
176
-continued
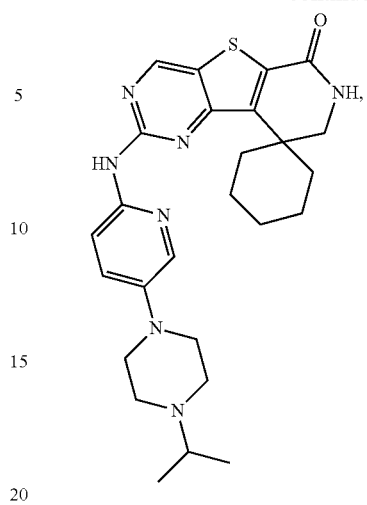
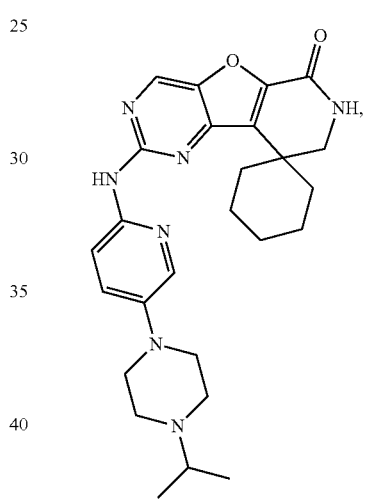
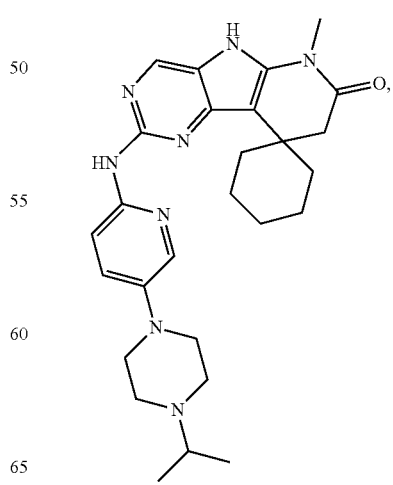

177
-continued
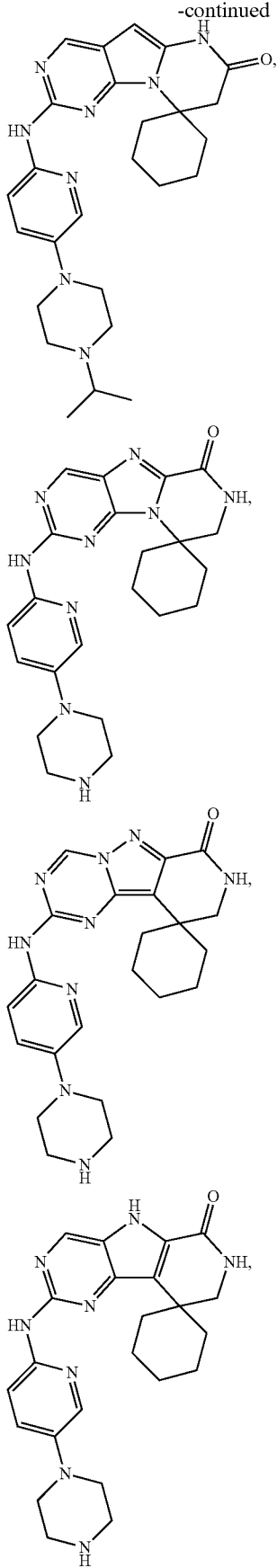
178
-continued
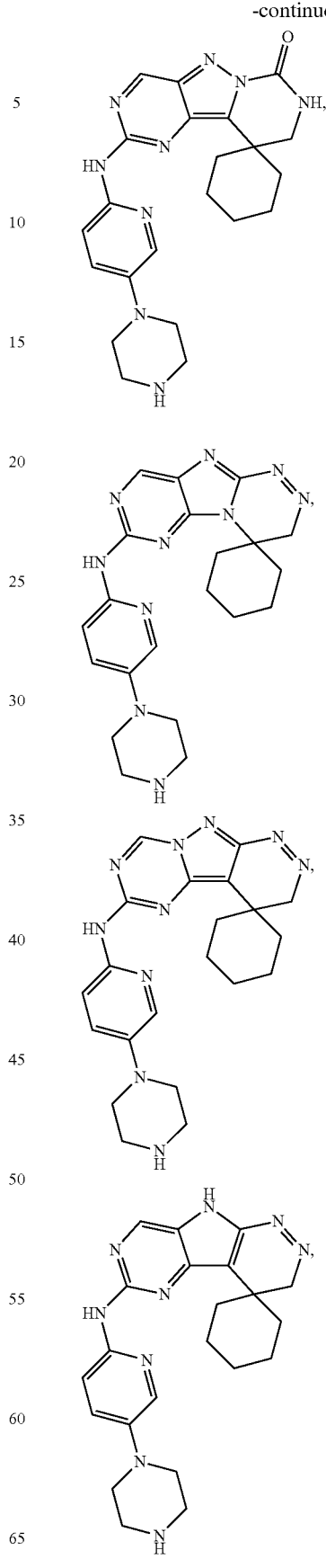

179
-continued
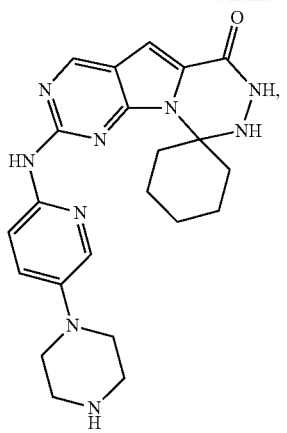
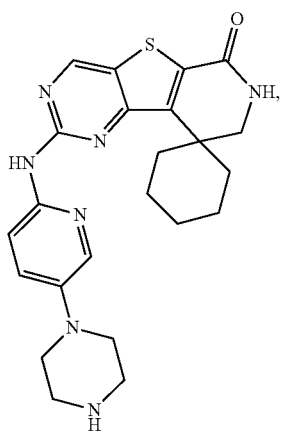
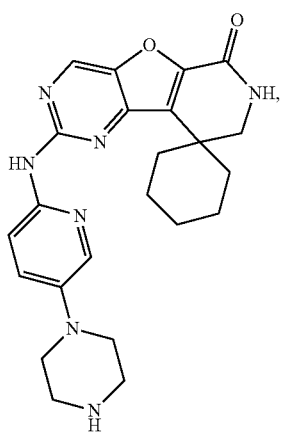
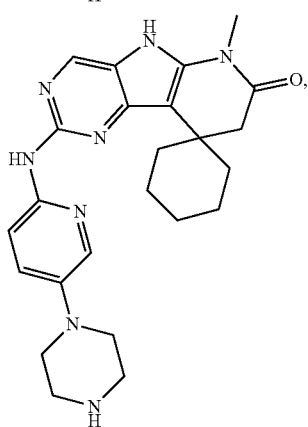
180
-continued
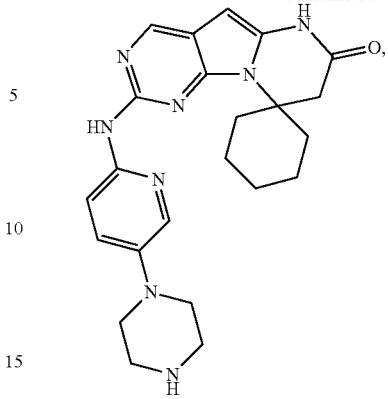
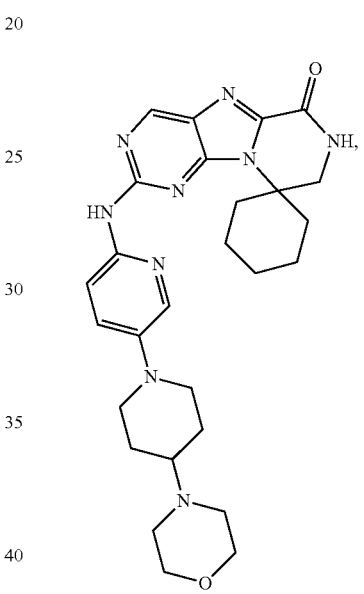
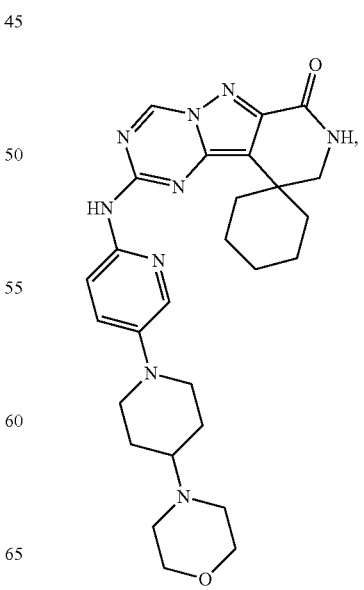

181
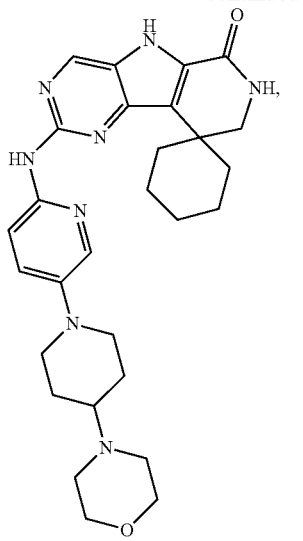
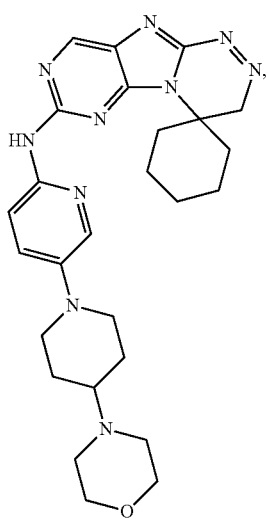
182
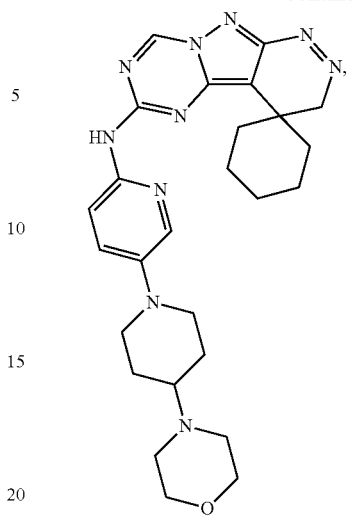
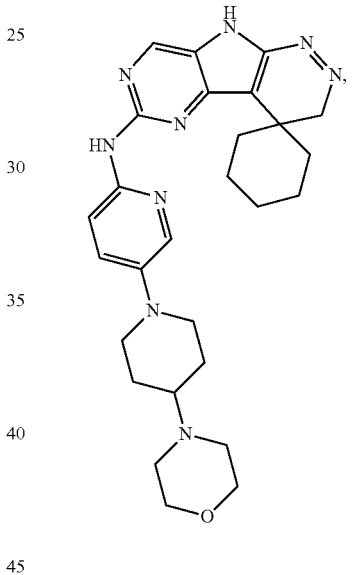
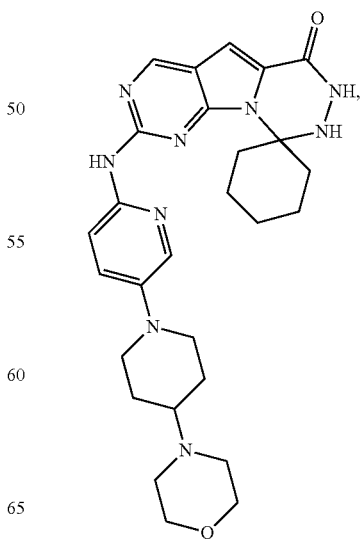

183
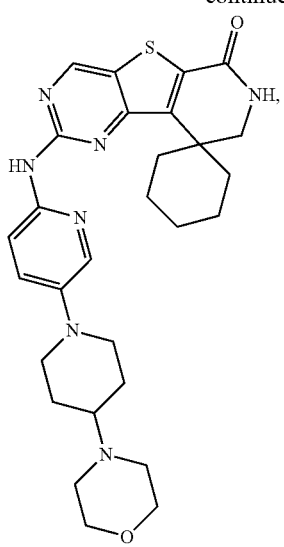
184
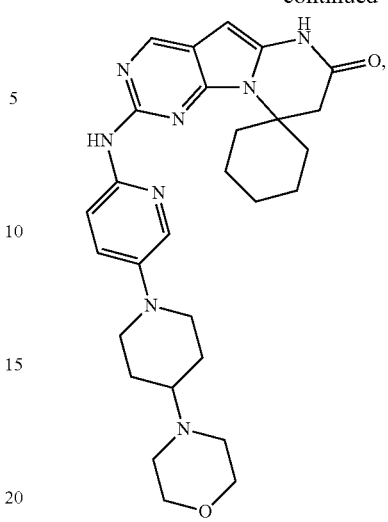
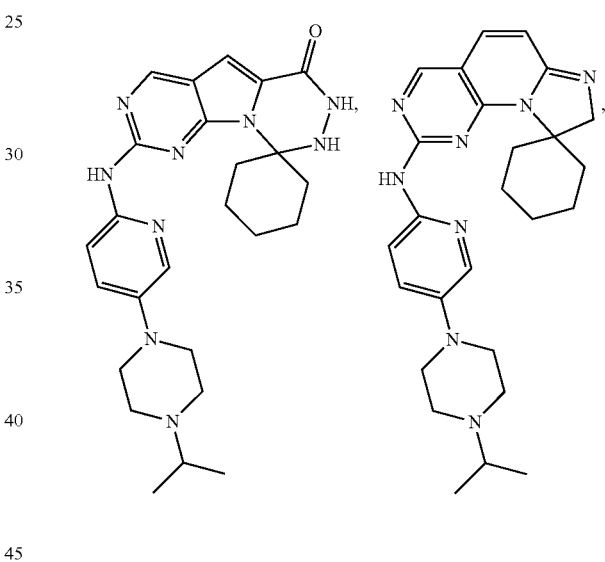
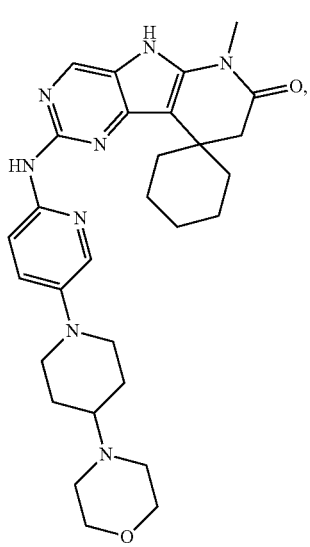
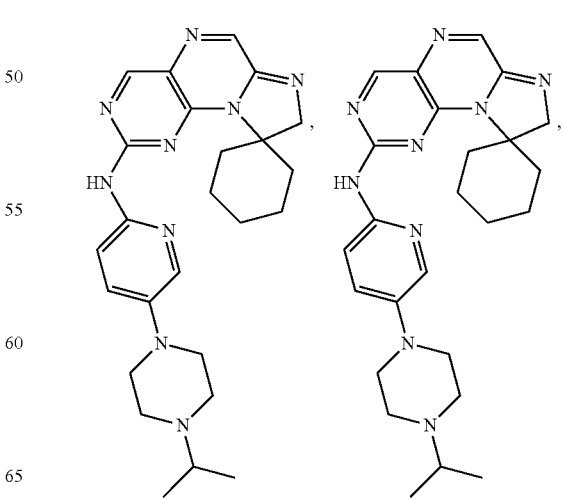

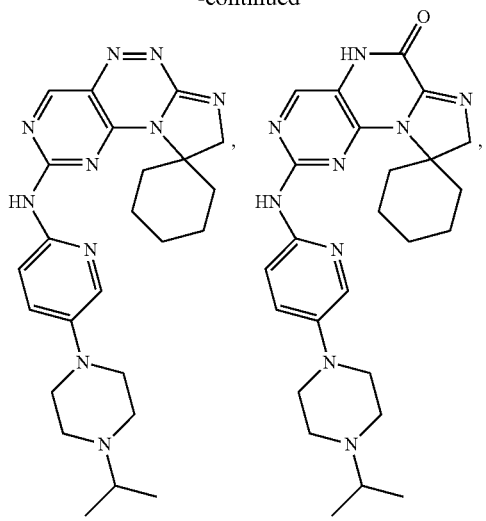
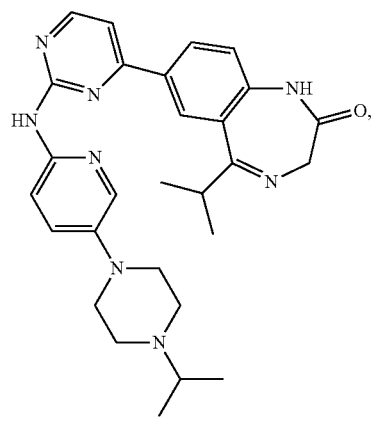
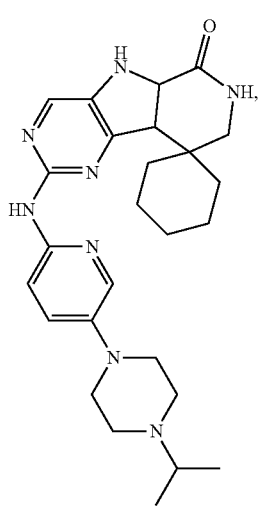
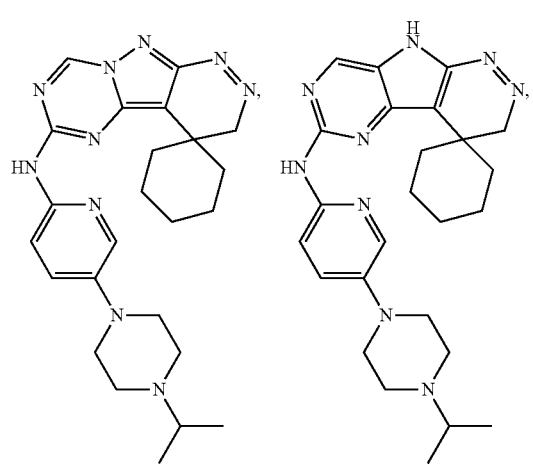
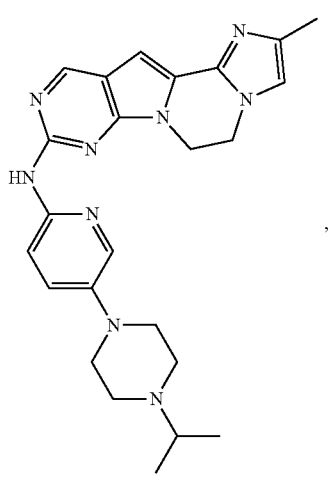
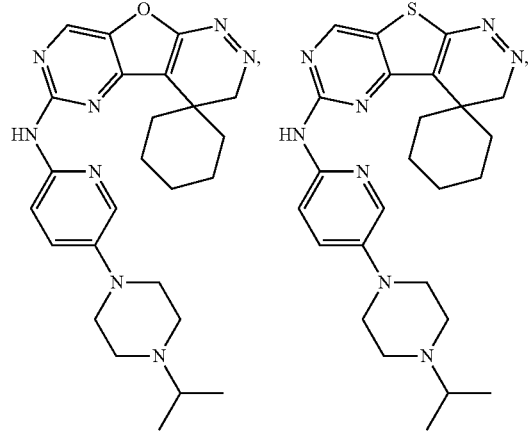

187
-continued
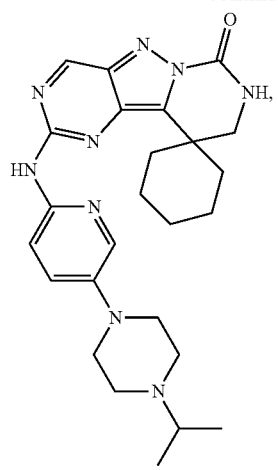
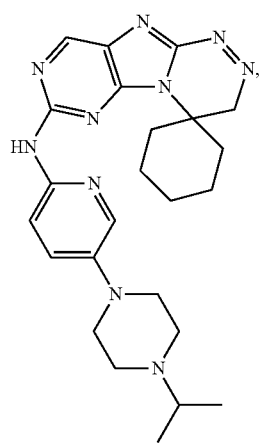
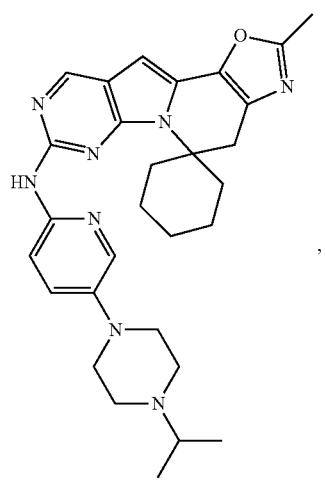
188
-continued
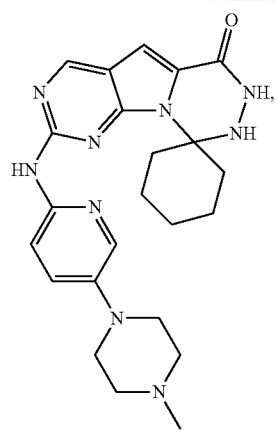
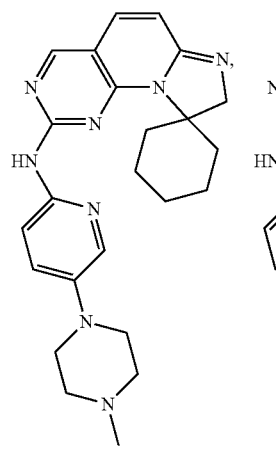
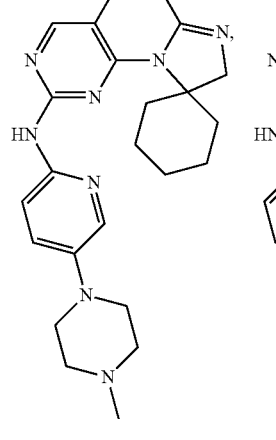

189
-continued
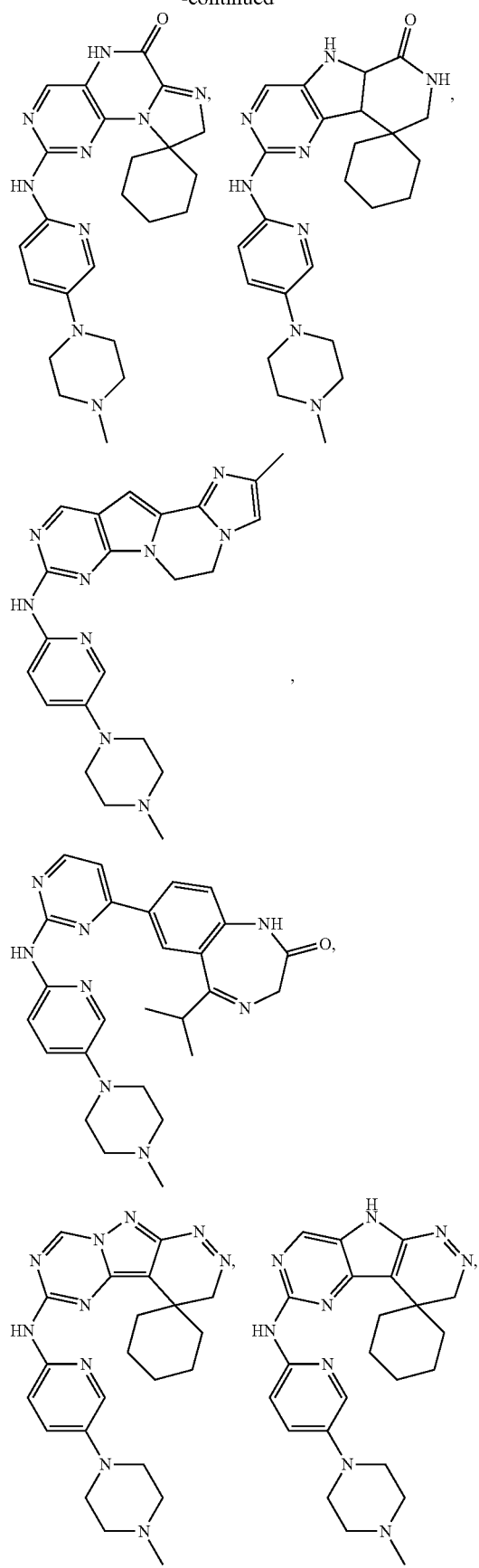
190
-continued
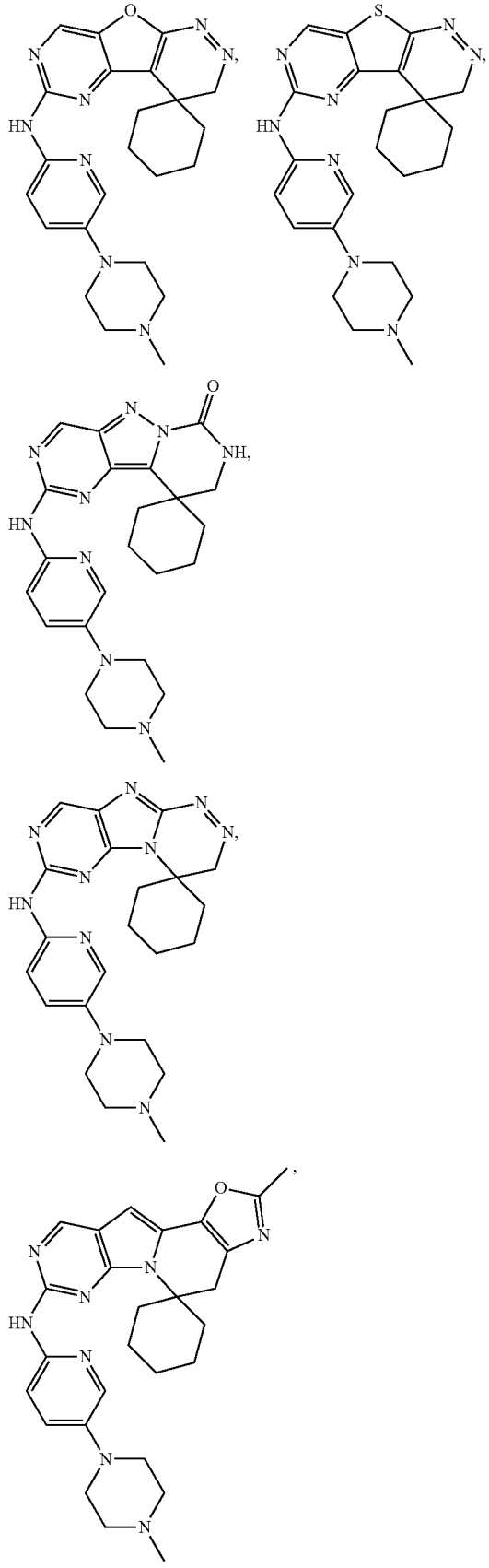

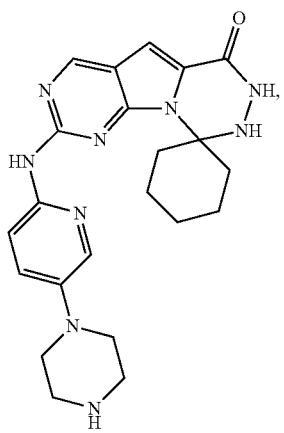
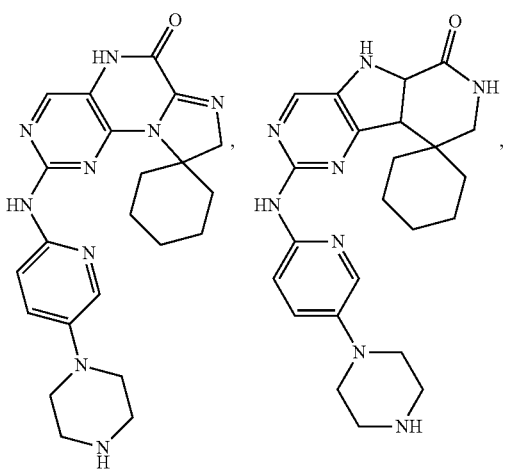
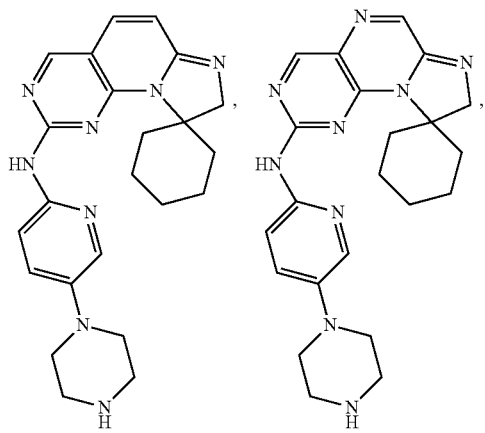
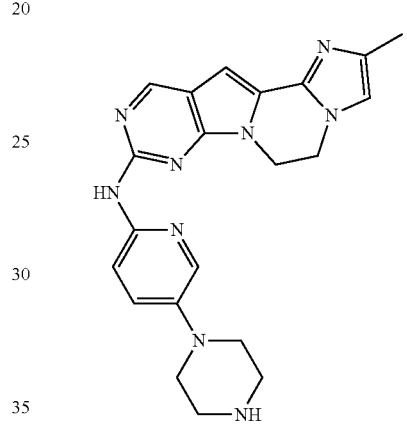
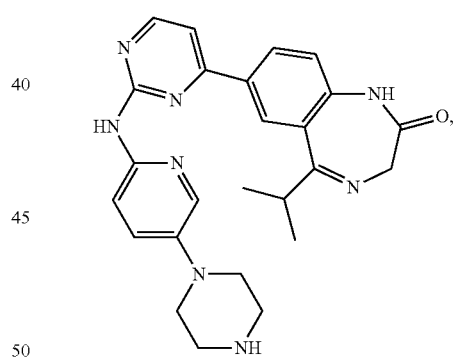
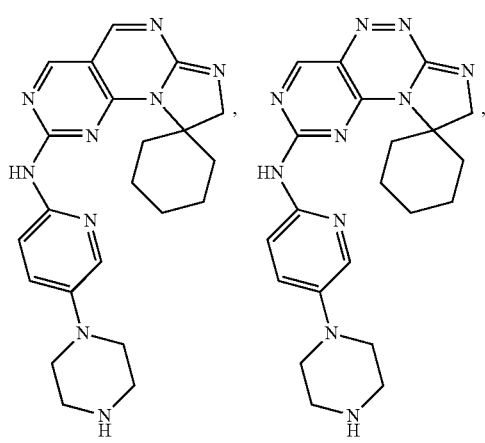
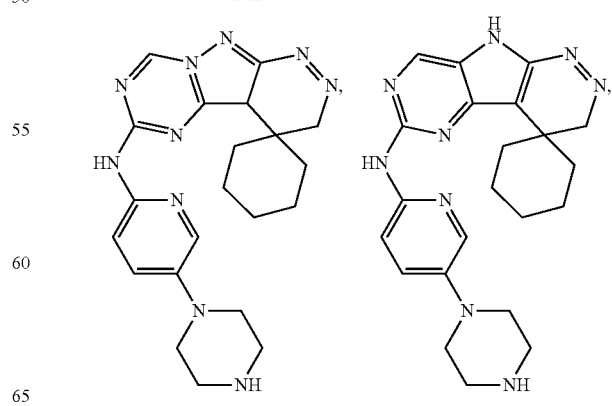

-continued
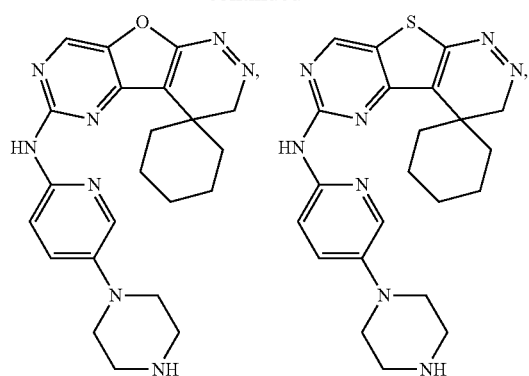
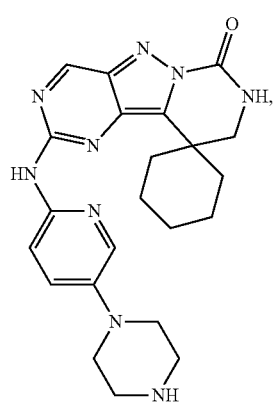
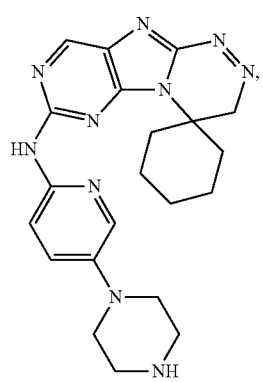
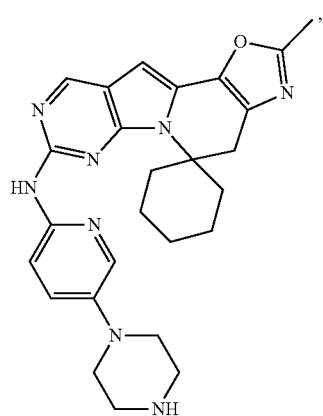
-continued
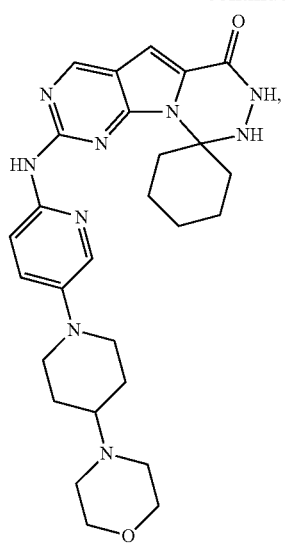
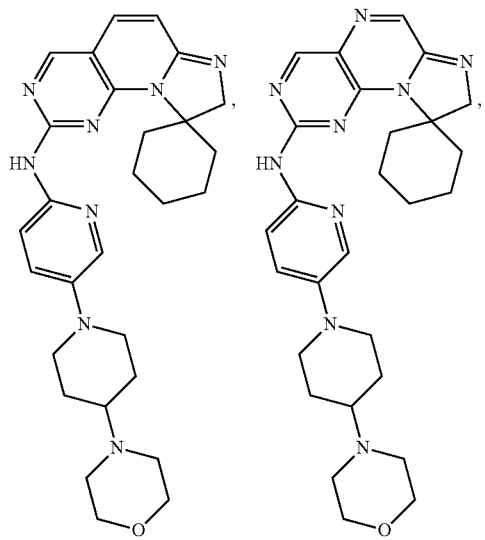
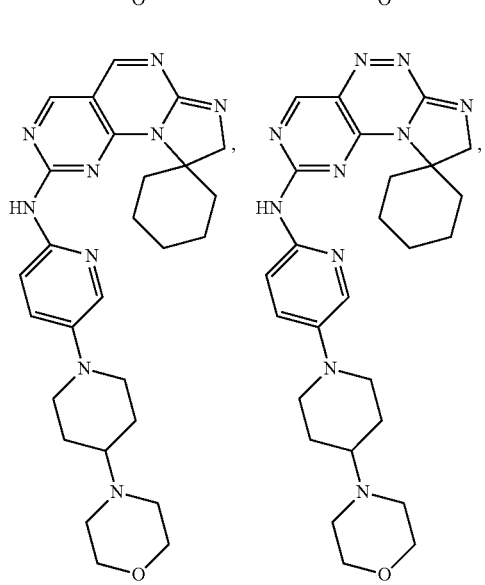

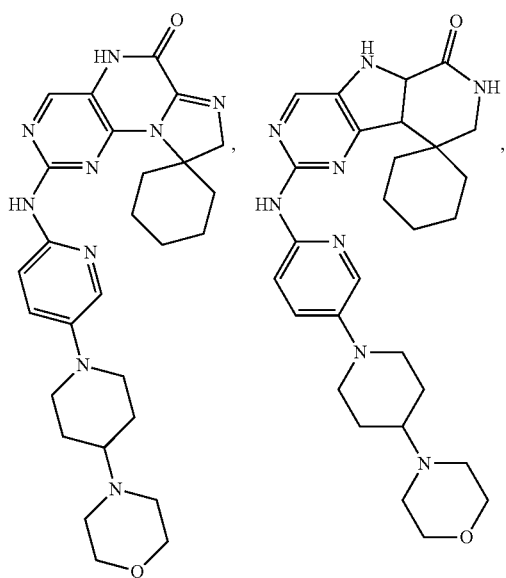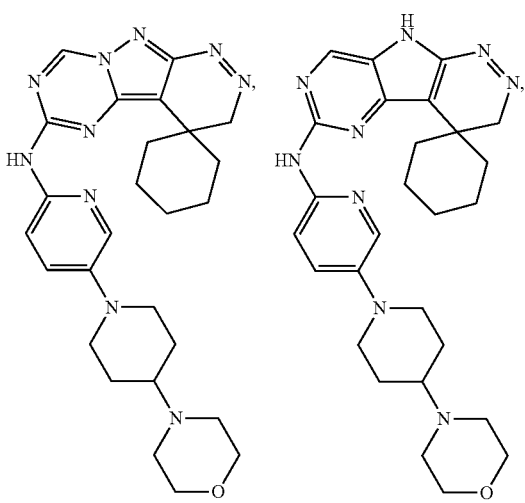

-continued

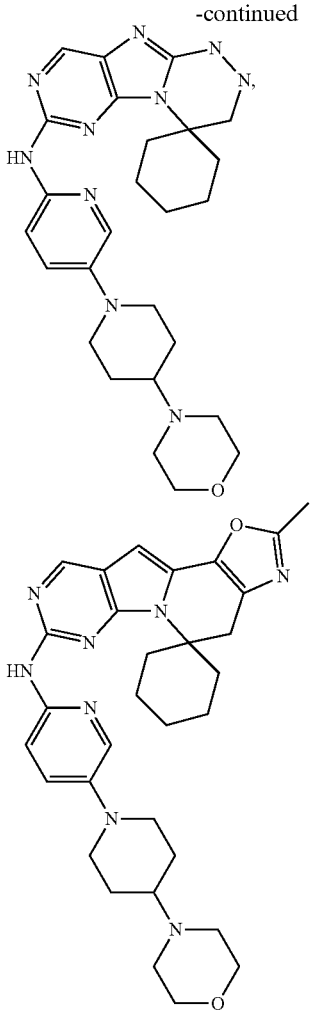

X. Examples

General Methods:

$^1$H NMR spectra were recorded on a 300 MHz Fourier transform Brücker spectrometer. Spectra were obtained from samples prepared in 5 mm diameter tubes in CDCl$_3$, CD$_3$OD or DMSO-d$_6$. The spin multiplicities are indicated by the symbols s (singlet), d (doublet), t (triplet), m (multiplet) and, br (broad). Coupling constants (J) are reported in Hz. MS spectra were obtained using electrospray ionization (ESI) on an Agilent Technologies 6120 quadrupole MS apparatus. The reactions were generally carried out under a dry nitrogen atmosphere using Sigma-Aldrich anhydrous solvents. All common chemicals were purchased from commercial sources.

Compounds of the present invention with stereocenters are drawn racemic for convenience. One skilled in the art will recognize that pure enantiomers can be prepared by methods known in the art. Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including simulated moving bed chromatography, is used in one embodiment. A wide variety of chiral stationary phases are commercially available.

Example 1. Preparation of Substituted 2-aminopyridines

1-Methyl-4-(6-nitro-3-pyridyl)piperazine

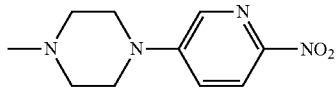 [SMILES: CN1CCN(c2ccc([N+](=O)[O-])nc2)CC1]

To 5-bromo-2-nitropyridine (4.93 g, 24.3 mmole) in DMF (20 mL) was added N-methylpiperazine (2.96 g, 1.1 eq) followed by the addition of DIPEA (4.65 mL, 26.7 mmole). The contents were heated at 90° C. for 24 hrs. After the addition of ethyl acetate (200 mL), water (100 mL) was added and the layers were separated. Drying followed by concentration afforded the crude product which was purified on a silica gel column using (0-10%) DCM/Methanol.

$^1$H NMR (DMSO-d$_6$) δ 8.26 (s, 1H), 8.15 (1H, d, J=9.3 Hz), 7.49 (1H, d, J=9.4 Hz), 3.50 (m, 4H), 2.49 (m, 4H), 2.22 (s, 3H).

5-(4-Methylpiperazin-1-yl)pyridin-2-amine

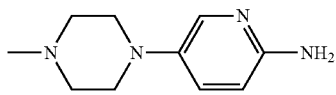

To 1-methyl-4-(6-nitro-3-pyridyl)piperazine 3.4 g in ethyl acetate (100 mL) and ethanol (100 mL) was added 10% Pd/c (400 mg) and then contents stirred under hydrogen (10 psi) overnight. After filtration through Celite®, the solvents were evaporated and the crude product was purified over silica gel using DCM/7N Ammonia in MeOH (0-5%) to afford 5-(4-methylpiperazin-1-yl)pyridin-2-amine (2.2 g).

$^1$HNMR (DMSO-d$_6$) δ 7.56 (1H, d, J=3 Hz), 7.13 (1H, m), 6.36 (1H, d, J=8.8 Hz), 5.33 (brs, 2H), 2.88 (m, 4H), 2.47 (m, 4H), 2.16 (s, 3H).

tert-Butyl 4-(6-amino-3-pyridyl)piperazine-1-carboxylate

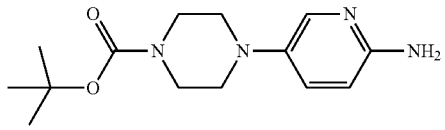 [SMILES: CC(C)(C)OC(=O)N1CCN(c2ccc(N)nc2)CC1]

The compound was prepared as described in WO 2010/020675 A1.

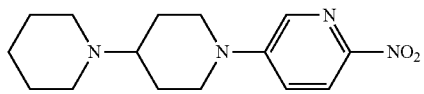

To 5-bromo-2-nitropyridine (1.2 g, 5.9 mmole) in DMSO (4 mL) was added 1-(4-piperidyl)piperidine (1.0 g, 5.9 mmole) and triethylamine (0.99 mL, 7.1 mmole). The contents were heated to 120° C. in a CEM Discovery microwave system for 3 hours. The crude reaction was then loaded over a silica gel column and eluted with DCM/methanol (0-20%) to afford 2-nitro-5-[4-(1-piperidyl)-1-piperidyl]pyridine as an oil (457 mg).

$^1$H NMR (600 MHz, DMSO-d$_6$) δ ppm 1.26-1.36 (m, 2H) 1.43 (m, 6H) 1.76 (m, 2H) 2.37 (m, 5H) 2.94 (t, J=12.74 Hz, 2H) 4.06 (d, J=13.47 Hz, 2H) 7.41 (dd, J=9.37, 2.64 Hz, 1H) 8.08 (d, J=9.37 Hz, 1H) 8.20 (d, J=2.64 Hz, 1H).

5-[4-(1-Piperidyl)-1-piperidyl]pyridin-2-amine

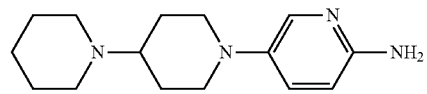 [SMILES: O=[N+]([O-])c1ccc(N2CCC(N3CCCCC3)CC2)cn1]

5-[4-(1-Piperidyl)-1-piperidyl]pyridin-2-amine was prepared in a manner similar to that used in the synthesis of 5-(4-methylpiperazin-1-yl)pyridin-2-amine.

$^1$H NMR (600 MHz, DMSO-d$_6$) δ ppm 1.13-1.37 (m, 6H) 1.40-1.63 (m, 6H) 1.71 (m, 2H), 2.24 (m, 1H) 2.43 (m, 2H) 3.33 (d, J=12.30 Hz, 2H) 5.31 (s, 2H) 6.33 (d, J=8.78 Hz, 1H) 7.10 (dd, J=8.78, 2.93 Hz, 1H) 7.55 (d, J=2.64 Hz, 1H). LCMS (ESI) 261 (M+H).

4-[1-(6-Nitro-3-pyridyl)-4-piperidyl] morpholine

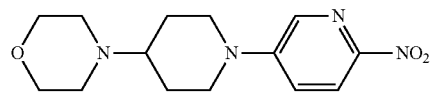 [SMILES: O=[N+]([O-])c1ccc(N2CCC(N3CCOCC3)CC2)cn1]

4-[1-(6-Nitro-3-pyridyl)-4-piperidyl]morpholine was synthesized in a manner similar to that used in the synthesis of 2-nitro-5-[4-(1-piperidyl)-1-piperidyl]pyridine.

1H NMR (600 MHz, DMSO-d$_6$) δ ppm 1.41 (m, 2H) 1.82 (m, 2H) 2.42 (m, 5H) 2.98 (t, J=12.44 Hz, 2H) 3.52 (s, 4H) 4.04 (d, J=12.88 Hz, 2H) 7.42 (d, J=9.37 Hz, 1H) 8.08 (d, J=9.08 Hz, 1H) 8.21 (s, 1H).

5-(4-Morpholino-1-piperidyl) pyridin-2-amine

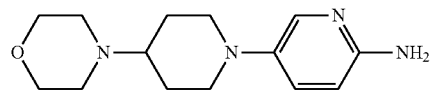 [SMILES: Nc1ccc(N2CCC(N3CCOCC3)CC2)cn1]

5-(4-Morpholino-1-piperidyl)pyridin-2-amine was prepared in a manner similar to that used in the synthesis of 5-(4-methylpiperazin-1-yl)pyridin-2-amine.

$^1$H NMR (600 MHz, DMSO-d$_6$) δ ppm 1.34-1.52 (m, 2H) 1.78 (m, 2H) 2.14 (m, 1H) 2.43 (m, 4H) 3.32 (d, J=12.30 Hz, 4H) 3.47-3.59 (m, 4H) 5.32 (s, 2H) 6.34 (d, J=8.78 Hz, 1H) 7.11 (dd, J=8.93, 2.78 Hz, 1H) 7.47-7.62 (m, 1H). LCMS (ESI) 263 (M+H).

4-[1-(6-Nitro-3-pyridyl)-4-piperidyl] thiomorpholine

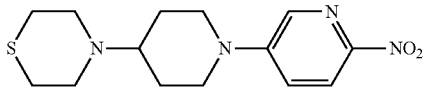

4-[1-(6-Nitro-3-pyridyl)-4-piperidyl] thiomorpholine was synthesized in a manner similar to that used in the synthesis of 2-nitro-5-[4-(1-piperidyl)-1-piperidyl]pyridine.

$^1$H NMR (600 MHz, DMSO-$d_6$) δ ppm 1.40-1.52 (m, 2H) 1.71 (m, 2H) 2.49-2.55 (m, 4H) 2.56-2.63 (m, 1H) 2.68-2.75 (m, 4H) 2.88-2.98 (m, 2H) 4.09 (d, J=13.18 Hz, 2H) 7.42 (dd, J=9.22, 3.07 Hz, 1H) 8.08 (d, J=9.37 Hz, 1H) 8.20 (d, J=3.22 Hz, 1H).

5-(4-Thiomorpholino-1-piperidyl) pyridin-2-amine

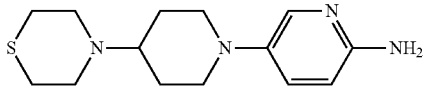

5-(4-Thiomorpholino-1-piperidyl) pyridin-2-amine was prepared in a manner similar to that used in the synthesis of 5-(4-methylpiperazin-1-yl)pyridin-2-amine.

$^1$H NMR (600 MHz, DMSO-$d_6$) δ ppm 1.47-1.59 (m, 2H) 1.65 (m, 2H) 2.22-2.38 (m, 1H) 2.50-2.59 (m, 6H) 2.68-2.82 (m, 4H) 3.33 (d, J=12.00 Hz, 2H) 5.31 (s, 2H) 6.33 (d, J=9.08 Hz, 1H) 7.10 (dd, J=8.78, 2.93 Hz, 1H) 7.55 (d, J=2.64 Hz, 1H). LCMS (ESI) 279 (M+H).

2-Nitro-5-(1-piperidyl)pyridine

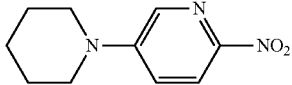 [SMILES: O=[N+]([O-])c1ccc(N2CCCCC2)cn1]

2-Nitro-5-(1-piperidyl) pyridine was synthesized in a manner similar to that used in the synthesis of 2-nitro-5-[4-(1-piperidyl)-1-piperidyl]pyridine.

$^1$H NMR (600 MHz, DMSO-$d_6$) δ ppm 1.56 (m, 6H) 3.49 (d, J=4.39 Hz, 4H) 7.30-7.47 (m, 1H) 8.02-8.12 (m, 1H) 8.15-8.26 (m, 1H).

5-(1-Piperidyl)pyridin-2-amine

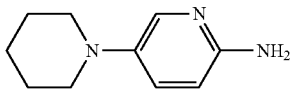 [SMILES: Nc1ccc(N2CCCCC2)cn1]

5-(1-Piperidyl) pyridin-2-amine was prepared in a manner similar to that used in the synthesis of 5-(4-methylpiperazin-1-yl)pyridin-2-amine.

$^1$H NMR (600 MHz, DMSO-$d_6$) δ ppm 1.39-1.46 (m, 2H) 1.51-1.62 (m, 4H) 2.75-2.92 (m, 4H) 5.30 (s, 2H) 6.34 (d, J=8.78 Hz, 1H) 7.09 (dd, J=8.78, 2.93 Hz, 1H) 7.54 (d, J=2.93 Hz, 1H). LCMS (ESI) 178 (M+H).

4-(6-Nitro-3-pyridyl) thiomorpholine

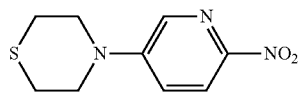

4-(6-nitro-3-pyridyl) thiomorpholine was synthesized in a manner similar to that used in the synthesis of 2-nitro-5-[4-(1-piperidyl)-1-piperidyl]pyridine.

$^1$H NMR (600 MHz, DMSO-$d_6$) δ ppm 2.56-2.69 (m, 4H) 3.79-3.92 (m, 4H) 7.43 (dd, J=9.22, 3.07 Hz, 1H) 8.10 (d, J=9.37 Hz, 1H) 8.20 (d, J=2.93 Hz, 1H).

5-Thiomorpholinopyridin-2-amine

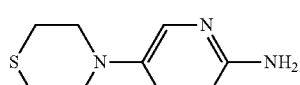

5-Thiomorpholinopyridin-2-amine was prepared in a manner similar to that used in the synthesis of 5-(4-methylpiperazin-1-yl) pyridin-2-amine.

$^1$H NMR (600 MHz, DMSO-$d_6$) δ ppm 2.59-2.73 (m, 4H) 3.04-3.20 (m, 4H) 5.41 (s, 2H) 6.35 (d, J=8.78 Hz, 1H) 7.10 (dd, J=8.78, 2.93 Hz, 1H) 7.57 (d, J=2.64 Hz, 1H). LCMS (ESI) 196 (M+H).

tert-Butyl (4R)-5-(6-nitro-3-pyridyl)-2,5-diazabicyclo [2.2.1]heptane-2-carboxylate

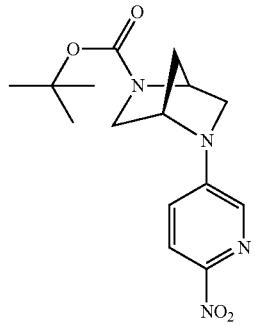 [SMILES: CC(C)(C)OC(=O)N1C[C@H]2CC1CN2c1ccc([N+](=O)[O-])nc1]

tert-Butyl (4R)-5-(6-nitro-3-pyridyl)-2,5-diazabicyclo [2.2.1]heptane-2-carboxylate was synthesized in a manner similar to that used in the synthesis of 2-nitro-5-[4-(1-piperidyl)-1-piperidyl]pyridine.

$^1$H NMR (600 MHz, DMSO-$d_6$) δ ppm 1.33 (d, J=32.21 Hz, 11H) 1.91 (m, 2H) 3.15 (d, J=10.25 Hz, 1H) 3.58 (m, 1H) 4.46 (m, 1H) 4.83 (s, 1H) 7.16 (s, 1H) 7.94 (s, 1H) 8.05-8.16 (m, 1H).

tert-Butyl (4R)-5-(6-amino-3-pyridyl)-2,5-diazabicyclo[2.2.1]heptane-2-carboxylate

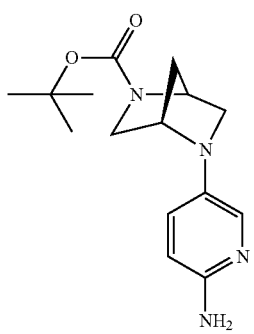 [SMILES: CC(C)(C)OC(=O)N1C[C@H]2CC1CN2c1ccc(N)nc1]

tert-Butyl (4R)-5-(6-amino-3-pyridyl)-2,5-diazabicyclo[2.2.1]heptane-2-carboxylate was prepared in a manner similar to that used in the synthesis of 5-(4-methylpiperazin-1-yl)pyridin-2-amine.

$^1$H NMR (600 MHz, DMSO-d$_6$) δ ppm 1.31 (d, J=31.91 Hz, 11H) 1.83 (m, 2H) 2.71-2.82 (m, 1H) 3.44 (m, 1H) 4.30 (d, 2H) 5.08 (s, 2H) 6.35 (d, J=8.78 Hz, 1H) 6.77-6.91 (m, 1H) 7.33 (s, 1H). LCMS (ESI) 291 (M+H).

N,N-dimethyl-1-(6-nitro-3-pyridyl)piperidin-4-amine

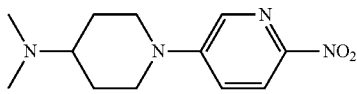 [SMILES: CN(C)C1CCN(c2ccc([N+](=O)[O-])nc2)CC1]

N,N-dimethyl-1-(6-nitro-3-pyridyl)piperidin-4-amine was synthesized in a manner similar to that used in the synthesis of 2-nitro-5-[4-(1-piperidyl)-1-piperidyl]pyridine.

$^1$H NMR (600 MHz, DMSO-d$_6$) δ ppm 1.30-1.45 (m, 2H) 1.79 (m, 2H) 2.14 (s, 6H) 2.33 (m, 1H) 2.92-3.04 (m, 2H) 4.03 (d, J=13.76 Hz, 2H) 7.42 (dd, J=9.22, 3.07 Hz, 1H) 8.04-8.11 (m, 1H) 8.21 (d, J=2.93 Hz, 1H).

5-[4-(Dimethylamino)-1-piperidyl] pyridin-2-amine

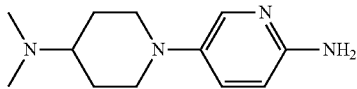 [SMILES: CN(C)C1CCN(c2ccc(N)nc2)CC1]

5-[4-(dimethylamino)-1-piperidyl]pyridin-2-amine was prepared in a manner similar to that used in the synthesis of 5-(4-methylpiperazin-1-yl)pyridin-2-amine.

$^1$H NMR (600 MHz, DMSO-d$_6$) δ ppm 1.35-1.50 (m, 2H) 1.69-1.81 (m, 2H) 2.00-2.10 (m, 1H) 2.11-2.22 (s, 6H) 3.17-3.36 (m, 4H) 5.19-5.38 (s, 2H) 6.34 (d, J=8.78 Hz, 1H) 7.10 (dd, J=8.78, 2.93 Hz, 1H) 7.55 (d, J=2.63 Hz, 1H). LCMS (ESI) 221 (M+H).

4-(6-Nitro-3-pyridyl) morpholine

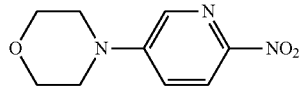 [SMILES: O=[N+]([O-])c1ccc(N2CCOCC2)cn1]

4-(6-Nitro-3-pyridyl) morpholine was synthesized in a manner similar to that used in the synthesis of 2-nitro-5-[4-(1-piperidyl)-1-piperidyl] pyridine.

5-Morpholinopyridin-2-amine

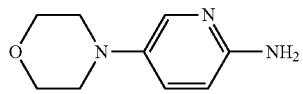

5-Morpholinopyridin-2-amine was prepared in a manner similar to that used in the synthesis of 5-(4-methylpiperazin-1-yl) pyridin-2-amine.

$^1$H NMR (600 MHz, CHCl$_3$-d) δ ppm 2.91-3.00 (m, 4H) 3.76-3.84 (m, 4H) 4.19 (br. s., 2H) 6.45 (d, J=8.78 Hz, 1H) 7.12 (dd, J=8.78, 2.93 Hz, 1H) 7.72 (d, J=2.93 Hz, 1H).

5-(4-Isobutylpiperazin-1-yl) pyridin-2-amine

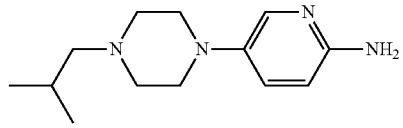

1-Isobutyl-4-(6-nitro-3-pyridyl)piperazine was synthesized in a manner similar to that used in the synthesis of 2-nitro-5-[4-(1-piperidyl)-1-piperidyl]pyridine which was then converted 5-(4-isobutylpiperazin-1-yl)pyridin-2-amine in a manner similar to that used in the synthesis of 5-(4-methylpiperazin-1-yl)pyridin-2-amine.

$^1$H NMR (600 MHz, CHCl$_3$-d) δ ppm 0.88 (d, J=6.73 Hz, 6H) 1.71-1.84 (m, 1H) 2.10 (d, J=7.32 Hz, 2H) 2.46-2.58 (m, 4H) 2.97-3.07 (m, 4H) 4.12 (s, 2H) 6.45 (d, J=8.78 Hz, 1H) 7.14 (dd, J=8.78, 2.93 Hz, 1H) 7.75 (d, J=2.93 Hz, 1H). LCMS (ESI) 235 (M+H).

5-(4-Isopropylpiperazin-1-yl) pyridin-2-amine

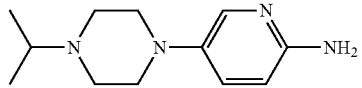 [SMILES: CC(C)N1CCN(c2ccc(N)nc2)CC1]

1-Isopropyl-4-(6-nitro-3-pyridyl)piperazine was synthesized in a manner similar to that used in the synthesis of 2-nitro-5-[4-(1-piperidyl)-1-piperidyl]pyridine which was then converted to 5-(4-isopropylpiperazin-1-yl)pyridin-2-amine in a manner similar to that used in the synthesis of 5-(4-methylpiperazin-1-yl)pyridin-2-amine.

$^1$H NMR (600 MHz, CHCl$_3$-d) δ ppm 1.06 (d, J=6.44 Hz, 6H) 2.59-2.75 (m, 5H) 2.97-3.10 (m, 4H) 4.13 (s, 2H) 6.45

(d, J=8.78 Hz, 1H) 7.15 (dd, J=9.08, 2.93 Hz, 1H) 7.76 (d, J=2.93 Hz, 1H). LCMS (ESI) 221 (M+H).

5-[(2R,6S)-2,6-Dimethylmorpholin-4-yl]pyridin-2-amine

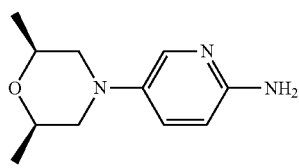

(2S,6R)-2,6-Dimethyl-4-(6-nitro-3-pyridyl)morpholine was synthesized in a manner similar to that used in the synthesis of 2-nitro-5-[4-(1-piperidyl)-1-piperidyl]pyridine which was then converted to 5-[(2R,6S)-2,6-dimethylmorpholin-4-yl]pyridin-2-amine in a manner similar to that used in the synthesis of 5-(4-methylpiperazin-1-yl)pyridin-2-amine. $^1$H NMR (600 MHz, CHCl$_3$-d) δ ppm 1.20 (d, J=6.44 Hz, 6H) 2.27-2.39 (m, 2H) 3.11-3.21 (m, 2H) 3.70-3.84 (m, 2H) 4.15 (s, 2H) 6.45 (d, J=8.78 Hz, 1H) 7.12 (dd, J=8.78, 2.93 Hz, 1H) 7.72 (d, J=2.63 Hz, 1H). LCMS (ESI) 208 (M+H).

5-[(3R,5S)-3,5-Dimethylpiperazin-1-yl]pyridin-2-amine

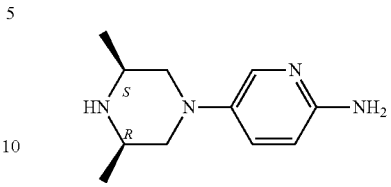

(3S,5R)-3,5-Dimethyl-1-(6-nitro-3-pyridyl)piperazine was synthesized in a manner similar to that used in the synthesis of 2-nitro-5-[4-(1-piperidyl)-1-piperidyl]pyridine which was then converted to 5-[(3R,5S)-3,5-dimethylpiperazin-1-yl]pyridin-2-amine in a manner similar to that used in the synthesis of 5-(4-methylpiperazin-1-yl)pyridin-2-amine. $^1$H NMR (600 MHz, CHCl$_3$-d) δ ppm 1.09 (d, J=6.44 Hz, 6H) 2.20 (t, J=10.83 Hz, 2H) 2.95-3.08 (m, 2H) 3.23 (dd, J=11.71, 2.05 Hz, 2H) 4.13 (s, 2H) 6.45 (d, J=8.78 Hz, 1H) 7.14 (dd, J=8.78, 2.93 Hz, 1H) 7.73 (d, J=2.63 Hz, 1H). LCMS (ESI) 207 (M+H).

Example 2: Compounds of the Present Invention

| Final Cmpd # | Structure | Name |
|---|---|---|
| 1 | 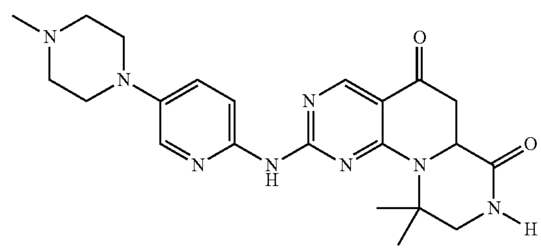 [SMILES: CN1CCN(c2ccc(Nc3ncc4c(n3)N3C(CC4=O)C(=O)NCC3(C)C)nc2)CC1] | 10,10-dimethyl-2-((5-(4-methylpiperazin-1-yl)pyridin-2-yl)amino)-6,6a,9,10-tetrahydro-5H-pyrazino[1',2':1,6]pyrido[2,3-d]pyrimidine-5,7(8H)-dione |
| 2 | 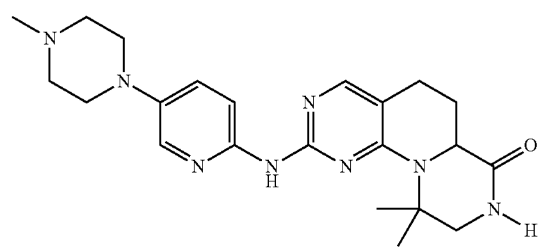 [SMILES: CN1CCN(c2ccc(Nc3ncc4c(n3)N3C(CC4)C(=O)NCC3(C)C)nc2)CC1] | 10,10-dimethyl-2-((5-(4-methylpiperazin-1-yl)pyridin-2-yl)amino)-6,6a,9,10-tetrahydro-5H-pyrazino[1',2':1,6]pyrido[2,3-d]pyrimidin-7(8H)-one |
| 3 | 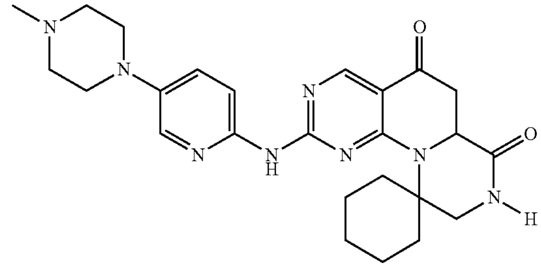 [SMILES: CN1CCN(c2ccc(Nc3ncc4c(n3)N3C(CC4=O)C(=O)NCC34CCCCC4)nc2)CC1] | 2'-((5-(4-methylpiperazin-1-yl)pyridin-2-yl)amino)-6',6a',8',9'-tetrahydrospiro[cyclohexane-1,10'-pyrazino[1',2':1,6]pyrido[2,3-d]pyrimidine1-5',7'-dione |

| Final Cmpd # | Structure | Name |
|---|---|---|
| 4 | 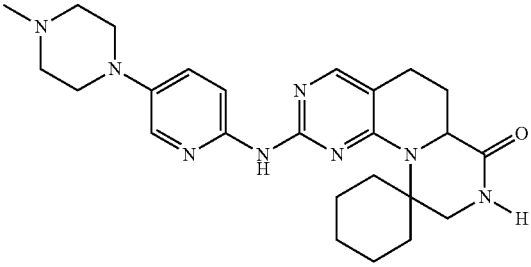 [SMILES: CN1CCN(c2ccc(Nc3ncc4c(n3)N3C(CC4)C(=O)NCC34CCCCC4)nc2)CC1] | 2'-((5-(4-methylpiperazin-1-yl)pyridin-2-yl)amino)-6',6a',8',9'-tetrahydrospiro[cyclohexane-1,10'-pyrazino[1',2':1,6]pyrido[2,3-d]pyrimidin]-7'(5'H)-one |
| 5 | 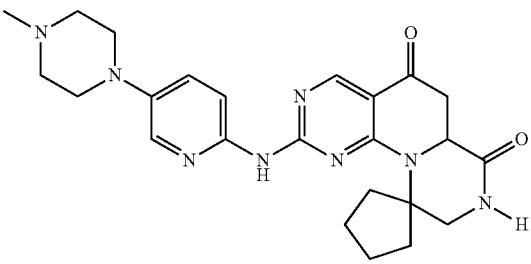 [SMILES: CN1CCN(c2ccc(Nc3ncc4c(n3)N3C(CC4=O)C(=O)NCC34CCCC4)nc2)CC1] | 2'-((5-(4-methylpiperazin-1-yl)pyridin-2-yl)amino)-6',6a',8',9'-tetrahydrospiro[cyclopentane-1,10'-pyrazino[1',2':1,6]pyrido[2,3-d]pyrimidine]-5',7'-dione |
| 6 | 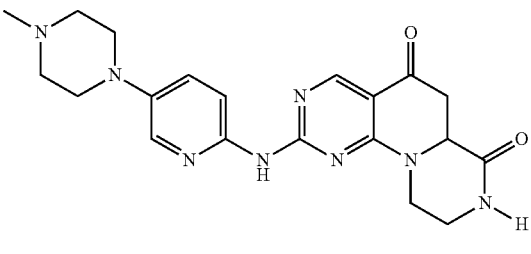 [SMILES: CN1CCN(c2ccc(Nc3ncc4c(n3)N3CCNC(=O)C3CC4=O)nc2)CC1] | 2-((5-(4-methylpiperazin-1-yl)pyridin-2-yl)amino)-6,6a,9,10-tetrahydro-5H-pyrazino[1',2':1,6]pyrido[2,3-d]pyrimidine-5,7(8H)-dione |
| 7 | 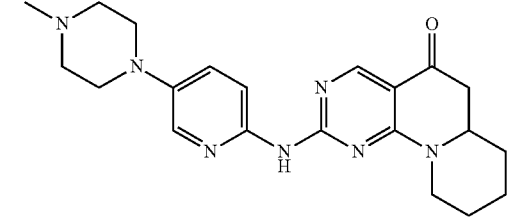 [SMILES: CN1CCN(c2ccc(Nc3ncc4c(n3)N3CCCCC3CC4=O)nc2)CC1] | 2-((5-(4-methylpiperazin-1-yl)pyridin-2-yl)amino)-6,6a,7,8,9,10-hexahydro-5H-pyrimido[5,4-c]quinolizin-5-one |
| 8 | 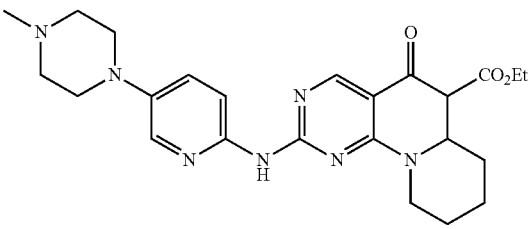 [SMILES: CCOC(=O)C1C(=O)c2cnc(Nc3ccc(N4CCN(C)CC4)cn3)nc2N2CCCCC12] | ethyl 2-((5-(4-methylpiperazin-1-yl)pyridin-2-yl)amino)-5-oxo-6,6a,7,8,9,10-hexahydro-5H-pyrimido[5,4-c]quinolizine-6-carboxylate |
| 9 | 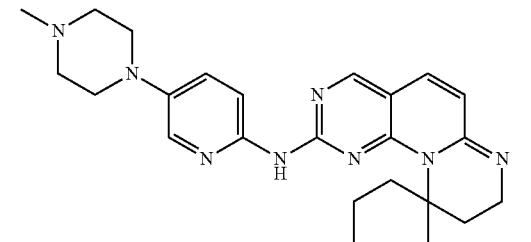 | N-(5-(4-methylpiperazin-1-yl)pyridin-2-yl)-8',9'-dihydrospiro[cyclohexane-1,10'-pyrido[1,6-a:2,3-d']dipyrimidin]-2'-amine |

Example 3: Biological Data for Compounds of the Present Invention
BIOLOGICAL TABLE 1
| Final Cmpd # | Compound | CDK4/ CycD IC$_{50}$ (μM) | CDK6/ CycD3 IC$_{50}$ (μM) | CDK2/ CycE IC$_{50}$ (μM) | CDK2/ CycA IC$_{50}$ (μM) | CDK5/ p35 IC$_{50}$ (μM) |
|---|---|---|---|---|---|---|
| 1 | 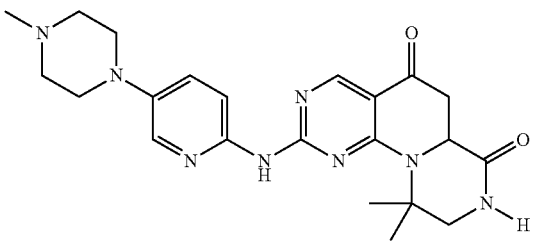 [SMILES: CN1CCN(c2ccc(Nc3ncc4c(n3)N3C(CC4=O)C(=O)NCC3(C)C)nc2)CC1] | 8.06 | 30.6 | >100 | >100 | >100 |
| 2 | 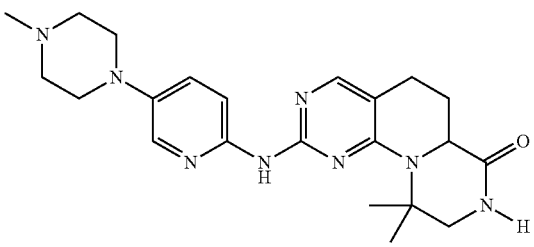 [SMILES: CN1CCN(c2ccc(Nc3ncc4c(n3)N3C(CC4)C(=O)NCC3(C)C)nc2)CC1] | >100 | >100 | >100 | >100 | >100 |
| 3 | 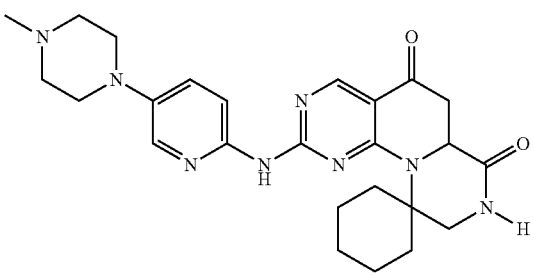 [SMILES: CN1CCN(c2ccc(Nc3ncc4c(n3)N3C(CC4=O)C(=O)NCC34CCCCC4)nc2)CC1] | >100 | >100 | >100 | >100 | >100 |
| 4 | 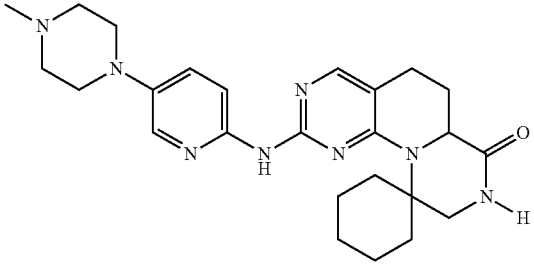 [SMILES: CN1CCN(c2ccc(Nc3ncc4c(n3)N3C(CC4)C(=O)NCC34CCCCC4)nc2)CC1] | 47.7 | 75.9 | >100 | 86.4 | >100 |
| 5 | 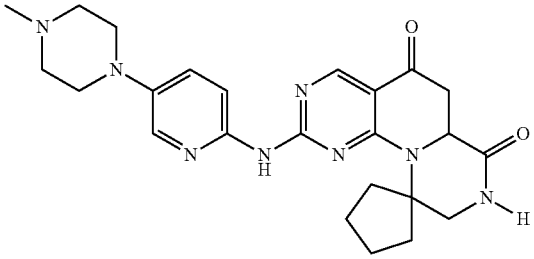 [SMILES: CN1CCN(c2ccc(Nc3ncc4c(n3)N3C(CC4=O)C(=O)NCC34CCCC4)nc2)CC1] | >100 | >100 | >100 | >100 | >100 |

BIOLOGICAL TABLE 1-continued

| Final Cmpd # | Compound | CDK4/ CycD IC$_{50}$ (μM) | CDK6/ CycD3 IC$_{50}$ (μM) | CDK2/ CycE IC$_{50}$ (μM) | CDK2/ CycA IC$_{50}$ (μM) | CDK5/ p35 IC$_{50}$ (μM) |
|---|---|---|---|---|---|---|
| 6 | [structure] | 14.4 | 50.4 | >100 | >100 | >100 |
| 7 | [structure] | 4.7 | 1.8 | >100 | >100 | >100 |
| 8 | [structure] | 4.1 | 3.5 | >100 | >100 | >100 |
| 9 | [structure] | 2.6 | 1.8 | >100 | >100 | >100 |

BIOLOGICAL TABLE 2

| Final cmpd # | Compound | CDK5/ p25 IC$_{50}$ (μM) | CDK7/ CycH/ MAT1 IC$_{50}$ (μM) | CDK9/ CycT IC$_{50}$ (μM) |
|---|---|---|---|---|
| 1 | [structure] | >100 | >100 | >100 |

BIOLOGICAL TABLE 2-continued

| Final cmpd # | Compound | CDK5/ p25 IC$_{50}$ (μM) | CDK7/ CycH/ MAT1 IC$_{50}$ (μM) | CDK9/ CycT IC$_{50}$ (μM) |
|---|---|---|---|---|
| 2 | | >100 | | >100 |
| 3 | | >100 | >100 | >100 |
| 4 | | >100 | >100 | >100 |
| 5 | | >100 | >100 | >100 |
| 6 | | >100 | >100 | >100 |

BIOLOGICAL TABLE 2-continued
| Final cmpd # | Compound | CDK5/ p25 IC$_{50}$ (μM) | CDK7/ CycH/ MAT1 IC$_{50}$ (μM) | CDK9/ CycT IC$_{50}$ (μM) |
|---|---|---|---|---|
| 7 | | >100 | >100 | >100 |
| 8 | | >100 | >100 | >100 |
| 9 | | >100 | >100 | >100 |
Example 4. Preparation of Final Compounds
Scheme 25: Synthesis of 2'-((5-(4-Methylpiperazin-1-yl)pyridin-2-yl)amino)-7',8'-dihydro-6'H-spiro[cyclohexane-1,9'-pyrazino[1,2-e]purin]-6'-one (Compound 10)
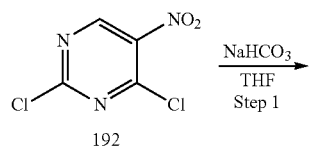
192
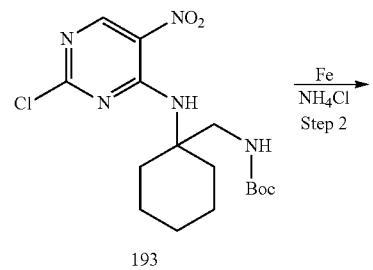
193
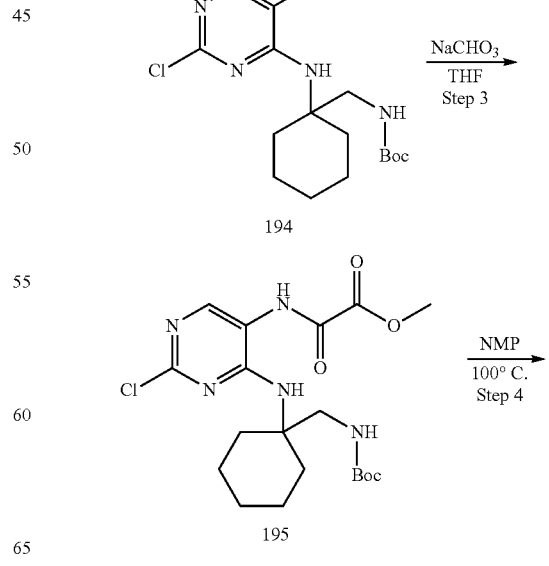
-continued
194
195

-continued

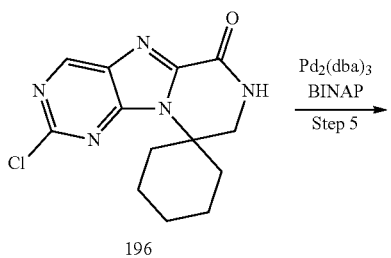

196

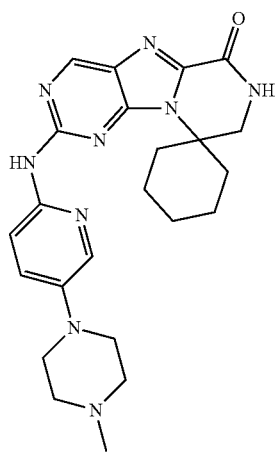

COMPOUND 10

Step 1: Synthesis of tert-Butyl ((1-((2-chloro-5-nitropyrimidin-4-yl)amino)cyclohexyl)methyl)carbamate (193)

To a solution of 2,4-dichloro-5-nitropyrimidine (192, 3 g, 15.5 mmol), tert-butyl ((1-aminocyclohexyl)methyl)carbamate (3.5 g, 15.5 mmol) in THF (20 mL) was added followed by NaHCO$_3$(4.0 g, 47.6 mmol). After stirring at room temperature for 3 hours, the reaction mixture was quenched with water (20 mL) and extracted with EtOAc (20 mL). The organic layer was separated and washed with brine, dried over MgSO$_4$, filtered and concentrated in vacuo. The resulting residue was purified by column chromatography to afford tert-butyl ((1-((2-chloro-5-nitropyrimidin-4-yl)amino)cyclohexyl)methyl)carbamate (193, 3.5 g, 9.1 mmol).

MS (ESI+): m/z 386 [M+H]$^+$.

Step 2: Synthesis of tert-Butyl ((1-((5-amino-2-chloropyrimidin-4-yl)amino)cyclohexyl)methyl)carbamate (194)

To a solution of tert-butyl ((1-((2-chloro-5-nitropyrimidin-4-yl)amino)cyclohexyl) methyl)carbamate (193, 3 g, 7.8 mmol) in EtOH (30 mL) was added Fe powder (6 g, 107 mmol) and sat. aq. NH$_4$Cl (1 mL). The reaction mixture was refluxed overnight. After cooling to room temperature, the reaction mixture was filtered and the filtrate was concentrated to afford the crude product, which was purified by column chromatography to afford tert-butyl ((1-((5-amino-2-chloropyrimidin-4-yl)amino)cyclohexyl)methyl)carbamate (194, 2.2 g, 6.2 mmol).

MS (ESI+): m/z 356 [M+H]$^+$.

Step 3: Synthesis of Methyl 2-((4-((1-(((tert-butoxycarbonyl)amino)methyl) cyclohexyl)amino)-2-chloropyrimidin-5-yl)amino)-2-oxoacetate (195)

To a solution of tert-butyl ((1-((5-amino-2-chloropyrimidin-4-yl)amino) cyclohexyl)methyl)carbamate (194, 2 g, 5.6 mmol) in THF (10 mL) was added methyl 2-chloro-2-oxoacetate (0.7 g, 5.7 mmol) and NaHCO$_3$(3 g, 35.7 mmol). After stirring at room temperature for 4 h, the reaction mixture was quenched with H$_2$O (20 mL) and extracted with EtOAc (20 mL). The organic layer was separated and washed with brine, dried over MgSO$_4$, filtered and concentrated in vacuo. The resulting residue was purified by column chromatography to afford methyl 2-((4-((1-(((tert-butoxycarbonyl)amino)methyl)cyclohexyl)amino)-2-chloropyrimidin-5-yl)amino)-2-oxoacetate (195, 2.5 g, 5.6 mmol). MS (ESI): m/z 442 [M+H]$^+$.

Step 4: Synthesis of 2'-Chloro-7',8'-dihydro-6'H-spiro[cyclohexane-1,9'-pyrazino [1,2-e]purin]-6'-one (196)

A solution of methyl 2-((4-((1-(((tert-butoxycarbonyl) amino)methyl)cyclohexyl) amino)-2-chloropyrimidin-5-yl) amino)-2-oxoacetate (195, 1.5 g, 3.4 mmol) in NMP (50 mL) was stirred at 100° C. for 5h. The reaction mixture was cooled to room temperature and purified by column chromatography to afford 2'-chloro-7',8'-dihydro-6'H-spiro[cyclohexane-1,9'-pyrazino[1,2-e]purin]-6'-one (196, 300 mg, 1.0 mmol). MS (ESI+): m/z 292 [M+H]$^+$.

Step 5: Synthesis of 2'-((5-(4-Methylpiperazin-1-yl)pyridin-2-yl)amino)-7',8'-dihydro-6'H-spiro[cyclohexane-1,9'-pyrazino[1,2-e]purin]-6'-one (COMPOUND 10)

Under N$_2$ atmosphere, to a solution of 2'-chloro-7',8'-dihydro-6'H— spiro[cyclohexane-1,9'-pyrazino[1,2-e]purin]-6'-one (196, 300 mg, 1.0 mmol), 5-(4-methylpiperazin-1-yl)pyridin-2-amine (193 mg, 1.0 mmol), Pd$_2$(dba)$_3$ (92.23 mg, 0.1 mmol) and BINAP (125.4 mg, 0.2 mmol) in toluene (25 mL) was added LHMDS (1.5 mL, 1 M in THF). The reaction mixture was kept at 100° C. overnight. After cooling to room temperature, the reaction mixture was quenched with water (25 mL) and extracted with EtOAc (25 mL). The organic layer was separated and concentrated in vacuo. The resulting residue was purified by prep TLC to provide 2'-((5-(4-methylpiperazin-1-yl)pyridin-2-yl)amino)-7',8'-dihydro-6'H-spiro [cyclohexane-1,9'-pyrazino [1,2-e]purin]-6'-one (COMPOUND 10, 1.1 mg, 0.0025 mmol). MS (ESI+): m/z 448 [M+H]+; $^1$H NMR (300 MHz, MeOD): δ 8.05-7.95 (m, 2H), 7.86 (d, J=9.0 Hz, 1H), 7.49 (d, J=8.4 Hz, 1H), 4.03 (s, 2H), 3.28-3.22 (m, 4H), 3.08-2.91 (m, 2H), 2.78-2.70 (m, 4H), 2.42 (s, 3H), 1.82-1.70 (m, 5H), 1.47-1.39 (m, 3H).

Scheme 26: Synthesis of (4aR,12aR)-10-((5-(4-Methylpiperazin-1-yl)pyridin-2-yl)amino)-1,3,4,4a,5,12a-hexahydropyrimido[5',4':4,5]pyrrolo[1,2-a]quinoxalin-6(2H)-one (COMPOUND 22)

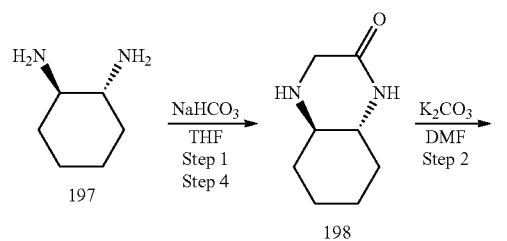

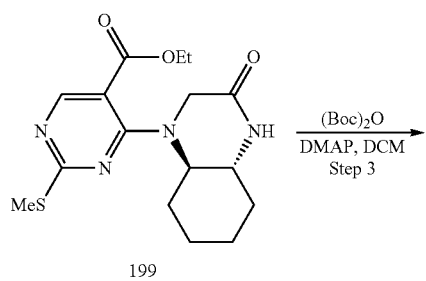

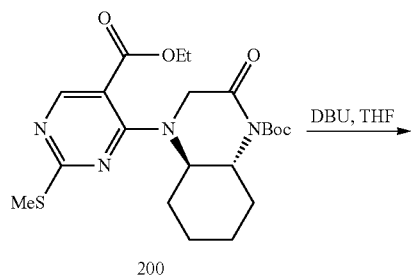

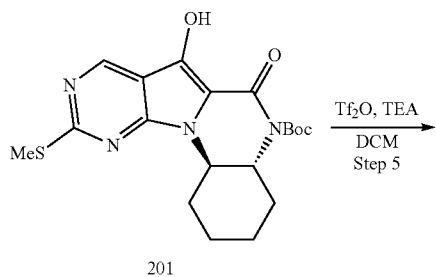

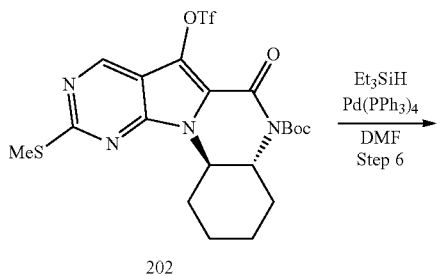

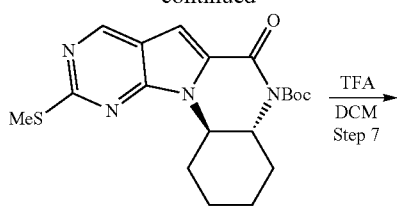

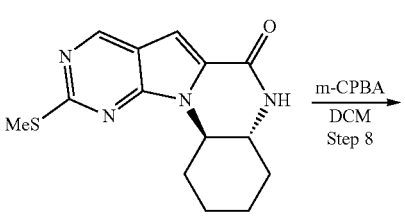

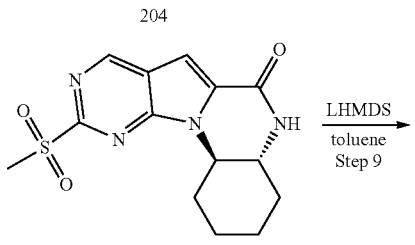

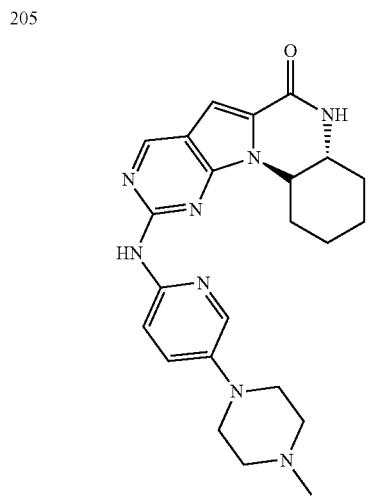

COMPOUND 22

Step 1: Synthesis of (4aR,8aR)-Octahydroquinoxalin-2(1H)-one (198)

To a mixture of (1R,2R)-cyclohexane-1,2-diamine (197, 1 g, 8.75 mmol) and NaHCO$_3$ (2.2 g, 26.2 mmol) in THF (40 mL) at 0° C. was added a solution of methyl 2-bromoacetate (1.34 g, 8.75 mmol) in THF (20 mL) in dropwise. After stirring at 0° C. for 2 h, the reaction mixture was warmed to room temperature and stirred for an additional 1 h. The reaction mixture was then quenched with water (40 mL) and extracted with EtOAc (50 mL×2). The combined organic phases were dried over MgSO$_4$, filtered and concentrated in vacuo. The resulting residue was purified by column chromatography to provide (4aR,8aR)-octahydroquinoxalin-2(1H)-one (198, 700 mg, 4.54 mmol).

Step 2: Synthesis of Ethyl 2-(methylthio)-4-((4aR, 8aR)-3-oxooctahydroquinoxalin-1(2H)-yl)pyrimidine-5-carboxylate (199)

To a solution of (4aR,8aR)-octahydroquinoxalin-2(1H)-one (198, 4.7 g, 30.5 mmol) in DMF (140 mL) was added ethyl chloro-2-(methylthio)pyrimidine-5-carboxylate (7 g, 30.1 mmol) and $K_2CO_3$ (12.6 g, 91.2 mmol). After stirring at 80° C. for 2 h, the reaction mixture was cooled to room temperature, quenched with water (250 mL) and extracted with EtOAc (150 mL×2). The combined organic phases were washed with water (100 mL×2) and brine (100 mL). After concentration in vacuo, the resulting residue was purified by column chromatography to afford ethyl 2-(methylthio)-4-((4aR,8aR)-3-oxooctahydroquinoxalin-1(2H)-yl)pyrimidine-5-carboxylate (199, 7.6 g, 21.6 mmol) as a white solid. MS (ESI+): m/z 351 [M+H]$^+$.

Step 3: Synthesis of tert-Butyl(4aR,8aR)-4-(5-(ethoxycarbonyl)-2-(methylthio)pyrimidin-4-yl)-2-oxooctahydroquinoxaline-1(2H)-carboxylate (200)

To a solution of ethyl 2-(methylthio)-4-((4aR,8aR)-3-oxooctahydroquinoxalin-1 (2H)-yl)pyrimidine-5-carboxylate (199, 7.6 g, 21.6 mmol) in DCM (200 mL) was added Boc$_2$O (7.1 g, 32.5 mmol) and DMAP (7.9 g, 64.7 mmol). After stirring at room temperature for 12 h, the reaction mixture was quenched with water (250 mL) and extracted with DCM (100 mL×2). The combined organic phases were washed with water (50 mL), brine (50 mL), dried over MgSO$_4$, and concentrated in vacuo. The resulting residue was purified by column chromatography to provide tert-butyl(4aR,8aR)-4-(5-(ethoxycarbonyl)-2-(methylthio)pyrimidin-4-yl)-2-oxooctahydroquinoxaline-1(2H)-carboxylate (200, 8.0 g, 17.7 mmol) as a colorless oil. MS (ESI+): m/z 451 [M+H]$^+$.

Step 4: Synthesis of tert-Butyl (4aR,12aR)-7-hydroxy-10-(methylthio)-6-oxo-1,2,3,4,4a,12a-hexahydropyrimido [5',4':4,5]pyrrolo [1,2-a]quinoxaline-5 (6H)-carboxylate (201)

To a solution of tert-butyl (4aR,8aR)-4-(5-(ethoxycarbonyl)-2-(methylthio) pyrimidin-4-yl)-2-oxooctahydroquinoxaline-1(2H)-carboxylate (200, 7.0 g, 15.5 mmol) in THF (100 mL) at 0° C. was added DBU (3.5 g, 23.0 mmol). The reaction was gradually warmed to room temperature. After stirring for 2 h, the reaction mixture was concentrated in vacuo. The resulting residue was purified by column chromatography to provide tert-butyl (4aR,12aR)-7-hydroxy-10-(methylthio)-6-oxo-1,2,3,4,4a, 12a-hexahydropyrimido[5',4':4,5]pyrrolo[1,2-a]quinoxaline-5(6H)-carboxylate (201, 4.8 g, 11.8 mmol) as a green solid. MS (ESI+): m/z 405 [M+H]$^+$.

Step 5: Synthesis of tert-Butyl (4aR,12aR)-10-(methylthio)-6-oxo-7-(((trifluoromethyl)sulfonyl)oxy)-1,2,3,4,4a,12a-hexahydropyrimido [5',4':4,5] pyrrolo[1,2-a]quinoxaline-5(6H)-carboxylate (202)

To a solution of tert-butyl (4aR,12aR)-7-hydroxy-10-(methylthio)-6-oxo-1,2,3,4,4a, 12a-hexahydropyrimido[5',4':4,5]pyrrolo[1,2-a]quinoxaline-5(6H)-carboxylate (201, 200 mg, 0.49 mmol) and Et$_3$N (0.3 mL, 2.16 mmol) in DCM (5 mL) at 0° C. was added Tf$_2$O (209 mg, 0.74 mmol). The reaction was gradually warmed to room temperature. After stirring for 2 h, the reaction mixture was concentrated in vacuo. The resulting residue was purified by column chromatography to provide tert-butyl (4aR,12aR)-10-(methylthio)-6-oxo-7-(((trifluoromethyl)sulfonyl)oxy)-1,2,3,4,4a, 12a-hexahydropyrimido[5',4':4,5]pyrrolo[1,2-a]quinoxaline-5(6H)-carboxylate (202, 180 mg, 0.34 mmol). MS (ESI+): m/z 536 [M+H]$^+$.

Step 6: Synthesis of tert-Butyl (4aR,12aR)-10-(methylthio)-6-oxo-1,2,3,4,4a,12a-hexahydropyrimido [5',4':4,5]pyrrolo [1,2-a]quinoxaline-5(6H)-carboxylate (203)

Under N$_2$ atmosphere, to a solution of tert-butyl (4aR, 12aR)-10-(methylthio)-6-oxo-7-(((trifluoromethyl)sulfonyl) oxy)-1,2,3,4,4a, 12a-hexahydropyrimido[5',4':4,5]pyrrolo [1,2-a]quinoxaline-5(6H)-carboxylate (202, 250 mg, 0.47 mmol) and Pd(PPh$_3$)$_4$ (54 mg, 0.47 mmol) in DMF (5 mL) was added Et$_3$SiH (81.4 mg, 0.70 mmol). After stirring at 50° C. for 12 h, the reaction mixture was quenched with water (20 mL) and extracted with EtOAc (10 mL×3). The combined organic layers were washed with water (5 mL×2) and brine (5 mL), dried over MgSO$_4$, and concentrated in vacuo. The resulting residue was purified by column chromatography to provide tert-butyl (4aR,12aR)-10-(methylthio)-6-oxo-1,2,3,4,4a,12a-hexahydropyrimido[5',4':4,5] pyrrolo[1,2-a]quinoxaline-5(6H)-carboxylate (203, 70 mg, 0.18 mmol).

Step 7: Synthesis of (4aR,12aR)-10-(Methylthio)-1,3,4,4a,5,12a-hexahydropyrimido [5',4':4,5]pyrrolo [1,2-a]quinoxalin-6(2H)-one (204)

To a solution of tert-butyl (4aR,12aR)-10-(methylthio)-6-oxo-1,2,3,4,4a,12a-hexahydropyrimido[5',4':4,5]pyrrolo[1,2-a]quinoxaline-5(6H)-carboxylate (203, 70 mg, 0.18 mmol) in DCM (1.5 mL) was added TFA (0.5 mL). After stirring at room temperature for 2 h, the reaction mixture was neutralized with saturated aqueous NaHCO$_3$(20 mL) and extracted with DCM (10 mL×3). The combined organic phases were dried over MgSO$_4$ and concentrated in vacuo. The resulting residue was purified by column chromatography to provide (4aR,12aR)-10-(methylthio)-1,3,4,4a,5,12a-hexahydropyrimido[5',4':4,5]pyrrolo[1,2-a]quinoxalin-6 (2H)-one (204, 70 mg, 0.24 mmol).

Step 8: Synthesis of (4aR,12aR)-10-(Methylsulfonyl)-1,3,4,4a,5,12a -hexahydropyrimido [5',4':4,5] pyrrolo[1,2-a]quinoxalin-6(2H)-one (205)

To a solution of (4aR,12aR)-10-(methylthio)-1,3,4,4a,5, 12a-hexahydropyrimido[5',4':4,5]pyrrolo[1,2-a]quinoxalin-6(2H)-one (204, 70 mg, 0.24 mmol) in DCM (5 mL) was added m-CPBA (126 mg, 0.73 mmol). After stirring at room temperature for 12 h, the reaction mixture was neutralized with saturated aqueous NaHCO$_3$(5 mL) and extracted with DCM (10 mL×2). The combined organic phases were dried over MgSO4, and concentrated in vacuo. The resulting residue was purified by column chromatography to provide (4aR,12aR)-10-(methylsulfonyl)-1,3,4,4a,5,12a-hexahydropyrimido[5',4':4,5]pyrrolo[1,2-a]quinoxalin-6(2H)-one (205, 30 mg, 0.09 mmol).

MS: m/z 321 (MH+).

Step 9: Synthesis of (4aR,12aR)-10-((5-(4-Methyl-piperazin-1-yl)pyridin-2-yl)amino)-1,3,4,4a,5,12a-hexahydropyrimido [5',4':4,5]pyrrolo [1,2-a]quinoxalin-6(2H)-one (COMPOUND 22)

To a solution of 5-(4-methylpiperazin-1-yl)pyridin-2-amine (180 mg, 0.94 mmol) in toluene (10 mL) at 0° C. was added LHMDS (1.1 mL, 1.1 mmol, 1 M in THF). After stirring at 0° C. for 1 h, a solution of (4aR,12aR)-10-(methylsulfonyl)-1,3,4,4a,5,12a-hexahydropyrimido[5',4':4,5]pyrrolo[1,2-a]quinoxalin-6(2H)-one (205, 300 mg, 0.94 mmol) in toluene (5 mL) was added. The reaction was kept at 80° C. for 12 h. After cooling to room temperature, the reaction mixture was quenched with saturated aqueous NaHCO3 (5 mL) and extracted with DCM (10 mL×3). The combined organic phases were dried over MgSO4, and concentrated in vacuo. The resulting residue was purified by column chromatography to provide ((4aR,12aR)-10-((5-(4-methylpiperazin-1-yl)pyridin-2-yl)amino)-1,3,4,4a,5,12a-hexahydropyrimido[5',4':4,5]pyrrolo[1,2-a]quinoxalin-6(2H)-one (COMPOUND 22, 3.0 mg, 0.007 mmol). MS (ESI+): m/z 433 [M+H]+; $^1$H NMR (300 MHz, MeOD+CDCl3): δ 9.35 (s, 1H), 8.69 (d, J=8.1 Hz, 1H), 8.52 (d, J=3.0 Hz, 1H), 7.95 (dd, J=9.0, 3.0 Hz, 1H), 7.80 (s, 1H), 4.62-4.44 (m, 2H), 4.23-4.13 (m, 1H), 3.78 (t, J=4.8 Hz, 4H), 3.25 (t, J=4.8 Hz, 4H), 2.97 (s, 3H), 2.75-2.60 (m, 1H), 2.52-2.40 (m, 2H), 2.26-2.04 (m, 4H).

Scheme 27: Synthesis of (4aS,12aS)-10-((5-(4-Methylpiperazin-1-yl)pyridin -2-yl)amino)-1,3,4,4a,5,12a-hexahydropyrimido[5',4':4,5]pyrrolo [1,2-a]quinoxalin-6(2H)-one (COMPOUND 23)

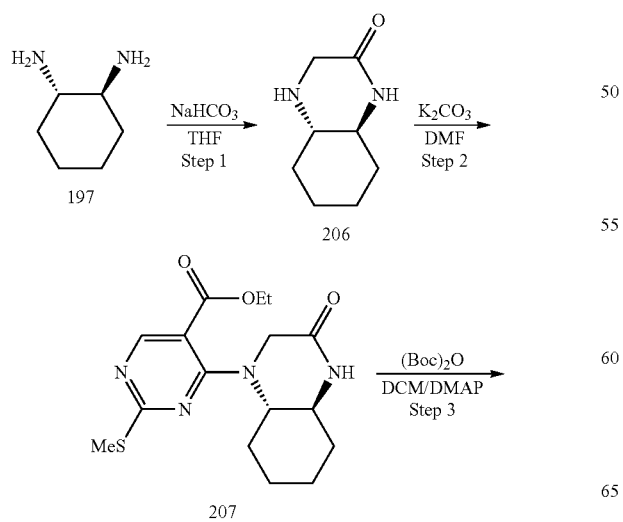

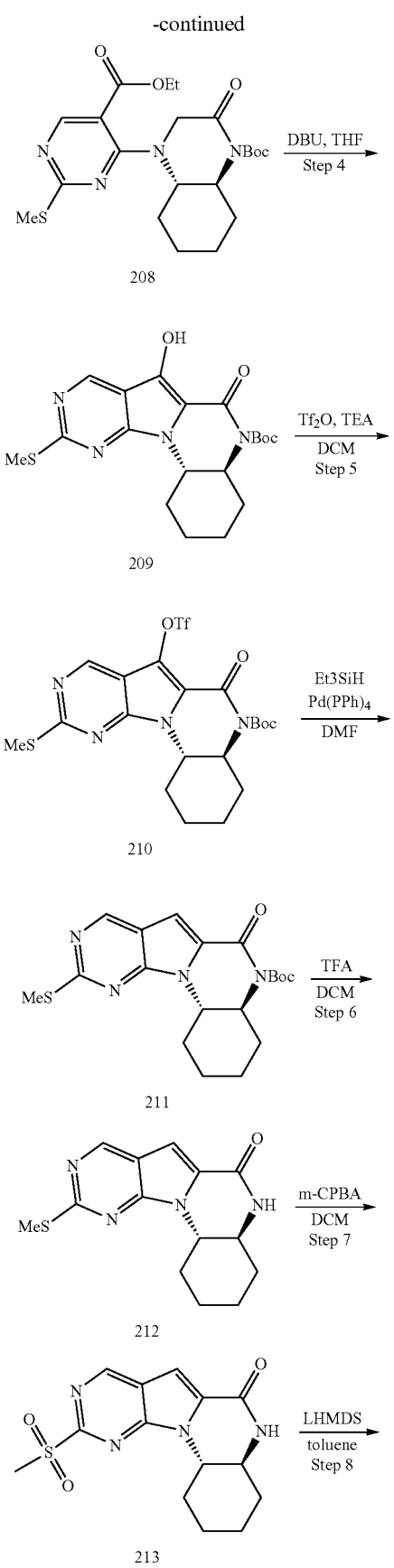

225
-continued
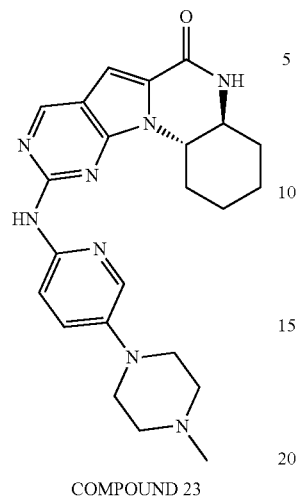
COMPOUND 23
COMPOUND 23 was prepared according to the experimental procedure described in Scheme 26 for the synthesis of COMPOUND 22. MS (ESI+): m/z 433 [M+H]+; $^1$H NMR (300 MHz, MeOD+CDCl$_3$): δ 8.81 (s, 1H), 8.13-8.10 (m, 1H), 7.96 (d, J=2.7 Hz, 1H), 7.48-7.44 (m, 1H), 7.24 (s, 1H), 4.01-3.94 (m, 2H), 3.66-3.63 (m, 1H), 3.29-3.25 (m, 4H), 2.81-2.78 (m, 4H), 2.48 (s, 3H), 2.19-2.08 (m, 2H), 1.99-1.86 (m, 2H), 1.71-1.46 (m, 3H).
Scheme 28: Synthesis of (4aS,12aR)-10-((5-(4-Methylpiperazin-1-yl)pyridin-2-yl)amino)-1,3,4,4a,5,12a-hexahydropyrimido [5′,4′:4,5]pyrrolo [1,2-a] quinoxalin-6(2H)-one (COMPOUND 24)
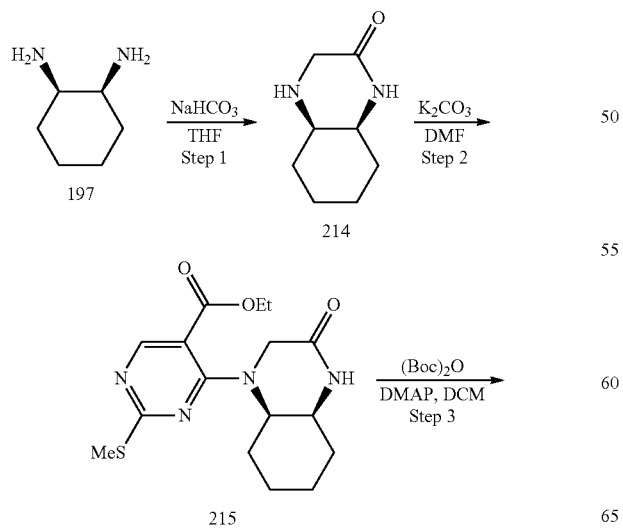
226
-continued
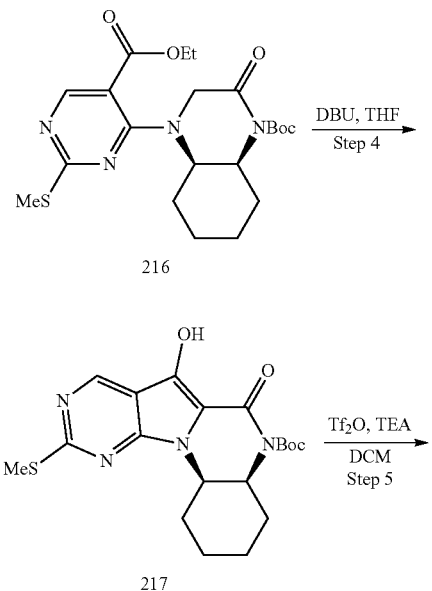
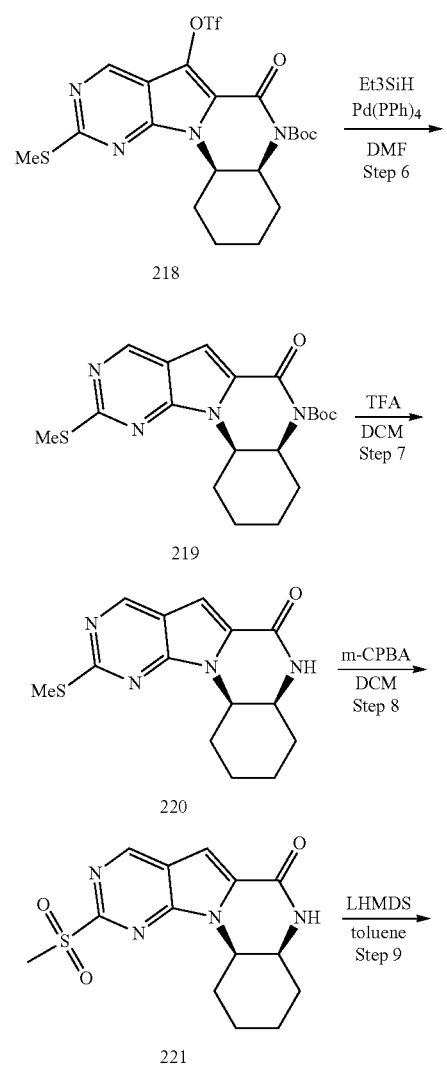

227

-continued

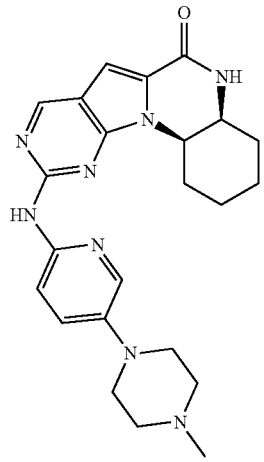

COMPOUND 24

COMPOUND 24 was prepared according to the experimental described in Scheme 26 for the synthesis of COMPOUND 22. MS (ESI+): m/z 433 [M+H]+; $^1$H NMR (300 MHz, MeOH+CDCl$_3$): δ 8.83 (s, 1H), 8.34 (s, 1H), 7.96 (s, 1H), 7.52-7.47 (m, 1H), 7.20 (s, 1H), 4.19-4.13 (m, 2H), 3.64 (s, 1H), 3.29-3.26 (m, 4H), 2.80-2.78 (m, 4H), 2.48 (s, 3H), 2.15-1.99 (m, 4H), 1.95-1.83 (m, 3H).

Scheme 29: Synthesis of N-(5-(4-Methylpiperazin-1-yl)pyridin-2-yl)-5'H -spiro[cyclohexane-1,6'-imidazo[2",1":3',4']pyrazino[1',2':1,5]pyrrolo[2,3-d]pyrimidin]-9'-amine (COMPOUND 25)

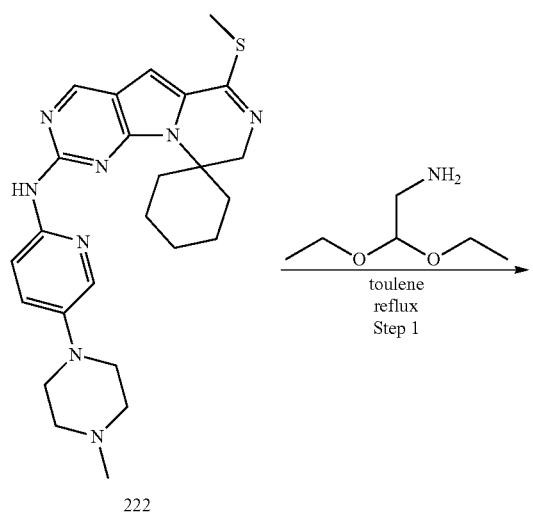

228

-continued

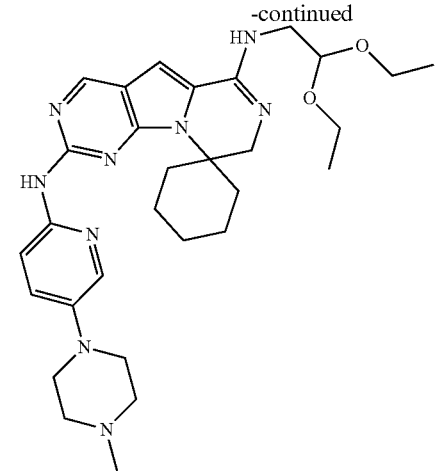

223

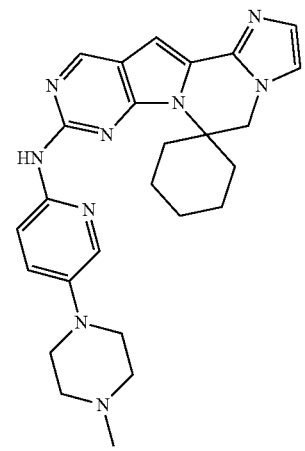

COMPOUND 25

Step 1: Synthesis of N$^{6'}$-(2,2-Diethoxyethyl)-N$^{2'}$-(5-(4-methylpiperazin-1-yl) pyridin-2-yl)-8'H-spiro[cyclohexane-1,9'-pyrazino[1',2':1,5]pyrrolo[2,3-d]pyrimidine]-2',6'-diamine (223)

To a solution of N-(5-(4-methylpiperazin-1-yl)pyridin-2-yl)-6'-(methylthio)-8'H-spiro[cyclohexane-1,9'-pyrazino[1',2': 1,5]pyrrolo[2,3-d]pyrimidin]-2'-amine (222, 100 mg, 0.20 mmol) in toluene (5 mL) was added 2,2-diethoxyethan-1-amine (100 mg, 0.37 mmol). After stirring under reflux for 48 h, the reaction mixture was cooled to room temperature and concentrated in vacuo. The resulting residue was purified by prep TLC to afford N6'-(2,2-diethoxyethyl)-N2'-(5-(4-methylpiperazin-1-yl)pyridin-2-yl)-8'H-spiro[cyclohexane-1,9'-pyrazino[11',2':1,5]pyrrolo[2,3-d]pyrimidine]-2',6'-diamine (223, 70 mg, 0.12 mmol). MS (ESI+): m/z 562 [M+H]$^+$.

Step 2: Synthesis of N-(5-(4-Methylpiperazin-1-yl) pyridin-2-yl)-5'H-spiro[cyclohexane-1,6'-imidazo [2",1":3',4']pyrazino [1',2':1,5]pyrrolo [2,3-d]pyrimidin]-9'-amine (COMPOUND 25)

To a solution of N$^{6'}$-(2,2-diethoxyethyl)-N2'-(5-(4-methylpiperazin-1-yl)pyridin-2-yl)-8'H-spiro[cyclohexane-1,9'-pyrazino[1',2': 1,5]pyrrolo[2,3-d]pyrimidine]-2',6'-diamine (223, 65 mg, 0.11 mmol) in toluene (3 mL) was added TFA (3 drops). After stirring under reflux for 1 h, the reaction mixture was cooled to room temperature and concentrated in vacuo. The resulting residue was purified by prep TLC to afford N-(5-(4-methylpiperazin-1-yl)pyridin-2-yl)-5'H-spiro[cyclohexane-1,6'-imidazo[2",1":3',4']pyrazino[1',2': 1,5]pyrrolo[2,3-d]pyrimidin]-9'-amine (COMPOUND 25, 6.9 mg, 0.015 mmol). MS (ESI+): m/z 470 [M+H]+; $^1$H NMR (300 MHz, MeOD): δ 8.74 (s, 1H), 8.06 (d, J=12.0 Hz, 1H), 7.98 (d, J=3.3 Hz, 1H), 7.58 (dd, J=9.9, 4.2 Hz, 1H), 7.24 (d, J=1.2 Hz, 1H), 7.18 (d, J=1.2 Hz, 1H), 7.04 (s, 1H), 4.55 (s, 2H), 3.41-3.37 (m, 4H), 3.16-3.12 (m, 6H), 2.73 (s, 3H), 1.95-1.86 (m, 5H), 1.75-1.44 (m, 3H).

Scheme 30: Synthesis of N-(5-(4-Methylpiperazin-1-yl)pyridin-2-yl)-8'H-spiro[cyclohexane-1,9'-imidazo[2,1-h]pteridin]-2'-amine (COMPOUND 26)

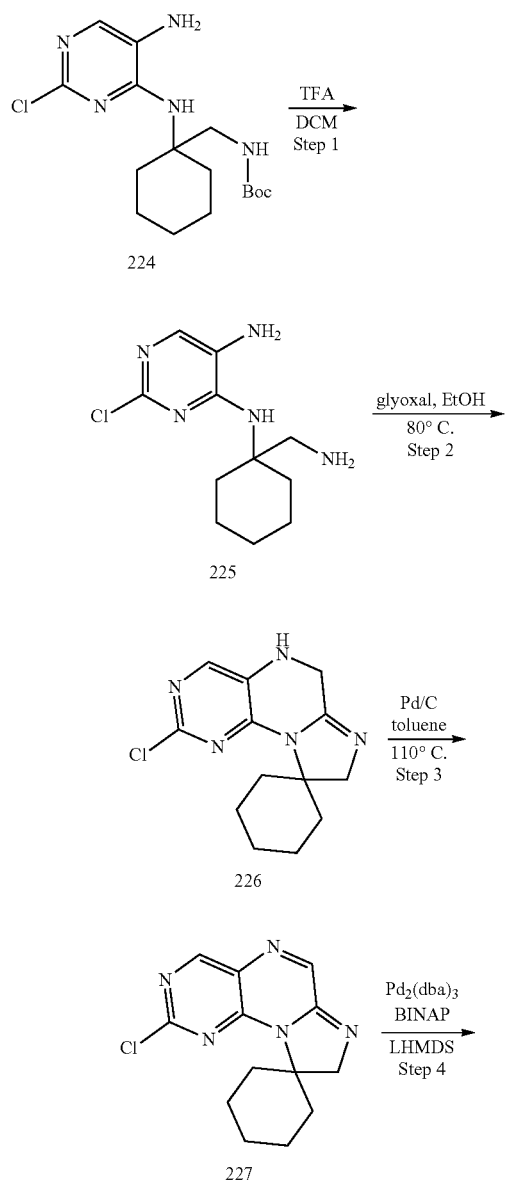

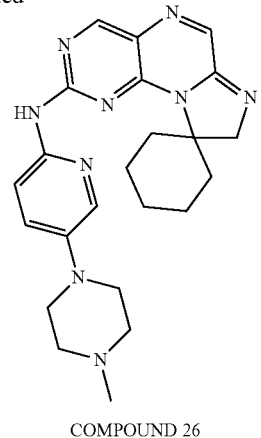

COMPOUND 26

Step 1: Synthesis of N$^4$-(1-(Aminomethyl)cyclohexyl)-2-chloropyrimidine-4,5-diamine (225)

To a solution of tert-butyl ((1-((5-amino-2-chloropyrimidin-4-yl)amino)cyclohexyl)methyl)carbamate (224, 300 mg, 0.84 mmol) in DCM (10 mL) was added TFA (3 mL). After stirring at room temperature for 2 h, the reaction mixture was neutralized with saturated aqueous NaHCO$_3$ and extracted with DCM (10 mL×3). The combined organic phases were dried over MgSO$_4$, filtered and concentrated in vacuo to provide N$^4$-(1-(aminomethyl)cyclohexyl)-2-chloropyrimidine-4,5-diamine (225, 200 mg, 0.78 mmol), which was used for the next step without further purification.

Step 2: Synthesis of 2'-Chloro-6',8'-dihydro-5'H-spiro[cyclohexane-1,9'-imidazo[2,1-h]pteridine] (226)

To a solution of N$^4$-(1-(aminomethyl)cyclohexyl)-2-chloropyrimidine-4,5-diamine (225, 200 mg, 0.78 mmol) in EtOH (10 mL) was added glyoxal (113 mg, 0.78 mmol). After stirred at 80° C. for 2 h, the reaction mixture was concentrated in vacuo. The resulting residue was purified by column chromatography to provide 2'-chloro-6',8'-dihydro-5'H-spiro[cyclohexane-1,9'-imidazo[2,1-h]pteridine] (226, 80 mg, 0.29 mmol). MS (ESI+): m/z 278 [M+H]+.

Step 3: Synthesis of 2'-Chloro-8'H-spiro[cyclohexane-1,9'-imidazo[2,1-h]pteridine] (227)

To a solution of 2'-chloro-6',8'-dihydro-5'H-spiro[cyclohexane-1,9'-imidazo[2,1-h]pteridine] (226, 60 mg, 0.22 mmol) in toluene (5 mL) was added Pd/C (10 mg). After stirred at 110° C. for 12 h, the reaction mixture was filtered. The filtrate was concentrated in vacuo. The resulting residue was purified by column chromatography to provide 2'-chloro-8'H-spiro[cyclohexane-1,9'-imidazo[2,1-h]pteridine] (227, 20 mg, 0.07 mmol). MS (ESI+): m/z 276 [M+H]$^+$.

Step 4: Synthesis of N-(5-(4-Methylpiperazin-1-yl)pyridin-2-yl)-8'H-spiro [cyclohexane-1,9'-imidazo[2,1-h]pteridin]-2'-amine (COMPOUND 26)

Under N$_2$ atmosphere, to a solution of 2'-chloro-8'H-spiro[cyclohexane-1,9'-imidazo[2,1-h]pteridine] (227, 80 mg, 0.29 mmol), 5-(4-methylpiperazin-1-yl)pyridin-2-amine (55 mg, 0.29 mmol), Pd$_2$(dba)$_3$ (26.4 mg, 0.03 mmol) and BINAP (35.2 mg, 0.06 mmol) in toluene (20 mL) was added LHMDS (0.4 mL, 0.4 mmol). After stirred at 100° C. for 12 h, the reaction mixture was cooled to room temperature, quenched with water (10 mL) and extracted with EtOAc (10 mL). The organic phase was separated and concentrated in vacuum. The resulting residue was purified by column chromatography to provide N-(5-(4-methylpiperazin-1-yl) pyridin-2-yl)-8'H-spiro[cyclohexane-1,9'-imidazo[2,1-h] pteridin]-2'-amine (COMPOUND 26, 11.1 mg, 0.02 mmol). MS (ESI+): m/z 432 [M+H]+; $^1$H NMR (300 MHz, MeOD): δ 8.47 (s, 1H), 8.03-8.09 (m, 2H), 7.90 (s, 1H), 7.39-7.43 (m, 1H), 4.00 (s, 2H), 3.28-3.36 (m, 4H), 2.88 (d, J=12.6 Hz, 2H), 2.76-2.82 (m, 4H), 2.49 (s, 3H), 1.68-1.89 (m, 5H), 1.28-1.47 (m, 3H).

Scheme 31: Synthesis of 2'-((5-(4-Methylpiperazin-1-yl)pyridin-2-yl) amino)-5'H-spiro[cyclohexane-1, 9'-imidazo[2,1-h]pteridin]-6'(8'H)-one (COMPOUND 27)

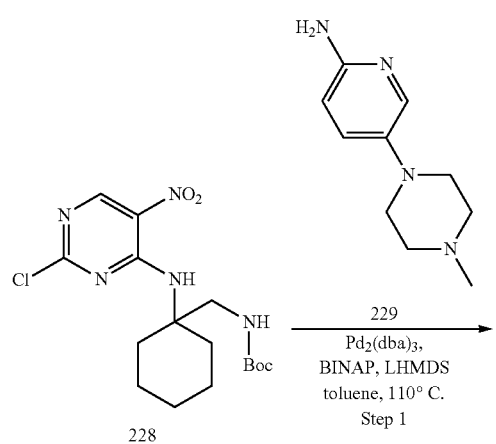

228

229
Pd$_2$(dba)$_3$,
BINAP, LHMDS
toluene, 110° C.
Step 1

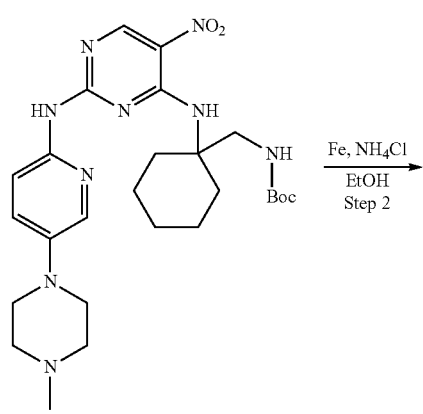

230

Fe, NH$_4$Cl
EtOH
Step 2

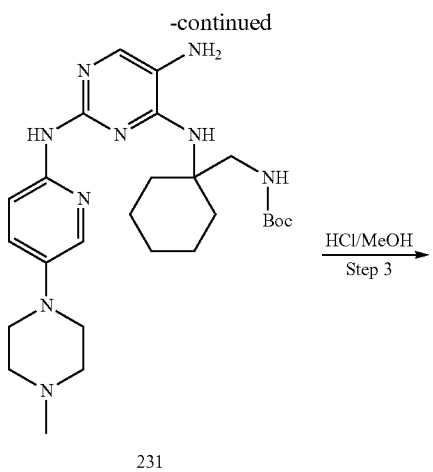

231

HCl/MeOH
Step 3

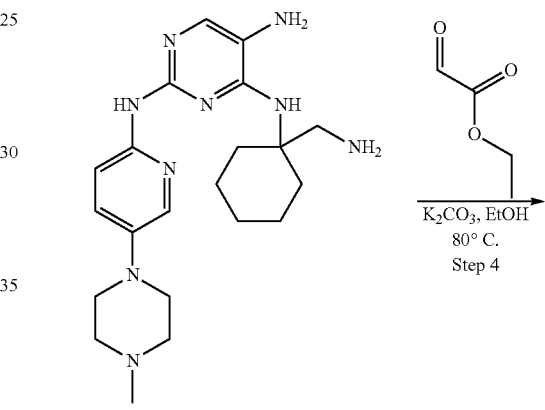

232

K$_2$CO$_3$, EtOH
80° C.
Step 4

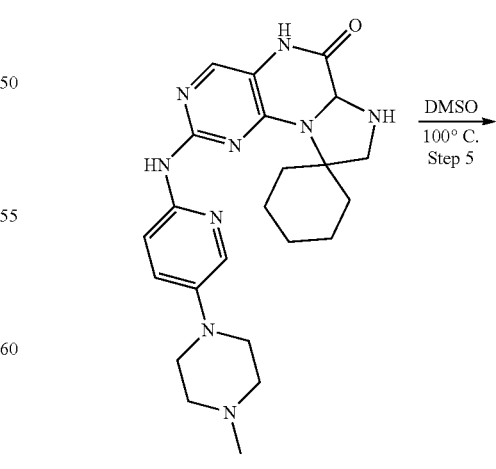

233

DMSO
100° C.
Step 5

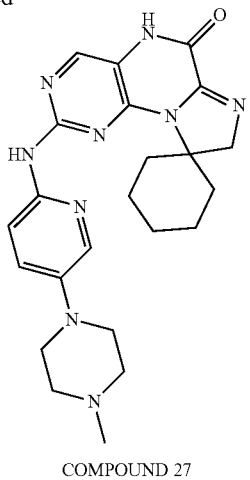

COMPOUND 27

Step 1: Synthesis of tert-Butyl ((1-((2-((5-(4-methylpiperazin-1-yl)pyridin-2-yl)amino)-5-nitropyrimidin-4-yl)amino)cyclohexyl)methyl)carbamate (230)

Under $N_2$ atmosphere, to a mixture of tert-butyl ((1-((2-chloro-5-nitropyrimidin-4-yl)amino)cyclohexyl)methyl) carbamate (228, 1.0 g, 2.6 mmol), 5-(4-methylpiperazin-1-yl)pyridin-2-amine (229, 0.6 g, 3.1 mmol), $Pd_2(dba)_3$ (120 mg, 0.13 mmol), and BINAP (160 mg, 0.25 mmol) in toluene (30 mL) was added LHMDS (0.52 mL, 1 M in THF). The reaction was kept at 100° C. overnight and was then quenched with water (50 mL) and extracted with EtOAc (50 mL). The organic layer was separated and concentrated in vacuo. The resulting residue was purified by column chromatography to afford tert-butyl ((1-((2-((5-(4-methylpiperazin-1-yl)pyridin-2-yl)amino)-5-nitropyrimidin-4-yl)amino)cyclohexyl)methyl)carbamate (230, 400 mg, 0.74 mmol). MS (ESI+): m/z 542 $[M+H]^+$.

Step 2: Synthesis of tert-Butyl ((1-((5-amino-2-((5-(4-methylpiperazin-1-yl) pyridin-2-yl)amino)pyrimidin-4-yl)amino)cyclohexyl)methyl)carbamate (231)

To a solution of tert-butyl ((1-((2-((5-(4-methylpiperazin-1-yl)pyridin-2-yl)amino)-5-nitropyrimidin-4-yl)amino)cyclohexyl)methyl)carbamate (230, 180 mg, 0.33 mmol) in EtOH (10 mL) was added Fe powder (200 mg, 3.57 mmol) and aqueous $NH_4Cl$ solution (1 mL). After stirring under reflux overnight, the reaction mixture was cooled to room temperature, filtered and concentrated in vacuo to afford the crude product, which was purified by column chromatography to afford tert-butyl ((1-((5-amino-2-((5-(4-methylpiperazin-1-yl)pyridin-2-yl)amino)pyrimidin-4-yl)amino)cyclohexyl)methyl)carbamate (231, 40 mg, 0.08 mmol). MS (ESI+): m/z 512 $[M+H]^+$.

Step 3: Synthesis of $N^4$-(1-(Aminomethyl)cyclohexyl)-$N^2$-(5-(4-methylpiperazin-1-yl)pyridin-2-yl)pyrimidine-2,4,5-triamine (232)

A solution of tert-butyl ((1-((5-amino-2-((5-(4-methylpiperazin-1-yl)pyridin-2-yl)amino)pyrimidin-4-yl)amino)cyclohexyl)methyl)carbamate (231, 270 mg, 0.53 mmol) in sat. HCl/MeOH solution (5 mL) was stirred at room temperature for 3 h. Then the mixture was concentrated in vacuo. To the resulting residue was added MeOH (5 mL) and $K_2CO_3$ (300 mg). The mixture was heated to reflux for 1 h. After cooling to room temperature, the mixture was filtered and the filtrate was concentrated to afford N4-(1-(aminomethyl)cyclohexyl)-N2-(5-(4-methylpiperazin-1-yl)pyridin-2-yl)pyrimidine-2,4,5-triamine (232, 180 mg, 0.44 mmol), which was used for the next step without further purification. MS (ESI): m/z 412 $[M+H]^+$.

Step 4: Synthesis of 2'-((5-(4-Methylpiperazin-1-yl)pyridin-2-yl)amino)-7',8'-dihydro-5'H-spiro [cyclohexane-1,9'-imidazo[2,1-h]pteridin]-6'(6a'H)-one (233)

To a mixture of $N^4$-(1-(aminomethyl)cyclohexyl)-$N^2$-(5-(4-methylpiperazin-1-yl)pyridin-2-yl)pyrimidine-2,4,5-triamine (232, 170 mg, 0.41 mmol), $K_2CO_3$ (300 mg, 2.17 mmol) in EtOH (3 mL) was added a solution of ethyl 2-oxoacetate (85 mg, 0.83 mmol) in toluene (0.1 mL). After stirring at 80° C. for 2 h, the reaction mixture was filtered and the filtrate was concentrated to afford the residue, which was purified by prep TLC to afford 2'-((5-(4-methylpiperazin-1-yl)pyridin-2-yl)amino)-7',8'-dihydro-5'H-spiro[cyclohexane-1,9'-imidazo[2,1-h]pteridin]-6'(6a'H)-one (233, 80 mg, 0.18 mmol). MS (ESI+): m/z 450 $[M+H]^+$.

Step 5: Synthesis of 2'-((5-(4-Methylpiperazin-1-yl)pyridin-2-yl)amino)-5'H-spiro[cyclohexane-1,9'-imidazo[2,1-h]pteridin]-6'(8'H)-one (COMPOUND 27)

A solution of 2'-((5-(4-methylpiperazin-1-yl)pyridin-2-yl)amino)-7',8'-dihydro-5'H-spiro[cyclohexane-1,9'-imidazo[2,1-h]pteridin]-6'(6a'H)-one (233, 65 mg, 0.14 mmol) in DMSO (2 mL) was kept at 100° C. for 6 h. After cooled to room temperature, the reaction mixture was purified by prep TLC to afford 2'-((5-(4-methylpiperazin-1-yl)pyridin-2-yl)amino)-5'H-spiro [cyclohexane-1,9'-imidazo[2,1-h]pteridin]-6'(8'H)-one (COMPOUND 27, 6.1 mg, 0.014 mmol). MS (ESI+): m/z 448 [M+H]+; $^1$H NMR (300 MHz, DMSO-$d_6$+$D_2O$): δ 8.04 (s, 1H), 7.97 (s, 1H), 7.93 (d, J=9.6 Hz, 1H), 7.46 (d, J=8.7 Hz, 1H), 3.91 (s, 2H), 3.10-3.05 (m, 2H), 3.05-3.03 (m, 2H), 3.00-2.96 (m, 2H), 2.84-2.76 (m, 5H), 2.02-1.96 (m, 2H), 1.72-1.61 (m, 5H), 1.40-1.30 (m, 3H).

Scheme 32: Synthesis of 2'-((5-(4-Methylpiperazin-1-yl)pyrimidin-2-yl) amino)-7',8'-dihydro-6'H-spiro [cyclohexane-1,9'-pyrazino[1',2':1,5]pyrrolo [2,3-d]pyrimidin]-6'-one (COMPOUND 28)

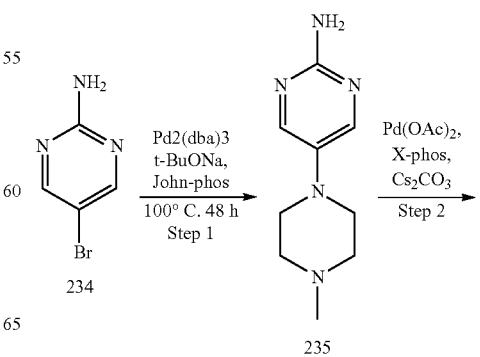

-continued

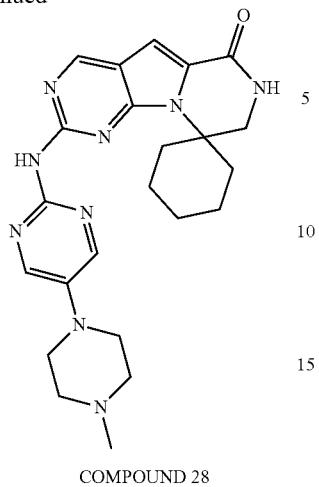

COMPOUND 28

Step 1: Synthesis of 5-(4-Methylpiperazin-1-yl)pyrimidin-2-amine (235)

Under N₂ atmosphere, to a solution of 5-bromopyrimidin-2-amine (234, 2 g, 11.5 mmol) in toluene (200 mL) was added 1-methylpiperazine (32 g, 319.5 mmol), t-BuONa (1.8 g, 18.7 mmol), Pd₂(dba)₃ (520 mg, 0.57 mmol) and John-phos (680 mg, 2.28 mmol). After stirred at 100° C. for 48 h, the reaction mixture was concentrated in vacuo. The resulting residue was purified by column chromatography to provide 5-(4-methylpiperazin-1-yl)pyrimidin-2-amine (235, 200 mg, 1.0 mmol). MS (ESI+): m/z 194 [M+H]+.

Step 2: synthesis of 2'-((5-(4-Methylpiperazin-1-yl)pyrimidin-2-yl)amino)-7',8'-dihydro-6'H-spiro[cyclohexane-1,9'-pyrazino[1',2':1,5]pyrrolo [2,3-d]pyrimidin]-6'-one (COMPOUND 28)

Under N₂ atmosphere, to a solution of 5-(4-methylpiperazin-1-yl)pyrimidin-2-amine (235, 13 mg, 0.07 mmol), 2'-chloro-7',8'-dihydro-6'H-spiro[cyclohexane-1,9'-pyrazino[1',2':1,5]pyrrolo[2,3-d]pyrimidin]-6'-one (20 mg, 0.07 mmol) in dioxane (40 mL) was added Pd(OAc)₂ (3 mg, 0.01 mmol), X-Phos (6 mg, 0.01 mmol) and Cs₂CO₃ (45 mg, 0.14 mmol). After stirred at 100° C. for 4 h, the reaction mixture was cooled to room temperature, quenched with water (20 mL) and extracted with EtOAc (10 mL×3). The combined organic phases were dried over Na₂SO₄, concentrated in vacuo. The resulting residue was purified by prep TLC to provide 2'-((5-(4-methylpiperazin-1-yl)pyrimidin-2-yl)amino)-7',8'-dihydro-6'H-spiro[cyclohexane-1,9'-pyrazino[1',2': 1,5]pyrrolo[2,3-d]pyrimidin]-6'-one (COMPOUND 28, 2.8 mg, 0.0063 mmol). MS (ESI+): m/z 448 [M+H]+; ¹H NMR (300 MHz, MeOD): δ 8.89 (s, 1H), 8.40 (br s, 2H), 7.26 (s, 1H), 3.77 (s, 2H), 3.29-3.20 (m, 4H), 3.07 (t, J=11.4 Hz, 2H), 2.80-2.72 (m 4H), 2.45 (s, 3H), 2.00-1.90 (m, 2H), 1.86-1.76 (m, 3H), 1.60-1.47 (m, 3H).

Scheme 33: Synthesis of 2'-((5-(4-Methylpiperazin-1-yl)pyridin-2-yl)amino)-6'H-spiro[cyclohexane-1, 9'-pyrazino[1',2':1,5]pyrrolo[2,3-d]pyrimidine]-6',8'(7'H)-dione (COMPOUND 30)

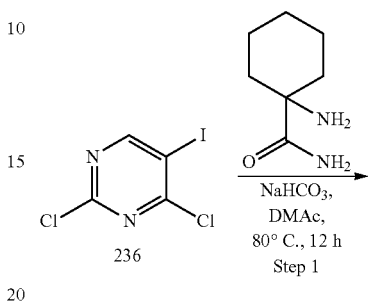

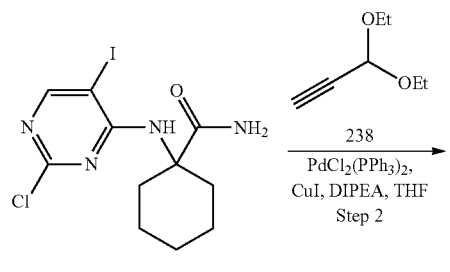

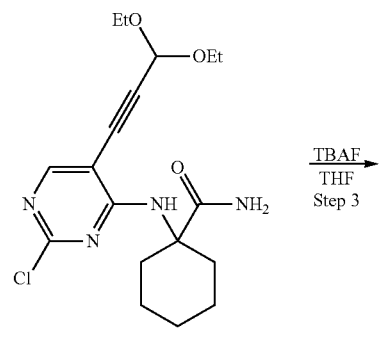

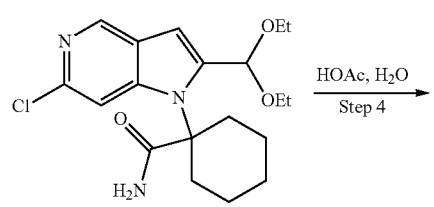

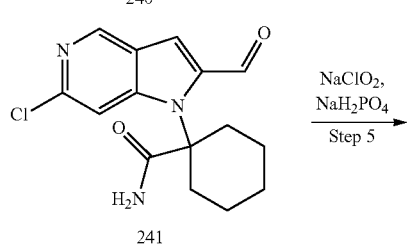

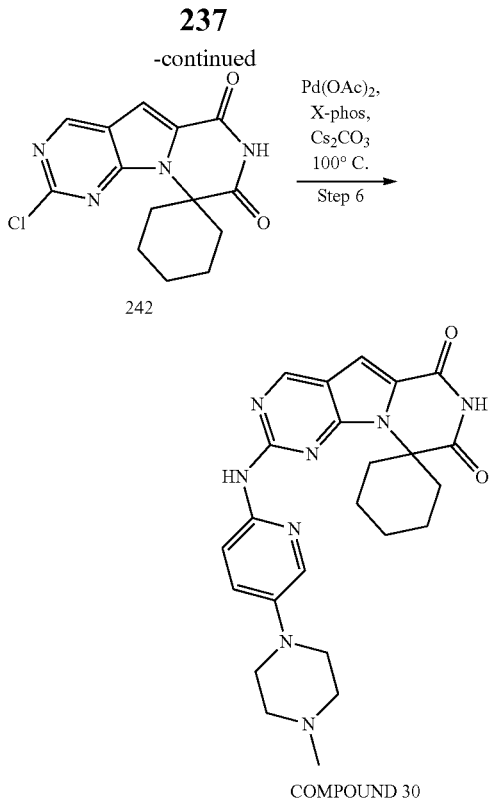

COMPOUND 30

Step 1: Synthesis of 1-((2-Chloro-5-iodopyrimidin-4-yl)amino)cyclohexane-1-carboxamide (237)

To a solution 2,4-dichloro-5-iodopyrimidine (236, 26 g, 94.6 mmol) and 1-aminocyclohexane-1-carboxamide (15 g, 105.4 mmol) in DMAc (260 mL) was added NaHCO$_3$ (33 g, 392.8 mmol). After stirring at 80° C. for 12 h, the reaction mixture was cooled to room temperature, quenched with water (700 mL) and extracted with EtOAc (300 mL×3). The combined organic phases were washed with water (200 mL×2), brine (100 mL) and dried over anhydrous Na$_2$SO$_4$. After concentration, the resulting residue was purified by column chromatography to provide 1-((2-chloro-5-iodopyrimidin-4-yl)amino)cyclohexane-1-carboxamide (237, 12 g, 31.5 mmol). MS (ESI+): m/z 381 [M+H]$^+$.

Step 2: Synthesis of 1-((2-Chloro-5-(3,3-diethoxyprop-1-yn-1-yl)pyrimidin-4-yl)amino)cyclohexane-1-carboxamide (239)

Under N$_2$ atmosphere, to a solution of 1-((2-chloro-5-iodopyrimidin-4-yl)amino)cyclohexane-1-carboxamide (237, 4 g, 10.5 mmol) and DIPEA (2.7 g, 20.9 mmol) in THF (170 mL) was added CuI (200 mg, 1.05 mmol) and Pd(PPh$_3$)$_2$Cl$_2$ (294 mg, 0.42 mmol). After stirring at room temperature for 10 min, a solution of 3,3-diethoxyprop-1-yne (238, 1.6 g, 12.5 mmol) in THF (5 mL) was added in dropwise and the reaction was stirred at room temperature for 12 h. After concentration of the mixture in vacuo, the resulting residue was purified by column chromatography to provide 1-((2-chloro-5-(3,3-diethoxyprop-1-yn-1-yl)pyrimidin-4-yl)amino)cyclohexane-1-carboxamide (239, 2.4 g, 6.3 mmol). MS (ESI+): m/z 381 [M+H]$^+$.

Step 3: Synthesis of 1-(2-Cloro-6-(diethoxymethyl)-7H-pyrrolo[2,3-d] pyrimidin-7-yl)cyclohexane-1-carboxamide (240)

To a solution of 1-((2-chloro-5-(3,3-diethoxyprop-1-yn-1-yl)pyrimidin-4-yl)amino)cyclohexane-1-carboxamide (239, 2 g, 5.25 mmol) was added TBAF (20 mL, 20 mmol, 1M in THF). After stirring at 60° C. for 2h, the reaction mixture was cooled to room temperature, quenched with water (70 mL) and extracted with EtOAc (50 mL×3). The combined organic phases were dried over Na$_2$SO$_4$, filtered and concentrated in vacuo. The resulting residue was purified by column chromatography to provide 1-(2-chloro-6-(diethoxymethyl)-7H-pyrrolo[2,3-d]pyrimidin-7-yl)cyclohexane-1-carboxamide (240, 400 mg, 1.05 mmol). MS (ESI+): m/z 381 [M+H]$^+$.

Step 4: synthesis of 1-(2-Chloro-6-formyl-7H-pyrrolo [2,3-d]pyrimidin-7-yl) cyclohexane-1-carboxamide (241)

To a solution of 1-(2-chloro-6-(diethoxymethyl)-7H-pyrrolo[2,3-d]pyrimidin-7-yl)cyclohexane-1-carboxamide (240, 800 mg, 2.1 mmol) in THF (4 mL) was added water (4 mL) and HOAc (4 mL). After stirring at 60° C. for 2h, the reaction mixture was quenched with saturated aqueous NaHCO$_3$ and extracted with EtOAc (100 mL×3). The combined organic phases were dried over Na$_2$SO$_4$, filtered and concentrated in vacuo. The resulting residue was purified by column chromatography to provide 1-(2-chloro-6-formyl-7H-pyrrolo[2,3-d]pyrimidin-7-yl)cyclohexane-1-carboxamide (241, 527 mg, 1.72 mmol).

Step 5: Synthesis of 2'-Chloro-6'H-spiro[cyclohexane-1,9'-pyrazino[1',2':1,5]pyrrolo[2,3-d]pyrimidine]-6',8'(7'H)-dione (242)

To a solution of 1-(2-chloro-6-formyl-7H-pyrrolo[2,3-d] pyrimidin-7-yl) cyclohexane-1-carboxamide (241, 100 mg, 0.33 mmol) in t-BuOH (5 mL) and acetonitrile (1 mL) was added NaH$_2$PO$_4$ (405 mg, 3.38 mmol) and 2-methyl-2-butene (183 mg, 2.6 mmol). The reaction mixture was brought to 0° C. was a solution of NaClO$_2$ (405 mg, 4.48 mmol) in water (10 mL) was added dropwise. After stirring at room temperature for 12 h, the reaction mixture was extracted with EtOAc (10 mL×2). The combined organic phases were washed with brine, dried over MgSO$_4$, filtered and concentrated in vacuo. The resulting residue was purified by column chromatography to provide 2'-chloro-6'H-spiro[cyclohexane-1,9'-pyrazino[1',2':1,5]pyrrolo[2,3-d]pyrimidine]-6',8'(7'H)-dione (242, 95 mg, 0.31 mmol).

Step 6: Synthesis of 2'-((5-(4-Methylpiperazin-1-yl) pyridin-2-yl)amino)-6'H-spiro[cyclohexane-1,9'-pyrazino[1',2':1,5]pyrrolo[2,3-d]pyrimidine]-6',8' (7'H)-dione (COMPOUND 30)

Under N$_2$ atmosphere, to a solution of 2'-chloro-6'H-spiro [cyclohexane-1,9'-pyrazino[1',2':1,5]pyrrolo[2,3-d]pyrimidine]-6',8'(7'H)-dione (242, 100 mg, 0.33 mmol), 5-(4-methylpiperazin-1-yl)pyridin-2-amine (76 mg, 0.4 mmol) in dioxane (5 mL) was added Pd(OAc)$_2$ (7.4 mg, 0.03 mmol), Cs$_2$CO$_3$ (320 mg, 0.98 mmol) and X-Phos (62 mg, 0.13 mmol). The reaction was stirred at 100° C. for 12 h. After cooled to room temperature, the reaction mixture was quenched with water (10 mL) and extracted with EtOAc (10 mL×2). The combined organic phases were concentrated in vacuo. The resulting residue was purified by prep TLC to prodive 2'-((5-(4-methylpiperazin-1-yl)pyridin-2-yl)amino)-6'H-spiro[cyclohexane-1,9'-pyrazino[1',2': 1,5]pyrrolo[2,3-d]pyrimidine]-6',8'(7'H)-dione (COMPOUND 30, 2.9 mg, 0.0063 mmol). MS (ESI+): m/z 461 [M+H]+; ¹HNMR (300 MHz, MeOD+CDCl₃): δ 8.93 (s, 1H), 8.34 (s, 1H), 8.02 (s, 1H), 7.48-7.42 (m, 2H), 3.32-3.21 (m, 6H), 2.93-2.84 (m, 4H), 2.55 (s, 3H), 2.30-2.15 (m, 2H), 2.13-2.02 (m, 2H), 2.00-1.91 (m, 1H), 1.91-1.78 (m, 2H), 1.70-1.59 (m, 1H).

Scheme 34: Synthesis of N-(5-(4-Methylpiperazin-1-yl)pyridin-2-yl)-6'H-spiro[cyclohexane-1,9'-pyrazino[1',2':1,5]pyrrolo[2,3-d]pyrimidin]-2'-amine (COMPOUND 31)

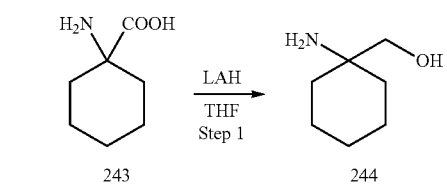

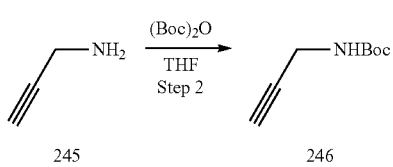

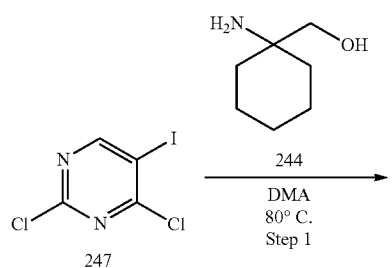

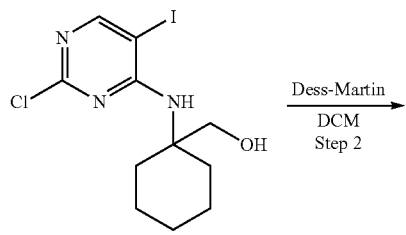

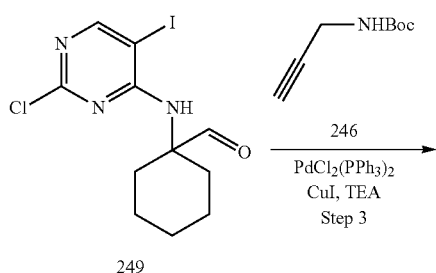

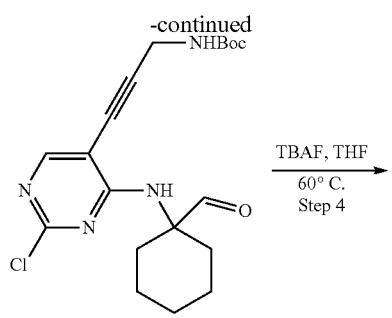

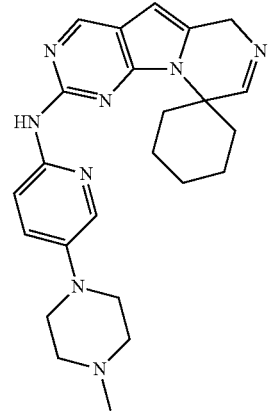

COMPOUND 31

Step 1: Synthesis of (1-Aminocyclohexyl)methanol Intermediate (244)

To a solution of 1-aminocyclohexane-1-carboxylic acid (243, 10 g, 69.9 mmol) in anhydrous THF (300 mL) at 5° C. was added LiAlH₄ (8 g, 210.5 mmol) in portions over 30 min. The reaction was then refluxed for 12 h. After cooling to 5° C. with an ice-bath, to the reaction mixture was added 8 mL of H₂O, 8 mL of 15% NaOH aqueous, followed by addition of 16 mL of H₂O. After the completion of addition, the mixture was stirred for 30 min. Anhydrous magnesium sulfate (20 g) was added. After stirring for 1 h, the mixture was filtered and the filter cake was washed with EtOAc (50 mL). The filtrate was concentrated to provide (1-aminocyclohexyl)methanol (244, 5.2 g, 40 mmol) as a yellow oil, which was used in the next step without further purification. MS (ESI+): m/z 130 [M+H]⁺.

Step 1: Synthesis of tert-Butyl prop-2-yn-1-ylcarbamate Intermediate (246)

To a solution of prop-2-yn-1-amine (245, 2.1 g, 38.2 mmol) in THF (30 mL) was added (Boc)$_2$O (15 g, 68.8 mmol). After stirring at room temperature for 1 h, the reaction mixture was concentrated in vacuo to afford the residue, which was purified by column chromatography with a gradient elution of hexane (100%) to hexane (80%) and EtOAc (20%) to provide tert-butyl prop-2-yn-1-ylcarbamate (246, 4.1 g, 26.4 mmol); $^1$H NMR (300 MHz, CDCl$_3$): δ 4.70 (s, 1H), 3.85 (d, J=3.0 Hz, 2H), 2.15 (t, J=2.7 Hz, 1H), 1.38 (s, 9H).

Step 1: Synthesis of (1-((2-Chloro-5-iodopyrimidin-4-yl)amino) cyclohexyl)methanol (248)

To a solution of 2,4-dichloro-5-iodopyrimidine (247, 2.7 g, 9.8 mmol) in DMA (20 mL) was added (1-aminocyclohexyl)methanol (244, 1.4 g, 10.8 mmol) and NaHCO$_3$ (5 g, 59.5 mol). The reaction was stirred at 80° C. for 4 h. After cooling to room temperature, the reaction mixture was quenched with water (40 mL) and extracted with EtOAc (50 mL×2). The combined organic phases were concentrated in vacuo to afford the residue, which was purified by column chromatography to afford (1-((2-chloro-5-iodopyrimidin-4-yl)amino)cyclohexyl)methanol (248, 1.5 g, 4.1 mmol). MS (ESI): m/z 368 [M+H]$^+$.

Step 2: Synthesis of 1-((2-Chloro-5-iodopyrimidin-4-yl)amino)cyclohexane-1-carbaldehyde (249)

To a solution of (1-((2-chloro-5-iodopyrimidin-4-yl)amino)cyclohexyl)methanol (248, 1 g, 2.7 mmol) in DCM (50 mL) at room temperature was added PCC (1.1 g, 5.1 mmol). After stirring at room temperature overnight, the solid was removed. The filter cake was washed with DCM (100 mL) and the filtrate was washed with saturated sodium bicarbonate solution (50 mL). The organic layer was separated and concentrated in vacuo to afford the residue, which was purified by column chromatography with a gradient elution hexane (95%) and EtOAc (5%) to hexane (80%) and EtOAc (20%) to provide 1-((2-chloro-5-iodopyrimidin-4-yl)amino)cyclohexane-1-carbaldehyde (249, 0.3 g, 0.8 mmol). MS (ESI+): m/z 366 [M+H]+.

Step 3: Synthesis of tert-Butyl (3-(2-Chloro-4-((1-formylcyclohexyl)amino) pyrimidin-5-yl)prop-2-yn-1-yl)carbamate (250)

Under N$_2$ atmosphere, to a solution of 1-((2-chloro-5-iodopyrimidin-4-yl)amino)cyclohexane-1-carbaldehyde (249, 300 mg, 0.8 mmol) and TEA (165 mg, 1.6 mmol) in anhydrous THF (15 mL) at room temperature was added CuI (15.5 mg, 0.1 mmol) and PdCl$_2$(PPh$_3$)$_2$ (28.7 mg, 0.04 mmol), followed by the addition of tert-butyl prop-2-yn-1-ylcarbamate (246, 165 mg, 1.1 mmol) dropwise. After stirring at room temperature overnight, the reaction mixture was quenched with water (20 mL) and extracted with EtOAc (20 mL). The organic layer was separated and washed with brine, dried over MgSO$_4$, filtered and concentrated in vacuo to afford the crude product, which was purified by column chromatography to provide tert-butyl (3-(2-chloro-4-((1-formylcyclohexyl)amino)pyrimidin-5-yl)prop-2-yn-1-yl)carbamate (250, 165 mg, 0.4 mmol). MS (ESI) m/z 393 [M+H]$^+$.

Step 4: Synthesis of tert-Butyl ((2-chloro-7-(1-formylcyclohexyl)-7H-pyrrolo [2,3-d]pyrimidin-6-yl)methyl)carbamate (251)

To a solution of tert-butyl (3-(2-chloro-4-((1-formylcyclohexyl)amino)pyrimidin-5-yl)prop-2-yn-1-yl)carbamate (250, 800 mg, 2.0 mmol) in anhydrous THF (5 mL) was added TBAF (12 mL, 12 mmol, 1 M in THF). The reaction was stirred at 60° C. for 1 h. After cooling to room temperature, the reaction mixture was quenched with H$_2$O (10 mL) and extracted with EtOAc (10 mL). The organic layer was separated and washed with brine, dried over MgSO$_4$, filtered and concentrated in vacuo to afford the crude product, which was purified by column chromatography to afford tert-butyl((2-chloro-7-(1-formylcyclohexyl)-7H-pyrrolo[2,3-d]pyrimidin-6-yl)methyl)carbamate (251, 370 mg, 0.94 mmol). MS (ESI+): m/z 393 [M+H]$^+$.

Step 5: Synthesis of 2'-Chloro-6'H-spiro[cyclohexane-1,9'-pyrazino [1',2':1,5]pyrrolo [2,3-d]pyrimidine] (252)

To a solution of tert-butyl ((2-chloro-7-(1-formylcyclohexyl)-7H-pyrrolo[2,3-d]pyrimidin-6-yl)methyl)carbamate (251, 100 mg, 0.25 mmol) in DCM (1 mL) was added TFA (3 mL). After stirring at room temperature for 2 h, the reaction mixture was neutralized with saturated sodium bicarbonate solution (5 mL) and extracted with EtOAc (5 mL×2). The combined organic phases were concentrated in vacuo and purified by prep TLC to afford 2'-chloro-6'H-spiro[cyclohexane-1,9'-pyrazino[1',2': 1,5]pyrrolo[2,3-d]pyrimidine] (252, 55 mg, 0.20 mmol) as a white solid. MS (ESI+): m/z 275 [M+H]$^+$.

Step 6: Synthesis of N-(5-(4-Methylpiperazin-1-yl)pyridin-2-yl)-6'H-spiro [cyclohexane-1,9'-pyrazino [1',2':1,5]pyrrolo[2,3-d]pyrimidin]-2'-amine (COMPOUND 31)

Under N$_2$ atmosphere, to a solution of 2'-chloro-6'H-spiro[cyclohexane-1,9'-pyrazino[1',2':1,5]pyrrolo[2,3-d]pyrimidine (252, 100 mg, 0.36 mmol) and 5-(4-methylpiperazin-1-yl)pyridin-2-amine (80 mg, 0.41 mmol) in anhydrous 1,4-dioxane (5 mL) was added Pd(OAc)$_2$ (40 mg, 0.18 mmol), X-phos (100 mg, 0.21 mmol) and Cs$_2$CO$_3$ (520 mg, 1.60 mmol). The reaction mixture was stirred at 110° C. overnight. After cooling to room temperature, the reaction mixture was quenched with water (10 mL) and extracted with EtOAc (20 mL). The organic phase was separated and concentrated in vacuo to afford the residue, which was purified by prep HPLC to provide N-(5-(4-methylpiperazin-1-yl)pyridin-2-yl)-6'H-spiro[cyclohexane-1,9'-pyrazino[1',2': 1,5]pyrrolo[2,3-d]pyrimidin]-2'-amine (COMPOUND 31, 15.2 mg, 0.03 mmol). MS (ESI+): m/z 431 [M+H]+; $^1$H NMR (300 MHz, CDCl$_3$): δ 8.68 (s, 1H), 8.30 (s, 1H), 8.22 (d, J=9.3 Hz, 1H), 7.96 (d, J=2.7 Hz, 1H), 7.93 (s, 1H), 7.25 (dd, J=9.0, 3.0 Hz, 1H), 6.55 (s, 1H), 4.00 (s, 2H), 3.17-3.14 (m, 4H), 2.83 (td, J=13.5, 4.2 Hz, 2H), 2.62-2.59 (m, 4H), 2.34 (s, 3H), 1.82-1.72 (m, 6H), 1.59-1.46 (m, 2H).

243

Scheme 35: Synthesis of 2'-((5-(4-Methylpiperazin-1-yl)pyridin-2-yl)amino)-6',7'-dihydro-8'H-spiro[cyclohexane-1,9'-pyrazino [1',2':1,5]pyrrolo[2,3-d]pyrimidin]-8'-one (COMPOUND 33)

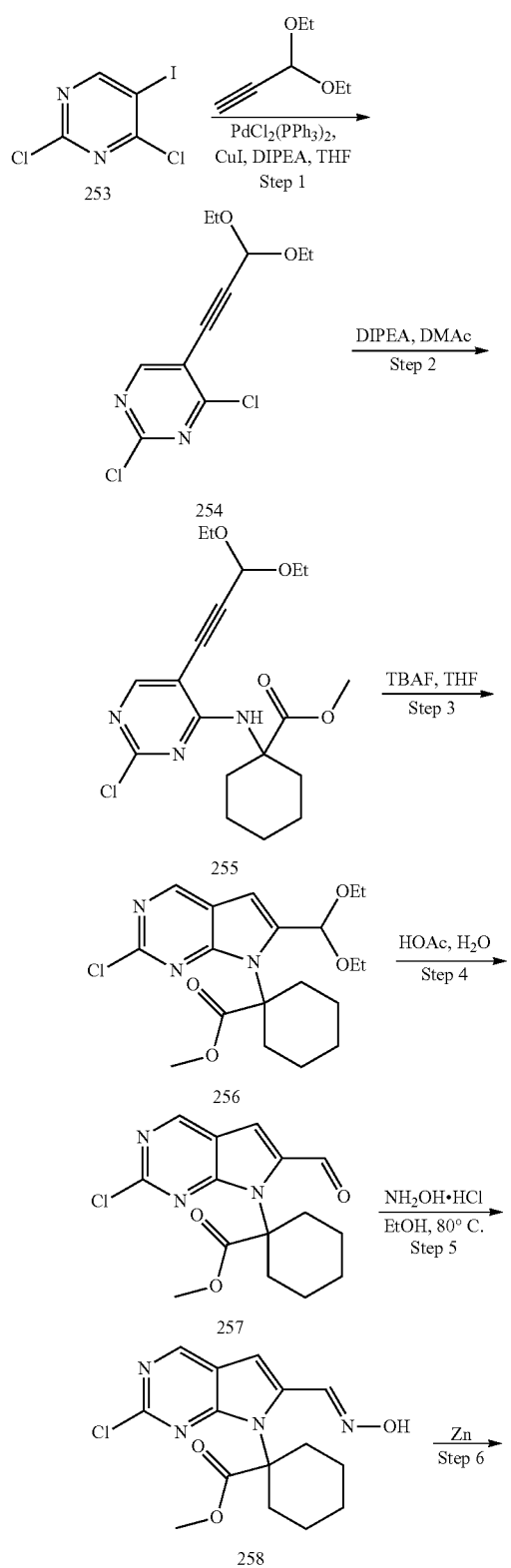

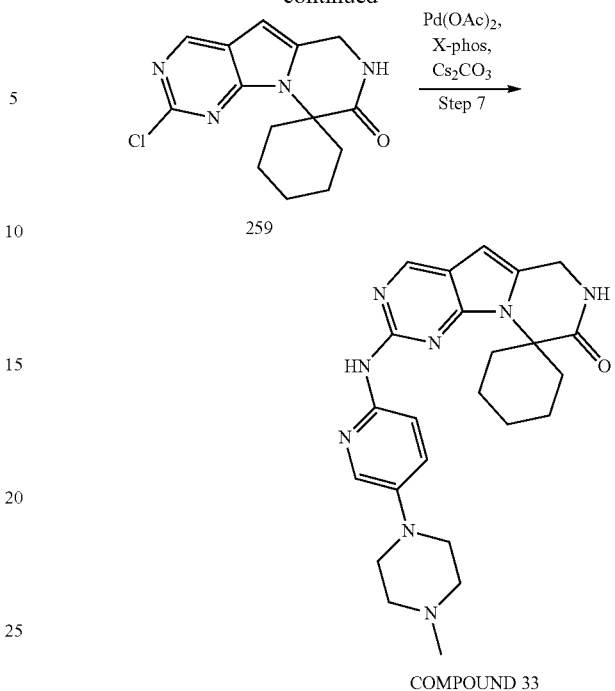

Step 1: Synthesis of 2,4-Dichloro-5-(3,3-diethoxyprop-1-yn-1-yl)pyrimidine (254)

Under N₂ atmosphere, to a solution of 2,4-dichloro-5-iodopyrimidine (253, 1 g, 3.65 mmol) and DIEA (1.42 g, 10.99 mmol) in THF (20 mL) was added CuI (70 mg, 0.37 mmol) and Pd(PPh₃)₂Cl₂ (100 mg, 0.14 mmol). After stirring at room temperature for 10 min, a solution of 3,3-diethoxyprop-1-yne (470 mg, 3.67 mmol) in THF (5 mL) was added. After stirring at room temperature for 12 h, the reaction mixture was quenched with water (20 mL) and extracted with EtOAc (20 mL×2). The combined organic phases were concentrated in vacuo. The resulting residue was purified by column chromatography to provide 2,4-dichloro-5-(3,3-diethoxyprop-1-yn-1-yl)pyrimidine (254, 1.1 g, 4.0 mmol).

Step 2: Synthesis of Methyl 1-((2-chloro-5-(3,3-diethoxyprop-1-yn-1-yl) pyrimidin-4-yl)amino)cyclohexane-1-carboxylate (255)

A solution of 2,4-dichloro-5-(3,3-diethoxyprop-1-yn-1-yl)pyrimidine (254, 600 mg, 2.18 mmol) and methyl 1-aminocyclohexane-1-carboxylate (336 mg, 2.14 mmol) and DIEA (619 mg, 4.8 mmol) in DMAc (20 mL) was stirred at 60° C. for 12 h. After cooling to room temperature, the reaction mixture was quenched with water (50 mL) and extracted with EtOAc (30 mL×3). The combined organic phases were washed with brine (30 mL), dried over Na₂SO₄ and concentrated in vacuo. The resulting residue was purified by column chromatography to afford methyl 1-((2-chloro-5-(3,3-diethoxyprop-1-yn-1-yl)pyrimidin-4-yl)amino)cyclohexane-1-carboxylate (255, 200 mg, 0.50 mmol).

Step 3: Synthesis of Methyl 1-(2-chloro-6-(diethoxymethyl)-7H-pyrrolo [2,3-d]pyrimidin-7-yl)cyclohexane-1-carboxylate (256)

To a solution of methyl 1-((2-chloro-5-(3,3-diethoxyprop-1-yn-1-yl)pyrimidin-4-yl)amino)cyclohexane-1-carboxylate (255, 50 mg, 0.13 mmol) in THF (1 mL) was added TBAF (0.4 mL, 0.4 mmol, 1M in THF). After stirring at 60° C. for 2 h, the reaction mixture was quenched with water (15 mL) and extracted with EtOAc (10 mL×3). The combined organic phases were dried over Na$_2$SO$_4$, filtered and concentrated in vacuo. The resulting residue was purified by column chromatography to provide methyl 1-(2-chloro-6-(diethoxymethyl)-7H-pyrrolo[2,3-d]pyrimidin-7-yl)cyclohexane-1-carboxylate (256, 20 mg, 0.05 mmol). MS (ESI+): m/z 396 [M+H]$^+$.

Step 4: Synthesis of Methyl 1-(2-chloro-6-formyl-7H-pyrrolo[2,3-d]pyrimidin-7-yl)cyclohexane-1-carboxylate (257)

To a solution of methyl 1-(2-chloro-6-(diethoxymethyl)-7H-pyrrolo[2,3-d]pyrimidin-7-yl)cyclohexane-1-carboxylate (256, 300 mg, 0.75 mmol) in THF (4 mL) was added water (4 mL) and HOAc (4 mL). After stirring at 60° C. for 2 h, the reaction mixture was quenched with saturated aqueous NaHCO$_3$ and extracted with EtOAc (100 mL×3). The combined organic phases were dried over Na$_2$SO$_4$ and concentrated in vacuo. The resulting residue was purified by column chromatography to provide methyl 1-(2-chloro-6-formyl-7H-pyrrolo[2,3-d]pyrimidin-7-yl)cyclohexane-1-carboxylate (257, 250 mg, 0.78 mmol).

Step 5: Synthesis of Methyl (E)-1-(2-chloro-6-((hydroxyimino)methyl)-7H-pyrrolo[2,3-d]pyrimidin-7-yl)cyclohexane-1-carboxylate (258)

To a solution of methyl 1-(2-chloro-6-formyl-7H-pyrrolo[2,3-d]pyrimidin-7-yl)cyclohexane-1-carboxylate (257, 250 mg, 0.78 mmol) in EtOH (2 mL) at room temperature was added hydroxylamine hydrochloride (107 mg, 1.54 mmol). After stirring at 80° C. for 30 min, the reaction mixture was quenched with water (15 mL) and extracted with EtOAc (10 mL×3). The combined organic phases were dried over Na$_2$SO$_4$, filtered and concentrated in vacuo.

The resulting residue was purified by column chromatography to provide methyl (E)-1-(2-chloro-6-((hydroxyimino)methyl)-7H-pyrrolo[2,3-d]pyrimidin-7-yl)cyclohexane-1-carboxylate (258, 220 mg, 0.65 mmol). MS (ESI+): m/z 337 [M+H]$^+$.

Step 6: Synthesis of 2'-Chloro-6',7'-dihydro-8'H-spiro [cyclohexane-1,9'-pyrazino [1',2':1,5]pyrrolo [2,3-d]pyrimidin]-8'-one (259)

Under N$_2$ atmosphere, to a solution of methyl (E)-1-(2-chloro-6-((hydroxyimino)methyl)-7H-pyrrolo[2,3-d]pyrimidin-7-yl)cyclohexane-1-carboxylate (258, 200 mg, 0.59 mmol) in EtOH (4 mL) was added saturated aqueous NH$_4$Cl (8 drops) and Zn power (193 mg, 2.95 mmol). After stirring at 80° C. for 2 h, the reaction mixture was cooled to room temperature and filtered. The filtrate was concentrated in vacuo. The resulting residue was purified by column chromatography to provide 2'-chloro-6',7'-dihydro-8'H-spiro[cyclohexane-1,9'-pyrazino[1',2': 1,5]pyrrolo[2,3-d]pyrimidin]-8'-one (259, 150 mg, 0.52 mmol). MS (ESI-): m/z 289 [M–H]—.

Step 7: Synthesis of 2'-((5-(4-Methylpiperazin-1-yl)pyridin-2-yl)amino)-6',7'-dihydro-8'H-spiro [cyclohexane-1,9'-pyrazino [1',2':1,5]pyrrolo [2,3-d]pyrimidin]-8'-one (COMPOUND 33)

Under N$_2$ atmosphere, to a solution of 5-(4-methylpiperazin-1-yl)pyrimidin-2-amine (40 mg, 0.21 mmol), 2'-chloro-6',7'-dihydro-8'H-spiro[cyclohexane-1,9'-pyrazino[1',2':1,5] pyrrolo[2,3-d]pyrimidin]-8'-one (259, 50 mg, 0.17 mmol) in dioxane (4 mL) at room temperature was added Cs$_2$CO$_3$ (160 mg, 0.49 mmol), Pd(OAc)$_2$ (4 mg, 0.02 mmol) and X-Phos (16 mg, 0.03 mmol). After stirring at 100° C. for 12 h, the reaction mixture was cooled to room temperature and quenched with water (10 mL) and extracted with EtOAc (10 mL×2). The combined organic phases were concentrated in vacuo. The resulting residue was purified by prep TLC to provide 2'-((5-(4-methylpiperazin-1-yl)pyridin-2-yl)amino)-6',7'-dihydro-8'H-spiro[cyclohexane-1,9'-pyrazino [1',2': 1,5]pyrrolo[2,3-d]pyrimidin]-8'-one (COMPOUND 33, 4.6 mg, 0.01 mmol). MS (ESI+): m/z 447 [M+H]+; $^1$H NMR (300 MHz, MeOD): δ 8.64 (s, 1H), 8.12 (d, J=9.4 Hz, 1H), 7.99 (s, 1H), 7.59 (d, J=9.6 Hz, 1H), 6.38 (s, 1H), 4.64 (s, 2H), 3.42-3.33 (m, 4H), 3.23-3.13 (m, 6H), 2.75 (s, 3H), 2.25-2.02 (m, 4H), 1.91-1.72 (m, 3H), 1.67-1.45 (m, 1H).

Scheme 36: Synthesis of 2'-((5-(4-Methylpiperazin-1-yl)pyridin-2-yl)amino)-2,3,5,6,7',8'-hexahydro-6'H-spiro [pyran-4,9'-pyrazino [1',2':1,5]pyrrolo [2,3-d]pyrimidin]-6'-one (COMPOUND 34)

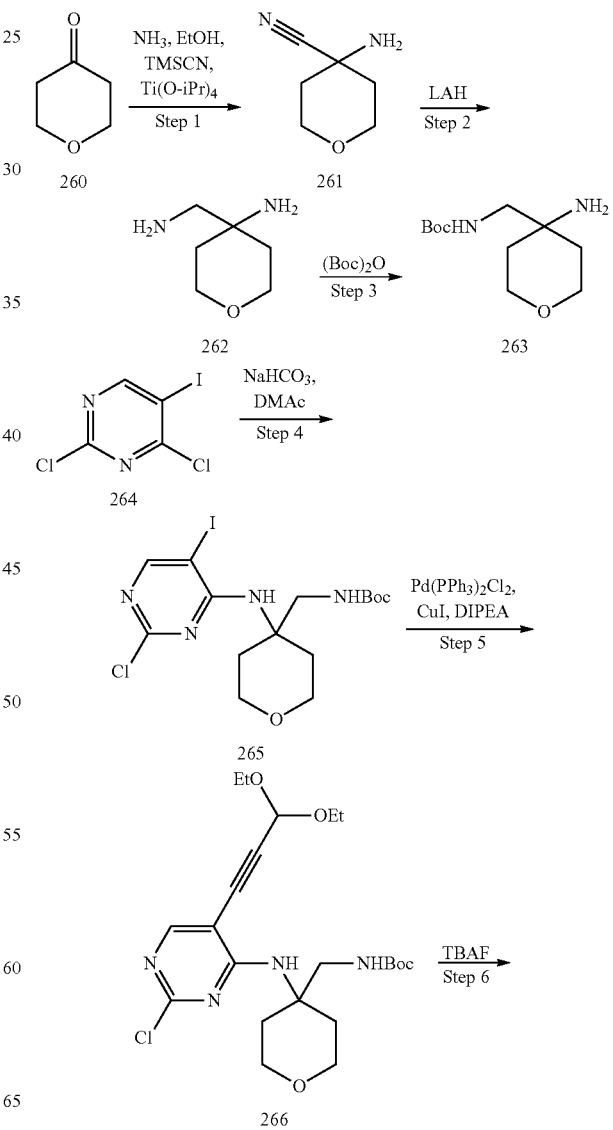

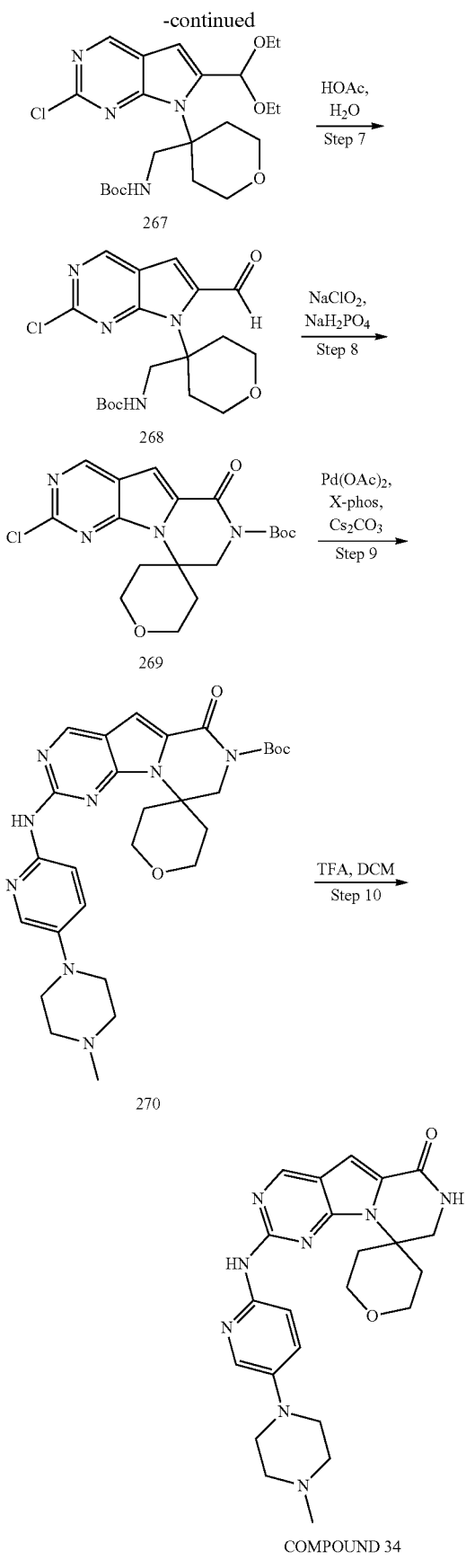

COMPOUND 34

Step 1: Synthesis of
4-Aminotetrahydro-2H-pyran-4-carbonitrile (261)

Under $N_2$ atmosphere, to a solution of Ti(O-iPr)$_4$ (68 g, 239 mmol) in NH$_3$/EtOH (300 mL) at room temperature was added tetrahydro-4H-pyran-4-one (260, 20 g, 200 mmol). After stirring at 20° C. for 2 h, the reaction was cooled to −5° C. TMSCN (20.6 g, 208 mmol) was added dropwise and the reaction was continued to stir at −5° C. for 3 h. The reaction was then warmed to room temperature and stirred for 12 h. The reaction mixture was quenched with water (20 mL), filtered, and the filter cake was washed with EtOH (20 mL×2). The filtrate was concentrated in vacuo. The resulting residue was purified by column chromatography to provide 4-aminotetrahydro-2H-pyran-4-carbonitrile (261, 20.8 g, 165 mmol) as a yellow oil.

Step 2: Synthesis of
4-(Aminomethyl)tetrahydro-2H-pyran-4-amine (262)

To a suspension of LiAlH$_4$ (9.1 g, 240 mmol) in MTBE (120 mL) at room temperature was added 4-aminotetrahydro-2H-pyran-4-carbonitrile (261, 10 g, 80 mmol). After stirring at 40° C. for 2 h, the reaction mixture was quenched with water (9.1 mL) and 15% aqueous NaOH (9.1 mL), followed by the addition of water (27.3 mL). After stirring for 1 h, the mixture was filtered and the filter cake was washed with MTBE (20 mL×2). The filtrate was concentrated in vacuo to provide 4-(aminomethyl)tetrahydro-2H-pyran-4-amine (262, 6 g, 46.1 mmol), which was carried forward in the next step without further purification.

Step 3: Synthesis of tert-Butyl ((4-aminotetrahydro-2H-pyran-4-yl)methyl)carbamate (263)

Under $N_2$ atmosphere, to a solution of 4-(aminomethyl)tetrahydro-2H-pyran-4-amine (262, 6 g, 46.1 mmol) in DCM (230 mL) at −78° C. was added Boc$_2$O (8.5 g, 39 mmol) dropwise over 1 h. After stirring at −78° C. for an additional 2 h, the reaction was gradually warmed to room temperature. 1 M HCl was added to adjust pH=5. The aqueous phase was extracted with EtOAc (200 mL). The aqueous phase was collected and adjusted to pH=10 with 15% aqueous NaOH and extracted with DCM (200 mL×3). The combined organic phases were dried over Na$_2$SO$_4$, filtered and concentrated to provide tert-butyl ((4-aminotetrahydro-2H-pyran-4-yl)methyl)carbamate (263, 6.05 g, 26.3 mmol).

Step 4: Synthesis of tert-Butyl ((4-((2-chloro-5-iodopyrimidin-4-yl)amino) tetrahydro-2H-pyran-4-yl)methyl)carbamate (265)

To a solution of 2,4-dichloro-5-iodopyrimidine (264, 8.7 g, 31.6 mmol) and tert-butyl ((4-aminotetrahydro-2H-pyran-4-yl)methyl)carbamate (263, 5 g, 21.7 mmol) in DMAc (200 mL) was added NaHCO$_3$(11.1 g, 132 mmol). After stirring at 80° C. for 12 h, the reaction mixture was quenched with water (50 mL) and extracted with EtOAc (300 mL×3). The combined organic phases were washed with water (200 mL×2) and brine (100 mL), dried over Na$_2$SO$_4$, filtered and concentrated in vacuo. The resulting residue was purified by column chromatography to provide tert-butyl ((4-((2-chloro-5-iodopyrimidin-4-yl)amino)tetrahydro-2H-pyran-4-yl) methyl) carbamate (265, 5.02 g, 10.7 mmol).

Step 5: Synthesis of tert-Butyl ((4-((2-chloro-5-(3,3-diethoxyprop-1-yn-1-yl) pyrimidin-4-yl)amino) tetrahydro-2H-pyran-4-yl)methyl)carbamate (266)

Under $N_2$ atmosphere, to a solution of tert-butyl((4-((2-chloro-5-iodopyrimidin-4-yl)amino) tetrahydro-2H-pyran-4-yl) methyl)carbamate (265, 5.70 g, 12.2 mmol) and DIEA (3.11 g, 24.1 mmol) in THF (170 mL) was added CuI (228 mg, 1.2 mmol) and Pd(PPh$_3$)$_2$Cl$_2$ (342 mg, 0.49 mmol). After stirring at room temperature for 10 min, 3,3-diethoxyprop-1-yne (1.9 g, 14.8 mmol) in THF (5 mL) was added dropwise and the reaction was stirred at room temperature for 12 h. The reaction was quenched with water (20 mL) and extracted with EtOAc (20 mL×2). The combined organic phases were concentrated in vacuo. The resulting residue was purified by column chromatography to provide tert-butyl ((4-((2-chloro-5-(3,3-diethoxyprop-1-yn-1-yl)pyrimidin-4-yl)amino)tetrahydro-2H-pyran-4-yl)methyl)carbamate (266, 5.03 g, 10.7 mmol). MS (ESI+): m/z 469 [M+H]$^+$.

Step 6: Synthesis of tert-Butyl ((4-(2-chloro-6-(diethoxymethyl)-7H-pyrrolo [2,3-d]pyrimidin-7-yl) tetrahydro-2H-pyran-4-yl)methyl)carbamate (267)

To a solution of tert-butyl ((4-((2-chloro-5-(3,3-diethoxyprop-1-yn-1-yl)pyrimidin-4-yl)amino)tetrahydro-2H-pyran-4-yl)methyl)carbamate (266, 4.90 g, 10.4 mmol) in THF (50 mL) was added TBAF (50 mL, 50 mmol, 1 M in THF). After stirring at 65° C. for 2 h, the reaction was cooled to room temperature and quenched with water (150 mL). The aqueous solution was extracted with EtOAc (100 mL×3). The combined organic phases were dried over Na$_2$SO$_4$, filtered and concentrated in vacuo. The resulting residue was purified by column chromatography to provide tert-butyl ((4-(2-chloro-6-(diethoxymethyl)-7H-pyrrolo[2,3-d]pyrimidin-7-yl)tetrahydro-2H-pyran-4-yl)methyl)carbamate (267, 1.8 g, 3.84 mmol). MS (ESI+): m/z 491 [M+Na]$^+$.

Step 7: Synthesis of tert-Butyl ((4-(2-chloro-6-formyl-7H-pyrrolo[2,3-d] pyrimidin-7-yl)tetrahydro-2H-pyran-4-yl)methyl)carbamate (268)

To a solution of tert-butyl ((4-(2-chloro-6-(diethoxymethyl)-7H-pyrrolo[2,3-d]pyrimidin-7-yl)tetrahydro-2H-pyran-4-yl)methyl)carbamate (267, 800 mg, 1.71 mmol) in THF (4 mL) was added water (4 mL) and AcOH (4 mL). After stirring at 60° C. for 2 h, the reaction mixture was neutralized with saturated aqueous NaHCO$_3$ and extracted with EtOAc (100 mL×3). The combined organic phases were dried over Na$_2$SO$_4$ and concentrated in vacuo. The resulting residue was purified by column chromatography to provide tert-butyl ((4-(2-chloro-6-formyl-7H-pyrrolo[2,3-d] pyrimidin-7-yl)tetrahydro-2H-pyran-4-yl)methyl)carbamate (268, 527 mg, 1.33 mmol).

Step 8: Synthesis of tert-Butyl 2'-chloro-6'-oxo-2,3,5,6-tetrahydro-6'H— spiro[pyran-4,9'-pyrazino[1',2':1,5]pyrrolo[2,3-d]pyrimidine]-7'(8'H)— carboxylate (269)

To a solution of tert-butyl ((4-(2-chloro-6-formyl-7H-pyrrolo[2,3-d]pyrimidin-7-yl)tetrahydro-2H-pyran-4-yl) methyl)carbamate (268, 200 mg, 0.51 mmol) in t-BuOH (5 mL) and acetonitrile (1 mL) at 0° C. was added NaH$_2$PO$_4$ (610 mg, 5.08 mmol) and 2-methyl-2-butene (280 mg, 3.99 mmol). Then a solution of NaClO$_2$ (360 mg, 3.98 mmol) in H$_2$O (3 mL) at 0° C. was added dropwise. After completion of the addition, the reaction was warmed to room temperature and stirred for 2 h. The reaction mixture was quenched with water (10 mL) and extracted with EtOAc (30 mL×3). The combined organic phases were dried over Na$_2$SO$_4$, filtered and concentrated in vacuo. The resulting residue was purified by column chromatography to provide tert-butyl 2'-chloro-6'-oxo-2,3,5,6-tetrahydro-6'H-spiro[pyran-4,9'-pyrazino[1',2':1,5]pyrrolo[2,3-d]pyrimidine]-7'(8'H)-carboxylate (269, 130 mg, 0.33 mmol).

Step 9: Synthesis of tert-Butyl 2'-((5-(4-methylpiperazin-1-yl)pyridin-2-yl) amino)-6'-oxo-2,3,5,6-tetrahydro-6'H-spiro [pyran-4,9'-pyrazino[1',2':1,5] pyrrolo[2,3-d]pyrimidine]-7'(8'H)-carboxylate (270)

Under $N_2$ atmosphere, to a mixture of tert-butyl 2'-chloro-6'-oxo-2,3,5,6-tetrahydro-6'H-spiro[pyran-4,9'-pyrazino[1',2':1,5]pyrrolo[2,3-d]pyrimidine]-7'(8'H)-carboxylate (269, 20 mg, 0.05 mmol), 5-(4-methylpiperazin-1-yl)pyridin-2-amine (11 mg, 0.06 mmol) and Cs$_2$CO$_3$ (33 mg, 0.10 mmol) in dioxane (2 mL) was added Pd(OAc)$_2$ (1.1 mg, 0.005 mmol) and X-Phos (9.6 mg, 0.02 mmol). The reaction was stirred at 100° C. for 12 h. After cooling to room temperature, the reaction was concentrated in vacuo. The resulting residue was purified by prep TLC to provide tert-butyl 2'-((5-(4-methylpiperazin-1-yl)pyridin-2-yl)amino)-6'-oxo-2,3,5,6-tetrahydro-6'H-spiro[pyran-4,9'-pyrazino[1',2': 1,5]pyrrolo[2,3-d]pyrimidine]-7'(8'H)-carboxylate (270, 10 mg, 0.02 mmol). MS (ESI+): m/z 549 [M+H]$^+$.

Step 10: Synthesis of 2'-((5-(4-Methylpiperazin-1-yl)pyridin-2-yl)amino)-2,3,5,6,7',8'-hexahydro-6'H-spiro [pyran-4,9'-pyrazino [1',2':1,5]pyrrolo [2,3-d] pyrimidin]-6'-one (COMPOUND 34)

To a solution of tert-butyl 2'-((5-(4-methylpiperazin-1-yl) pyridin-2-yl)amino)-6'-oxo-2,3,5,6-tetrahydro-6'H-spiro [pyran-4,9'-pyrazino[1',2':1,5]pyrrolo[2,3-d]pyrimidine]-7' (8'H)-carboxylate (270, 10 mg, 0.02 mmol) in DCM (3 mL) at 0° C. was added TFA (1 mL) dropwise over 5 min. After stirring for 2 h, the reaction mixture was neutralized with saturated aqueous NaHCO$_3$ and extracted with i-PrOH/DCM=1/3 (20 mL×2). The combined organic phases were dried over Na$_2$SO$_4$ and concentrated in vacuo. The resulting residue was purified by prep TLC to provide 2'-((5-(4-methylpiperazin-1-yl)pyridin-2-yl)amino)-2,3,5,6,7',8'-hexahydro-6'H-spiro[pyran-4,9'-pyrazino[1',2':1,5]pyrrolo [2,3-d]pyrimidin]-6'-one (COMPOUND 34, 5.9 mg, 0.01 mmol). MS (ESI+): m/z 449 [M+H]+; $^1$H NMR (300 MHz, MeOD+CDCl$_3$): δ 8.83 (s, 1H), 8.26 (d, J=9.1 Hz, 1H), 7.99 (d, J=2.8 Hz, 1H), 7.63 (s, 1H), 7.53 (dd, J=9.2, 2.8 Hz, 1H), 4.09 (dd, J=12.0, 4.8 Hz, 2H), 3.90 (s, 2H), 3.70 (t, J=12.0 Hz, 2H), 3.47 (td, J=13.4, 5.1 Hz, 2H), 3.33-3.29 (m, 4H), 2.92-2.82 (m, 4H), 2.54 (s, 3H), 1.94 (d, J=13.2 Hz, 2H).

Scheme 37: Synthesis of 2'-(((1R,4R)-4-(4-(Cyclopropylmethyl)piperazin-1-yl)cyclohexyl)amino)-7',8'-dihydro-6'H-spiro [cyclohexane-1,9'-pyrazino[1',2':1,5]pyrrolo[2,3-d]pyrimidin]-6'-one (COMPOUND 36) and 2'-(((1S,4S)-4-(4-(Cyclopropylmethyl)piperazin-1-yl)cyclohexyl)amino)-7',8'-dihydro-6'H-spiro [cyclohexane-1,9'-pyrazino[1',2':1,5]pyrrolo[2,3-d]pyrimidin]-6'-one (COMPOUND 40)
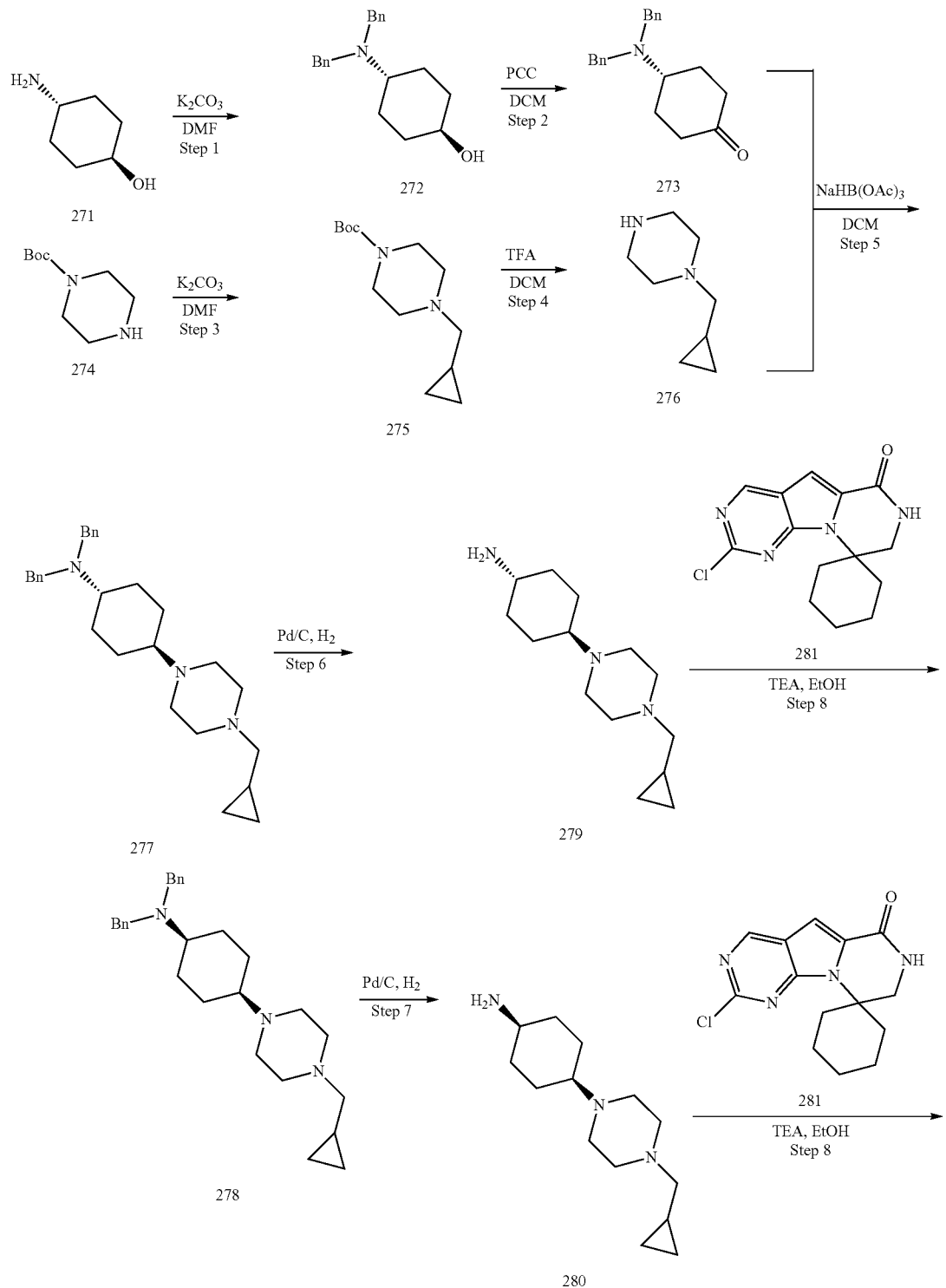

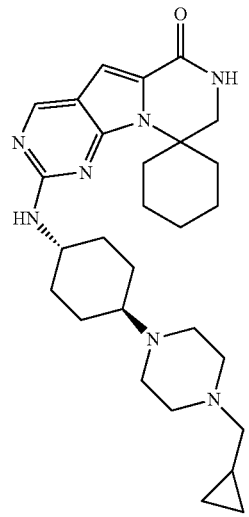

COMPOUND 36

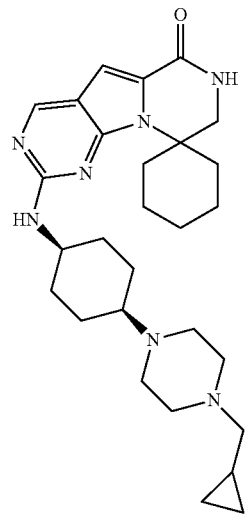

COMPOUND 40

Step 1: Synthesis of (1R,4R)-4-(Dibenzylamino)cyclohexan-1-ol (272)

To a solution of (1R,4R)-4-aminocyclohexan-1-ol (270, 30 g, 261 mmol) and $K_2CO_3$ (80 g, 575 mmol) in DMF (250 mL) was added benzyl bromide (44 g, 257 mmol) dropwise over 30 min. After stirring at room temperature overnight, the reaction mixture was poured into 2 L of ice-water. The precipitated solid was collected, washed with water (2×100 mL) and dried to provide (1R,4R)-4-(dibenzylamino)cyclohexan-1-ol (272, 69.3 g, 234 mmol). MS (ESI+): m/z 296 [M+H]+.

Step 2: Synthesis of 4-(Dibenzylamino)cyclohexan-1-one (273)

To a solution of (1R,4R)-4-(dibenzylamino)cyclohexan-1-ol (272, 40 g, 136 mmol) in DCM (250 mL) was added PCC (75 g, 348 mmol) and silica gel (75 g). After stirring at room temperature overnight, the reaction mixture was filtered. The filter cake was washed with DCM (50 mL×2) and the filtrate was washed with 100 mL of saturated sodium bicarbonate solution. The organic layer was separated and concentrated in vacuo. The resulting residue was purified by column chromatography with a gradient elution of hexane (90%) and EtOAc (10%) to hexane (75%) and EtOAc (25%) to provide 4-(dibenzylamino)cyclohexan-1-one (273, 25 g, 85 mmol). MS (ESI+): m/z 294 [M+H]+.

Step 3: Synthesis of tert-Butyl 4-(cyclopropylmethyl)piperazine-1-carboxylate To a solution of tert-butyl piperazine-1-carboxylate (274, 32 g, 172 mmol) and (bromomethyl)cyclopropane (25 g, 185 mmol) in DCM (100 mL) at room temperature was added TEA (20 mL, 144 mmol). After stirring at room temperature for 48 h, the reaction mixture was filtered and the filtrate was concentrated in vacuo. The resulting residue was purified by column chromatography to afford tert-butyl 4-(cyclopropylmethyl)piperazine-1-carboxylate (275, 30 g, 124 mmol). MS (ESI): m/z 241 [M+H]+.

Step 4: Synthesis of 1-(Cyclopropylmethyl)piperazine (276)

To a solution of tert-butyl 4-(cyclopropylmethyl)piperazine-1-carboxylate (275, 30 g, 124 mmol) in DCM (100 mL) was added TFA (50 mL). After stirring at room temperature overnight, the reaction mixture was neutralized with saturated sodium bicarbonate solution (500 mL) and extracted with DCM (200 mL×2). The combined organic phases were dried over $MgSO_4$, filtered and concentrated in vacuo to provide 1-(cyclopropylmethyl)piperazine (276, 13 g, 92 mmol), which was used carried forward in the next step without further purification. MS (ESI+): m/z 141 [M+H]+.

Step 5: Synthesis of (1R,4R)—N,N-Dibenzyl-4-(4-(cyclopropylmethyl) piperazin-1-yl)cyclohexan-1-amine (277) and (1S,4S)—N,N-Dibenzyl-4-(4-(cyclopropylmethyl)piperazin-1-yl)cyclohexan-1-amine (278)

To a solution of 4-(dibenzylamino)cyclohexan-1-one (273, 5 g, 17.0 mmol) and 1-(cyclopropylmethyl)piperazine (276, 2.4 g, 17.1 mmol) in DCM (30 mL) was added HOAc (1 mL). $NaHB(OAc)_3$ (20 g, 94.4 mmol) was then added in portions. After stirring at room temperature for 48 h, the reaction mixture was neutralized with saturated sodium bicarbonate solution and extracted with DCM (50 mL×3). The combined organic phases were dried over $MgSO_4$ and concentrated in vacuo. The resulting residue was purified by column chromatography to afford (1r,4r)-N,N-dibenzyl-4-(4-(cyclopropylmethyl)piperazin-1-yl)cyclohexan-1-amine (277, 670 mg, 1.6 mmol) and (1s,4s)-N,N-dibenzyl-4-(4-(cyclopropylmethyl)piperazin-1-yl)cyclohexan-1-amine (278, 1.2 g, 2.9 mmol).

(1R,4R)—N,N-Dibenzyl-4-(4-(cyclopropylmethyl) piperazin-1-yl)cyclohexan-1-amine (277)

$^1$H NMR (300 MHz, $CDCl_3$): δ 7.29-7.26 (m, 4H), 7.24-7.18 (m, 4H), 7.15-7.10 (m, 2H), 3.53 (s, 4H), 2.81-2.60 (m, 6H), 2.44-2.36 (m, 2H), 2.29 (d, J=6.6 Hz, 2H), 1.96-1.88 (m, 4H), 1.58-1.29 (m, 4H), 1.21-1.10 (m, 2H), 0.88-0.77 (m, 1H), 0.50-0.42 (m, 2H), 0.10-0.02 (m, 2H).

(1S,4S)—N,N-Dibenzyl-4-(4-(cyclopropylmethyl) piperazin-1-yl)cyclohexan-1-amine (278)

$^1$H NMR (300 MHz, $CDCl_3$): δ 7.29-7.27 (m, 4H), 7.23-7.18 (m, 4H), 7.14-7.09 (m, 2H), 3.57 (s, 4H), 2.96-2.49 (m, 8H), 2.40 (d, J=6.6 Hz, 2H), 2.20 (s, 1H), 1.89-1.85 (m, 2H), 1.77-1.66 (m, 2H), 1.48-1.44 (m, 2H), 1.26-1.17 (m, 3H), 1.00-0.82 (m, 1H), 0.55-0.49 (m, 2H), 0.16-0.11 (m, 2H).

Step 6: Synthesis of (1R,4R)-4-(4-(Cyclopropylmethyl)piperazin-1-yl)cyclohexan-1-amine (279)

To a solution of (1R,4R)—N,N-dibenzyl-4-(4-(cyclopropylmethyl)piperazin-1-yl)cyclohexan-1-amine (277, 500 mg, 1.2 mmol) in IPA (30 mL) was added Pd/C (10%, 200 mg). The reaction mixture was stirred at 40° C. under 1.8 MPa of hydrogen pressure for 24 h. After completion of the reaction, the mixture was filtered and the filtrate was concentrated to provide (1R,4R)-4-(4-(cyclopropylmethyl)piperazin-1-yl)cyclohexan-1-amine (279, 160 mg, 0.67 mmol). MS (ESI+): m/z 238 [M+H]+.

Step 7: Synthesis of (1S,4S)-4-(4-(Cyclopropylmethyl)piperazin-1-yl)cyclohexan-1-amine (280)

(1S,4S)-4-(4-(cyclopropylmethyl)piperazin-1-yl)cyclohexan-1-amine (280) was prepared from (1S,4S)—N,N-dibenzyl-4-(4-(cyclopropylmethyl)piperazin-1-yl)cyclohexan-1-amine (278) according to the experimental procedure as described in Step 6 for the synthesis of (1R,4R)-4-(4-(cyclopropylmethyl)piperazin-1-yl)cyclohexan-1-amine (279). MS (ESI+): m/z 238 [M+H]+.

Step 8: Synthesis of 2'-(((1R,4R)-4-(4-(Cyclopropylmethyl)piperazin-1-yl)cyclohexyl)amino)-7',8'-dihydro-6'H-spiro [cyclohexane-1,9'-pyrazino[1',2':1,5]pyrrolo[2,3-d]pyrimidin]-6'-one (COMPOUND 36)

To a solution of (1R,4R)-4-(4-(cyclopropylmethyl)piperazin-1-yl)cyclohexan-1-amine (279, 40 mg, 0.17 mmol) and 2'-chloro-7',8'-dihydro-6'H-spiro[cyclohexane-1,9'-pyrazino[1',2':1,5]pyrrolo[2,3-d]pyrimidin]-6'-one (280, 40 mg, 0.14 mmol) in 95% EtOH (5 mL) was added TEA (0.3 mL). The reaction was stirred in a sealed tube at 140° C. overnight. After cooling to room temperature, the reaction mixture was concentrated to the residue, which was purified by prep TLC to provide 2'-(((1R,4R)-4-(4-(cyclopropylmethyl)piperazin-1-yl)cyclohexyl)amino)-7',8'-dihydro-6'H-spiro[cyclohexane-1,9'-pyrazino[1',2':1,5]pyrrolo[2,3-d]pyrimidin]-6'-one (COMPOUND 36, 4.3 mg, 0.008 mmol). MS (ESI+): m/z 492 [M+H]+; $^1$H NMR (300 MHz, MeOD): δ 8.60 (s, 1H), 7.11 (s, 1H), 3.73 (s, 2H), 3.73-3.72 (m, 1H), 3.04 (td, J=13.5, 3.9 Hz, 4H), 2.89-2.75 (m, 4H), 2.33-1.79 (m, 10H), 1.56-1.28 (m, 11H), 1.09-1.00 (m, 1H), 0.71-0.68 (m, 2H), 0.36 (s, 2H).

Step 9: Synthesis of 2'-(((1S,4S)-4-(4-(Cyclopropylmethyl)piperazin-1-yl) cyclohexyl)amino)-7',8'-dihydro-6'H-spiro [cyclohexane-1,9'-pyrazino[1',2':1,5]pyrrolo[2,3-d]pyrimidin]-6'-one (COMPOUND 40)

2'-(((1S,4S)-4-(4-(cyclopropylmethyl)piperazin-1-yl)cyclohexyl)amino)-7',8'-dihydro-6'H-spiro[cyclohexane-1,9'-pyrazino[1',2': 1,5]pyrrolo[2,3-d]pyrimidin]-6'-one (COMPOUND 40) was prepared according to the procedure in Step 8 for the synthesis of COMPOUND 36. MS (ESI+): m/z 492 [M+H]+; $^1$H NMR (300 MHz, MeOD): δ 8.62 (s, 1H), 7.12 (s, 1H), 4.04 (s, 1H), 3.73 (s, 2H), 3.04 (td, J=13.5, 3.6 Hz, 4H), 2.86-2.80 (m, 4H), 2.18-2.10 (m, 3H), 1.95-1.78 (m, 10H), 1.60-1.46 (m, 3H), 1.39-1.29 (m, 5H), 1.13-1.02 (m, 1H), 0.71-0.68 (m, 2H), 0.36 (s, 2H).

Scheme 38: Synthesis of 2'-(((1R,4R)-4-(4-Methyl-piperazin-1-yl)cyclohexyl) amino)-7',8'-dihydro-6'H-spiro [cyclohexane-1,9'-pyrazino[1',2':1,5]pyrrolo [2,3-d]pyrimidin]-6'-one (COMPOUND 37) and 2'-(((1S,4S)-4-(4-Methylpiperazin-1-yl) cyclohexyl) amino)-7',8'-dihydro-6'H-spiro [cyclohexane-1,9'-pyrazino[1',2':1,5]pyrrolo[2,3-d]pyrimidin]-6'-one (COMPOUND 41)
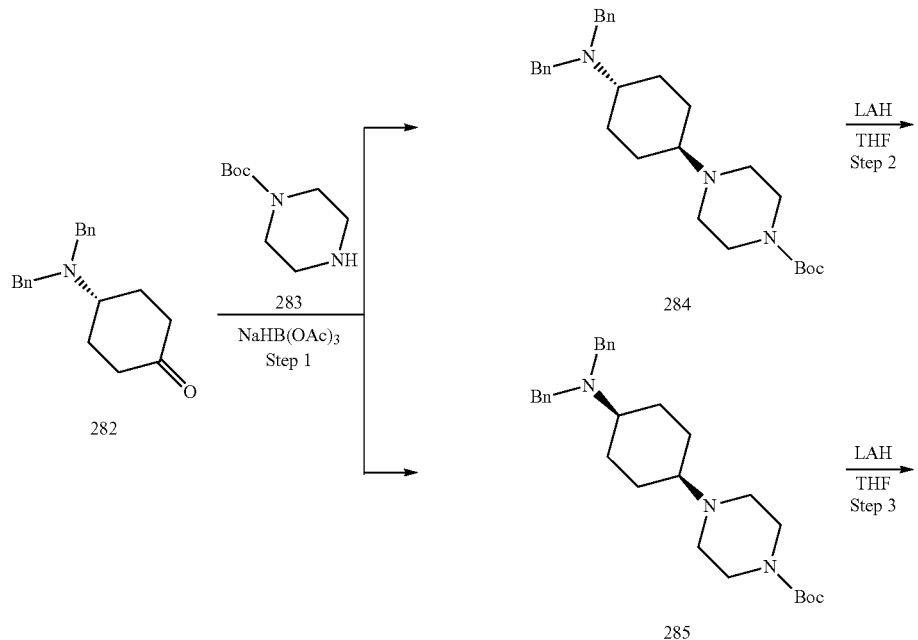
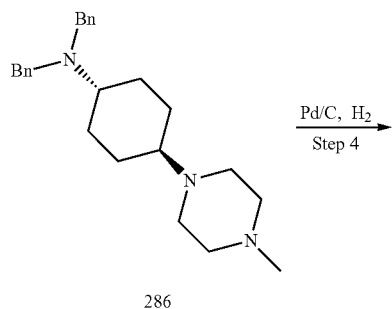
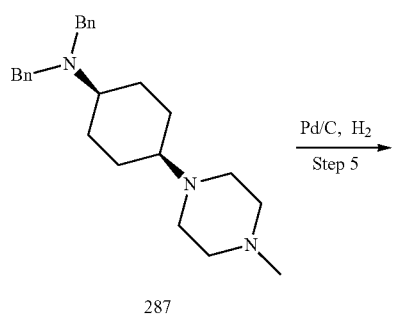

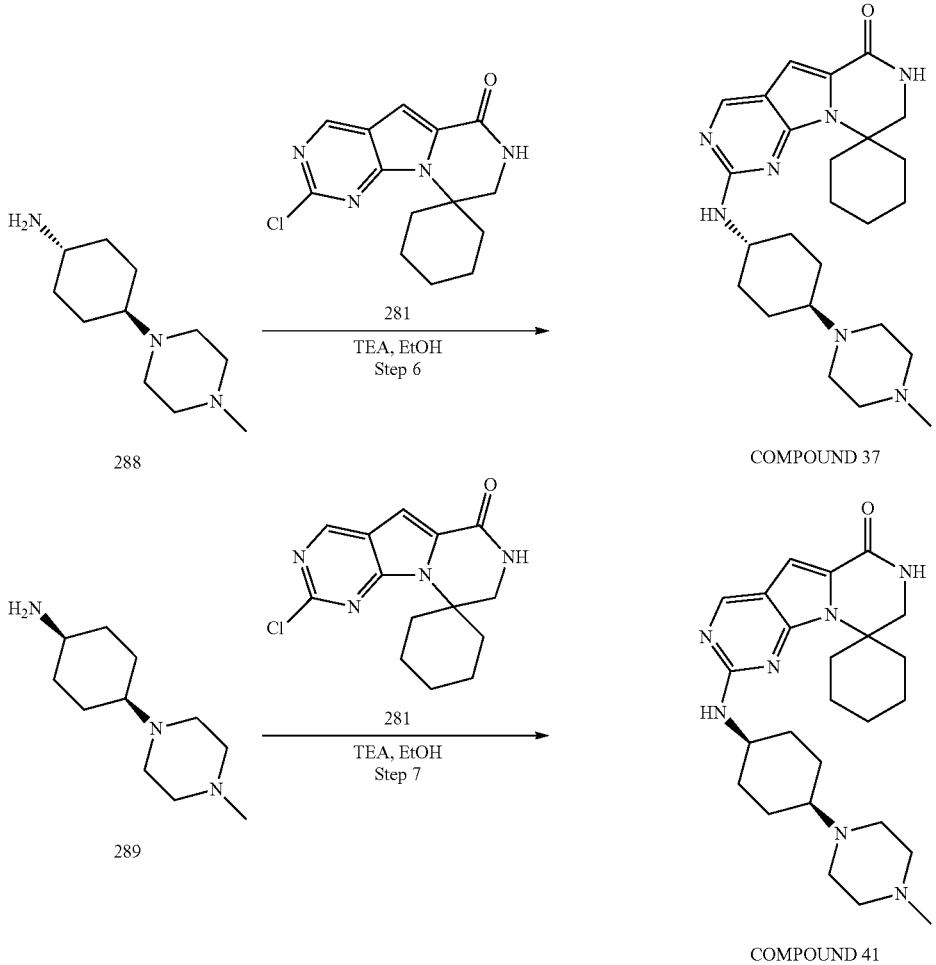

Step 1: Synthesis of tert-Butyl 4-((1R,4R)-4-(dibenzylamino)cyclohexyl)piperazine-1-carboxylate (284) and tert-Butyl 4-((1S,4S)-4-(dibenzylamino)cyclohexyl)piperazine-1-carboxylate (285)

To a solution of 4-(dibenzylamino)cyclohexan-1-one (282, 5 g, 17.0 mmol) and tert-butyl piperazine-1-carboxylate (283, 3.17 g, 22.6 mmol) in DCM (30 mL) was added HOAc (1 mL). NaHB(OAc)$_3$ (20 g, 94.4 mmol) was then added in portions. After stirring at room temperature for 48 h, the reaction mixture was neutralized with saturated sodium bicarbonate solution and extracted with DCM (50 mL×5). The combined organic phases were dried over anhydrous MgSO$_4$ and concentrated in vacuo. The resulting residue was purified by column chromatography to afford tert-butyl 4-((1R,4R)-4-(dibenzylamino)cyclohexyl)piperazine-1-carboxylate (284, 400 mg, 0.86 mmol) and tert-butyl 4-((1S,4S)-4-(dibenzylamino)cyclohexyl)piperazine-1-carboxylate (285, 1.4 g, 3.02 mmol).

tert-Butyl 4-((1R,4R)-4-(Dibenzylamino)cyclohexyl)piperazine-1-carboxylate $^1$H NMR (300 MHz, CDCl$_3$): δ 7.29-7.20 (m, 8H), 7.15-7.10 (m, 2H), 3.54 (s, 4H), 3.41-3.29 (m, 4H), 2.47-2.33 (m, 4H), 1.95-1.81 (m, 4H), 1.38 (s, 9H), 1.31-1.06 (m, 6H).

tert-Butyl 4-((1S,4S)-4-(dibenzylamino)cyclohexyl) piperazine-1-carboxylate $^1$H NMR (300 MHz, CDCl$_3$): δ 7.31-7.21 (m, 8H), 7.15-7.10 (m, 2H), 3.54 (s, 4H), 3.38-3.32 (m, 3H), 2.60-2.46 (m, 1H), 2.36-2.26 (m, 4H), 2.20-1.99 (m, 2H), 1.92-1.87 (m, 2H), 1.78-1.66 (m, 2H), 1.38 (s, 9H), 1.28-1.14 (m, 4H).

Step 2: Synthesis of (1R,4R)—N,N-Dibenzyl-4-(4-methylpiperazin-1-yl)cyclohexan-1-amine (286)

To a solution of tert-butyl 4-((1R,4R)-4-(Dibenzylamino)cyclohexyl)piperazine-1-carboxylate (284, 900 mg, 1.94 mmol) in anhydrous THF (20 mL) under ice-water bath was added LiAlH$_4$ (300 mg, 7.90 mmol) in portions. After completion of the addition, the reaction mixture was refluxed for 3 h. After cooling to room temperature, the mixture was quenched with 0.3 mL of water, 0.3 mL of 15% sodium hydroxide aqueous solution, followed by the addition of 0.6 mL of water. The mixture was stirred for 30 min. and 1 g of anhydrous magnesium sulfate was added and the reaction was stirred for 1 h. After filtration, the filter cake was washed with EtOAc (30 mL×2). The filtrate was concentrated to afford the residue, which was purified by a column chromatography with a gradient elution of EtOAc (100%) to EtOAc (83%) and MeOH (16%) and NH$_3$.H$_2$O (1%) to provide (1R,4R)—N,N-dibenzyl-4-(4-methylpiperazin-1-yl)cyclohexan-1-amine (286, 500 mg, 1.32 mmol). MS (ESI+): m/z 378 [M+H]$^+$.

Step 3: Synthesis of (1S,4S)—N,N-Dibenzyl-4-(4-methylpiperazin-1-yl)cyclohexan-1-amine (287)

(1S,4S)—N,N-dibenzyl-4-(4-methylpiperazin-1-yl)cyclohexan-1-amine (287) was prepared from 4-((1S,4S)-4-(dibenzylamino)cyclohexyl)piperazine-1-carboxylate (285) according to the experimental procedure of Step 2 for the synthesis of (1R,4R)—N,N-dibenzyl-4-(4-methylpiperazin-1-yl)cyclohexan-1-amine (286) MS (ESI+): m/z 378 [M+H]+.

Step 4: Synthesis of (1R,4R)-4-(4-Methylpiperazin-1-yl)cyclohexan-1-amine (288)

(1R,4R)-4-(4-methylpiperazin-1-yl)cyclohexan-1-amine (288) was prepared from (1R,4R)—N,N-dibenzyl-4-(4-methylpiperazin-1-yl)cyclohexan-1-amine (286) according to the experimental procedure for the synthesis of (1R,4R)-4-(4-(cyclopropylmethyl)piperazin-1-yl)cyclohexan-1-amine (279, Scheme 37, Step 6). MS (ESI+): m/z 198 [M+H]$^+$.

Step 5: Synthesis of (1S,4S)-4-(4-Methylpiperazin-1-yl)cyclohexan-1-amine (289)

(1S,4S)-4-(4-methylpiperazin-1-yl)cyclohexan-1-amine (289) was prepared from (1S,4S)—N,N-dibenzyl-4-(4-methylpiperazin-1-yl)cyclohexan-1-amine (287) according to the experimental procedure for the synthesis of (1R,4R)-4-(4-(cyclopropylmethyl)piperazin-1-yl)cyclohexan-1-amine (279, Scheme 37, Step 6). MS (ESI+): m/z 198 [M+H]$^+$.

Step 6: Synthesis of 2'-(((1R,4R)-4-(4-Methylpiperazin-1-yl)cyclohexyl)amino)-7',8'-dihydro-6'H-spiro[cyclohexane-1,9'-pyrazino[1',2':1,5]pyrrolo[2,3-d]pyrimidin]-6'-one (COMPOUND 37)

2'-(((1R,4R)-4-(4-methylpiperazin-1-yl)cyclohexyl)amino)-7',8'-dihydro-6'H-spiro[cyclohexane-1,9'-pyrazino[1',2': 1,5]pyrrolo[2,3-d]pyrimidin]-6'-one (COMPOUND 37) was prepared from (1R,4R)-4-(4-methylpiperazin-1-yl)cyclohexan-1-amine (288) according to the experimental procedure for the synthesis of COMPOUND 36 as shown in Step 8, Scheme 37. MS (ESI+): m/z 452 [M+H]+; $^1$H NMR (300 MHz, MeOD): δ 8.60 (s, 1H), 7.11 (s, 1H), 3.73 (s, 2H), 3.73-3.68 (m, 1H), 3.03 (td, J=13.2, 3.3 Hz, 4H), 2.67 (br s, 3H), 2.33-2.28 (m, 2H), 2.19-2.13 (m, 2H), 1.96-1.92 (m, 2H), 1.83-1.79 (m, 3H), 1.57-1.36 (m, 9H), 1.31-1.25 (m, 5H).

Step 7: Synthesis of 2'-(((1S,4S)-4-(4-Methylpiperazin-1-yl)cyclohexyl)amino)-7',8'-dihydro-6'H-spiro[cyclohexane-1,9'-pyrazino[1',2':1,5]pyrrolo[2,3-d]pyrimidin]-6'-one (COMPOUND 41)

2'-(((1S,4S)-4-(4-methylpiperazin-1-yl)cyclohexyl)amino)-7',8'-dihydro-6'H-spiro[cyclohexane-1,9'-pyrazino[1',2': 1,5]pyrrolo[2,3-d]pyrimidin]-6'-one (COMPOUND 41) was prepared from (1S,4S)-4-(4-methylpiperazin-1-yl)cyclohexan-1-amine (289) according to the experimental procedure for the synthesis of COMPOUND 36 as shown in Step 8, Scheme 37. MS (ESI+): m/z 452 [M+H]+; $^1$H NMR (300 MHz, MeOD): δ 8.64 (s, 1H), 7.14 (s, 1H), 4.06 (s, 1H), 3.73 (s, 2H), 3.00 (td, J=13.2, 3.9 Hz, 4H), 2.69 (br s, 3H), 2.21-2.11 (m, 3H), 1.96-1.74 (m, 12H), 1.60-1.47 (m, 3H), 1.33-1.29 (m, 5H).

Scheme 39: Synthesis of (1S,4S)-4-Methoxy-2'-((5-(4-methylpiperazin-1-yl) pyridin-2-yl)amino)-7',8'-dihydro-6'H-spiro [cyclohexane-1,9'-pyrazino[1',2':1,5]pyrrolo[2,3-d]pyrimidin]-6'-one (COMPOUND 38) and (1R,4R)-4-Methoxy-2'-((5-(4-methylpiperazin-1-yl)pyridin-2-yl)amino)-7',8'-dihydro-6'H-spiro [cyclohexane-1,9'-pyrazino [1',2':1,5]pyrrolo[2,3-d]pyrimidin]-6'-one (COMPOUND 39)

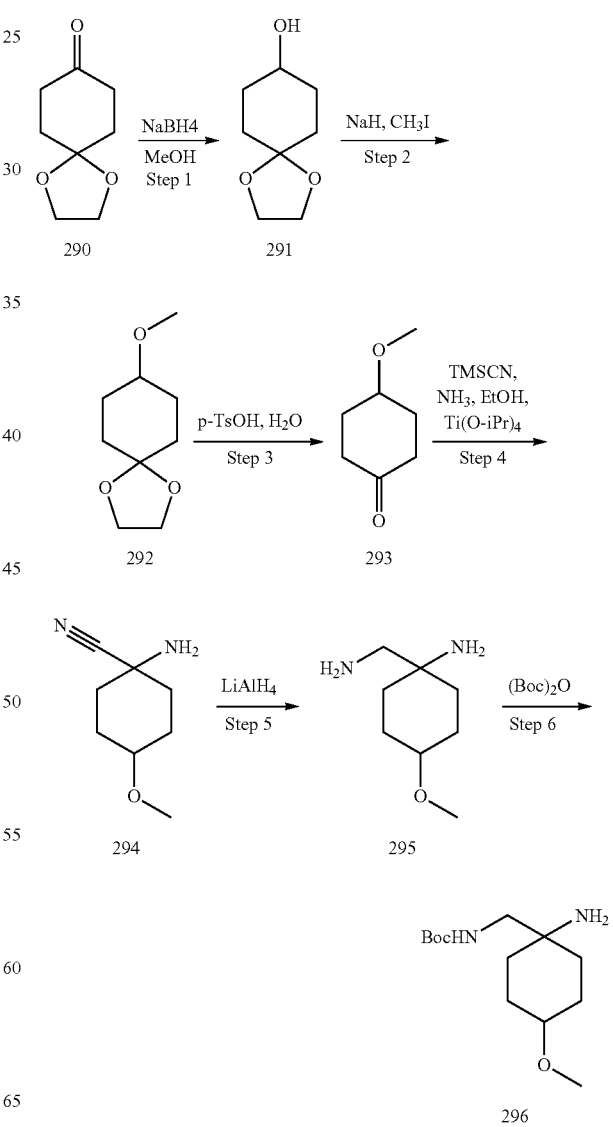

-continued
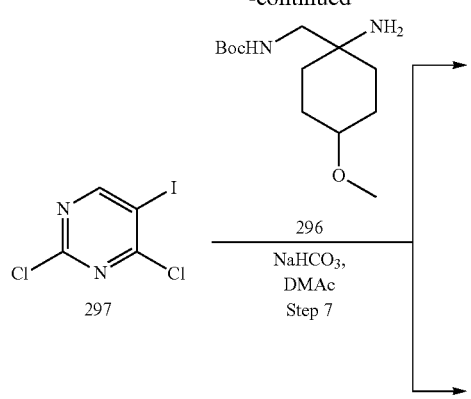
297
296
NaHCO₃,
DMAc
Step 7
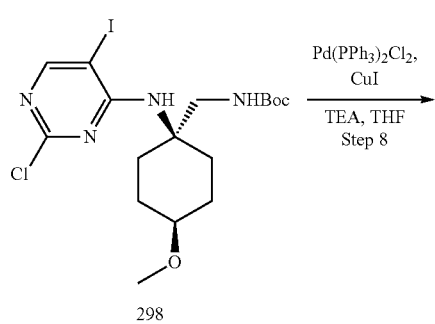
298
Pd(PPh₃)₂Cl₂,
CuI
TEA, THF
Step 8
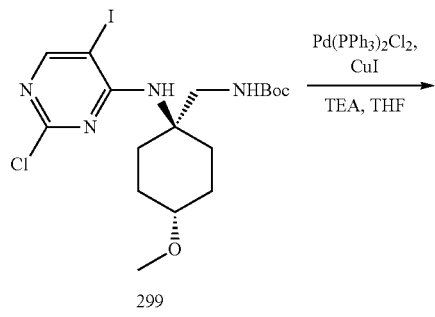
299
Pd(PPh₃)₂Cl₂,
CuI
TEA, THF
300
TBAF
Step 9
-continued
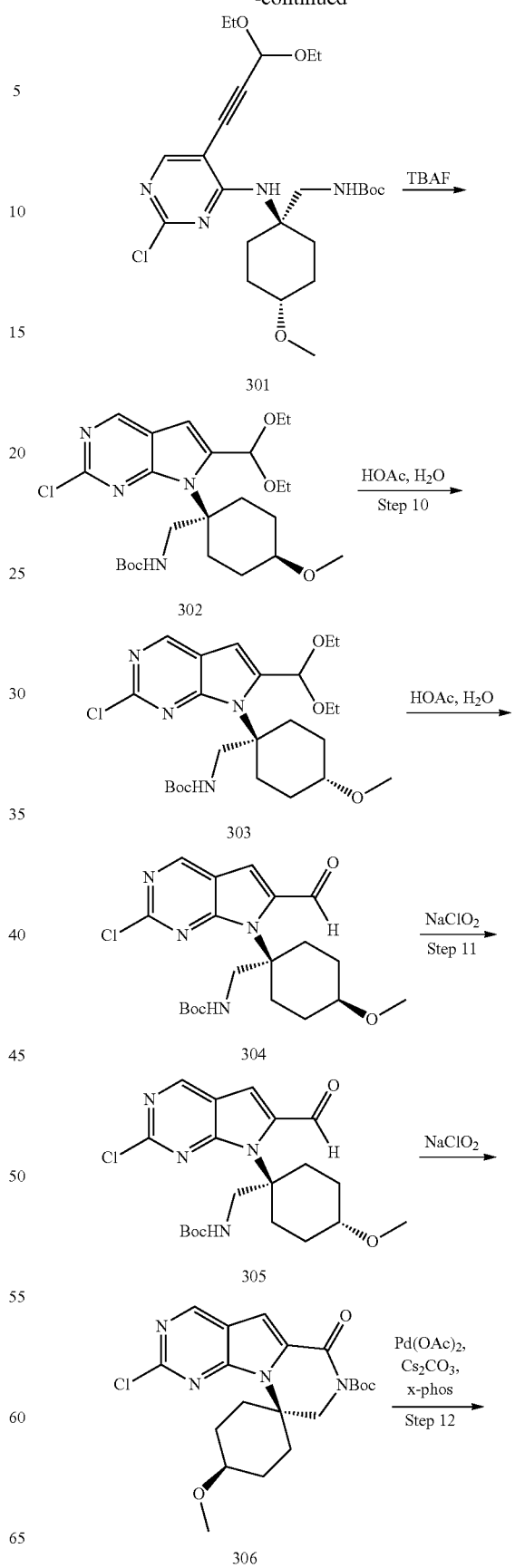
301  TBAF
302  HOAc, H₂O
     Step 10
303  HOAc, H₂O
304  NaClO₂
     Step 11
305  NaClO₂
306  Pd(OAc)₂,
     Cs₂CO₃,
     x-phos
     Step 12

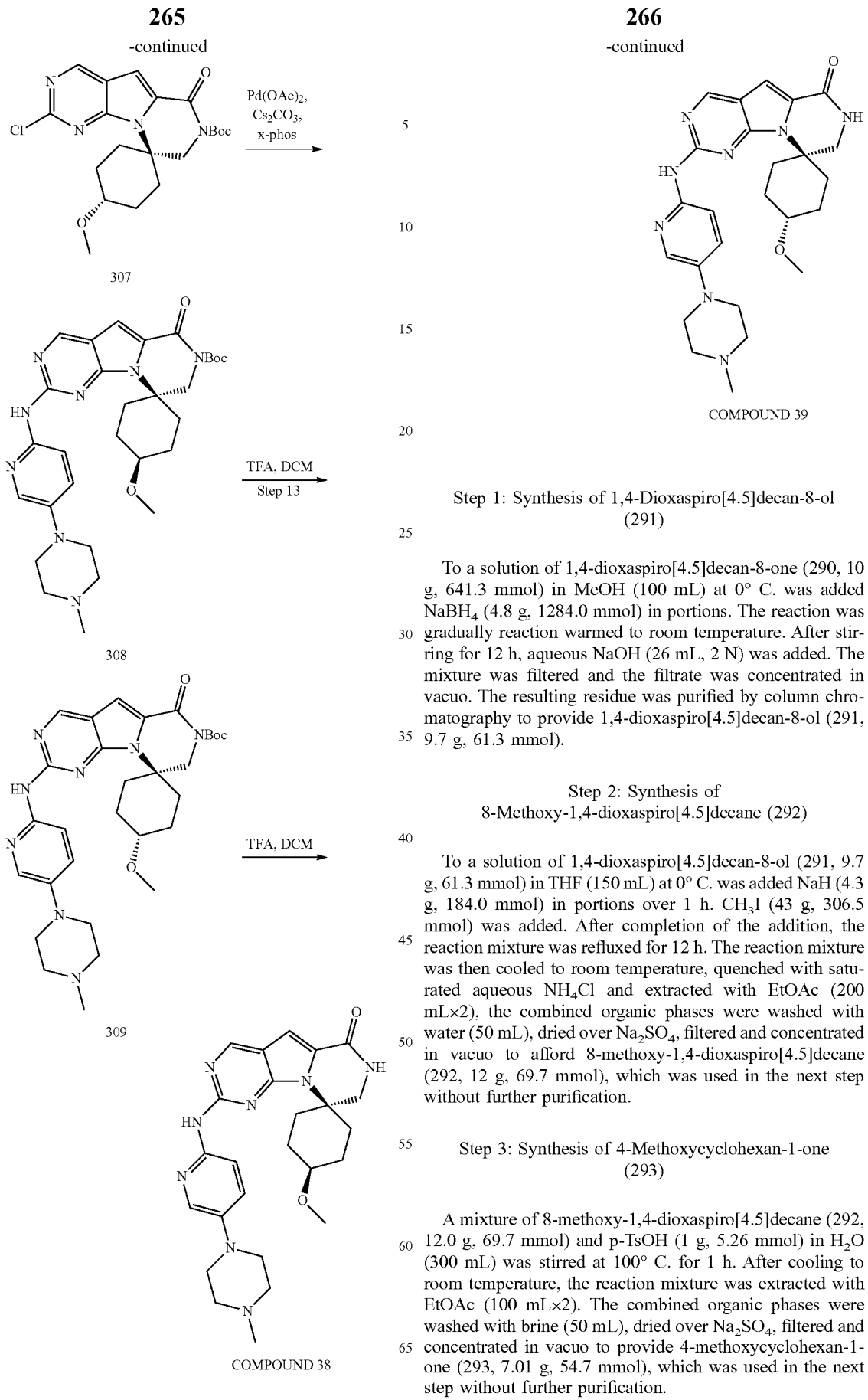

Step 1: Synthesis of 1,4-Dioxaspiro[4.5]decan-8-ol (291)

To a solution of 1,4-dioxaspiro[4.5]decan-8-one (290, 10 g, 641.3 mmol) in MeOH (100 mL) at 0° C. was added NaBH₄ (4.8 g, 1284.0 mmol) in portions. The reaction was gradually reaction warmed to room temperature. After stirring for 12 h, aqueous NaOH (26 mL, 2 N) was added. The mixture was filtered and the filtrate was concentrated in vacuo. The resulting residue was purified by column chromatography to provide 1,4-dioxaspiro[4.5]decan-8-ol (291, 9.7 g, 61.3 mmol).

Step 2: Synthesis of 8-Methoxy-1,4-dioxaspiro[4.5]decane (292)

To a solution of 1,4-dioxaspiro[4.5]decan-8-ol (291, 9.7 g, 61.3 mmol) in THF (150 mL) at 0° C. was added NaH (4.3 g, 184.0 mmol) in portions over 1 h. CH₃I (43 g, 306.5 mmol) was added. After completion of the addition, the reaction mixture was refluxed for 12 h. The reaction mixture was then cooled to room temperature, quenched with saturated aqueous NH₄Cl and extracted with EtOAc (200 mL×2), the combined organic phases were washed with water (50 mL), dried over Na₂SO₄, filtered and concentrated in vacuo to afford 8-methoxy-1,4-dioxaspiro[4.5]decane (292, 12 g, 69.7 mmol), which was used in the next step without further purification.

Step 3: Synthesis of 4-Methoxycyclohexan-1-one (293)

A mixture of 8-methoxy-1,4-dioxaspiro[4.5]decane (292, 12.0 g, 69.7 mmol) and p-TsOH (1 g, 5.26 mmol) in H₂O (300 mL) was stirred at 100° C. for 1 h. After cooling to room temperature, the reaction mixture was extracted with EtOAc (100 mL×2). The combined organic phases were washed with brine (50 mL), dried over Na₂SO₄, filtered and concentrated in vacuo to provide 4-methoxycyclohexan-1-one (293, 7.01 g, 54.7 mmol), which was used in the next step without further purification.

Step 4: Synthesis of 1-Amino-4-methoxycyclohexanecarbonitrile (294)

1-amino-4-methoxycyclohexanecarbonitrile (294) was prepared according to the synthesis of 4-methoxycyclohexan-1-one (261) described in Step 1 of Scheme 36.

Step 5: Synthesis of 1-(Aminomethyl)-4-methoxycyclohexanamine (295)

1-(aminomethyl)-4-methoxycyclohexanamine (295) was prepared from 1-amino-4-methoxycyclohexanecarbonitrile (294) according to the experimental procedure for the synthesis of 4-(aminomethyl)tetrahydro-2H-pyran-4-amine (262) described in Step 2, Scheme 36.

Step 6: Synthesis of tert-Butyl ((1-amino-4-methoxycyclohexyl)methyl)carbamate (296)

Tert-butyl ((1-amino-4-methoxycyclohexyl)methyl)carbamate (296) was prepared from 1-(aminomethyl)-4-methoxycyclohexanamine (295) according to the experimental procedure for the synthesis of tert-butyl ((4-aminotetrahydro-2H-pyran-4-yl)methyl)carbamate (263) shown in Step 3, Scheme 36.

Step 7: Synthesis of tert-Butyl (((1S,4S)-1-((2-chloro-5-iodopyrimidin-4-yl) amino)-4-methoxycyclohexyl)methyl)carbamate (298) and tert-Butyl (((1R,4R)-1-((2-chloro-5-iodopyrimidin-4-yl) amino)-4-methoxycyclohexyl)methyl)carbamate (299)

To a solution 2,4-dichloro-5-iodopyrimidine (297, 10.3 g, 37.5 mmol) and tert-butyl ((1-amino-4-methoxycyclohexyl)methyl)carbamate (296, 9 g, 34.8 mmol) in DMAc (180 mL) was added NaHCO$_3$(10.8 g, 128 mmol). After stirring at 80° C. for 12 h, the reaction was quenched with water (500 ml) and extracted with EtOAc (300 mL×3). The combined organic layers were washed with water (200 mL×2) and brine (100 mL). The organic layer was dried over Na$_2$SO$_4$, filtered and concentrated in vacuo. The resulting residue was purified by column chromatography to provide tert-butyl (((1S,4S)-1-((2-chloro-5-iodopyrimidin-4-yl)amino)-4-methoxycyclohexyl)methyl)carbamate (298, 3.2 g, 6.44 mmol) and tert-butyl (((1R,4R)-1-((2-chloro-5-iodopyrimidin-4-yl)amino)-4-methoxycyclohexyl)methyl)carbamate (299, 5.1 g, 10.3 mmol). MS (ESI+): m/z 497 [M+H]$^+$.

tert-Butyl (((1S,4S)-1-((2-chloro-5-iodopyrimidin-4-yl)amino)-4-methoxycyclohexyl)methyl)carbamate (298)

$^1$H NMR (300 MHz, CDCl$_3$): δ 8.21 (s, 1H), 3.53 (d, J=6.6 Hz, 2H), 3.49 (d, J=6.3 Hz, 1H), 3.37-3.32 (m, 1H), 3.25 (s, 3H), 3.23-3.22 (m, 1H), 2.08-1.98 (m, 2H), 1.79-1.64 (m, 5H), 1.52-1.47 (m, 1H), 1.36 (s, 9H).

tert-Butyl (((1R,4R)-1-((2-chloro-5-iodopyrimidin-4-yl)amino)-4-methoxycyclohexyl)methyl)carbamate (299)

$^1$H NMR (300 MHz, CDCl$_3$): δ 8.22 (s, 1H), 3.56 (d, J=6.6 Hz, 2H), 3.52 (s, 1H), 3.28 (s, 3H), 3.27-3.25 (m, 1H), 3.19-3.12 (m, 1H), 2.30-2.17 (m, 2H), 1.95-1.82 (m, 2H), 1.79-1.65 (m, 2H), 1.45-1.39 (m, 2H), 1.36 (s, 9H).

Step 8: Synthesis of tert-Butyl (((1S,4S)-1-((2-chloro-5-(3,3-diethoxyprop-1-yn-1-yl)pyrimidin-4-yl)amino)-4-methoxycyclohexyl)methyl)carbamate (300)

Under N$_2$ atmosphere, to a solution of tert-butyl (((1s,4s)-1-((2-chloro-5-iodopyrimidin-4-yl)amino)-4-methoxycyclohexyl)methyl)carbamate (298, 3.2 g, 6.45 mmol) and Et$_3$N (1.4 g, 13.8 mmol) in THF (70 mL) was added CuI (122 mg, 0.64 mmol) and Pd(PPh$_3$)$_2$Cl$_2$ (181 mg, 0.26 mmol). After the reaction was stirred at 20° C. for 10 min, 3,3-diethoxyprop-1-yne (990 mg, 7.72 mmol) was added dropwise and the reaction was stirred at 20° C. for 12 h. The reaction mixture was then quenched with water (100 mL) and extracted with EtOAc (100 mL×3). The combined organic phases were washed with brine (100 mL), dried over Na$_2$SO$_4$, filtered and concentrated in vacuo. The resulting residue was purified by column chromatography to provide tert-butyl (((1s,4s)-1-((2-chloro-5-(3,3-diethoxyprop-1-yn-1-yl)pyrimidin-4-yl)amino)-4-methoxycyclohexyl)methyl)carbamate (300, 2.60 g, 5.23 mmol).

Step 9: Synthesis of tert-Butyl (((1S,4S)-1-(2-chloro-6-(diethoxymethyl)-7H-pyrrolo[2,3-d]pyrimidin-7-yl)-4-methoxycyclohexyl)methyl)carbamate (302)

To a solution of tert-butyl (((1s,4s)-1-((2-chloro-5-(3,3-diethoxyprop-1-yn-1-yl)pyrimidin-4-yl)amino)-4-methoxycyclohexyl)methyl)carbamate (300, 2.60 g, 5.23 mmol) in THF (50 mL) was added TBAF (25 mL, 25 mmol, 1 M in THF). After stirring at 65° C. for 2 h, the reaction mixture was cooled room temperature, quenched with water (150 mL) and extracted with EtOAc (100 mL×3). The combined organic phases were dried over Na$_2$SO$_4$, filtered and concentrated in vacuo. The resulting residue was purified by column chromatography to provide tert-butyl (((1s,4s)-1-(2-chloro-6-(diethoxymethyl)-7H-pyrrolo[2,3-d]pyrimidin-7-yl)-4-methoxycyclohexyl)methyl)carbamate (302, 1.2 g, 2.41 mmol).

Step 10: Synthesis of tert-Butyl (((1S,4S)-1-(2-chloro-6-formyl-7H-pyrrolo [2,3-d]pyrimidin-7-yl)-4-methoxycyclohexyl)methyl)carbamate (304)

To a solution of tert-butyl (((1s,4s)-1-(2-chloro-6-(diethoxymethyl)-7H-pyrrolo[2,3-d]pyrimidin-7-yl)-4-methoxycyclohexyl)methyl)carbamate (302, 1.2 g, 2.41 mmol) in THF (4 mL) was added H$_2$O (4 mL) and HOAc (4 mL). After stirring at 60° C. for 2 h, the reaction was quenched with saturated aqueous NaHCO$_3$and extracted with EtOAc (100 mL×3). The combined organic phases were dried over Na$_2$SO$_4$, filtered and concentrated in vacuo. The resulting residue was purified by column chromatography to provide tert-butyl (((1s,4s)-1-(2-chloro-6-formyl-7H-pyrrolo[2,3-d]pyrimidin-7-yl)-4-methoxycyclohexyl)methyl)carbamate (304, 700 mg, 1.66 mmol).

Step 11: Synthesis of tert-Butyl (1S,4S)-2'-chloro-4-methoxy-6'-oxo-6'H-spiro [cyclohexane-1,9'-pyrazino [1',2':1,5]pyrrolo[2,3-d]pyrimidine]-7'(8'H)-carboxylate (306)

To a solution of tert-butyl (((1 S,4S)-1-(2-chloro-6-formyl-7H-pyrrolo[2,3-d]pyrimidin-7-yl)-4-methoxycyclohexyl)methyl)carbamate (304, 240 mg, 0.57 mmol) in t-BuOH (15 mL) and acetonitrile (3 mL) was added NaH$_2$PO$_4$ (709 mg, 4.55 mmol) and 2-methyl-2-butene (318 mg, 4.53 mmol). After stirring at 0° C. for 5 min, a solution of NaClO$_2$ (318 mg, 3.52 mmol) in H$_2$O (3 mL) was added dropwise over 1 h. After warming to room temperature and stirring for another 2 h, the reaction mixture was quenched with water (50 mL) and extracted with EtOAc (30 mL×3). The combined organic phases were dried over Na$_2$SO$_4$, filtered and concentrated in vacuo. The resulting residue was purified by column chromatography to provide tert-butyl (1 S,4S)-2'-chloro-4-methoxy-6'-oxo-6'H-spiro[cyclohexane-1,9'-pyrazino[1',2':1,5]pyrrolo[2,3-d]pyrimidine]-7'(8'H)-carboxylate (306, 200 mg, 0.47 mmol).

Step 12: Synthesis of tert-Butyl (1S,4S)-4-methoxy-2'-((5-(4-methylpiperazin -1-yl)pyridin-2-yl)amino)-6'-oxo-6'H-spiro [cyclohexane-1,9'-pyrazino [1',2':1, 5]pyrrolo [2,3-d]pyrimidine]-7'(8'H)-carboxylate (308)

Under N$_2$ atmosphere, to a solution of tert-butyl (1S,4S)-2'-chloro-4-methoxy-6'-oxo-6'H-spiro[cyclohexane-1,9'-pyrazino[1',2': 1,5]pyrrolo[2,3-d]pyrimidine]-7'(8'H)-carboxylate (306, 100 mg, 0.24 mmol), 5-(4-methylpiperazin-1-yl)pyridin-2-amine (55.4 mg, 0.28 mmol) in dioxane (5 mL) was added Cs$_2$CO$_3$ (232 mg, 0.71 mmol), Pd(OAc)$_2$ (5.3 mg, 0.02 mmol) and X-Phos (59 mg, 0.12 mmol). After stirring at 100° C. for 12 h, the reaction was quenched with water (10 mL) and extracted with EtOAc (10 mL×2). The organic phases were concentrated in vacuo and the resulting residue was purified by column chromatography to provide tert-butyl (1s,4s)-4-methoxy-2'-((5-(4-methylpiperazin-1-yl)pyridin-2-yl)amino)-6'-oxo-6'H-spiro[cyclohexane-1,9'-pyrazino[1',2': 1,5]pyrrolo[2,3-d]pyrimidine]-7'(8'H)-carboxylate (308, 50 mg, 0.09 mmol). MS (ESI+): m/z 577 [M+H]$^+$.

Step 13: Synthesis of (1S,4S)-4-Methoxy-2'-((5-(4-methylpiperazin-1-yl) pyridin-2-yl)amino)-7',8'-dihydro-6'H-spiro[cyclohexane-1,9'-pyrazino[1',2':1, 5]pyrrolo [2,3-d]pyrimidin]-6'-one (COMPOUND 38)

To a solution of tert-butyl (1S,4S)-4-methoxy-2'-((5-(4-methylpiperazin-1-yl)pyridin-2-yl)amino)-6'-oxo-6'H-spiro [cyclohexane-1,9'-pyrazino[1',2': 1,5]pyrrolo[2,3-d]pyrimidine]-7'(8'H)-carboxylate (308, 50 mg, 0.09 mmol) in DCM (3 mL) at 0° C. was added TFA (1 mL) in dropwise. After stirring for 2 h, the reaction mixture was neutralized with saturated aqueous NaHCO$_3$ and extracted with i-PrOH/DCM=1/3 (20 mL×2). The combined organic phases were dried over Na$_2$SO$_4$, filtered and concentrated in vacuo. The resulting residue was purified by prep TLC to provide (1S,4S)-4-methoxy-2'-((5-(4-methylpiperazin-1-yl)pyridin-2-yl) amino)-7',8'-dihydro-6'H-spiro[cyclohexane-1,9'-pyrazino[1',2': 1,5]pyrrolo[2,3-d]pyrimidin]-6'-one (COMPOUND 38, 6.7 mg, 0.01 mmol). MS (ESI+): m/z 477 [M+H]+; $^1$H NMR (300 MHz, MeOD+CDCl$_3$): δ 8.84 (s, 1H), 8.15 (s, 1H), 8.01 (s, 1H), 7.51-7.41 (m, 1H), 7.27 (s, 1H), 3.78 (s, 2H), 3.46 (s, 3H), 3.45-3.36 (m, 6H), 3.23-3.06 (m, 5H), 2.73 (s, 3H), 2.27-2.17 (m, 2H), 2.15-2.04 (m, 2H), 1.54-1.40 (m, 2H).

Synthesis of (1R,4R)-4-Methoxy-2'-((5-(4-methyl-piperazin-1-yl)pyridin-2-yl)amino)-7',8'-dihydro-6'H-spiro [cyclohexane-1,9'-pyrazino[1',2':1,5]pyrrolo [2,3-d]pyrimidin]-6'-one (COMPOUND 39)

COMPOUND 39 was prepared according to the experimental procedures in the synthesis of COMPOUND 38. MS (ESI+): m/z 477 [M+H]$^+$; $^1$H NMR (300 MHz, MeOD+CDCl$_3$): δ 8.82 (s, 1H), 8.39 (br s, 1H), 7.98 (d, J=2.5 Hz, 1H), 7.55 (d, J=9.7 Hz, 1H), 7.26 (s, 1H), 3.77 (s, 2H), 3.63 (s, 1H), 3.41 (s, 3H), 3.40-3.34 (m, 6H), 3.16-2.94 (m, 4H), 2.67 (s, 3H), 2.19-2.09 (m, 2H), 1.87-1.76 (m, 2H), 1.72-1.59 (m, 2H).

Example 5. Non-Limiting Examples of Compounds

TABLE 3

Non-limiting Examples of Final Compounds

| Compd # | Compound Structure |
|---|---|
| 10 | 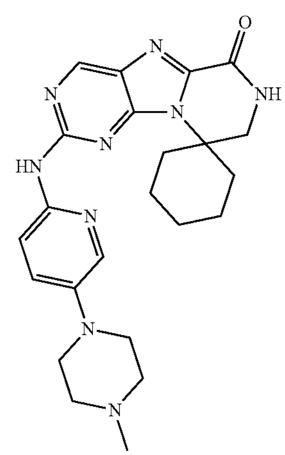 [SMILES: CN1CCN(c2ccc(Nc3ncc4nc5n(c4n3)C3(CCCCC3)CNC5=O)nc2)CC1] |
| 11 | 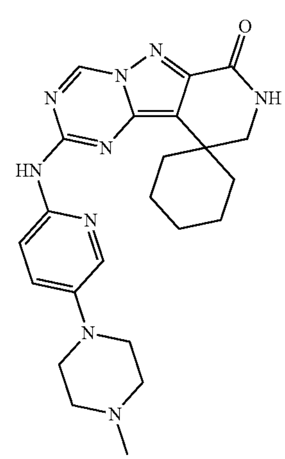 [SMILES: CN1CCN(c2ccc(Nc3ncn4nc5c(c4n3)C3(CCCCC3)CNC5=O)nc2)CC1] |

TABLE 3-continued

Non-limiting Examples of Final Compounds

| Compd # | Compound Structure |
|---|---|
| 12 | 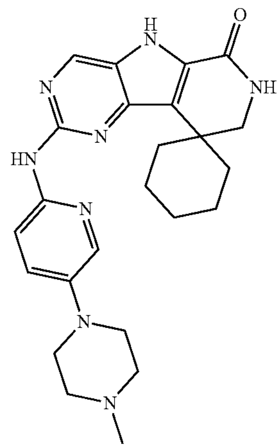 [SMILES: CN1CCN(c2ccc(Nc3ncc4[nH]c5c(c4n3)C3(CCCCC3)CNC5=O)nc2)CC1] |
| 13 | 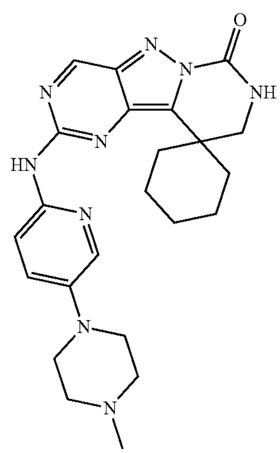 [SMILES: CN1CCN(c2ccc(Nc3ncc4nn5c(c4n3)C3(CCCCC3)CNC5=O)nc2)CC1] |
| 14 | 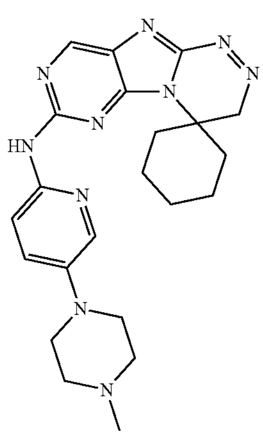 [SMILES: CN1CCN(c2ccc(Nc3ncc4nc5n(c4n3)C3(CCCCC3)CN=N5)nc2)CC1] |
| 15 | |
| 16 | |
| 17 | |

TABLE 3-continued

Non-limiting Examples of Final Compounds

| Compd # | Compound Structure |
|---|---|
| 18 | 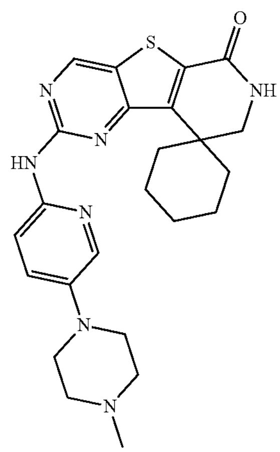 [SMILES: CN1CCN(c2ccc(Nc3ncc4sc5c(c4n3)C3(CCCCC3)CNC5=O)nc2)CC1] |
| 19 | 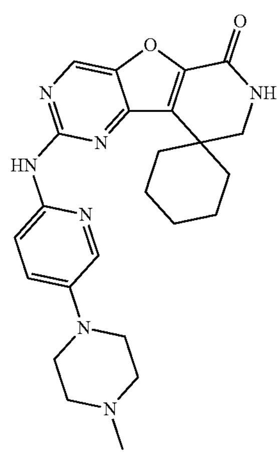 [SMILES: CN1CCN(c2ccc(Nc3ncc4oc5c(c4n3)C3(CCCCC3)CNC5=O)nc2)CC1] |
| 20 | 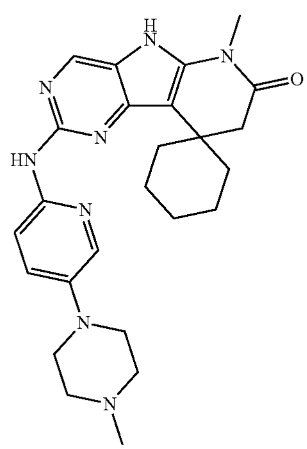 [SMILES: CN1CCN(c2ccc(Nc3ncc4[nH]c5c(c4n3)C3(CCCCC3)CC(=O)N5C)nc2)CC1] |
| 21 | |
| 22 | |
| 23 | |

TABLE 3-continued

Non-limiting Examples of Final Compounds

| Compd # | Compound Structure |
|---|---|
| 24 | 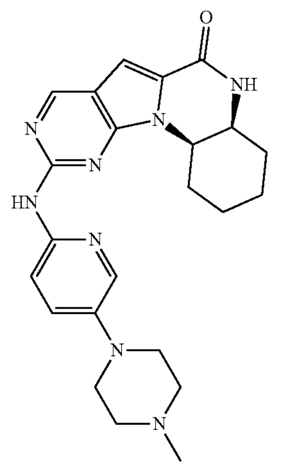 [SMILES: CN1CCN(c2ccc(Nc3ncc4cc5n(c4n3)[C@@H]3CCCC[C@@H]3NC5=O)nc2)CC1] |
| 25 | 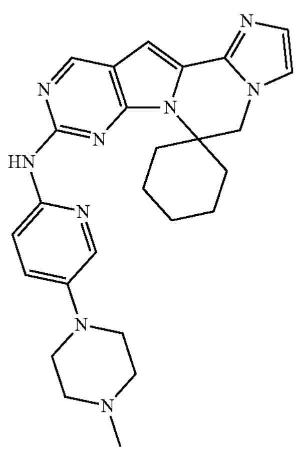 [SMILES: CN1CCN(c2ccc(Nc3ncc4cc5n(c4n3)C3(CCCCC3)Cn3ccnc3-5)nc2)CC1] |
| 26 | 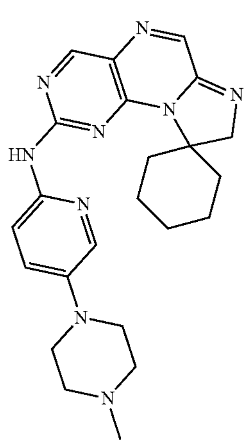 [SMILES: CN1CCN(c2ccc(Nc3ncc4c(n3)N3C(=NCC35CCCCC5)C=N4)nc2)CC1] |
| 27 | |
| 28 | |
| 29 | |

TABLE 3-continued

Non-limiting Examples of Final Compounds

| Compd # | Compound Structure |
|---|---|
| 30 | 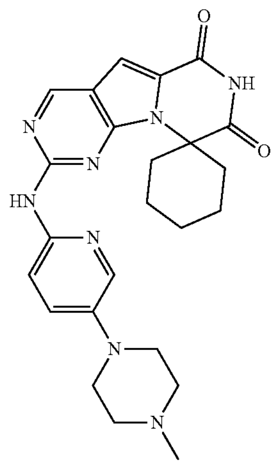 [SMILES: CN1CCN(c2ccc(Nc3ncc4cc5n(c4n3)C3(CCCCC3)C(=O)NC5=O)nc2)CC1] |
| 31 | 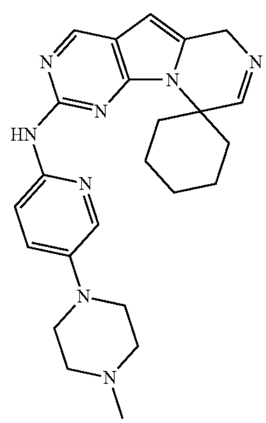 [SMILES: CN1CCN(c2ccc(Nc3ncc4cc5n(c4n3)C3(C=NC5)CCCCC3)nc2)CC1] |
| 32 | 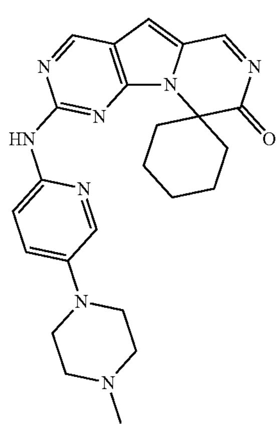 [SMILES: CN1CCN(c2ccc(Nc3ncc4cc5n(c4n3)C3(CCCCC3)C(=O)N=C5)nc2)CC1] |
| 33 | |
| 34 | |
| 35 | |

TABLE 3-continued

Non-limiting Examples of Final Compounds

| Compd # | Compound Structure |
|---|---|
| 36 | (structure) |
| 37 | (structure) |
| 38 | (structure) |
| 39 | (structure) |
| 40 | (structure) |
| 41 | (structure) |

Example 6: CDK4/6 Inhibition In Vitro Assay

Selected compounds disclosed herein were tested in CDK4/cyclinD1, CDK2/CycA and CDK2/cyclinE kinase assays by Nanosyn (Santa Clara, Calif.) to determine their inhibitory effect on these CDKs. The assays were performed using microfluidic kinase detection technology (Caliper Assay Platform). The compounds were tested in 12-point dose-response format in singlicate at Km for ATP. Phospho-acceptor substrate peptide concentration used was 1 µM for all assays and Staurosporine was used as the reference compound for all assays. Specifics of each assay are as described below:

CDK2/CyclinA: Enzyme concentration: 0.2 nM; ATP concentration: 50 µM; Incubation time: 3 hr.

CDK2/CyclinE: Enzyme concentration: 0.28 nM; ATP concentration: 100 µM; Incubation time: 1 hr.

CDK4/CyclinD1: Enzyme concentration: 1 nM; ATP concentration: 200 µM; Incubation time: 10 hr.

BIOLOGICAL TABLE 3

| Compd # | Compound Structure | CDK4/ Cyclin D1 (µM) | CDK6/ Cyclin D3 (µM) | CDK2/ Cyclin E (µM) | CDK2/ Cyclin A (µM) | CDK9/ Cyclin T (µM) |
| --- | --- | --- | --- | --- | --- | --- |
| 25 | 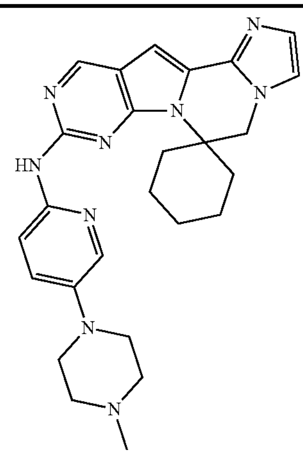 | 0.03 | 0.1 | 99 | 59 | 6.3 |
| 27 | 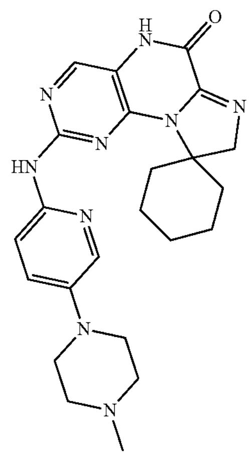 [SMILES: CN1CCN(c2ccc(Nc3ncc4c(n3)N3C(=NCC35CCCCC5)C(=O)N4)nc2)CC1] | 9.4 | 21 | >100 | >100 | >100 |
| 28 | 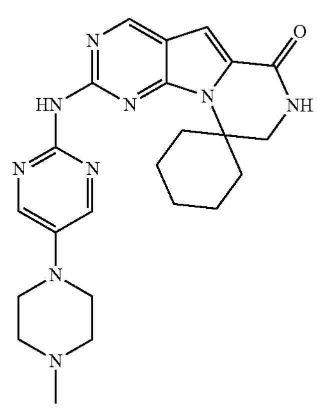 [SMILES: CN1CCN(c2cnc(Nc3ncc4cc5n(c4n3)C3(CCCCC3)CNC5=O)nc2)CC1] | 0.02 | 0.06 | >100 | 13.5 | 1 |

BIOLOGICAL TABLE 3-continued

| Compd # | Compound Structure | CDK4/ Cyclin D1 (μM) | CDK6/ Cyclin D3 (μM) | CDK2/ Cyclin E (μM) | CDK2/ Cyclin A (μM) | CDK9/ Cyclin T (μM) |
|---|---|---|---|---|---|---|
| 31 | 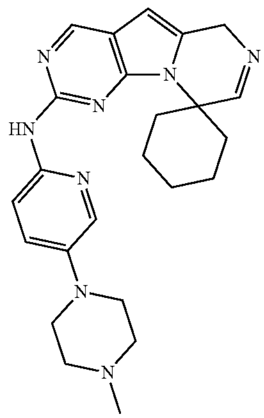 [SMILES: CN1CCN(c2ccc(Nc3ncc4cc5n(c4n3)C3(C=NC5)CCCCC3)nc2)CC1] | 0.0006 | 0.001 | 0.04 | 0.1 | 0.04 |
| 33 | 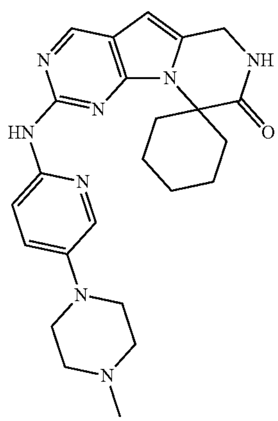 [SMILES: CN1CCN(c2ccc(Nc3ncc4cc5n(c4n3)C3(CCCCC3)C(=O)NC5)nc2)CC1] | 0.006 | 0.02 | 4 | 2 | 3 |
| 34 | 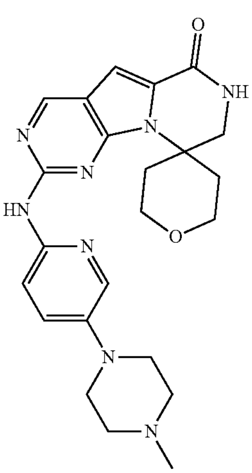 [SMILES: CN1CCN(c2ccc(Nc3ncc4cc5n(c4n3)C3(CCOCC3)CNC5=O)nc2)CC1] | 0.02 | 0.02 | 23 | 14 | 0.4 |

BIOLOGICAL TABLE 3-continued
| Compd # | Compound Structure | CDK4/ Cyclin D1 (μM) | CDK6/ Cyclin D3 (μM) | CDK2/ Cyclin E (μM) | CDK2/ Cyclin A (μM) | CDK9/ Cyclin T (μM) |
|---|---|---|---|---|---|---|
| 36 | 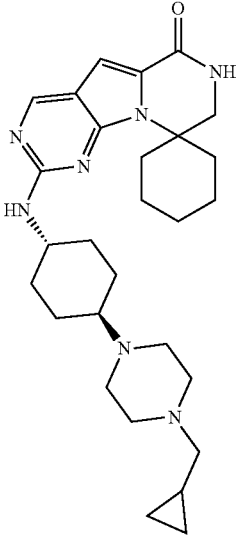 [SMILES: O=C1NCC2(CCCCC2)n2c1cc1cnc(N[C@H]3CC[C@H](N4CCN(CC5CC5)CC4)CC3)nc12] | 0.004 | 0.03 | 0.3 | 0.1 | 0.002 |
| 37 | 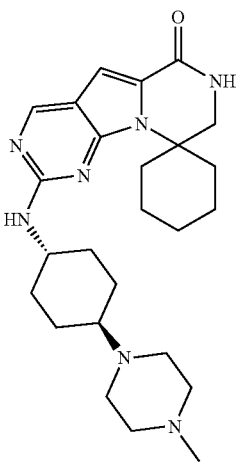 [SMILES: CN1CCN([C@H]2CC[C@H](Nc3ncc4cc5n(c4n3)C3(CCCCC3)CNC5=O)CC2)CC1] | 0.006 | 0.04 | 0.4 | 0.02 | 0.003 |
| 38 | 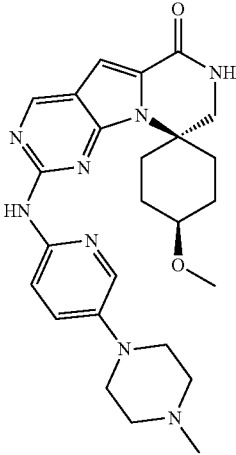 [SMILES: CO[C@H]1CC[C@@]2(CC1)CNC(=O)c1cc3cnc(Nc4ccc(N5CCN(C)CC5)cn4)nc3n12] | 0.007 | 0.01 | 14 | 5 | 0.2 |

BIOLOGICAL TABLE 3-continued

| Compd # | Compound Structure | CDK4/ Cyclin D1 (μM) | CDK6/ Cyclin D3 (μM) | CDK2/ Cyclin E (μM) | CDK2/ Cyclin A (μM) | CDK9/ Cyclin T (μM) |
|---|---|---|---|---|---|---|
| 39 | 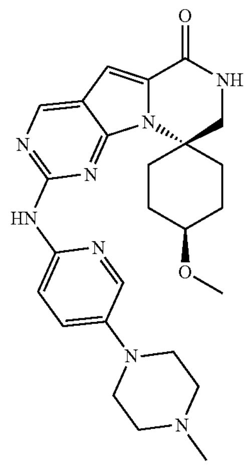 [SMILES: CO[C@H]1CC[C@]2(CC1)CNC(=O)c1cc3cnc(Nc4ccc(N5CCN(C)CC5)cn4)nc3n12] | 0.06 | 0.09 | 33 | 19 | 0.2 |
| 40 | 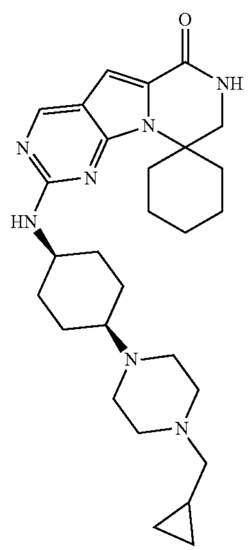 [SMILES: O=C1NCC2(CCCCC2)n2c1cc1cnc(N[C@H]3CC[C@@H](N4CCN(CC5CC5)CC4)CC3)nc12] | 0.09 | 0.5 | 5 | 2 | 0.05 |
| 41 | 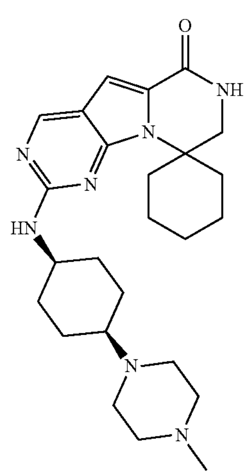 [SMILES: CN1CCN([C@H]2CC[C@@H](Nc3ncc4cc5n(c4n3)C3(CCCCC3)CNC5=O)CC2)CC1] | 0.14 | 0.8 | 6 | 2 | 0.07 |

We claim:
1. A compound selected from the group consisting of:

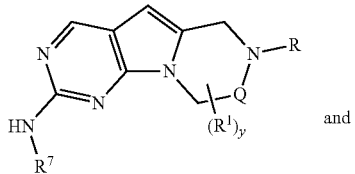

and

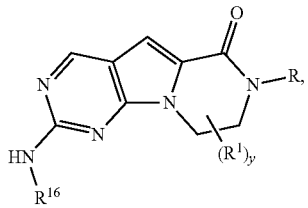

or a pharmaceutically acceptable salt thereof,
wherein:
y is 1 or 2;
Q is —C(O)—;
R is hydrogen, $C_1$-$C_6$alkyl, —($C_0$-$C_2$alkyl)($C_3$-$C_8$carbocyclyl), —($C_0$-$C_2$alkyl)($C_3$-$C_8$heterocyclyl), —C(O)—O—H, —($C_0$-$C_2$alkyl)(aryl), —($C_0$-$C_2$alkyl)(heteroaryl), —C(O)—O-alkyl, or —C(O)—O-arylalkyl;
each $R^1$ is independently alkyl, haloalkyl, cycloalkyl, or aryl, wherein each alkyl, haloalkyl, and cycloalkyl optionally includes in place of a chain carbon atom a heteroatom selected from the group consisting of nitrogen, oxygen, and sulfur; or
two geminal $R^1$ groups, together with the carbon atom to which they are attached, form a 3-8-membered ring; or
two vicinal $R^1$ groups, together with the carbon atoms to which they are attached, form a 3-8-membered ring;
$R^7$ is:

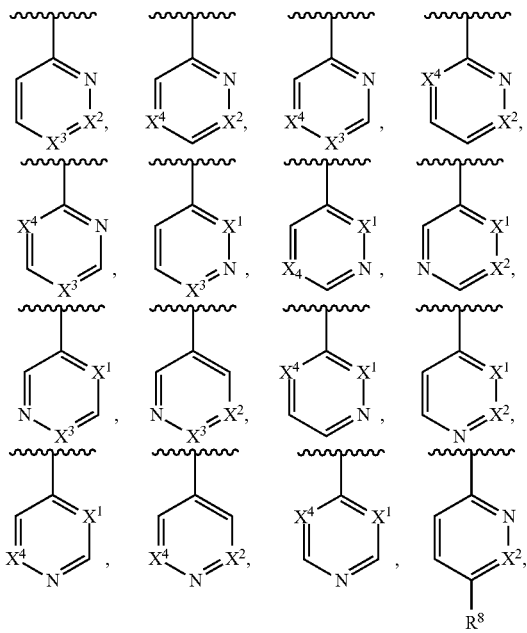

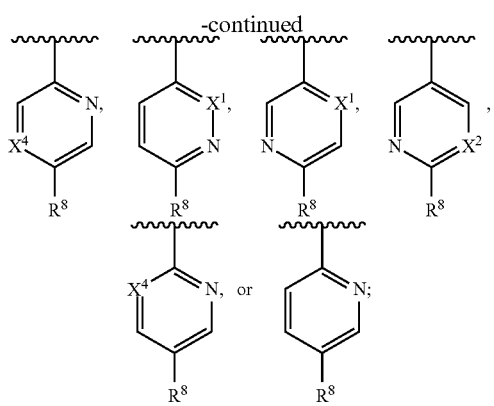

wherein:
$X^1$ is $CR^8$ or N;
$X^2$ is $CR^8$ or N;
$X^3$ is $CR^8$ or N;
$X^4$ is $CR^8$ or N; and
each $R^8$ is independently $R^2$ or $R^6$; or
$R^7$ is alkyl, cycloalkyl, or heterocyclyl, wherein the alkyl, cycloalkyl, and heterocyclyl are each optionally substituted with one or more substituents independently selected from the group consisting of —$NR^{14}R^{15}$, —$OR^{14}$, $R^2$, and $R^6$;
each $R^{14}$ is independently hydrogen, alkyl, arylalkyl, heteroarylalkyl, alkenyl, alkynyl, —C(O)H, —C(O)-alkyl, —C(S)-alkyl, —S(O)$_2$-alkyl, aryl, or heteroaryl;
each $R^{15}$ is independently hydrogen, alkyl, arylalkyl, heteroarylalkyl, alkenyl, alkynyl, —C(O)H, —C(O)-alkyl, —C(S)-alkyl, —S(O)$_2$-alkyl, aryl, or heteroaryl;
$R^{16}$ is cycloalkyl, wherein the cycloalkyl is substituted with one $R^2$;
each $R^2$ is independently -(alkylene)$_m$-heterocyclyl, wherein each -(alkylene)m-heterocyclyl is independently substituted with one or more independently selected $R^x$ substituents;
each $R^x$ is independently halo, cyano, nitro, oxo, alkyl, haloalkyl, -(alkylene)$_m$-CN, -(alkylene)$_m$-C(O)—$R^5$, -(alkylene)$_m$-C(O)—$OR^5$, -(alkylene)$_m$-C(S)—$R^5$, -(alkylene)$_m$-C(S)—$NR^3R^4$, -(alkylene)$_m$-C(S)—$OR^5$, -(alkylene)$_m$-$NR^3R^4$, -(alkylene)$_m$-N($R^3$)—C(O)—$R^5$, -(alkylene)$_m$-N($R^3$)—S(O)$_2$—$R^5$, -(alkylene)$_m$-$OR^5$, -(alkylene)$_m$-O—C(O)—$R^5$, -(alkylene)$_m$-O—C(O)—$NR^3R^4$, -(alkylene)$_m$-O—C(S)—$NR^3R^4$, -(alkylene)$_m$-C(O)-(alkylene)$_m$-$NR^3R^4$, -(alkylene)$_m$-N($R^3$)—C(O)—$NR^3R^4$, -(alkylene)$_m$-N($R^3$)—C(O)—$OR^5$, -(alkylene)$_m$-N($R^3$)—C(S)—$R^5$, -(alkylene)$_m$-N($R^3$)—C(S)—$OR^5$, -(alkylene)$_m$-N($R^3$)—S(O)$_2$—$NR^3R^4$, -(alkylene)$_m$-N($R^3$)—C(S)—$NR^3R^4$, -(alkylene)$_m$-O-alkylene-$OR^5$, -(alkylene)$_m$-S(O)—$R^5$, -(alkylene)$_m$-S(O)$_2$—$NR^3R^4$, cycloalkylalkyl, heterocycloalkyl, arylalkyl, heteroarylalkyl, alkenyl, alkynyl, cycloalkyl, heterocyclyl, aryl, or heteroaryl; or
two geminal $R^x$ groups, together with the atom to which they are attached, form a ring; or
two vicinal $R^x$ groups, together with the atoms to which they are attached, form a ring;
each $R^3$ is independently hydrogen, alkyl, cycloalkylalkyl, heterocyclylalkyl, arylalkyl, heteroarylalkyl, cycloalkyl, heterocyclyl, aryl, or heteroaryl;

each $R^4$ is independently hydrogen, alkyl, cycloalkyl-alkyl, heterocyclylalkyl, arylalkyl, heteroarylalkyl, cycloalkyl, heterocyclyl, aryl, or heteroaryl; or $R^3$ and $R^4$, together with the nitrogen atom to which they are attached, form a heterocyclyl ring;

each $R^5$ is independently hydrogen, alkyl, cycloalkyl-alkyl, heterocyclylalkyl, arylalkyl, heteroarylalkyl, alkenyl, alkynyl, cycloalkyl, heterocyclyl, aryl, or heteroaryl;

each $R^6$ is independently hydrogen, halogen, alkyl, cycloalkylalkyl, heterocyclylalkyl, arylalkyl, heteroarylalkyl, alkenyl, alkynyl, cycloalkyl, heterocyclyl, aryl, or heteroaryl;

each m is independently 0, 1, or 2; and each n is independently 0, 1, or 2;

with the provisos that:

(1) at least one of $X^1$, $X^2$, $X^3$, or $X^4$ is $CR^8$; and (2) one $R^8$ is $R^2$.

2. The compound of claim 1, wherein the compound is of formula:

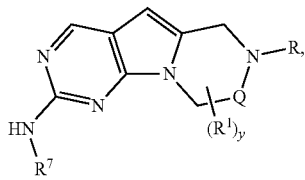

or a pharmaceutically acceptable salt thereof.

3. The compound of claim 2, or a pharmaceutically acceptable salt thereof, wherein R is hydrogen.

4. The compound of claim 1, wherein the compound is of formula:

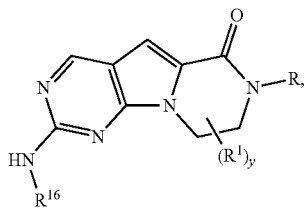

or a pharmaceutically acceptable salt thereof.

5. The compound of claim 4, or a pharmaceutically acceptable salt thereof, wherein R is hydrogen.

6. The compound of claim 4, or a pharmaceutically acceptable salt thereof, wherein each IV is independently heterocyclyl, wherein each heterocyclyl is independently substituted with one or more independently selected $R^x$ substituents.

7. The compound of claim 6, or a pharmaceutically acceptable salt thereof, wherein at least one $R^x$ substituent is cycloalkylalkyl, heterocycloalkyl, or heteroarylalkyl.

8. The compound of claim 1, or a pharmaceutically acceptable salt thereof, wherein y is 1.

9. The compound of claim 1, or a pharmaceutically acceptable salt thereof, wherein y is 2.

10. The compound of claim 9, or a pharmaceutically acceptable salt thereof, wherein:

two geminal $R^1$ groups, together with the carbon atom to which they are attached, form a 3-8-membered ring; or two vicinal $R^1$ groups, together with the carbon atoms to which they are attached, form a 3-8-membered ring.

11. The compound of claim 10, or a pharmaceutically acceptable salt thereof, wherein the 3-8-membered ring is a 6-membered ring.

12. The compound of claim 11, or a pharmaceutically acceptable salt thereof, wherein at least one $R^2$ is 4-(morpholino)piperidin-1-yl, piperazin-1-yl, 4-methylpiperazin-1-yl, or 4-isopropylpiperazin-1-yl.

13. The compound of claim 1, or a pharmaceutically acceptable salt thereof, wherein $R^7$ is:

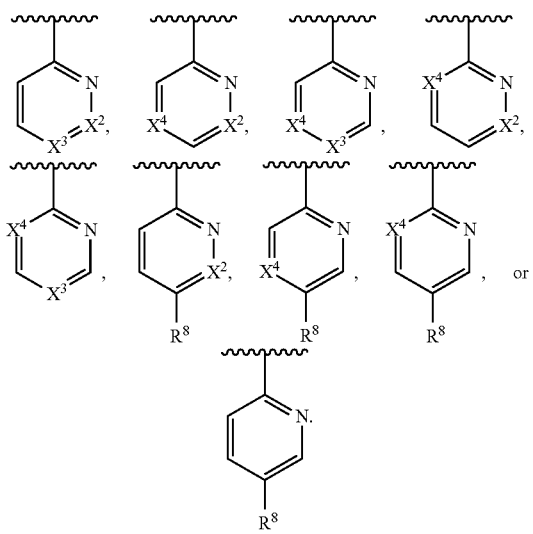

14. The compound of claim 1, or a pharmaceutically acceptable salt thereof, wherein $R^7$ is:

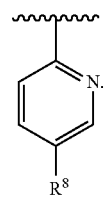

15. The compound of claim 14, or a pharmaceutically acceptable salt thereof, wherein:

$R^8$ is $R^2$; and $R^2$ is heterocyclyl, wherein the heterocyclyl is substituted with one or more independently selected $R^x$ substituents.

16. The compound of claim 15, or a pharmaceutically acceptable salt thereof, wherein each $R^x$ is independently halo, cyano, nitro, oxo, alkyl, haloalkyl, cycloalkylalkyl, heterocycloalkyl, arylalkyl, heteroarylalkyl, alkenyl, alkynyl, cycloalkyl, heterocyclyl, aryl, or heteroaryl.

17. The compound of claim 1, or a pharmaceutically acceptable salt thereof, wherein each $R^2$ is independently heterocyclyl, wherein each heterocyclyl is independently substituted with one or more independently selected $R^x$ substituents.

18. The compound of claim 17, or a pharmaceutically acceptable salt thereof, wherein each $R^x$ is independently halo, cyano, nitro, oxo, alkyl, haloalkyl, cycloalkylalkyl, heterocycloalkyl, arylalkyl, heteroarylalkyl, alkenyl, alkynyl, cycloalkyl, heterocyclyl, aryl, or heteroaryl.

19. The compound of claim 18, or a pharmaceutically acceptable salt thereof, wherein y is 2.

20. The compound of claim 1, or a pharmaceutically acceptable salt thereof, wherein each $R^2$ is independently 4-(morpholino)piperidin-1-yl, piperazin-1-yl, 4-methylpiperazin-1-yl, or 4-isopropylpiperazin-1-yl.

21. The compound of claim 1, or a pharmaceutically acceptable salt thereof, wherein:
each $R^3$ is independently hydrogen; and
each $R^4$ is independently hydrogen.

22. The compound of claim 1, or a pharmaceutically acceptable salt thereof, wherein each $R^5$ is independently alkyl.

23. The compound of claim 1, or a pharmaceutically acceptable salt thereof, wherein each m is independently 0.

24. The compound of claim 1, or a pharmaceutically acceptable salt thereof, wherein each n is independently 0.

25. The compound of claim 1, wherein the compound is:

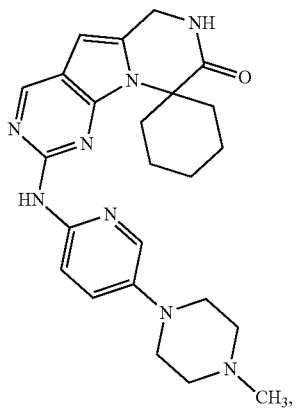 [SMILES: CN1CCN(c2ccc(Nc3ncc4cc5n(c4n3)C3(CCCCC3)C(=O)NC5)nc2)CC1]

or a pharmaceutically acceptable salt thereof.

26. The compound of claim 1, wherein the compound is:

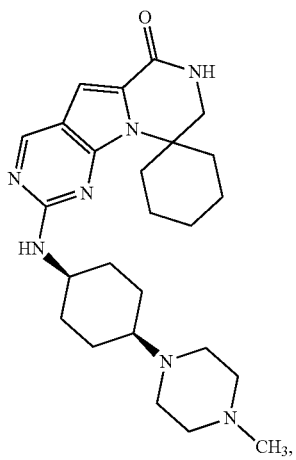 [SMILES: CN1CCN([C@H]2CC[C@@H](Nc3ncc4cc5n(c4n3)C3(CCCCC3)CNC5=O)CC2)CC1]

or a pharmaceutically acceptable salt thereof.

27. The compound of claim 1, wherein the compound is:

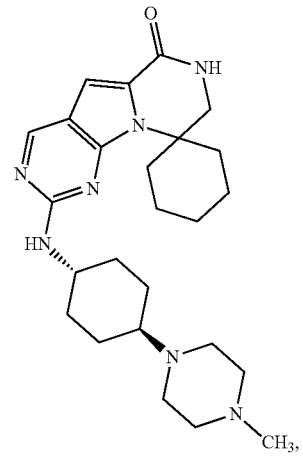 [SMILES: CN1CCN([C@H]2CC[C@H](Nc3ncc4cc5n(c4n3)C3(CCCCC3)CNC5=O)CC2)CC1]

or a pharmaceutically acceptable salt thereof.

28. The compound of claim 1, wherein the compound is:

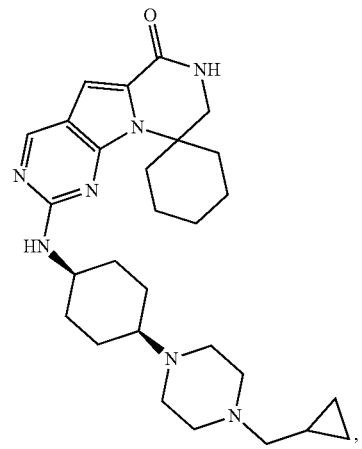 [SMILES: O=C1NCC2(CCCCC2)n2c1cc1cnc(N[C@H]3CC[C@@H](N4CCN(CC5CC5)CC4)CC3)nc12]

or a pharmaceutically acceptable salt thereof.

29. The compound of claim 1, wherein the compound is:

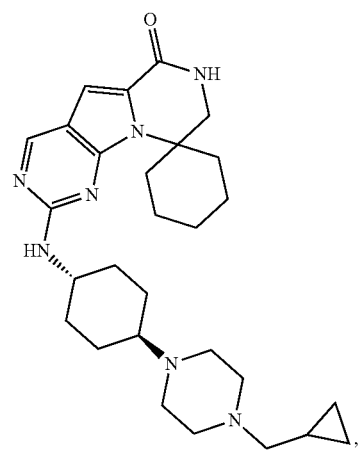 [SMILES: O=C1NCC2(CCCCC2)n2c1cc1cnc(N[C@H]3CC[C@H](N4CCN(CC5CC5)CC4)CC3)nc12]

or a pharmaceutically acceptable salt thereof.

* * * * *